US011230688B2

(12) United States Patent
Kerns et al.

(10) Patent No.: US 11,230,688 B2
(45) Date of Patent: Jan. 25, 2022

(54) IN VITRO GASTROINTESTINAL MODEL COMPRISING LAMINA PROPRIA-DERIVED CELLS

(71) Applicant: EMULATE, Inc., Boston, MA (US)

(72) Inventors: S. Jordan Kerns, Reading, MA (US); Jenifer Obrigewitch, Boston, MA (US); Michael Salmon, Boston, MA (US); Benjamin Richards Umiker, Cambridge, MA (US)

(73) Assignee: EMULATE, INC., Boston, MA (US)

( * ) Notice: Subject to any disclaimer, the term of this patent is extended or adjusted under 35 U.S.C. 154(b) by 0 days.

(21) Appl. No.: 15/820,011

(22) Filed: Nov. 21, 2017

(65) Prior Publication Data

US 2018/0230417 A1 Aug. 16, 2018

Related U.S. Application Data

(60) Provisional application No. 62/429,436, filed on Dec. 2, 2016.

(51) Int. Cl.
| | | |
|---|---|---|
| *C12M 3/06* | (2006.01) | |
| *G01N 33/50* | (2006.01) | |
| *B01L 3/00* | (2006.01) | |
| *C12N 5/077* | (2010.01) | |
| *C12N 5/071* | (2010.01) | |
| *C07K 16/28* | (2006.01) | |
| *C12M 1/12* | (2006.01) | |
| *C12N 5/0783* | (2010.01) | |

(52) U.S. Cl.
CPC ....... *C12M 23/16* (2013.01); *B01L 3/502753* (2013.01); *C07K 16/2809* (2013.01); *C07K 16/2818* (2013.01); *C12M 25/02* (2013.01); *C12N 5/0636* (2013.01); *C12N 5/0652* (2013.01); *C12N 5/0679* (2013.01); *C12N 5/0697* (2013.01); *G01N 33/505* (2013.01); *G01N 33/5088* (2013.01); *B01L 2300/0681* (2013.01); *C12N 2501/999* (2013.01); *C12N 2502/13* (2013.01); *C12N 2502/23* (2013.01); *C12N 2502/28* (2013.01); *C12N 2503/04* (2013.01); *C12N 2533/90* (2013.01); *C12N 2533/92* (2013.01)

(58) Field of Classification Search
CPC ... C12M 23/16; C12M 25/02; C07K 16/2809; C07K 16/2818; C12N 5/0636; C12N 5/0652; C12N 5/0679; C12N 2502/28; C12N 2502/23; C12N 2502/13; C12N 2501/999; C12N 2503/04; C12N 2533/90; C12N 2533/92; C12N 5/0697; G01N 33/505; G01N 33/5088; B01L 3/502753; B01L 2300/0681
See application file for complete search history.

(56) References Cited

U.S. PATENT DOCUMENTS

| 8,647,861 B2 | 2/2014 | Ingber et al. ............... 435/289.1 |
|---|---|---|
| 2003/0119185 A1* | 6/2003 | Berenson ............ A61L 27/3804 435/372 |
| 2016/0047735 A1* | 2/2016 | Grisham ............ G01N 15/1484 435/7.1 |
| 2016/0243738 A1 | 8/2016 | Katrycz ........................ 264/294 |
| 2016/0313306 A1* | 10/2016 | Ingber .................... C12M 21/08 |

FOREIGN PATENT DOCUMENTS

| WO | WO/2010/009307 | 1/2010 |
|---|---|---|
| WO | WO/2012/118799 | 9/2012 |
| WO | WO/2013/086486 | 6/2013 |
| WO | WO/2013/086502 | 6/2013 |
| WO | WO/2015/013332 | 1/2015 |
| WO | WO/2015/138032 | 9/2015 |
| WO | WO/2015/138034 | 9/2015 |

OTHER PUBLICATIONS

Dura, Burak et al. "Profiling Lymphocyte Interactions at the Single-Cell Level by Microfluidic Cell Pairing". Nature Communications, vol. 6, No. 1, pp. 1-13. (Year: 2015).*
Anand, B., (Ed.) (2016) *Microscopic Colitis (Lymphocytic Colitis and Collagenous Colitis)*.
Barker, N. et al. (2010) "Lgr5$^{+ve}$ Stem Cells Drive Self-Renewal in the Stomach and Build Long-Lived Gastric Units In Vitro," *Cell Stem Cell* 6(1), 25-36.
Bischel, L. L. et al. (2012) "A Practical Method for Patterning Lumens through ECM Hydrogels via Viscous Finger Patterning," *Journal of Laboratory Automation* 17(2), 96-103.
Cerilli, L. A. et al. (2012) "The Differential Diagnosis of Colitis in Endoscopic Biopsy Specimens: A Review Article," *Archives of Pathology & Laboratory Medicine* 136(8), 854-864.

(Continued)

*Primary Examiner* — Blaine Lankford
(74) *Attorney, Agent, or Firm* — Medlen & Carroll, LLP

(57) ABSTRACT

An in vitro microfluidic gut-on-chip is described herein that mimics the structure and at least one function of specific areas of the gastrointestinal system in vivo. In particular, a multicellular, layered, microfluidic culture is described, allowing for interactions between lamina propria-derived cells and gastrointestinal epithelial cells and endothelial cells. This in vitro microfluidic system can be used for modeling inflammatory gastrointestinal tissue, e.g., Crohn's disease, colitis and other inflammatory gastrointestinal disorders. These multicellular, layered microfluidic gut-on-chip further allow for comparisons between types of gastrointestinal tissues, e.g., small intestinal deuodejeum, small intestinal ileium, large intestinal colon, etc., and between disease states of gastrointestinal tissue, i.e. healthy, pre-disease and diseased areas. Additionally, these microfluidic gut-on-chips allow identification of cells and cellular derived factors driving disease states and drug testing for reducing inflammation.

20 Claims, 69 Drawing Sheets
(55 of 69 Drawing Sheet(s) Filed in Color)

(56) References Cited

OTHER PUBLICATIONS

Crohn's & Colitis Foundation of America. (2014) The Facts About Inflammatory Bowel Disease.

Gerlach, K. et al. (2014) "TH9 cells that express the transcription factor PU.1 drive T cell-mediated colitis via IL-9 receptor signaling in intestinal epithelial cells," *Nature Immunology* 15(7), 676-686.

Gerlach, K. et al. (2015) "IL-9 regulates intestinal barrier function in experimental T cell-mediated colitis," *Tissue Barriers* 3(1-2), e983777.

Jung, P. et al. (2011) "Isolation and in vitro expansion of human colonic stem cells," *Nature Medicine* 17(10), 1225-1227.

Kaplan, G. G. (2015) "The global burden of IBD: from 2015 to 2025," *Nature Reviews Gastroenterology & Hepatology* 12, 720.

Lichtenstein, G. R. et al. (2006) "Quality of life after proctocolectomy with ileoanal anastomosis for patients with ulcerative colitis," *Journal of Clinical Gastroenterology* 40(8), 669-677.

Lim, A. G. et al. (1999) "Diversion colitis: a trigger for ulcerative colitis in the in-stream colon?," *Gut* 44(2), 279.

Meunier, V. et al. (1995) "The human intestinal epithelial cell line Caco-2; pharmacological and pharmacokinetic applications," *Cell Biology and Toxicology* 11(3-4), 187-194.

Nalleweg, N. et al. (2015) "IL-9 and its receptor are predominantly involved in the pathogenesis of UC," *Gut* 64(5), 743.

Pageot, L. P. et al. (2000) "Human cell models to study small intestinal functions: Recapitulation of the crypt-villus axis," *Microscopy Research and Technique* 49(4), 394-406.

Powell, D. W. et al. (2011) "Mesenchymal Cells of the Intestinal Lamina Propria," *Annual Review of Physiology* 73(1), 213-237.

Salzmann, J. L. et al. (1989) "Morphometric study of colonic biopsies: a new method of estimating inflammatory diseases," *Laboratory Investigation* 60(6), 847-851.

Sato, T. et al. (2013) "Growing Self-Organizing Mini-Guts from a Single Intestinal Stem Cell: Mechanism and Applications," *Science* 340(6137), 1190.

Sato, T. et al. (2009) "Single Lgr5 stem cells build cryptvillus structures in vitro without a mesenchymal niche," *Nature* 459, 262.

Sinagra, E. et al. (2016) "Inflammation in irritable bowel syndrome: Myth or new treatment target?," *World Journal of Gastroenterology* 22(7), 2242-2255.

Wu, W. et al. (2011) "Omnidirectional Printing of 3D Microvascular Networks," *Advanced Materials* 23(24), H178-H183.

Wu, W. et al. (2010) "Direct-write assembly of biomimetic microvascular networks for efficient fluid transport," *Soft Matter* 6(4), 739-742.

Barker, N. et al., (2010) "LgrS+ve Stem Cells Drive Self-Renewal in the Stomach and Build Long-Lived Gastric Units In Vitro," Cell Stem Cell 6(1), 25-36.

Cerilli, L. A. and Greenson, J. K., (2012) "The Differential Diagnosis of Colitis in Endoscopic Biopsy Specimens: A Review Article," Arch. Pathol. Lab. Med. 136(8), 854-864.

Gerlach, K. R. et al., (2014) "TH9 cells that express the transcription factor PU.1 drive T cell-mediated colitis via IL-9 receptor signaling in intestinal epithelial cells," Nat. Immunol. 15(7), 676-686.

Jung, P. et al., (2011) "Isolation and in vitro expansion of human colonic stem cells," Nat. Med. 17(10), 1225-1227.

Kaplan, G. G., (2015) "The global burden of IBD: from 2015 to 2025," Nat. Rev. Gastroenterol. Hepatol. 12, 720.

Lichtenstein, G. R. et al., (2006) "Quality of life after proctocolectomy with ileoanal anastomosis for patients with ulcerative colitis," J. Clin. Gastroenterol. 40(8), 669-677.

Meunier, V. et al., (1995) "The human intestinal epithelial cell line Caco-2; pharmacological and pharmacokinetic applications," Cell Biol. Toxicol. 11(3-4), 187-194.

Pageot, L. P. et al., (2000) "Human cell models to study small intestinal functions: Recapitulation of the crypt-villus axis," Microsc. Res. Tech. 49(4), 394-406.

Powell, D. W. et al., (2011) "Mesenchymal Cells of the Intestinal Lamina Propria," Annu. Rev. Physiol. 73(1), 213-237.

Salzmann, J. L. et al., (1989) "Morphometric study of colonic biopsies: a new method of estimating inflammatory diseases," Lab. Invest. 60(6), 847-851.

Sato, T. and Clevers, H., (2013) "Growing Self-Organizing Mini-Guts from a Single Intestinal Stem Cell: Mechanism and Applications," Science 340(6137), 1190.

Sinagra, E. et al., (2016) "Inflammation in irritable bowel syndrome: Myth or new treatment target?," World J. Gastroenterol. 22(7), 2242-2255.

Wu, W. et al., (2011) "Omnidirectional Printing of 3D Microvascular Networks," Adv. Mater. 23(24), H178-H183.

\* cited by examiner

Fig. 2
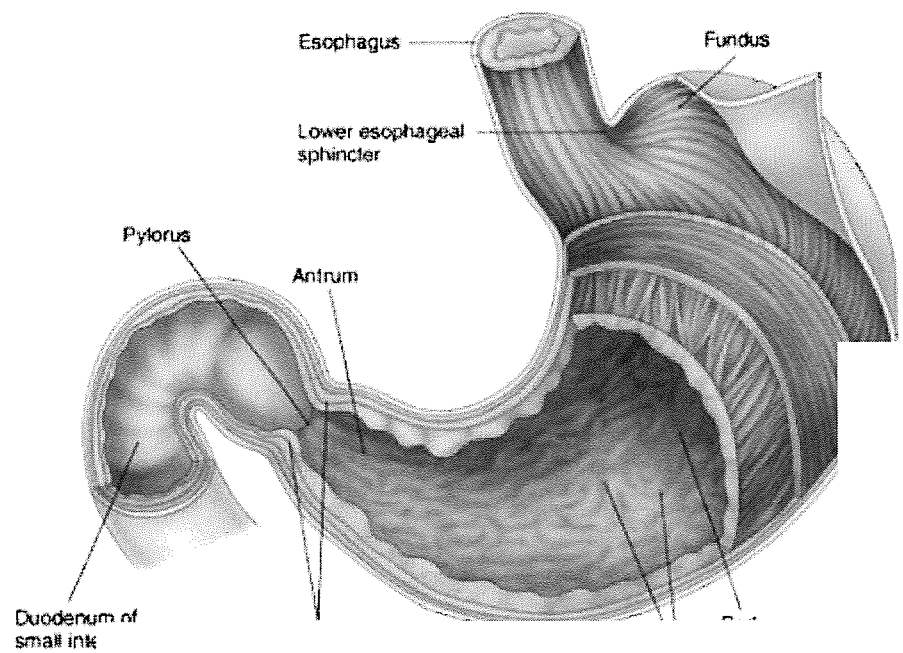
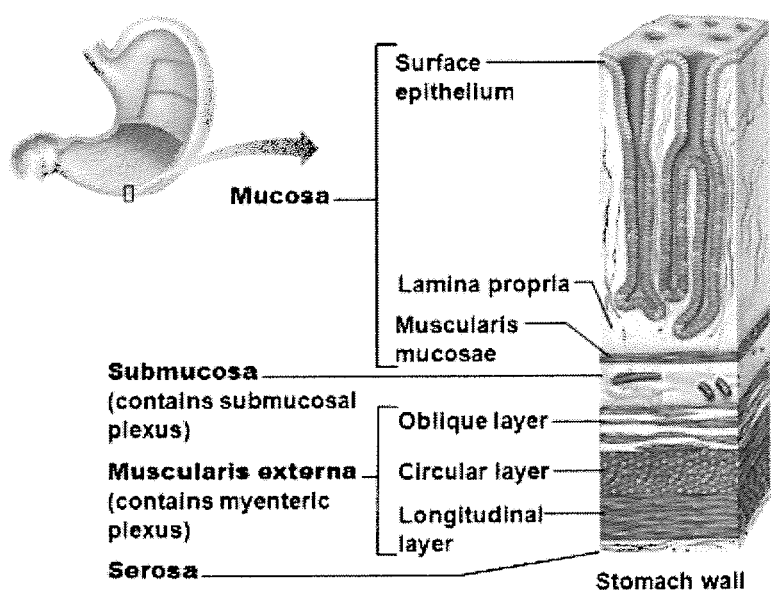

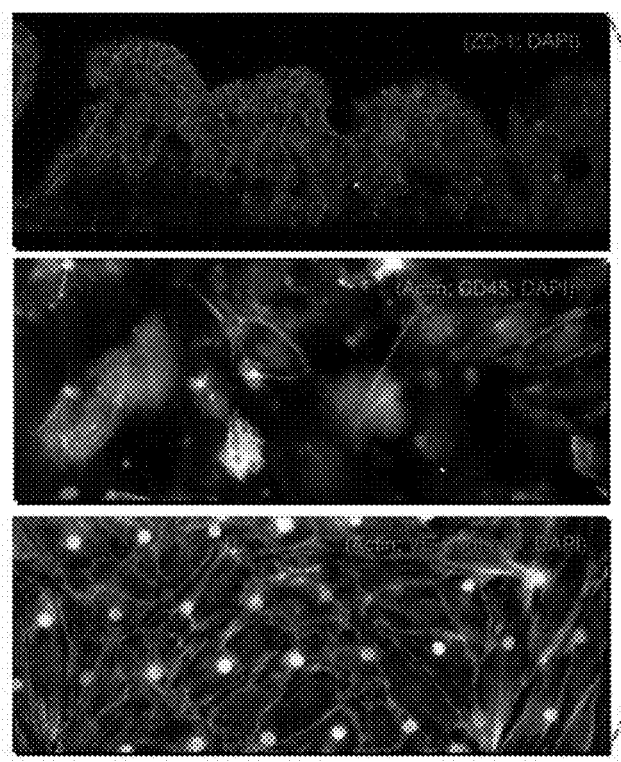
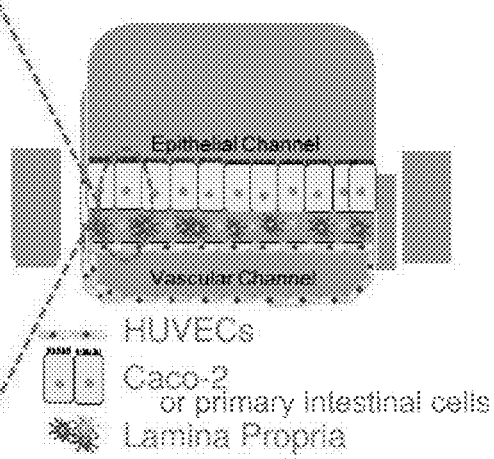
FIG. 5A
FIG. 5B
FIG. 5A - B

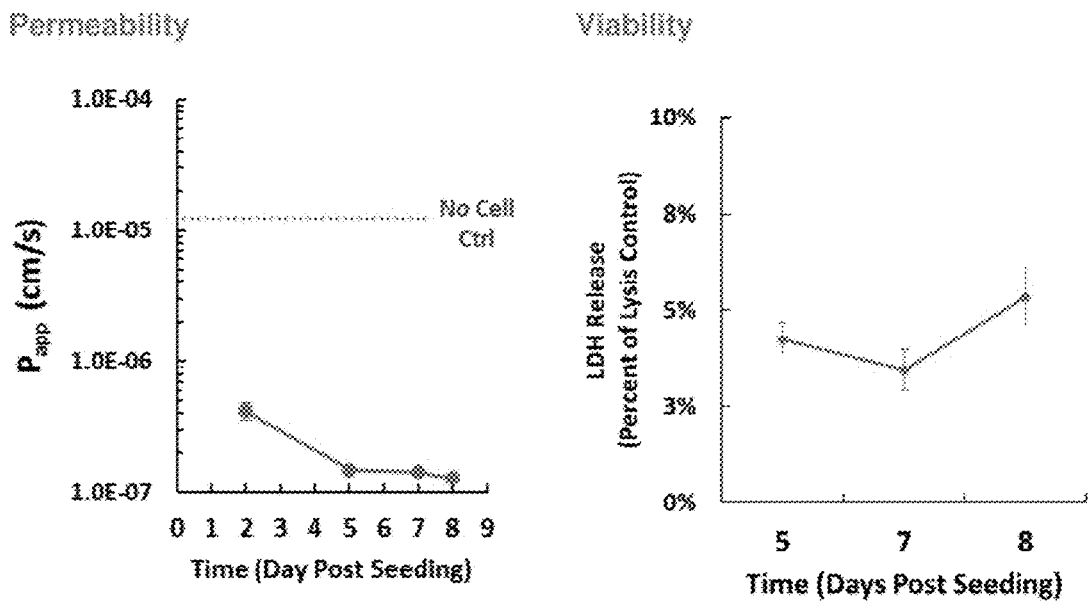
FIG. 9A
FIG. 9B
Fig. 10
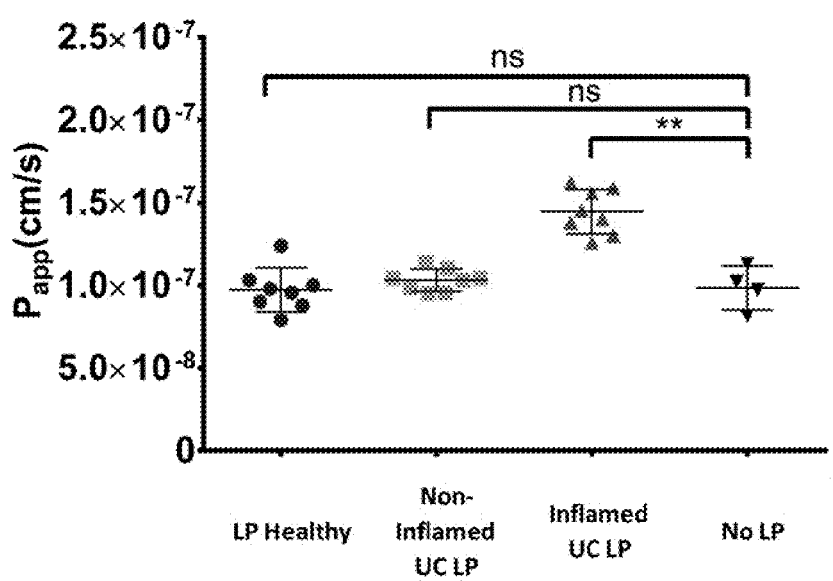

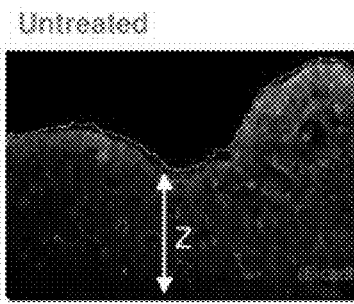 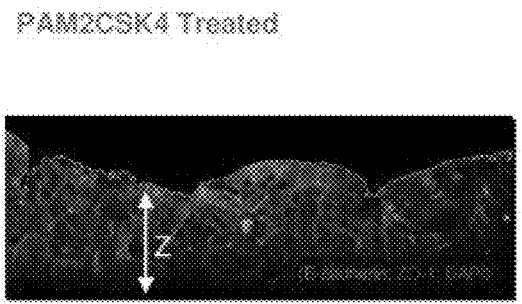
FIG. 14A
FIG. 14B

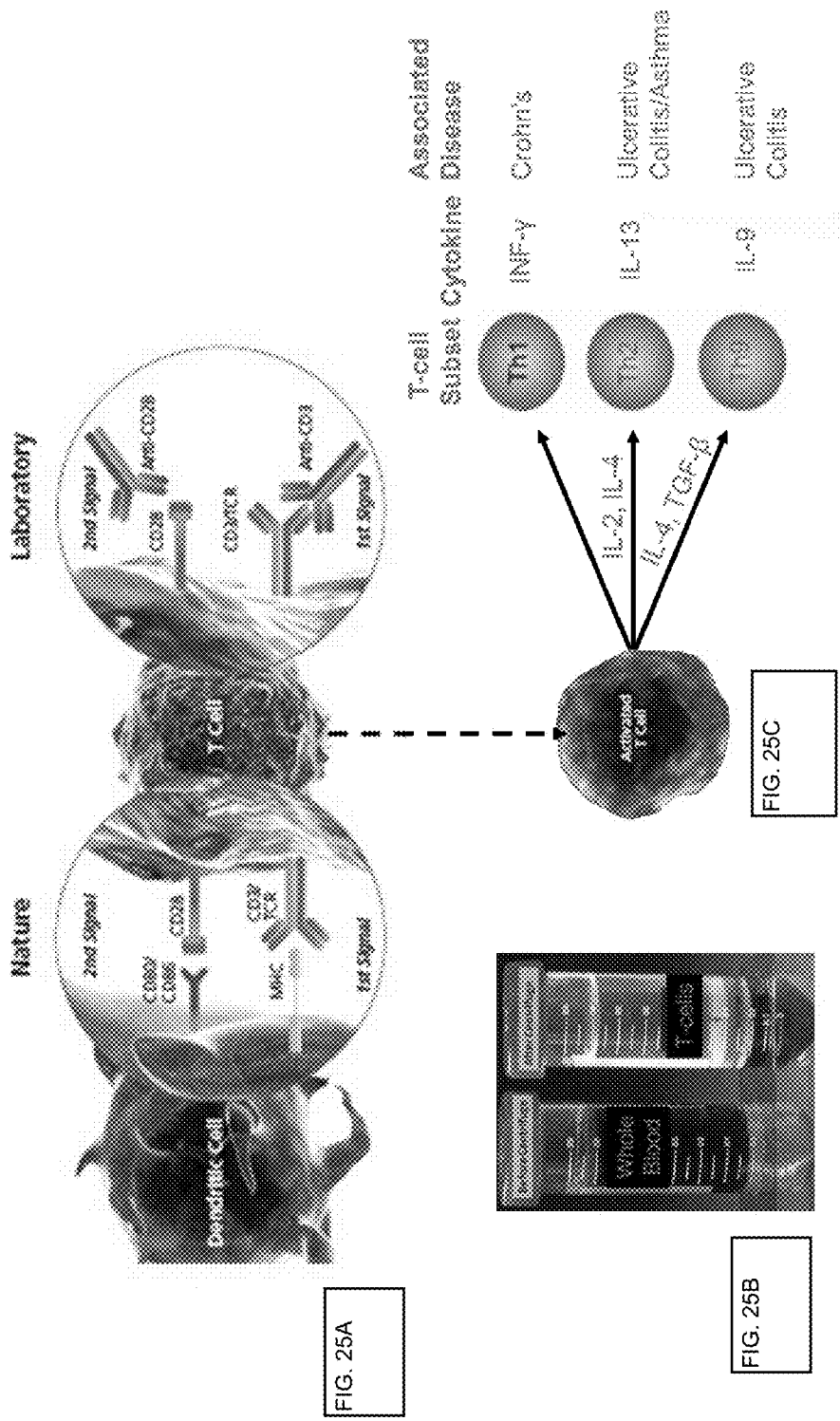

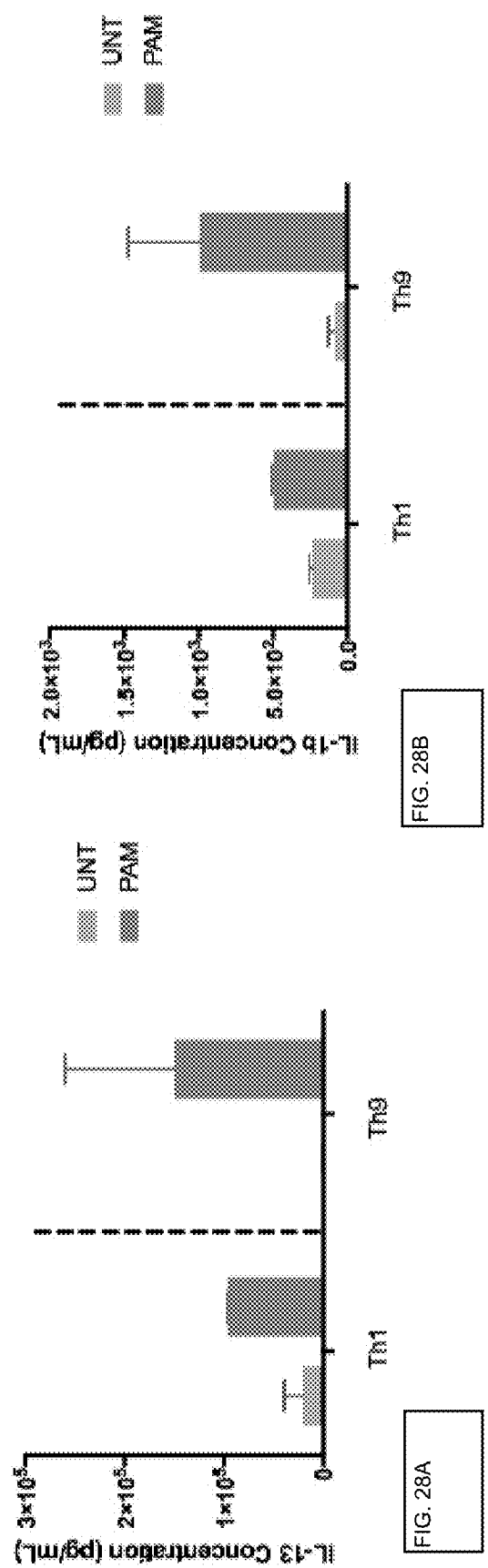

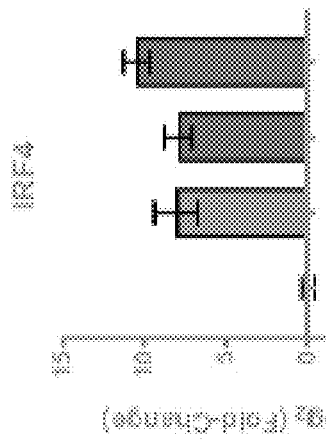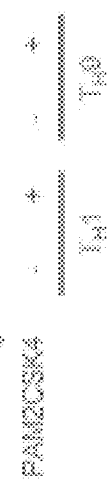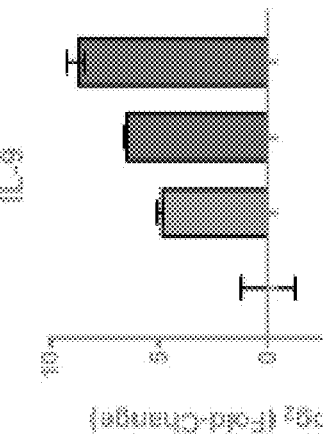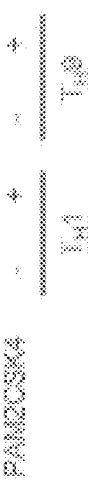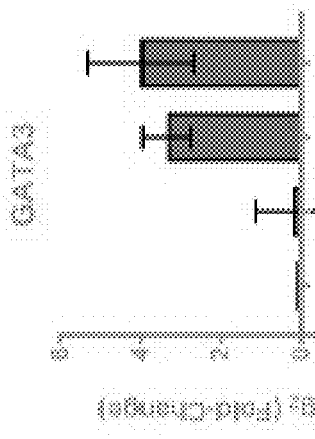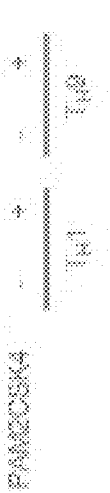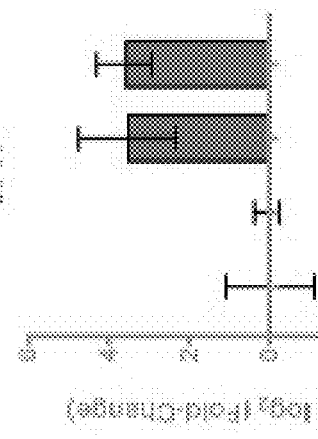
FIG. 30A  FIG. 30B  FIG. 30C  FIG. 30D

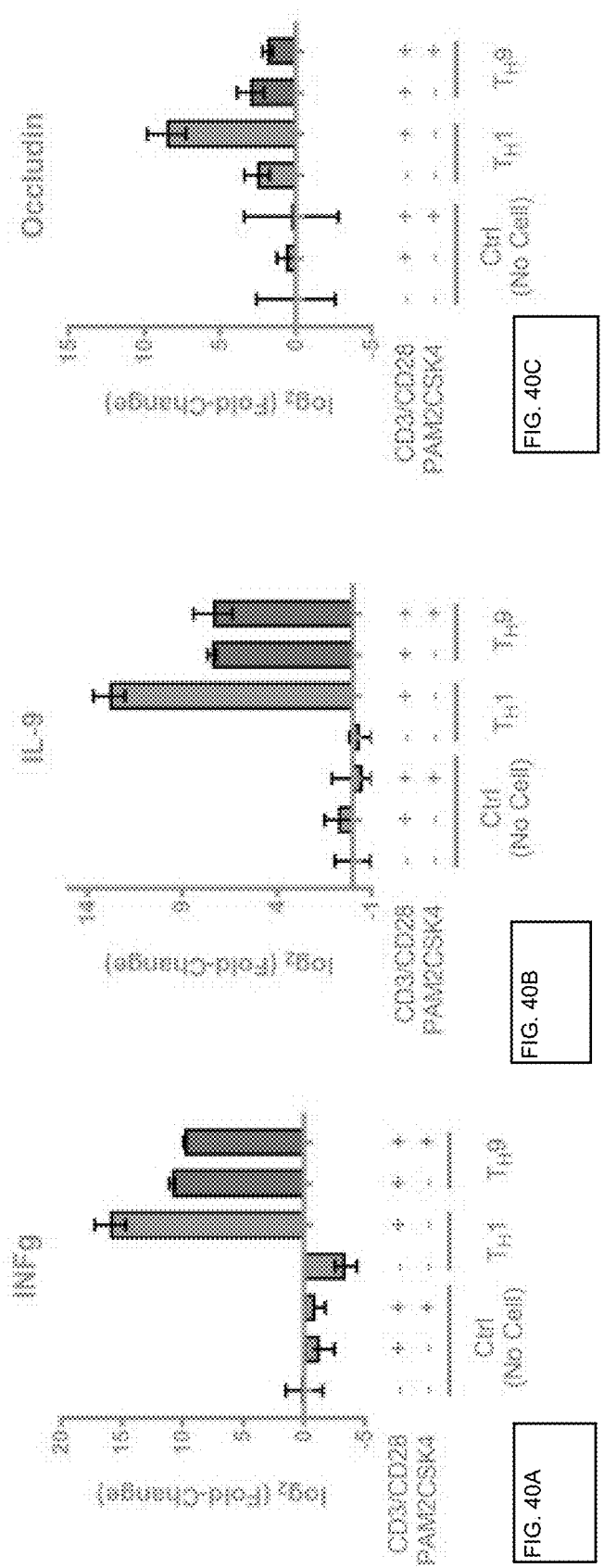

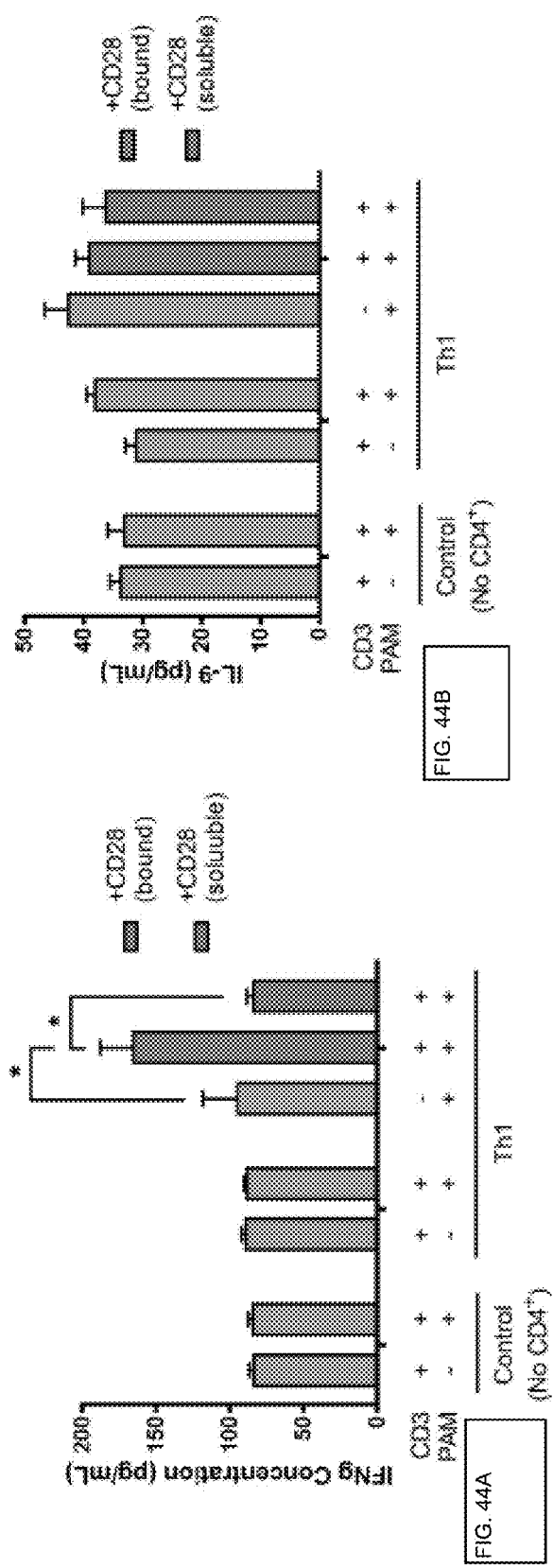
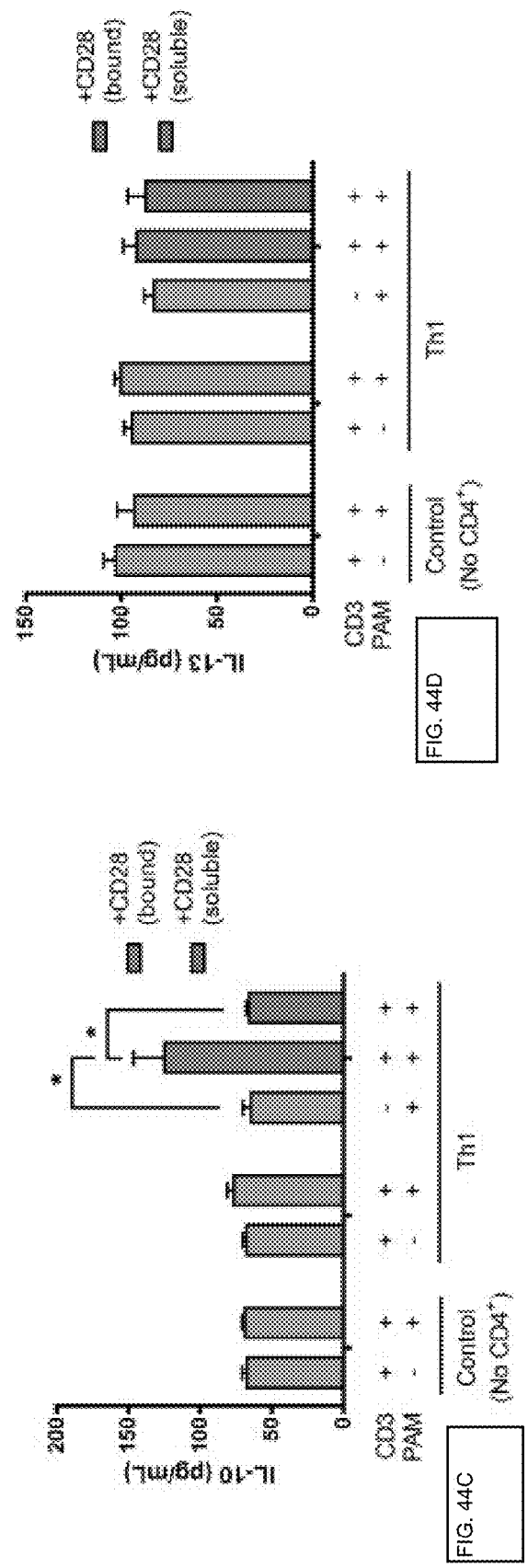
FIG. 44A, FIG. 44B, FIG. 44C, FIG. 44D

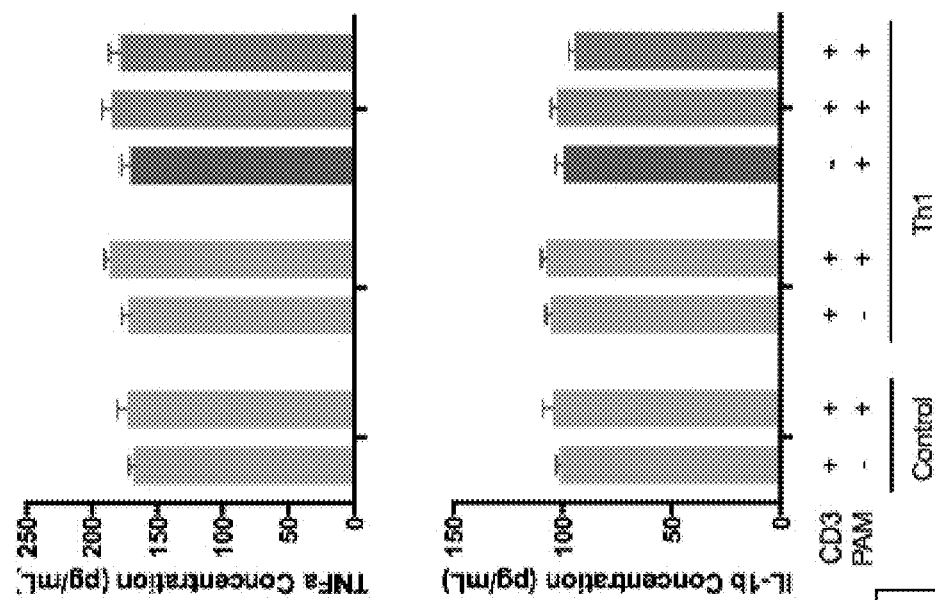

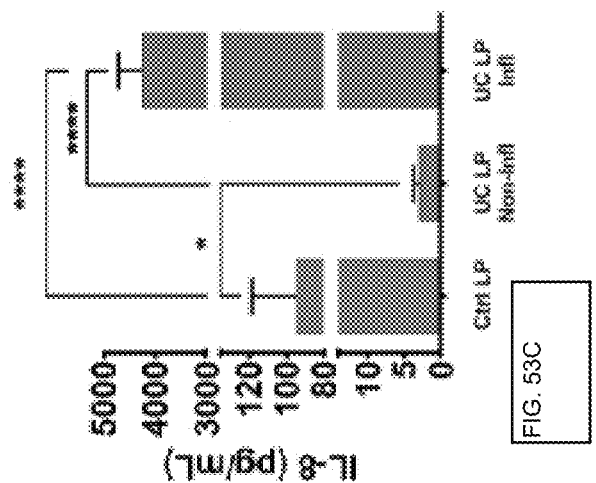
FIG. 53C
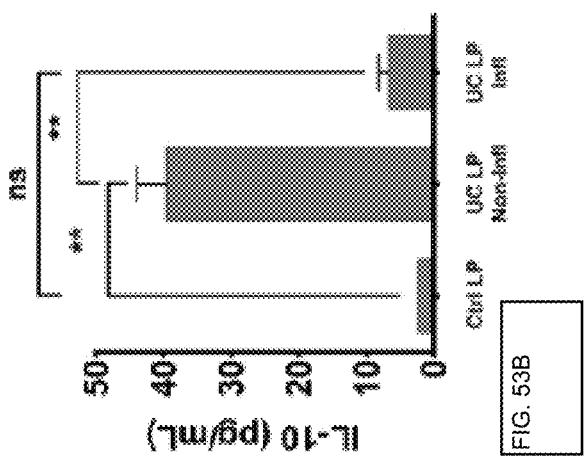
FIG. 53B
FIG. 53D
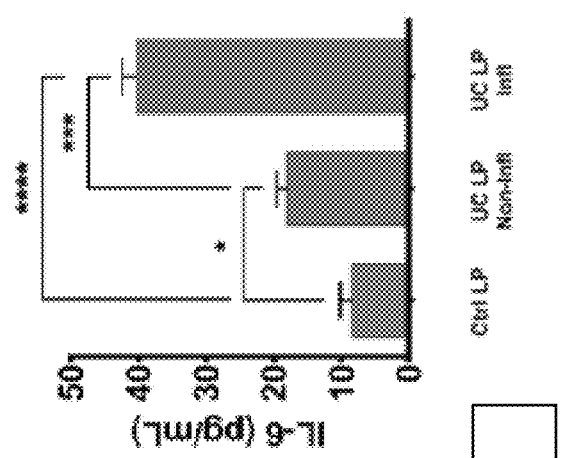
FIG. 53A

Prednisone:

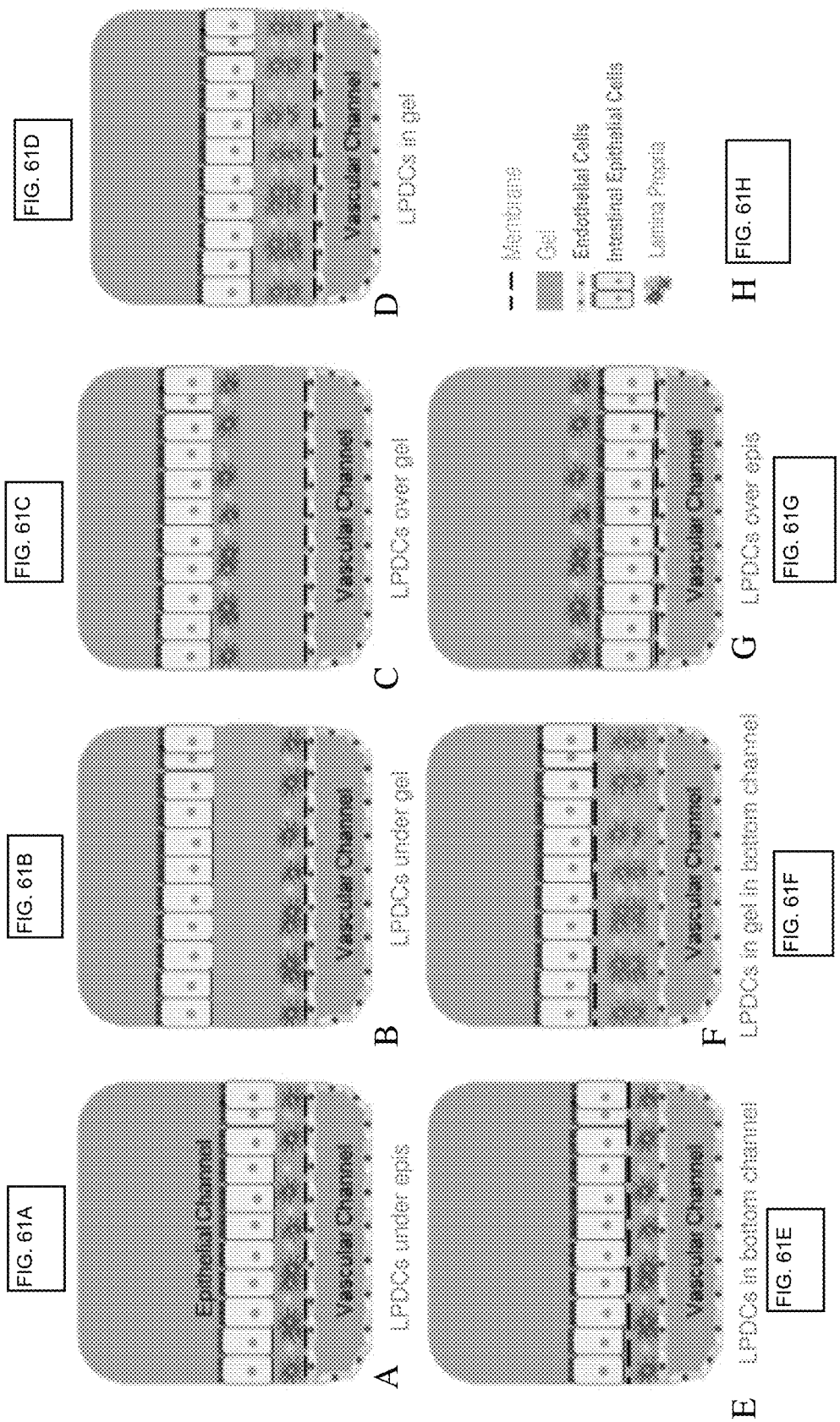

IN VITRO GASTROINTESTINAL MODEL COMPRISING LAMINA PROPRIA-DERIVED CELLS

FIELD OF THE INVENTION

An in vitro microfluidic gut-on-chip is described herein that mimics the structure and at least one function of specific areas of the gastrointestinal system in vivo. In particular, a multicellular, layered, microfluidic culture is described, allowing for interactions between lamina propria-derived cells and gastrointestinal epithelial cells and endothelial cells. This in vitro microfluidic system can be used for modeling inflammatory gastrointestinal tissue, e.g., Crohn's disease, colitis and other inflammatory gastrointestinal disorders. These multicellular, layered microfluidic gut-on-chip further allow for comparisons between types of gastrointestinal tissues, e.g., small intestinal deuodejeum, small intestinal ileium, large intestinal colon, etc., and between disease states of gastrointestinal tissue, i.e. healthy, pre-disease and diseased areas. Additionally, these microfluidic gut-on-chips allow identification of cells and cellular derived factors driving disease states and drug testing for reducing inflammation.

BACKGROUND

In vitro gastrointestinal tissue model systems include cell lines, primary cell explant cultures and three-dimensional primary cell organoid culture systems. However, these models have significant limitations. Limitations of both cell lines and primary cell explant cultures are reviewed in part by Pageot, et al. "Human cell models to study small intestinal functions; recapitulation of the crypt-villus axis." Microsc Res Tech.; 49; 394-406, 2000. Explant cultures, which have organotypic properties such as complex 3-dimensional (3D) architecture and cellular heterogeneity are limited in part by their lack of reproducibility of growing conditions between laboratories and their short-term nature.

What is needed is a better in vitro platform for gastrointestinal tissue modeling and drug testing, specifically in combination with modeling gastrointestinal inflammatory diseases.

SUMMARY OF THE INVENTION

An in vitro microfluidic gut-on-chip; is described herein that mimics the structure and at least one function of specific areas of the gastrointestinal system in vivo. In particular, a multicellular, layered, microfluidic culture is described, allowing for interactions between lamina propria-derived cells and gastrointestinal epithelial cells and endothelial cells. This in vitro microfluidic system can be used for modeling inflammatory gastrointestinal tissue, e.g., Crohn's disease, colitis and other inflammatory gastrointestinal disorders. These multicellular, layered microfluidic gut-on-chip further allow for comparisons between types of gastrointestinal tissues, e.g., small intestinal deuodejeum, small intestinal ileium, large intestinal colon, etc., and between disease states of gastrointestinal tissue, i.e. healthy, predisease and diseased areas. Additionally, these microfluidic gut-on-chips allow identification of cells and cellular derived factors driving disease states and drug testing for reducing inflammation or for disease modification.

The intestinal mucosa is the innermost layer of the gastrointestinal tract and is composed of the epithelium and the supporting loose connective tissue called the lamina propria. The lamina propria in vivo includes a dense, irregular network of resident immune cells that act as sentinels for constantly monitoring and modulating the immune state of intestinal tissue. To build a more accurate model of the human intestine that recapitulates key embodiments of intestinal physiology and pathophysiology, we have developed an Intestine-on-Chip model which. In some embodiments. Includes the following components: 1) intestinal epithelial cells (age Caco-2 BBE adenocarcinoma cells) to model the epithelium, 2) primary resident immune cells isolated from intestinal lamina propria as lamina propria-derived cells, 3) and vascular endothelial cells (e.g. HUVEC cells) to model the microvasculature. Together these three cells types better recapitulate intestinal homeostatic functions including barrier function, biochemical cross-talk between tissue-tissue interfaces, and participation in host immune responses.

Thus, embodiments described herein relate to the design of microfluidic devices providing controllable and physiologically realistic models of gastrointestinal tissue in a variety of conditions. Including but not limited to healthy, pre-disease and disease states. In one embodiment, the present invention contemplates a microfluidic device containing a plurality of gastrointestinal cell types. For example. In one embodiment, the present invention contemplates co-culture of gastrointestinal lamina propria-derived cells (LP-derived cells) and gastrointestinal epithelial cells, with or without endothelial cells. These cells may be mixed in culture (e.g. together in a microfluidic channel, chamber, etc.) or separated (e.g. by a porous membrane) in a layered structure to establish a gastrointestinal environment in vitro.

Non-limiting examples of cells contemplated for use in the microfluidic device or chip for in vitro modeling of gastrointestinal tissue. Include epithelial cells, (e.g. epithelial cell lines, caco-2 intestinal epithelial cancer cells. Intestinal cancer-derived epithelial cell lines, non-cancer derived intestinal cell-lines, epithelial intestinal cell lines, primary gastrointestinal epithelial cells, primary healthy gastrointestinal epithelial cells, primary diseased gastrointestinal epithelial cells, cultures of gastrointestinal epithelial cells, cultures of expanded primary gastrointestinal epithelial cells, epithelial cells derived from 3D intestinal enteroids, epithelial intestinal cells derived from induced pluripotent stem cells, etc.); lamina propria-derived cells (LP-derived cells) including but not limited to stromal cells, fibroblasts, and resident immune cells (e.g. primary immune cells isolated from gastrointestinal tissue, immune cells differentiated from naïve T-cells); and intestinal vascular endothelial cells (e.g. HUVEC, human primary intestinal vascular endothelial cells, human intestinal microvascular endothelial cells, cultures of intestinal vascular endothelial cells, etc.).

To more accurately model the mucosal tissue-tissue interface, conditions were developed to co-culture the epithelial cells and endothelial cells (e.g. Caco-2 and HUVEC cell-lines) on opposing surfaces of the semi-permeable chip membrane. The proximity of these two cell types facilitates paracrine and biochemical communication recapitulating key embodiments of intestinal functionality.

Thus, one embodiment, the present invention contemplates a microfluidic Intestine-On-Chip (or "Gut-on-chip") comprising 1) intestinal epithelial cells (e.g. Caco-2 BBE adenocarcinoma cells) to model the intestinal epithelium; 2) primary resident immune cells isolated from intestinal lamina propria as lamina propria-derived cells; and 3) endothelial cells (e.g. HUVEC cells) to model the microvasculature. Together these three cells types recapitulate intestinal homeostatic functions including barrier function, biochemical cross-talk between tissue-tissue interfaces, and participation in host immune responses.

In one embodiment, endothelial cells (e.g. human umbilical vein endothelial cells or "HUVECs") are seeded on the bottom channel for at least 1.5 hours at high density to create a vascular lumen. Second, lamina propria-derived cells are seeded, e.g. thawed, counted, and seeded on the top channel and allowed to incubate overnight, for providing resident immune cells. Third. Intestinal epithelial cells (e.g. Caco-2 cells) are seeded on the top channel to create a contiguous epithelial cell layer that covers the resident immune population on the same channel. In one embodiment, resident immune cells obtained from donor lamina propria-derived cells were provided frozen and conditions were developed, described herein, for seeding and culturing of these cells on the intestine On-Chip. In another embodiment, the donor lamina propria-derived cells and/or LP-derived cells were provided fresh as primary cells. In yet another embodiment, LP-derived cells undergo pre-differentiation of naïve T-cells towards a particular T-helper cell profile (e.g. TH9).

Without intending to limit the invention to any particular mechanism, it is believed that immune cells of the mucosal microenvironment assist in guiding intestinal physiology and pathophysiology. These immune cells are responsible for continuous monitoring of the intestinal milieu for possible infection. Initiating an effective innate immune response, then, under appropriate conditions, mounting an adaptive immune response. Under healthy conditions, resident immune cells then turn off the immune response.

To establish that the presence of intestinal resident immune cells (isolated from lamina propria as lamina propria-derived cells) modulates signaling across the Intestine-on-Chip tissue-tissue interface, we performed multiplex measurements of secreted cytokines and assessed epithelial barrier function with small molecule permeability. Further, we contacted the epithelial cell layer with a representative bacterial antigen, e.g. PAM2CSK4. The data from these tests show that the lamina propria-derived cells (e.g. resident immune cells) impact intercellular signaling and weaken the epithelial barrier in response to a simulated bacterial infection.

In one embodiment, resident primary intestinal immune cells were isolated (as lamina propria-derived cells) from control and ulcerative colitis patients (e.g. isolated from inflamed and non-inflamed regions of an ulcerative colitis patient colon resection.). Resident immune cells from inflamed regions of the ulcerative colitis patient retained the inflammatory phenotype resulting in weakened epithelial barrier function as compared to cells from healthy patients.

In one embodiment, the Intestine-on-Chip model incorporating lamina propria-derived cells (e.g., resident immune cells) recapitulates the pathogenesis of ulcerative colitis including immune cell dependent weakening of epithelial barrier function.

In one embodiment, the Intestine-on-Chip incorporating intestinal resident immune cells demonstrated an immune cell dependent production of the proinflammatory cytokine IL-9. IL-9 has been identified as a key mediator of ulcerative colitis. Therefore, our Intestine-Chip is a model for studying the mechanism of action and regulation of IL-9 mediated colitis. In one embodiment, the production of IL-9 by is linked to the presence of primary lamina propria-derive) cells, e.g. primary immune cells isolated from the lamina propria-derived cells, on the chip. Indeed, IL-9 production is LP dependent. The most significant source of IL-9 from human mucosal biopsies comes from Th9 effector cells.

Without intending to limit the invention to any particular mechanism, it is believed that weakened barrier function is dependent on the density of seeded LP-derived cells and in particular, the density of the resident immune cells. The incorporation of intestinal resident immune cells on the Intestine-Chip and corresponding weakening of intestinal barrier function is dependent on the initial (lamina propria-derived) cell seeding density.

In one embodiment, two or more enclosed, microfluidic channels or chambers are aligned (e.g., vertically or horizontally) with each other with one or more membranes separating them from each other ("gut-on-a-chip"). The gut-on-a-chip devices were developed and optimized with improvements based on the basic design of an organ-on-a-chip as described in the U.S. Pat. No. 8,647,861, and International Patent App. No. PCT/US2014/071611, the entire contents of each of which are incorporated herein by reference. In particular for U.S. Pat. No. 8,647,861, the basic features of microchannels, e.g. fluid flow; fluid pressure, such as providing a pressure differential between channels, by suction or vacuum; surface features of membranes; porosity of membranes; perfusion of cells by media; testing cells by changing media used for perfusion; cyclic mechanical strain of the membrane to observe morphological and functional characteristics of the co-cultured cells; a membrane to permit direct cellular interaction across the membrane; a blood-gas barrier or interface, are incorporated herein.

In particular for PCT/US2014/071611 (published as WO2015138034), the entire contents of which are incorporated herein by reference, features such as a gas-liquid interface formed by a gaseous fluid added to fluid in a channel; a blood vessel channel; mucus secreting cells and the like, are incorporated by reference herein.

In some embodiments, the inventors optimized the design of the gut-on-a chip devices and culture conditions to provide long-term culture of gastrointestinal cells with physiologically relevant environments (e.g., healthy, predisease and disease states) for different types of human inflammatory gastrointestinal diseases, e.g. Ulcerative colitis.

In one embodiment, the present invention contemplates a method of culturing cells, comprising: a) providing a microfluidic device, viable human lamina propria-derived cells and viable human gastrointestinal epithelial cells; b) introducing said human lamina propria-derived cells and human gastrointestinal epithelial cells into said microfluidic device so as to create a co-culture; and c) perfusing said co-culture with media under flow conditions. It is not intended that the present invention be limited by the nature of the microfluidic device. However, it is preferred that said microfluidic device comprises one or more microfluidic channels in fluidic communication with a source of media. It is also preferred that said microfluidic device comprises first and second microfluidic channels separated by a membrane, said membrane comprising first and second surfaces. In one embodiment, said human lamina propria-derived cells and human gastrointestinal epithelial cells are cultured on said top surface of said membrane. In one embodiment, the method further comprises introducing endothelial cells on said bottom surface of said membrane. In one embodiment, said endothelial cells are introduced before step c). In one embodiment, said endothelial cells are gastrointestinal endothelial cells. In one embodiment, said human lamina propria-derived cells and viable human gastrointestinal epithelial cells are introduced in step b) simultaneously. In one embodiment, said human lamina propria-derived cells and viable human gastrointestinal epithelial cells are introduced in step b) sequentially. It is not intended that the present invention be limited by where or how the lamina propria-derived cells are obtained. In one embodiment, said human lamina propria-derived cells were obtained from inflamed human gastrointestinal tissue. In one embodiment, said human lamina propria-derived cells comprise resident immune cells of human gastrointestinal tissue.

The present invention further contemplates an embodiment of a method of culturing cells, comprising: a) providing a microfluidic device comprising a membrane, said membrane comprising a top surface and a bottom surface; b) seeding viable human lamina propria-derived cells on said top surface and viable human endothelial cells on said bottom surface so as to create seeded cells; and c) culturing said seeded cells under flow conditions. In one embodiment, prior to step b), said top surface of said membrane is treated with at least one extracellular matrix protein. In one embodiment, said lamina propria-derived cells are covered by at least one extracellular matrix protein. In one embodiment, said cells are covered by an overlay of Matrigel. In one embodiment, said overlay is subsequently removed. In one embodiment, the method further comprises step d) adding a population of human gastrointestinal epithelial cells to said seeded lamina propria-derived cells. In one embodiment, said human epithelial cells are selected from the group consisting of Caco-2 epithelial cells, primary small intestinal epithelial cells and primary large intestinal epithelial cell. In one embodiment, said human lamina propria-derived cells comprise resident immune cells. In one embodiment, said human lamina propria-derived cells comprise immune cells from healthy tissue. In one embodiment, said human lamina propria-derived cells comprise immune cells from disease tissue. In one embodiment, said human lamina propria-derived cells are selected from the group consisting of stromal cells, fibroblasts, and resident immune cells. In one embodiment, said resident immune cells are selected from the group consisting of lymphocytes, mononuclear cells, macrophages, immature dendritic cells, mature dendritic cells, eosinophils, basophils, roast cells and combinations thereof. In one embodiment, said human lamina propria derived cells are obtained from intestinal tissue selected from the group consisting of small intestine and large intestine. In one embodiment, said small intestine tissue is selected from the group consisting of duodenum, duodenojejunal flexure, jejunum, ileum, and terminal ileum. In one embodiment, said large intestine tissue is selected from the group consisting of cecum, ascending colon, hepatic flexure, descending colon, sigmoid colon, rectum and anus. In one embodiment, said human lamina propria-derived cells are obtained from gastrointestinal tissue selected from the group consisting of stomach, esophagus, and mouth. In one embodiment, said human lamina propria-derived cells are primary cells. In one embodiment, said human lamina propria-derived cells were cryopreserved and then thawed prior to step b). In one embodiment, the method further comprises after step d) assessing viability. In one embodiment, viability is assessed by measuring the relative amount of lactate dehydrogenase released by the cells over time. In one embodiment, said flow conditions comprise a moving flow of medium (e.g. culture media) through said device. In one embodiment, the method further comprises a step after step c) comprising sampling cytokines present in said flow media. In one embodiment, said cytokines are selected from the group consisting of interleukin-6 and interleukin-9. In one embodiment, said epithelial cells form a monolayer of cells, wherein said monolayer has an apical region and a basal region. In one embodiment, the method further comprises after step d) adding an agent to said apical region of said epithelial cells. In one embodiment, said agent is PAM2CSK4. In one embodiment, the method further comprises after step d) assessing permeability of said monolayer between said apical region and said basal region. In one embodiment, said assessing permeability comprises applying an agent at said apical region of said epithelial cells then measuring the amount of said agent released at said basal region. In one embodiment, said agent is a dye.

In one embodiment, the present invention also contemplates a microfluidic device, wherein said microfluidic device comprises one or more microfluidic channels, a membrane, said membrane comprising a top surface and a bottom surface, and a co-culture of human gastrointestinal epithelial cells and lamina propria-derived cells located on said top surface of said membrane, and human endothelial cells located on said bottom surface of said membrane. In one embodiment, said membrane is semi-permeable. In one embodiment, said lamina propria-derived cells comprise stromal cells and immune cells. In one embodiment, said immune cells are selected from the group consisting of lymphocytes, mononuclear cells, macrophages, immature dendritic cells, mature dendritic cells, eosinophils, basophils, mast cells and combinations thereof. In one embodiment, said top surface of said membrane comprises at least one extracellular matrix protein. In one embodiment, said lamina propria-derived cells were obtained from human gastrointestinal tissue selected from the group consisting of healthy tissue, pre-diseased tissue and diseased tissue. In one embodiment, said lamina propria-derived cells were obtained from inflamed human gastrointestinal tissue. In one embodiment, said lamina propria-derived cells were obtained from a human with inflammatory colitis. In one embodiment, the device further comprises media, wherein said media is located within said microfluidic channels and in contact with said co-culture.

In one embodiment, the present invention also contemplates a microfluidic system comprising a microfluidic device and a co-culture of human gastrointestinal epithelial cells, lamina propria derived cells and human endothelial cells, wherein said co-culture is perfused with media under flow conditions. In one embodiment, said device comprises a membrane, said membrane comprising a top surface and a bottom surface, and one or more microfluidic channels in fluidic communication with a source of said media. In one embodiment, said microfluidic device comprises first and second microfluidic channels separated by said membrane. In one embodiment, said top surface of said membrane comprises at least one extracellular matrix protein. In one embodiment, said gastrointestinal cells are located on said top surface of said membrane. In one embodiment, said endothelial cells are on said bottom surface of said membrane. In one embodiment, said human lamina propria-derived cells comprise stromal cells and immune cells. In one embodiment, said human lamina propria-derived cells comprise resident immune cells of human gastrointestinal tissue. In one embodiment, said lamina propria-derived cells are obtained from human gastrointestinal tissue are selected from the group consisting of healthy tissue, pre-diseased tissue and diseased tissue.

In another embodiment, the present invention contemplates a fluidic device comprising: a first fluidic channel in contact with a semi-permeable membrane, first cells comprising intestinal epithelial cells; and second cells comprising at least one stromal cell type. In one embodiment, said stromal cell type is a lamina propria-derived cell. In one embodiment, said stromal cell type comprises resident immune cells. In one embodiment, said stromal cell type comprises cells selected from the group consisting of fibroblasts, macrophages, and dendritic cells. In one embodiment, said stromal cell types comprises primary stromal cells. In one embodiment, said primary stromal cells comprise biopsy-derived cells or lavage derived cells. In one embodiment, said primary stromal cells are patient-derived cells. In one embodiment, said patient derived cells are from a patient with an inflammatory disease of the intestine. In one embodiment, at least a portion of said second cells are disposed in contact with said semi-permeable membrane.

In one embodiment, the present invention contemplates a method comprising: a) providing a fluidic device comprising i) a fluidic channel in contact with a semi-permeable membrane, ii) first cells comprising intestinal epithelial cells, and iii) second cells comprising at least one stromal cell type; and b) perfusing said first fluidic device with fluid. In one embodiment, said stromal cell type is a lamina propria-derived cell. In one embodiment, said stromal cell type comprises resident immune cells. In one embodiment, said stromal cell type comprises cells selected from the group consisting of fibroblasts, macrophages, and dendritic cells. In one embodiment, said stromal cell type comprises primary stromal cells. In one embodiment, said primary stromal cells comprise biopsy-derived cells or lavage-derived cells. In one embodiment, said primary cells are patient-derived cells. In one, embodiment, said patient-derived cells are from a patient with an inflammatory disease of the intestines. In one embodiment, the method further comprises c) contacting said first cells, said second cells or both with a first agent. In one embodiment, the method further comprises d) detecting at least one response to said first agent. In one embodiment, the said at least one response comprises modulation of the inflammation reaction.

In one embodiment, the present invention also contemplates a microfluidic device comprising one or more affinity reagents configured to stimulate immune cells. In one embodiment, said microfluidic device further comprises one or more microfluidic channels. In one embodiment, said one or more affinity reagents are positioned within said microfluidic device. In one embodiment, said one or more affinity reagents are retained within said microfluidic device. In one embodiment, said one or more affinity reagents are positioned on beads within said microfluidic device. In one embodiment, said affinity reagents are attached within said microfluidic device. In one embodiment, said affinity reagents are covalently attached within said microfluidic device. In one embodiment, said microfluidic device further comprises a membrane in contact with said one or more microfluidic channels. In one embodiment, said affinity reagents are positioned on said membrane. In one embodiment, said microfluidic device further comprises one or more extracellular matrix proteins in said one or more microfluidic channels. In one embodiment, said microfluidic device further comprises at least one gel in said microfluidic device. In one embodiment, said gel comprising at least one extracellular matrix protein. In one embodiment, said affinity reagents are immobilized in said gel. In one embodiment, said affinity reagents are immobilized in said one or more extracellular matrix proteins. In one embodiment, said one or more extracellular matrix proteins comprise an overlay, said overlay trapping said affinity reagents. In one embodiment, said one or more extracellular matrix proteins comprise a gel, said gel trapping said affinity reagents. In some embodiments, the microfluidic device has said affinity reagents comprising antibodies or binding fragments thereof. In one embodiment, said antibodies are anti-CD3 antibodies. In one embodiment, said antibodies are anti-CD28 antibodies. In one embodiment, said antibodies are a combination of anti-CD3 antibodies and anti-CD28 antibodies. In one embodiment, said microfluidic device further comprises epithelial cells. In one embodiment, said microfluidic device further comprises endothelial cells. In one embodiment, said microfluidic device further comprises immune cells. In one embodiment, said microfluidic device further comprises T cells. In one embodiment, said T cells comprise plate activated T cells. In one embodiment, said T cells are derived from peripheral blood mononuclear cells. In one embodiment, said T cells comprise $T_H1$ cells. In one embodiment, said T cells comprise $T_H9$ cells. In one embodiment, the T cells are derived from lamina propria tissue. In one embodiment, said device further comprises soluble antigen.

In one embodiment, the present invention also contemplates a method of stimulating immune cells, comprising; a) providing i) immune cells and ii) a microfluidic device comprising affinity reagents configured to stimulate said immune cells; and b) introducing said immune cells into said microfluidic device under conditions such that said immune cells become stimulated. In one embodiment, said microfluidic device comprises one or more microfluidic channels. In one embodiment, said affinity reagents are positioned within said microfluidic device. In one embodiment, said affinity reagents are retained within said microfluidic device. In one embodiment, said affinity reagents are positioned on beads within said microfluidic device. In one embodiment, said affinity reagents are attached within said microfluidic device. In one embodiment, said affinity reagents are covalently attached within said microfluidic device. In one embodiment, said microfluidic device further comprises a membrane in contact with said one or more microfluidic channels. In one embodiment, said affinity reagents are positioned on said membrane. In one embodiment, said microfluidic device further comprises one or more extracellular matrix proteins in said one or more microfluidic channels. In one embodiment, said microfluidic device further comprises at least one gel in said microfluidic device. In one embodiment, said gel comprising at least one extracellular matrix protein. In one embodiment, said affinity reagents are immobilized in said gel. In one embodiment, said affinity reagents are immobilized in said one or more extracellular matrix proteins. In one embodiment, said one or more extracellular matrix proteins comprise an overlay, said overlay trapping said affinity reagents. In one embodiment, said one or more extracellular matrix proteins comprise a gel, said gel trapping said affinity reagents. In some embodiments, the method has said affinity reagents comprising antibodies or binding fragments thereof. In one embodiment, said antibodies are anti-CD3 antibodies. In one embodiment, said antibodies are anti-CD28 antibodies. In one embodiment, said antibodies are a combination of anti-CD3 antibodies and anti-CD28 antibodies. In one embodiment, said method comprising prior to step b), providing epithelial cells, and adding said epithelial cells to said microfluidic device. In one embodiment, said method comprising prior to step b), providing endothelial cells, and adding said endothelial cells to said microfluidic device. In one embodiment, said immune cells comprise T cells. In one embodiment, the T cells are derived from lamina propria tissue. In one embodiment, said T cells comprise plate activated T cells. In one embodiment, said T cells are derived from peripheral blood mononuclear cells. In one embodiment, said T cells comprise $T_H1$ cells. In one embodiment, said wherein said T cells comprise $T_H9$ cells.

In one embodiment, said wherein said T cells comprise $T_H2$ cells. In one embodiment, said wherein said T cells comprise $T_H17$ cells. In one embodiment, said device further comprises soluble antigen. In one embodiment, said microfluidic device further comprising, providing, a soluble antigen and step c) introducing said soluble antigen into said microfluidic device. In one embodiment, said microfluidic device further comprising, providing, one or more test agents and step c) introducing said test agents into said microfluidic device. In one embodiment, said test agent is a drug or candidate drug. In one embodiment, said drug or candidate drug is tested for inhibiting said stimulated immune cells.

In one embodiment, the present invention also contemplates a microfluidic device comprising one or more reagents configured to activate T cells. In one embodiment, said one or more reagents comprise affinity reagents. In one embodiment, said one or more affinity reagents comprise antibodies or binding fragments thereof. In one embodiment, said microfluidic device further comprising, one or more microfluidic channels. In one embodiment, said one or more reagents are positioned within said microfluidic device. In one embodiment, said one or more reagents are retained within said microfluidic device.

In one embodiment, the present invention also contemplates a method, comprising, a) providing, i) a microfluidic device, comprising one or more reagents configured to activate T cells, and ii) T cells, and b) adding said T cells to said microfluidic device under conditions such that said T cells are activated. In one embodiment, said one or more reagents comprise affinity reagents. In one embodiment, said one or more affinity reagents comprise antibodies or binding fragments thereof. In one embodiment, said microfluidic device further comprises one or more microfluidic channels. In one embodiment, said one or more reagents are positioned within said microfluidic device. In one embodiment, said one or more reagents are retained within said microfluidic device. In one embodiment, the T cells are derived from lamina propria tissue.

In one embodiment, the present invention also contemplates a microfluidic device comprising affinity reagents configured to stimulate immune cells. In one embodiment, said microfluidic device further comprises one or more microfluidic channels. In one embodiment, said affinity reagents are positioned within said one or more microfluidic channels. In one embodiment, said affinity reagents are positioned on beads within said one or more microfluidic channels. In one embodiment, said affinity reagents are attached to said one or more microfluidic channels. In one embodiment, said affinity reagents are covalently attached to said one or more microfluidic channels. In one embodiment, said microfluidic device further comprises a membrane in said one or more microfluidic channels. In one embodiment, said affinity reagents are positioned on said membrane. In one embodiment, said microfluidic device further comprises one or more extracellular matrix proteins in said one or more microfluidic channels. In one embodiment, said affinity reagents are immobilized in said one or more extracellular matrix proteins. In one embodiment, said one or more extracellular matrix proteins comprise an overlay, said overlay trapping said affinity reagents. In one embodiment, said one or more extracellular matrix proteins comprise a gel, said gel trapping said affinity reagents. In some embodiments, said microfluidic device comprises said affinity reagents further comprising antibodies or binding fragments thereof. In one embodiment, said antibodies are anti-CD3 antibodies. In one embodiment, said antibodies are anti-CD28 antibodies. In one embodiment, said antibodies are a combination of anti-CD3 antibodies and anti-CD28 antibodies. In one embodiment, said microfluidic device further comprises epithelial cells in said one or more microfluidic channels. In one embodiment, said microfluidic device further comprises endothelial cells in said one or more microfluidic channels. In one embodiment, said microfluidic device further comprises immune cells in said one or more microfluidic channels. In one embodiment, said microfluidic device further comprises T cells in said one or more microfluidic channels. In one embodiment, said T cells comprise plate activated and differentiated T cell subsets derived from peripheral blood mononuclear cells. In one embodiment, said T cells comprise plate activated and differentiated TH11 cell subsets derived from peripheral blood mononuclear cells. In one embodiment, said T cells comprise plate activated and differentiated TH9 cell subsets derived from peripheral blood mononuclear cells. In one embodiment, said device further comprises soluble antigen.

In one embodiment, the present invention also contemplates a method of stimulating immune cells, comprising; a) providing i) immune cells and ii) a microfluidic device comprising affinity reagents configured to stimulate said immune cells; and b) introducing said immune cells into said microfluidic device under conditions such that said immune cells are stimulated. In one embodiment, said microfluidic device comprises one or more microfluidic channels. In one embodiment, said affinity reagents are positioned within said one or more microfluidic channels. In one embodiment, said affinity reagents are positioned on beads within said one or more microfluidic channels. In one embodiment, said affinity reagents are attached to said one or more microfluidic channels. In one embodiment, said affinity reagents are covalently attached to said one or more microfluidic channels. In one embodiment, said microfluidic device further comprises a membrane in said one or more microfluidic channels. In one embodiment, said affinity reagents are positioned on said membrane. In one embodiment, said microfluidic device further comprises one or more extracellular matrix proteins in said one or more microfluidic channels. In one embodiment, said affinity reagents are immobilized in said one or more extracellular matrix proteins. In one embodiment, said one or more extracellular matrix proteins comprise an overlay, said overlay trapping said affinity reagents. In one embodiment, said one or more extracellular matrix proteins comprise a gel, said gel trapping said affinity reagents. In some embodiments, said method has said affinity reagents comprising antibodies or binding fragments thereof. In one embodiment, said antibodies are anti-CD3 antibodies. In one embodiment, said antibodies are anti-CD28 antibodies. In one embodiment, said antibodies are a combination of anti-CD3 antibodies and anti-CD28 antibodies. In one embodiment, said microfluidic device further comprises epithelial cells in said one or more microfluidic channels. In one embodiment, said microfluidic device further comprises endothelial cells in said one or more microfluidic channels. In one embodiment, said immune cells comprise cells. In one embodiment, said T cells comprise plate activated and differentiated T cell subsets derived from peripheral blood mononuclear cells. In one embodiment, said T cells comprise plate activated and differentiated $T_H1$ cell subsets derived from peripheral blood mononuclear cells. In one embodiment, said T cells comprise plate activated and differentiated $T_H9$ cell subsets derived from peripheral blood mononuclear cells. In one embodiment, said method further comprising c) introducing soluble antigen into said microfluidic device. In one embodiment, said method further comprising c) introducing one or more test agents into said microfluidic device. In one embodiment, said test agent is a drug or candidate drug. In one embodiment, said drug or candidate drug is tested for inhibiting said stimulated immune cells.

In one embodiment, the present invention contemplates a method of culturing cells, comprising: a) providing, i) a microfluidic device, ii) viable lamina propria-derived cells and iii) viable gastrointestinal epithelial cells; b) introducing said lamina propria-derived cells and gastrointestinal epithelial cells into said microfluidic device so as to create a co-culture; and c) perfusing said co-culture with fluid under flow conditions. In one embodiment, said lamina propria-derived cells are human lamina propria-derived cells. However, it is not meant to limit lamina propria-derived cells from humans. Indeed, lamina propria-derived cells may be obtained from other species including, for examples, rodent, mouse, rat, dog, non-human primates, e.g., monkey. Insects, reptiles, etc. In one embodiment, said fluid in step c) comprises tissue-culture medium. In one embodiment, said fluid in step c) comprises blood or one or more blood components. In one embodiment, said microfluidic device comprises one or more microfluidic channels in fluidic communication with a source of fluid. In one embodiment, said microfluidic device comprises first and second microfluidic channels separated by a membrane, said membrane comprising first and second surfaces. In one embodiment, said method wherein at least one of said first and second channels comprises an open region. In one embodiment, said lamina propria-derived cells and said gastrointestinal epithelial cells are cultured on said top surface of said membrane. In one embodiment, said gastrointestinal epithelial cells are cultured in said first channel. In one embodiment, said lamina propria-derived cells are cultured in said first channel. In one embodiment, said lamina propria-derived cells are cultured in said second channel. In one embodiment, said perfusing in step c) comprises flowing said fluid in said first channel at a flow rate. In one embodiment, said perfusing in step c) comprises flowing said fluid in said second channel at a flow rate. In one embodiment, said method further comprising introducing endothelial cells on said bottom surface of said membrane. In one embodiment, said method further comprising introducing endothelial cells into said second channel. In one embodiment, said endothelial cells are introduced before step c). In one embodiment, said endothelial cells are gastrointestinal endothelial cells. In one embodiment, said lamina propria-derived cells and viable gastrointestinal epithelial cells are introduced in step b) simultaneously. In one embodiment, said lamina propria-derived cells and viable gastrointestinal epithelial cells are introduced in step b) sequentially. In one embodiment, said lamina propria derived cells are introduced in step b) prior to the introduction of said gastrointestinal epithelial cells. In one embodiment, said lamina propria-derived cells are introduced in step b) after the introduction of said gastrointestinal epithelial cells. In one embodiment, said lamina propria-derived cells were derived from inflamed gastrointestinal tissue. In one embodiment, said gastrointestinal epithelial cells were derived from inflamed gastrointestinal tissue. In one embodiment, said lamina propria-derived cells comprise cells derived from a site of an ulcer or injury. In one embodiment, said gastrointestinal epithelial cells comprise cells derived from a site of an ulcer or injury. In one embodiment, said lamina propria-derived cells comprise resident immune cells of gastrointestinal tissue.

In one embodiment, the present invention contemplates a method of culturing cells, comprising: a) providing a microfluidic device comprising a membrane, said membrane comprising a top surface and a bottom surface; b) seeding viable lamina propria-derived cells and viable parenchymal cells in said microfluidic device so as to create seeded cells; and c) culturing said seeded cells in fluid under flow conditions. In one embodiment, said microfluidic device further comprises a first and second microfluidic channels separated by said membrane. In one embodiment, said at least one of first and second channels comprise an open region. In one embodiment, said lamina propria derived cells are human lamina propria-derived cells. However, it is not meant to limit lamina propria-derived cells from humans. Indeed, lamina propria-derived cells may be obtained from other species including, for examples, rodent, mouse, rat, dog, non-human primates, e.g. monkey. Insects, reptiles, etc. In one embodiment, said parenchymal cells comprise epithelial cells. In one embodiment, said epithelial cells comprise gastrointestinal epithelial cells. In one embodiment, said method further comprising seeding endothelial cells as part of step b). In one embodiment, said seeding of endothelial cells in step b) comprises seeding said endothelial cells in said second channel. In one embodiment, said seeding of parenchymal cells in step b) comprises seeding said parenchymal cells in the first channel. In one embodiment, said seeding of lamina propria-derived cells in step b) comprises seeding said lamina propria-derived cells in the second channel. In one embodiment, said seeding of lamina propria-derived cells in step b) comprises seeding said lamina propria-derived cells in a gel. In one embodiment, wherein, prior to step b), said top surface of said membrane is treated with at least one extracellular matrix protein. In one embodiment, said lamina propria-derived cells are covered by at least one extracellular matrix protein. In one embodiment, said cells are covered by an overlay of Matrigel. In one embodiment, wherein step b) further comprises seeding a population of gastrointestinal epithelial cells to said seeded lamina propria-derived cells. In one embodiment, said overlay is subsequently removed. In one embodiment, said human epithelial cells are selected from the group consisting of Caco-2 epithelial cells, primary small intestinal epithelial cells and primary large intestinal epithelial cells. However, it is not meant to limit gastrointestinal epithelial cells from humans. Indeed, gastrointestinal epithelial cells may be obtained from other species including, for examples, rodent, mouse, rat, dog, non-human primates, e.g. monkey, insects, reptiles, etc. In one embodiment, said lamina propria-derived cells comprise resident immune cells. In one embodiment, said lamina propria-derived cells comprise immune cells from healthy tissue. In one embodiment, said lamina propria-derived cells comprise immune cells from disease tissue. In one embodiment, said lamina propria-derived cells comprise fibroblasts. In one embodiment, said lamina propria derived cells are selected from the group consisting of stromal cells and resident immune cells. In one embodiment, said resident immune cells are selected from the group consisting of lymphocytes, mononuclear cells, macrophages, immature dendritic cells, mature dendritic eosinophils, basophils, mast cells and combinations thereof. In one embodiment, said lamina propria derived cells are obtained from intestinal tissue selected from the group consisting of small intestine and large intestine. In one embodiment, said small intestine tissue is selected from the group consisting of duodenum, duodenojejunal flexure, jejunum, ileum, and terminal ileum. In one embodiment, said large intestine tissue is selected from the group consisting of cecum, ascending colon, hepatic flexure, descending colon, sigmoid colon, rectum and anus. In one embodiment, said lamina propria-derived cells are obtained from gastrointestinal tissue selected from the group consisting of stomach, esophagus, and mouth. In one embodiment, said lamina propria-derived cells are primary cells. In one embodiment, said lamina propria-derived cells were cryopreserved and then thawed prior to step b). In one embodiment, said method comprising after step b) assessing viability. In one embodiment, said method wherein viability is assessed by measuring the relative amount of lactate dehydrogenase released by the cells over time. In one embodiment, said flow conditions comprise flowing said fluid through said device at a flow rate. In one embodiment, said fluid comprises tissue-culture medium. In one embodiment, said fluid comprises blood or blood components. In one embodiment, said method further comprising a step after step e) sampling cytokines present in said fluid. In one embodiment, said cytokines are selected from the group consisting of interleukin-6 and interleukin-9. In one embodiment, said epithelial cells form a monolayer of cells, wherein said monolayer has an apical region and a basal region. In one embodiment, said method further comprising after step b) adding an agent to said apical region of said epithelial cells. In one embodiment, said agent is PAM2CSK4. In one embodiment, said method further comprising after step b) assessing permeability of said monolayer between said apical region and said basal region. In one embodiment, said assessing permeability comprises applying an agent at said apical region of said epithelial cells then measuring the amount of said agent released at said basal region. In one embodiment, said agent is a dye. In one embodiment, said method further comprising step d) contacting at least one of said lamina propria-derived cells and said parenchymal cells with a first agent. In one embodiment, said first agent comprises a drug. In one embodiment, said method further comprising step e) detecting a response to said first agent.

In one embodiment, the present invention contemplates a microfluidic device, wherein said microfluidic device comprises one or more microfluidic channels, a membrane, said membrane comprising a top surface and a bottom surface, and a co-culture of gastrointestinal epithelial cells and lamina propria-derived cells located on said top surface of said membrane, and endothelial cells located on said bottom surface of said membrane. In one embodiment, said membrane is semi-permeable. In one embodiment, said lamina propria-derived cells comprise stromal cells and immune cells. In one embodiment, said immune cells are selected from the group consisting of lymphocytes, mononuclear cells, macrophages, immature dendritic cells, mature dendritic cells, eosinophils, basophils, mast cells and combinations thereof. In one embodiment, said top surface of said membrane comprises at least one extracellular matrix protein. In one embodiment, said lamina propria-derived cells were obtained from human gastrointestinal tissue selected from the group consisting of healthy tissue, pre-diseased tissue and diseased tissue. In one embodiment, said lamina propria-derived cells were obtained from inflamed human gastrointestinal tissue. In one embodiment, said lamina propria-derived cells were obtained from a human with inflammatory colitis. However, it is not meant to limit lamina propria derived cells from humans. Indeed, lamina propria-derived cells may be obtained from other species including, for examples, rodent, mouse, rat, dog, non-human primates, e.g. monkey. Insects, reptiles, etc. In one embodiment, said fluidic device further comprising media, wherein said media is located within said microfluidic channels and in contact with said co-culture of said cells.

In one embodiment, the present invention contemplates a microfluidic system comprising a microfluidic device and a co-culture of gastrointestinal epithelial cells, and lamina propria-derived cells, wherein said co-culture is perfused with fluid under flow conditions. In one embodiment, said device further comprises endothelial cells. In one embodiment, said device comprises a membrane, said membrane comprising a top surface and a bottom surface, and one or more microfluidic channels in fluidic communication with a source of said fluid. In one embodiment, said microfluidic device comprises first and second microfluidic channels separated by said membrane. In one embodiment, said top surface of said membrane comprises at least one extracellular matrix protein. In one embodiment, said gastrointestinal cells are located on said top surface of said membrane. In one embodiment, said fluidic device further comprising endothelial cells on said bottom surface of said membrane. In one embodiment, said lamina propria-derived cells comprise stromal cells and immune cells. In one embodiment, said lamina propria derived cells comprise resident immune cells of human gastrointestinal tissue. However, it is not meant to limit gastrointestinal tissue from humans. Indeed, gastrointestinal tissue may be obtained from other species including, for examples, rodent, mouse, rat, dog, non-human primates, e.g. monkey. Insects, reptiles, etc. In one embodiment, said lamina propria-derived cells are obtained from gastrointestinal tissue and are selected from the group consisting of healthy tissue, pre-diseased tissue and diseased tissue.

In one embodiment, the present invention contemplates a fluidic device comprising; a) a first fluidic channel in contact with a semi-permeable membrane, b) first cells comprising intestinal epithelial cells; and c) second cells comprising at least one stromal cell type. In one embodiment, said fluidic device further comprising d) endothelial cells. In one embodiment, said endothelial cells are disposed within the said first fluidic channel. In one embodiment, said stromal cell type is a lamina propria-derived cell. In one embodiment, said stromal cell type comprises resident immune cells. In one embodiment, said stromal cell type comprises fibroblasts. In one embodiment, said stromal cell type comprises cells selected from the group consisting of macrophages and dendritic cells. In one embodiment, said stromal cell types comprise primary stromal cells. In one embodiment, said primary stromal cells comprise biopsy-derived cells or lavage-derived cells. In one embodiment, said primary stromal cells are patient-derived cells. In one embodiment, said patient-derived cells are from a patient with an inflammatory disease of the intestine. In one embodiment, wherein at least a portion of said second cells are disposed in contact with said semi-permeable membrane. In one embodiment, the fluidic device further comprises a gel. In one embodiment, said lamina propria-derived cells are disposed in said gel.

In one embodiment, the present invention contemplates a method comprising: a) providing a fluidic device comprising i) a fluidic channel in contact with a semi-permeable membrane, ii) first cells comprising intestinal epithelial cells, and iii) second cells comprising at least one stromal cell type; and b) perfusing said fluidic device with fluid. In one embodiment, said stromal cell type is a lamina propria-derived cell. In one embodiment, said stromal cell type comprises resident immune cells. In one embodiment, said stromal cell type comprises fibroblasts. In one embodiment, said stromal cell type comprises cells selected from the group consisting of macrophages and dendritic cells. In one embodiment, said stromal cell type comprises primary stromal cells. In one embodiment, said primary stromal cells comprise biopsy-derived cells or lavage-derived cells. In one embodiment, said primary stromal cells are patient-derived cells. In one embodiment, said patient-derived cells are from a patient with an inflammatory disease of the intestines. In one embodiment, the method further comprising step c) contacting said first cells, said second cells or both cells with a first agent. In one embodiment, the method further comprising step d) detecting at least one response to said first agent. In one embodiment, said at least one response comprises modulation of an inflammation reaction.

The novel features of using Gut-on-Chip microfluidic devices of the present inventions include but are not limited to: allowing the user to make multiple duplicate chips in one operation; Lamina propria-derived cells from primary sources can be co-cultured for up to 9 days without significant cell death; Immune cell populations from intestinal lamina propria-derived cells obtained from primary sources contribute to providing an inflammatory state (environment) of the Intestine-on-Chip, this microfluidic device was shown to mimic an Ulcerative Colitis-like disease phenotype; a resident immune cell population seeded on to the Intestine-Chip includes a $T_H9$ T-helper cell population which in vivo are highly correlated with ulcerative colitis inflammatory conditions; IL-9 production is linked to ulcerative colitis in vivo and in vitro on the Intestine-Chip IL-9 production is activated by treatment with a TLR2 bacterial agonist.

The present invention contemplates combining features from different embodiments. The present invention contemplates removing features from the above-indicated embodiments. For a non-limiting example, co-cultures of epithelial cells with endothelial cells and lamina propria-derived cells may have a feature removed. For example, subsets of cells isolated from lamina propria may be removed from the configuration in order to identify subsets of LP-derived cells contributing to specific disease phenotypes. The present invention contemplates adding features to the configuration in order to identify LP-cells initiating a specific disease phenotype, e.g. adding diseased LP-derived cells or Th9 cells isolated from diseased LP derived cells to microfluidic devices containing pre-disease or healthy gastrointestinal cells. The present invention, contemplates substituting features in the above-indicated embodiments. For a non-limiting example, ECM from commercial sources may be substituted with ECM isolated from humans.

DEFINITIONS

The terms "Intestine-on-Chip" and "Gut-On-Chip" are used interchangeably herein. A "Gut-On-Chip" or "chip" refers to a "microfluidic device" for modeling any one or more types of gastrointestinal tissue. Including but not limited to the small intestine, large intestine, stomach etc. A "Gut-On-Chip" device is not limited to modeling the upper or lower intestine. In fact, "Gut-On-Chip" refers to a "microfluidic device" for modeling any one or more subtypes of gastrointestinal tissue. Including but not limited to the small intestinal ileum, large intestine colon, large intestine rectum, etc.

Additionally, the term "microfluidic" as used herein relates to components where moving fluid is constrained in or directed through one or more channels wherein one or more dimensions are 1 mm or smaller (microscale). Microfluidic channels may be larger than microscale in one or more directions, though the channels) will be on the microscale in at least one direction. In some instances the geometry of a microfluidic channel may be configured to control the fluid flow rate through the channel (e.g. increase channel height to reduce shear). Microfluidic channels can be formed of various geometries to facilitate a wide range of flow rates through the channels.

"Channels" are pathways (whether straight, curved, single, multiple, in a network, etc.) through a medium (e.g., silicon) that allow for movement of liquids and gasses. Channels thus can connect other components, i.e., keep components "in communication" and more particularly, "in fluidic communication" and still more particularly, "in liquid communication." Such components include, but are not limited to, liquid-intake ports and gas vents. Microchannels are channels with dimensions less than 1 millimeter and greater than 1 micron.

As used herein, the phrases "connected to," "coupled to," "in contact with" and "in communication with" refer to any form of interaction between two or more entities, including mechanical, electrical, magnetic, electromagnetic, fluidic, and thermal interaction. For example, in one embodiment, channels in a microfluidic device are in fluidic communication with cells and (optionally) a fluid reservoir. Two components may be coupled to each other even though they are not in direct contact with each other. For example, two components may be coupled to each other through an intermediate component (e.g. tubing or other conduit).

Other than in the operating examples, or where otherwise indicated, all numbers expressing quantities of ingredients or reaction conditions used herein should be understood as modified in all instances by the term "about." The term "about" when used to describe the present invention. In connection with percentages means ±5%.

As used herein, the term "substantially" is a relative term that can be used to indicate similar dimensions (e.g. height, width, etc.) or similar features (e.g. porosity, linearity, etc.) that need not be identical to a reference, e.g. preferably at least 80% of the dimension or feature, more typically, at least 90%, or at least 95%, or at least 97% or at least 99% or more.

As used herein, the term "biopsy" refers to a sample of the tissue that is removed from a body.

As used herein, the terms "lamina propria-derived cells" and "LP-derived cells" refers to cells used in the context of specific tissues (e.g. mucosal tissues), including but not limited to stromal cells, fibroblasts, and immune cells (including resident immune cells or immune cells that may be transiently present in said tissues).

As used herein, "lamina propria-derived cells" and "LP-derived cells" shall include all cell types that one could derive from lamina propria. For example, the term LP-derived cells as used herein may include macrophages that have been differentiated in vitro from monocytes, as the macrophages are a cell type that could be derived from lamina propria. In one embodiment, LP-derived cells are isolated from specific tissues (e.g. mucosal tissues), LP-derived cells are not limited to mucosal tissues, as they may be isolated from tissues extending into mucosal areas, for example, cells in stromal areas. LP-derived cells may be used directly after isolation or under go culture to expand cell numbers prior to use. LP-derived cells may undergo isolation techniques before or after culturing or freezing. In other embodiments, LP-derived cells may be cryopreserved (frozen) prior to use.

As used herein, the term "stromal" refer to connective tissue cells including but not limited to multipotent stromal cells (MSCs), e.g. Bone marrow derived mesenchymal stem, cells, fibroblasts, myofibroblasts, mural cells (pericytes) of the vasculature, etc. Such cells may be found in or near sites of inflammation, such as in or near the lamina propria in vivo, e.g. mucosa, submucosa, etc. In some embodiments, stromal cells are contemplated for use in microfluidic devices of the present inventions. In some embodiments, "stromal cells" are contemplated for use after isolation from lamina propria-derived cells. In some embodiments, stromal cells are contemplated for use derived from regions that do not include lamina propria. In some embodiments, stromal cells are contemplated for use that are a mixture of LP-derived and non-LP-derived cells, e.g. when biopsy tissue used for isolating cells includes both mucosa and submucosal cells. In some embodiments, stromal cells are isolated from healthy and diseased individuals, and/or from different sites within the same individual. For example, stromal cells may be from the site of an IBD ulcer vs. from a macroscopically healthy region.

As used herein, the term "parenchymal cells" encompass epithelial cells for all organs. In many cases, the "parenchyma" refers to the 'bulk' of an organ, i.e. mass of it.

As used herein, the term "irritant" refers to a stimulus or agent that induces the state of irritation in an epithelial lining, for example, a bacterial toxin or an allergen that causes activation of resident mononuclear white blood cells, leukocytes, lymphocytes, etc. In the lamina propria (in vivo), lamina propria-derived cells (in vitro), or actual damage to epithelial cells, in vivo or in vitro, that in turn triggers activation of resident immune cells any of which may induce irritation.

As used herein, the term "irritation" refers to initiation of inflammation. By way of example only, this may be due to an allergy or damage to epithelial cells in the lining of the gastrointestinal system.

As used herein, the term "inflammation" refers to an in vivo physical condition in which a part of tissue in a body may become reddened, swollen (enlarged), or damaged (ulcerated) especially as a reaction to injury or an irritant. Areas of inflammation can have increased blood flow and capillary permeability, i.e. changes in endothelial cells lining capillaries resulting in capillary dilation and leukocyte infiltration into the irritated and/or inflamed tissues, along with activated immune cells. Including white blood cells, leukocytes, lymphocytes, etc., including substances produced by activated immune cells. Inflammation may occur suddenly (acute) or gradually over time (chronic). Inflammation may be local, i.e. in one location as a "patch" or "spot" or may be in several areas as numerous patches. Including ulcers, or contiguous involving a large area of tissue. Inflammation may be limited to epithelial regions and underlying lamina propria (for example, mucosal areas), or may extend to the submucosa, or extend to the muscularis propria and may further extent to the outermost layer, adventitia, in contact with other parts of the body. Inflammation may also refer to a physiological condition in vitro, as described herein; where lamina propria-derived cells are isolated from inflammatory or pre-inflammatory tissue, such that resident immune cells may be preactivated or activated.

As used herein, "Caco-2" or "Caco2" refer to a human epithlial intestinal cell line demonstrating a well-differentiated brush border on the apical surface with tight junctions between cells. Although this cell line was originally derived from a large intestine (colon) carcinoma, also called an epithelial colorectal adenocarcinoma, this cell line can express typical small-intestinal microvillus hydrolases and nutrient transporters, see, Meunier, et al., "The human intestinal epithelial cell line Caco-2; pharmacological and pharmacokinetic applications." Cell Biot Toxicol, 11(3-4): 187-94, 1995, abstract. Examples of Caco-2 cell lines include but are not limited to CRL-2102, American Type Culture Collection (Rockville, Md.); a BBE subclone of Caco-2 cells; etc.

As used herein, "reagent" refers to a substance or compound, including but not limited to substances or compounds that a) react, b) cause a reaction (whether chemical or cellular), or c) bind to a target. As used herein, "affinity reagent" refers to a reagent that binds to a target. Including but not limited to an antibody (or binding fragment thereof), a peptide, an oligonucleotide, a small molecule, or a drug. A "target" can be an antigen (whether soluble or cell-bound), a cell surface molecule. Including but not limited to a receptor molecule, etc. The binding of an affinity reagent is typically non-covalent.

As used herein, a "binding fragment" of an antibody can be a "Fab fragment" such as a F(ab'), fragment or a F(ab') fragment or other fragment that is smaller than the intact antibody, i.e. that does not include the entire antibody molecule.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIG. 2 shows an exemplary anatomy schematic of a healthy human stomach (upper diagram) with labeled regions: from the esophagus through the lower esophageal sphincter, fundus, body with rugae folds, antrum through the pyloric sphincter and pylorus to the duodenum of the small intestine. The lower diagram shows a schematic of the stomach wall. In particular the mucosal layer of surface epithelium and lamina propria above a muscularis mucosae and submucosal area.

FIGS. 5A-B shows FIG. 5A) an exemplary immunofluorescently stained histological micrograph showing three layers in a cross section and FIG. 5B) an exemplary schematic of an Intestine-on-chip. Note that the apical microvilli are depicted facing away from the other cells in the chip. FIG. 5B) Top layer is an epithelial channel of Caco-2 cells which is shown in FIG. 5A) in a top micrograph as cells outlined in red ZO-1 (Zonula occludens-1, also known as Tight junction protein-1) outlining cells with nuclei stained by DAPI (4′,6-diamidino-2-phenylindole) fluorescent stain in blue. Underneath the epithelium (FIG. 5B), on the basal side, is the layer of resident immune cells (lamina propria derived cells), which in the middle (FIG. 5A) micrograph shows C45+ (a lymphocyte common antigen expressed on leucocytes) cells in pink, with intracellular green actin fibers and nuclei stained by DAPI in blue. The lower vascular channel (FIG. 5B) shows a channel formed by HUVECS which in the lower (FIG. 5A) micrograph shows red VE-Cadherin (vascular endothelial cadherin) outlining the cells. Intracellular green actin fibers, and nuclei stained by DAPI, in blue.

FIGS. 9A-B shows an exemplary embodiment for Intestine-on-Chip: Quality Control, FIG. 9A) permeability ($P_{app}$ (cm/s)) and FIG. 9B) viability (LDH release as a percent of lysis control) of cells over time.

FIG. 10 shows an exemplary disrupted barrier function ($P_{app}$ (cm/s)) (apparent permeability) by co-culture of epithelial cells and HUVECS with leukocytes from inflamed UC tissue. Untreated control use LP-derived healthy cells. Treated used non-inflamed UC LP, inflamed UC LP, which weakened barrier function, and no LP for comparisons.

FIG. 11A) Comparison of IL-6 (pg/ml) production between chips containing healthy LP, UC LP non-inflamed, UC LP inflamed and no LP. FIG. 11B) Comparison of IL-9 (pg/ml) production between chips containing healthy LP, UC LP non-inflamed, UC LP inflamed and no LP. IL-6 production foreshold for chips with UC LP tissue is different than in control LP and no LP chips; TLR2 activation of IL-9 production is LP dependent; and no priming for IL-9 production is observed for UC LP.

FIGS. 14A-B shows an exemplary reduced 'Villus' Height in Infected Chips as representative immunofluorescent micrograph cross-sections of one embodiment of Intestine On-Chip indicating changes in exemplary heights of the Caco-2 epithelial layer as a readout for barrier function. FIG. 14A) Untreated Control Caco-2 epithelial layer (Avg. Z Height (z arrow) 157+/−1.5 um) and FIG. 14B) Caco-2 epithelial layer+Bacterial Challenge—PAM2CSK4 Treated (Avg. Z Height (z-arrow) 84 um+/−11 m). The epithelial boundary is marked by a thick yellow line. Immunohistochemistry shows ZO-1 (red) outlining cells, E-cadherin (green) and nuclei (blue: DAPI stained). A decrease in barrier function in infected chips correlates with reduced 'villus' heights on the chip.

FIG. 16A) Apical IL-9 (pg/ml) cytokine secretion at 1, 2 or 4 LP (mil/ml), FIG. 16B) Basal IL-9 (pg/ml) cytokine secretion at 1, 2 or 4 LP (mil/ml). Loss of barrier function correlates with presence of IL-9 in the basal channel.

FIGS. 25A-C shows an exemplary schematic model for translating in vivo T cell activation and differentiation of T-Cell effector subsets derived from blood to an in vitro method for providing human activated immune cells simulating CD as $T_H1$ subsets and simulating UC as $T_H9$ subsets. FIG. 25A shows one embodiment as an exemplary schematic of T cell activation in vivo (nature) where antigen presentation in the context of cell bound MHCII-antigen triggers a CD3 signaling complex on a T cell, while cell bound CD80 and CD86 molecules co-activate CD28 signaling on the same cell, as compared to T cell activation in vivo (laboratory) where activation factors such as anti-CD3 and anti-CD28 antibodies are soluble (in solution) that activate the T cell bound CD3 complex bypassing recognition of TCR (T cell receptor) antigen specific MHC molecules and the CD28 receptor. FIG. 25B shows one embodiment as an exemplary schematic for lymphocyte isolation from peripheral blood (i.e. PBMCs), including T cells, as a buffy coat layer (right) obtained after centrifugation of a mixture of whole blood, i.e. peripheral whole blood mononuclear (PBMCs) cells, in a solution comprising a gradient forming particle (left). FIG. 25C shows one embodiment as an exemplary schematic for post-activation of a population of CD4+ enriched T cells differentiated into T cell subsets depending upon differential levels cytokine additions for inducing differentiation into the exemplary T cell subsets depicted.

FIG. 26A shows exemplary comparative IFN-gamma cytokine protein expression. FIG. 26B shows exemplary IL-9 cytokine protein expression. For each CD4+ T cell subset, the left bar represents expression without an additional stimulus whiles the right bar represents expression after exposure to soluble PAM2CSK4. PAM2CSK4 increases in the concentration of protein signaling in both $T_H1$ (CD) and $T_H9$ (UC) cells.

FIG. 27A shows exemplary comparative IL-6 cytokine protein. FIG. 27B shows exemplary comparative IL-8 cytokine protein expression. For each CD4+ T cell subset, the left bar represents expression without an additional stimulus while the right bar represents expression after exposure to soluble PAM2CSK4.

FIGS. 28A-C shows exemplary results of measuring cytokine expression post differentiation as described in FIGS. 26A-B. FIG. 28A shows exemplary comparative IL-13 cytokine protein expression. FIG. 28B shows exemplary comparative IL-1beta cytokine protein expression. FIG. 28C shows exemplary comparative TNF-alpha cytokine protein expression.

FIGS. 30A-D shows exemplary results comparing post differentiation CD4+ $T_H9$ T cell activation factors and IL-9 cytokine secretion from activation of CD4+ T cell subsets using soluble CD3 and CD28 antibodies, with or without stimulation by soluble PAM2CSK4, on-plates. FIG. 30A shows exemplary results for GATA3 protein production. FIG. 30B shows exemplary results for SPI1 protein production. FIG. 30C shows exemplary results for IRF4 protein production. FIG. 30D shows exemplary results for IL-9 protein production.

FIG. 32B shows results from Day 8 microfluidic chips treated with Tofacitinib citrate with or without PAM2CSK4 (PAM).

FIG. 33A shows exemplary IL-6 secretion. FIG. 33B shows exemplary IL-10 secretion.

FIG. 36A shows exemplary apparent permeability representative of barrier function of treated Intestine-Chip with $T_H1$-Activated populations (simulating Crohn's). FIG. 36B shows exemplary apparent permeability representative of barrier function of treated Intestine-Chip with $T_H9$ Activated populations (simulating Ulcerative Colitis).

FIG. 37A shows exemplary IFN-gamma secretion. FIG. 37B shows exemplary IL-9 secretion.

FIG. 38A shows exemplary IL-6 secretion. FIG. 38B shows exemplary IL-8 secretion.

FIG. 39A IL-10 Cytokine Expression after 48 hr stimulation with soluble anti-CD3/CD28. FIG. 39B IL-13 Cytokine Expression after 48 hr stimulation with soluble CD3/CD28. FIG. 39C IL-1b Cytokine Expression after 48 hr stimulation with soluble CD3/CD28.

FIG. 40A-C shows exemplary results comparing pro-inflammatory cytokine gene expression between $TH_1$ and $T_H9$ cell populations stimulated with either soluble anti-CD3/CD28 or PAM or both. FIG. 40A shows exemplary IFN-gamma gene expression. FIG. 40B shows exemplary IL-9 gene expression. FIG. 40C shows exemplary Occludin (cell adhesion protein) gene expression.

FIG. 41A shows exemplary comparisons where dendritic cells in vivo activate T cells simulated by soluble activation factor induction in vitro (laboratory). The enlarged area inside of the circle highlights $1^{st}$ the and second soluble signals used in vivo. FIG. 41B indicates the types of cytokines or growth factors present during activation (i.e. co-stimulation) that produce specific differentiated T cell subsets. FIG. 41C is a schematic representation showing immune activating factors (reagents) covalently attached to the chip membrane, alternatively trapped within or located on top of the ECM, i.e. activated ECM.

FIGS. 44A-D shows exemplary results of measuring immune cytokine expression after the addition of bound activation reagents on-chip with exposure to antigen. The graphs demonstrate that bound antiCD3 with soluble or bound anti-CD28 for co-stimulation of $T_H1$ cells in the presence of antigen. $T_H1$ cells show a significant increased in IFN-gamma but not IL-9 using bound anti-CD3 and anti-CD28 in the presence of soluble antigen. Thus, binding both anti-CD3 and anti-CD28 to the membrane causes a significant upregulation in inflammatory cytokine production on Intestine On-Chip for $T_H1$ cells. FIG. 44A shows IFN-gamma production. FIG. 44B shows IL-9 production. FIG. 44C shows IL-10 production. FIG. 44D shows IL-13 production.

FIG. 45A shows IL-6 production. FIG. 45B IL-8 production.

FIGS. 46A-C shows exemplary results of measuring epithelial cytokine expression in the presence of T cells and activated ECM. In this embodiment as intestine on-chips having bound CD3 antibodies. In combination with bound anti-CD28 or soluble anti-CD28 co-stimulation of $T_H1$ cells. FIG. 46A TNF alpha cytokine expression. FIG. 46B IL-1b cytokine expression. FIG. 46C shows an exemplary key for experimental conditions: control, antigen stimulation (PAM). In the presence of soluble CD28, bound CD28 and T cells without activated ECM (i.e. inactivated).

FIG. 52A shows an exemplary schematic of one embodiment of an intestine on-chip with an upper epithelial channel seeded with CD45+ resident immune cells and a lower vascular channel seeded with endothelial cells. FIG. 52C shows an exemplary fluorescent micrograph image of the chip where green dots represent immune cells labeled with Cell Tracker.

FIGS. 53A-C shows exemplary results of measuring an inflammatory response (secreted cytokines) of CD45+ resident immune cells on plates. FIG. 53A shows exemplary IL-6 protein secretion. FIG. 53B shows exemplary IL-10 protein secretion. FIG. 53C shows exemplary IL-8 protein secretion. FIG. 53D shows a key for experimental conditions in FIGS. 53A-C. Ctrl LP, Non-Infl (non-inflammatory) LP UC (Ulcerative Colitis) and Infl (inflammatory) LP UC (Ulcerative Colitis).

FIG. 55A shows exemplary TNF alpha protein secretion. FIG. 55B shows exemplary IL-6 protein secretion. FIG. 55C shows exemplary IL-8 protein secretion.

FIG. 57A shows exemplary IL-6 protein secretion. FIG. 57B shows exemplary IL-8 protein secretion. FIG. 57C shows exemplary apparent permeability increase after CD45+ resident immune cells from an inflammatory region of UC LP.

FIG. 59A shows exemplary IL-8 protein secretion. FIG. 59B shows exemplary IL-9 protein secretion.

FIGS. 61A-G shows exemplary embodiments of epithelial channels and vascular channels, with or without a gel, in a gut-on-chip with symbol information provided in FIG. 61H. FIG. 61A shows LPDCs located under epithelial cells. FIG. 61B shows LPDCs located under gel. FIG. 61C shows LPDCs located over gel, FIG. 61D shows LPDCs located in gel, FIG. 61E shows LPDCs located in bottom channel. FIG. 61F shows LPDCs located in gel in bottom channel. FIG. 61G shows LPDCs located over epithelial cells. FIG. 61H shows symbols representing: Membrane, Gel, Endothelial Cells, e.g. HUVEC. Intestinal Epithelial Cells (epis) and lamina Propria (LP) Derived Cells (LPDC).

FIG. 63A Human primary colonic epithelial cells obtained from Endoscopic Biopsies then cultured as human Enteroids/Colonoids. FIG. 63B Human colonic microvascular endothelial cells. FIG. 63C Human intestinal fibroblasts (e.g. obtained commercially from Cell Biologics).

GENERAL DESCRIPTION OF THE INVENTION

Figure 1A:
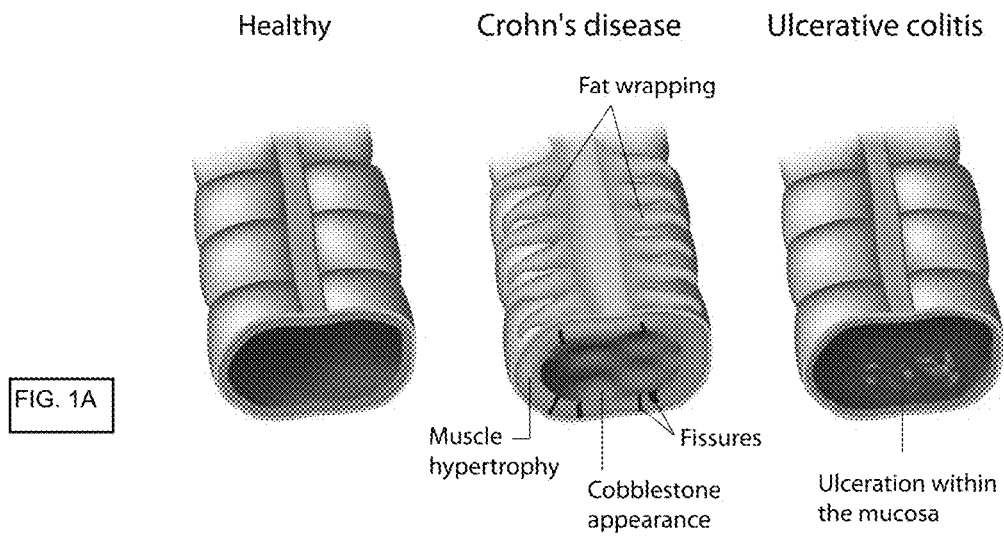
FIG. 1A shows exemplary comparative anatomy schematics of cross sections between healthy large intestine, an inflammatory large intestine, such as in Cretan's disease, that may involve the entire wall (mucosal to serosa layers) including muscle hypertrophy, an atypical cobblestone appearance of the epithelium, and may have damaged areas (i.e. lose of barrier function) as fissures that leak intestinal contents into the abdomen, and inflammatory large intestine limited to an inflammatory inner lining (mucosal region which may extend to the submucosal regions) such as in ulcerative colitis tissues (UC). For UC ulceration within the mucosa represented in the schematic, i.e. (i.e. lose of barrier function) may occur over time.
Figure 1B:
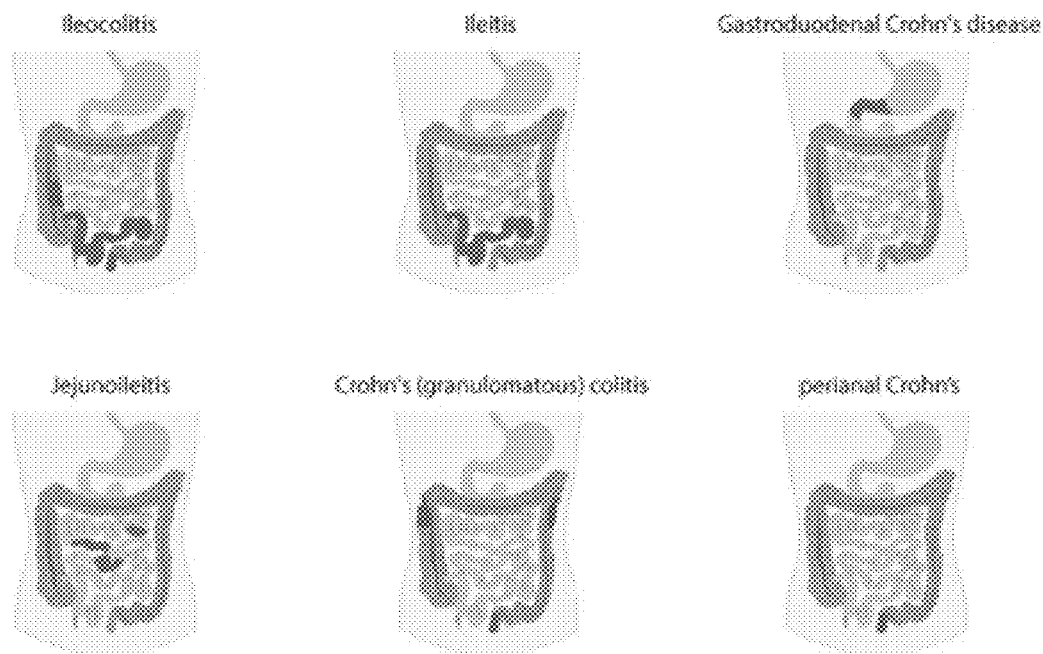
FIG. 1B shows an exemplary anatomy schematic of Crohn's Disease (CD) in a human small intestine with red-labeled regions corresponding to the areas that may be affected by each type of CD. Types of CD shown are, from top to bottom, left to right, ileocolitis, ileitis, gastroduodenal CD, jejunoilitis, Crohn's (granulomatous) colitis, and perianal CD. These types of CD and the areas that may be affected are further described below.
Figure 1C:
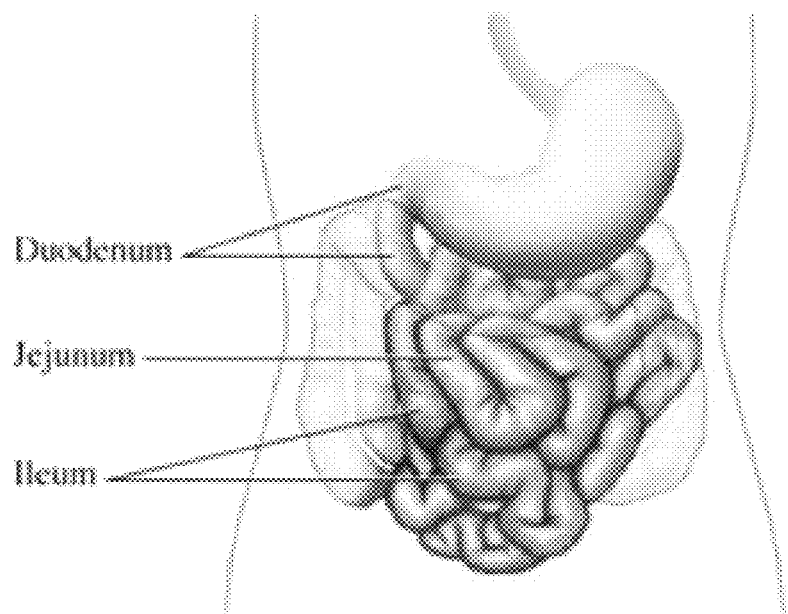
FIG. 1C shows an exemplary anatomy schematic of a small intestine showing regions of the stomach transitioning to the duodenum, jejunum, and ileum.
Figure 1D:
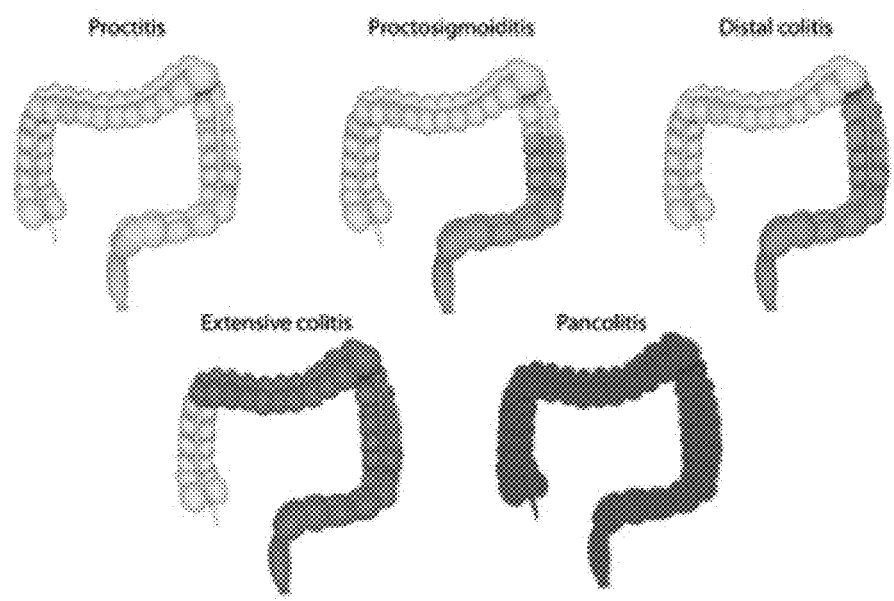
FIG. 1D shows an exemplary anatomy schematic of a human large intestines showing types of ulcerative colitis with yellow-, orange- and red-labeled regions corresponding to the areas affected by each type of colitis from the most limited to the most extensive, from left to right, top to bottom: proctitis (yellow region), proctosigmoiditis (orange region), distal colitis (orange region), extensive colitis (dark orange region) and pancolitis (red region) involving the entire large intestine.
Figure 1E:
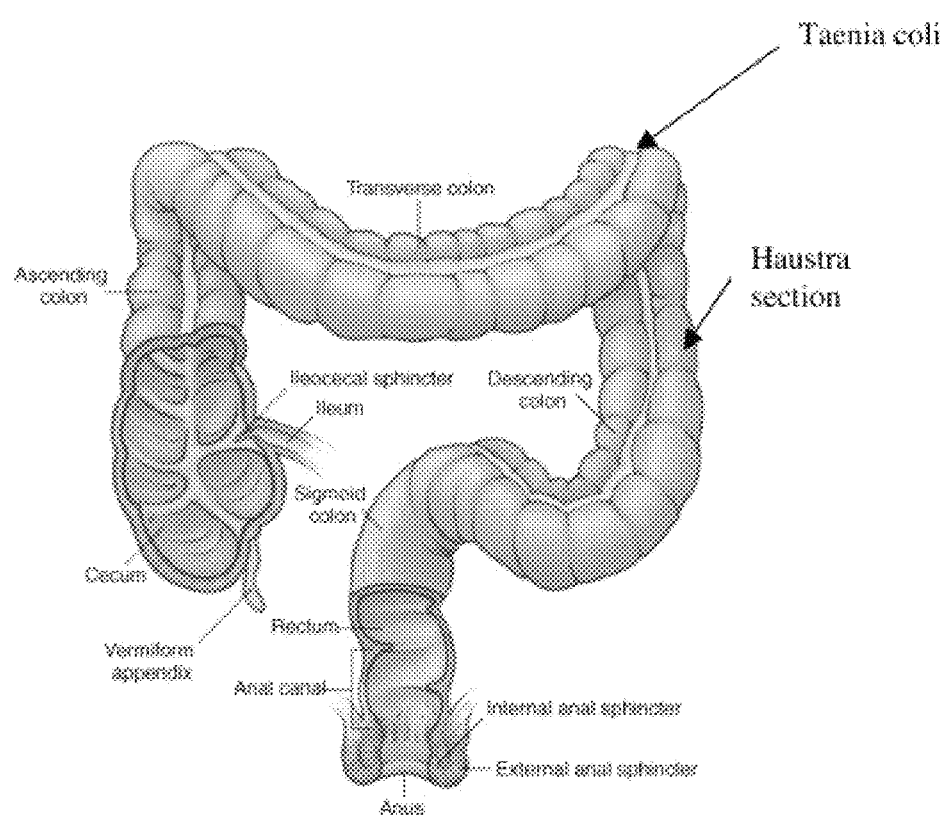
FIG. 1E shows an exemplary anatomy schematic of a healthy human large intestine with labeled regions: transitioning from the ileium region of the small intestine through the ileocecal sphincter, into the cecum (where the appendix is located at the end of the cecum), ascending colon, transverse colon, descending colon, sigmoid colon, rectum, anal canal to the internal anal sphincter to the external anal sphincter of the anus.
Figure 3A:
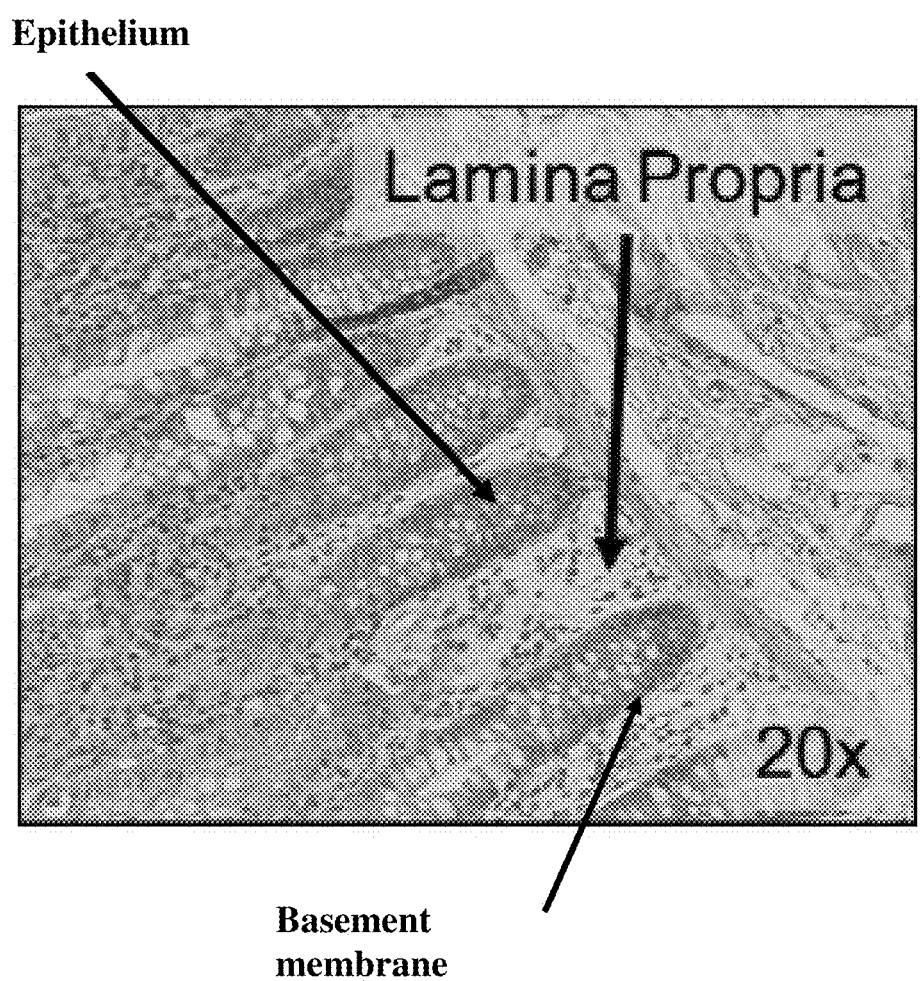
FIGS. 3A-B shows an exemplary FIG. 3A) histological view of a biopsy obtained from Ulcerative Colitis (UC) patients' intestine showing regions of lamina propria. The lamina propria is the irregular connective tissue that support the intestinal epithelium and is rich with resident immune cells, FIG. 3B) Schematic of a relationship between an epithelial layer and lamina propria.
Figure 3B:
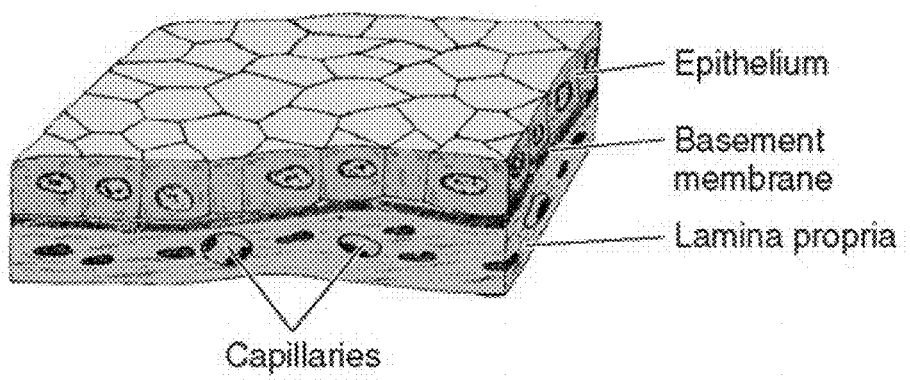
Figure 3C:
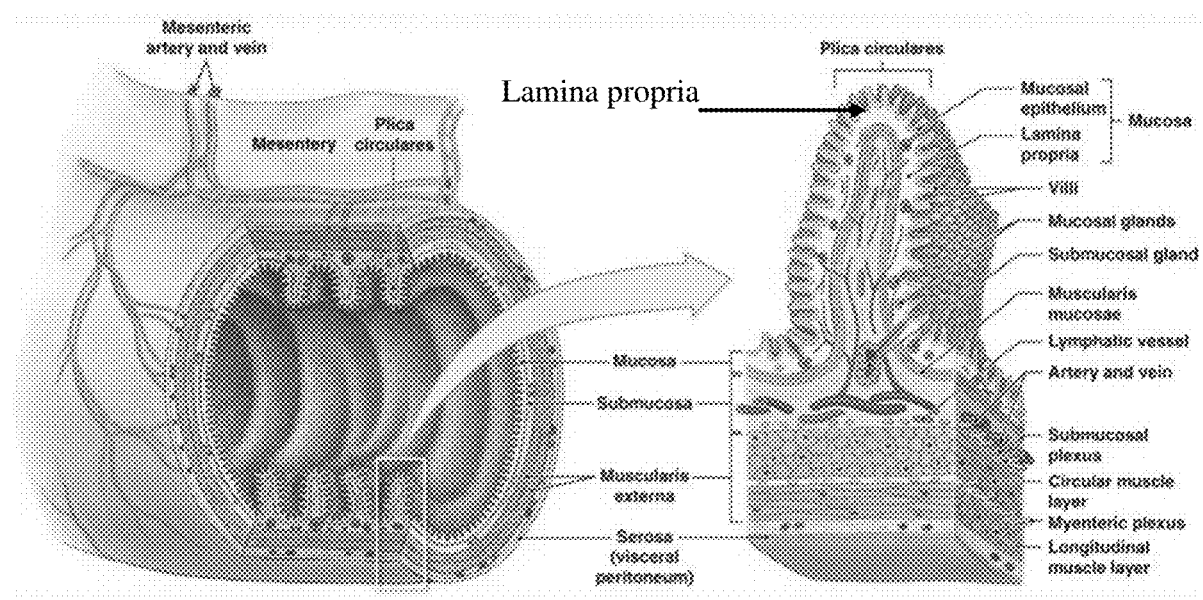
FIG. 3C shows an exemplary schematic of general anatomy and histology of an intestinal region. A villus projection is formed of epithelial cells and goblet cells that form plicae circulates (plica). Epithelial cells have microvilli on the apical side and a basement membrane on the basal side. Plica extend into the lumen area.

An in vitro microfluidic gut-on-chip is described herein that mimics the structure and at least one function of specific areas of the gastrointestinal system in vivo. In particular, a multicellular, layered, microfluidic culture is described, allowing for interactions between lamina propria-derived cells and gastrointestinal epithelial cells and endothelial cells. This in vitro microfluidic system can be used for modeling inflammatory gastrointestinal tissue, e.g., Crohn's disease, colitis and other inflammatory gastrointestinal disorders. These multicellular, layered microfluidic gut-on-chip further allow for comparisons between types of gastrointestinal tissues, e.g., small intestinal deuodejeum, small intestinal ileium, large intestinal colon, etc., and between disease states of gastrointestinal tissue, i.e. healthy, pre-disease and diseased areas. Additionally, these microfluidic gut-on-chips allow identification of cells and cellular derived factors driving disease states and drug testing for reducing inflammation.

As healthy, pre-inflammatory and inflammatory conditions are contemplated for simulation using microfluidic devices described herein; embodiments include using human cells derived from each of these types of tissues. In particular, pre-inflammatory areas of tissue adjacent to inflamed areas and inflammatory areas of the gastrointestinal system, acute and chronic, are contemplated, including but not limited to the diseases described herein, such as colitis, inflammatory bowel disease and other inflammatory conditions of the gastrointestinal tract.

Thus, biopsies of healthy, pre-inflammatory and inflammatory areas of human gastrointestinal tissue are contemplated as sources of cells for use in the present inventions. Further, human tissue may be obtained from surgical resections. In some embodiments, cadavers (e.g. beating heart cadavers) are contemplated for use in providing tissues and cells. Additionally, cells may also be obtained from commercial. sources, including but not limited to companies, blood banks, tissue banks, organ banks etc. However, it is not meant to limit gastrointestinal tissue, gastrointestinal cells, stromal cells, LPDCs, immune cells, or other cell types or tissues from humans. Indeed, cells and tissues may be obtained from other species for use herein, including Rodentia, i.e. rodent, e.g., mouse, rat, Canidae, i.e. canine, e.g. dog, non-human primates, e.g. monkey, Insecta, i.e. insects, Reptilia, i.e. reptiles.

The following describes diseases contemplated for modeling using a microfluidic device of the present inventions.
I. General Inflammation in the Gastrointestinal System.

Inflammation in tissue of the gastrointestinal system has descriptive terms ranging from general terms to terms identifying specific regions. General disease terms include but are not limited to gastroenteritis, enteritis, colitis, etc., while specific diseased area designations include terms such as small intestinal ileitis, proctitis, etc. The following descriptions relate to general terms that may also refer to overlapping conditions or diseases. In one embodiment, biopsies are contemplated as sources of these cells for use with the microfluidic devices described herein.

A. Gastroenteritis.

Gastroenteritis generally refers to irritation and inflammation anywhere in the digestive tract, i.e. involving the epithelial cell (keratinocyte) lining and underlying immune cells of the lamina propria. Gastroenteritis may be mild or severe. Mild gastroenteritis may result from, for example. Indigestion or stress. As another example, a form of localized gastroenteritis in the stomach may be viral, also referred to as the stomach flu or the 24/48-hour bug. Gastroenteritis may also refer to life-threatening conditions resulting from food poisoning or a toxic ingestion, for example, after eating a substance that contains a toxin, such as a poisonous plant, mushroom or anthrax toxin. Gastroenteritis may also occur as the result of a disorder or disease, such as inflammatory bowel disease, irritable bowel syndrome, a side effect of medication, chemotherapy or radiation, as examples.

Thus, in some embodiments, a toxin is tested on healthy, pre-inflammatory and inflammatory gastrointestinal tissue with devices of the present inventions. In some embodiments, a potential toxin is tested on healthy, pre-inflammatory and inflammatory gastrointestinal tissue with devices of the present inventions. In some embodiments, a virus is tested on healthy, pre-inflammatory and inflammatory gastrointestinal tissue with devices of the present inventions.

B. Enteritis.

Enteritis generally refers to conditions arising from an initial irritation and inflammation of the small intestine (i.e. walls), usually accompanied by diarrhea. Enteritis may further involve other areas such as the stomach, and often further involves inflammation in the large intestine. Enteritis may also indicate or trigger the onset of an IBD (discussed below). Enteritis may also be caused by an autoimmune condition resulting in chronic inflammation, such as in Crohn's disease when inflammation is restricted to the small intestine.

Enteritis is typically caused by eating or drinking food items that are contaminated with bacteria, parasites, such as amoebae, or viruses, Pathogenic triggers typically settle in the small intestine and cause inflammation and swelling which may extend to the stomach and/or large intestine.

Enteritis may also be initiated by radiation, where radiation is an irritant resulting in radiation enteritis in the small intestine, where symptoms may occur during or shortly after radiation treatment. Radiation enteritis may be acute and/or chronic.

Thus, in some embodiments, radiation is tested on healthy, pre-inflammatory and inflammatory gastrointestinal tissue with devices of the present inventions. In some embodiments, healthy, pre-inflammatory and inflammatory gastrointestinal tissue are radiated in devices of the present inventions. In some embodiments, healthy, pre-inflammatory and inflammatory gastrointestinal tissue are radiated prior to placement in devices of the present inventions.
II. Colitis.

Colitis is a general term referring to inflammation of the colon, i.e. large intestine, however colitis may also refer to disorders/diseases additionally associated with inflammation of the small intestine and other parts of the gastrointestinal system. Colitis may be acute, self-limited, or chronic, i.e. persistent. Colitis in humans is associated with intermittent, watery, diarrhea (with or without blood in the stool) and may include inflammation causing acute or chronic abdominal pain, cramping, and bloating. Additional symptoms depend upon the cause of colitis and may include fever, chills, fatigue, dehydration, eye inflammation, joint swelling, canker sores, and skin inflammation. Thus, identifying contributing factors and treatments would be useful. In one embodiment, biopsies are contemplated as sources of these cells for use with the microfluidic devices described herein.

Colitis inflammation may be due to infection by virus, ameba, or a bacterium (such as *Campylobacter*) that produce toxins that irritate the lining of the intestine inducing inflammation. Colitis may also be caused by bacteria that directly infect the colon lining, i.e. mucosal region including epithelium.

Types of colitis include autoimmune colitis covering a range of inflammatory bowel disease (IBD) as a group of chronic colitides, ulcerative colitis (a chronic colitis that affects the large intestine), and Crohn's disease, a type of IBD that often leads to colitis and idiopathic inflammatory conditions. These last two types are described in separate sections under section III.

Colitis generally includes diseases in their inflammatory stages, such as enteritis, infectious colitis, Pseudomembranous colitis, necrotizing enterocolitis, ischemic colitis, acute mesenteric ischemia, radiation, allergic (response) colitis, several types of microscopic colitis, proctitis, and inflammatory bowel disease (IBD) (including Crohn's (colitis) disease, ulcerative colitis, etc.). The following descriptions provide more infomiation on different forms of colitis that contemplated for modeling using the devices described herein. Because different types of colitis in humans may have similar symptoms and overlapping causes, biopsies of human gastrointestinal tissue are frequently obtained.

A. Necrotizing Enterocolitis (NEC).

Necrotizing Enterocolitis (NEC) refers to when portions of the inner lining, i.e. epithelium, of the large and/or small intestine. Including an immature intestine, become inflamed then undergoes necrosis (tissue death). NEC is characterized by damage to the intestinal tract, ranging from mucosal injury to full-thickness necrosis and perforation. There is no one cause for NEC which is consider a multifactoral condition having risk factors that include premature birth and the presence of bacteria in an immature GI tract. As an example, NEC may occur after normal gut bacteria cause a local infection and inflammation by infecting the intestinal epithelium. In one embodiment, biopsies are contemplated as sources of these cells for use with the microfluidic devices described herein.

NEC is a common type of colitis in human newborns, premature, formula-fed infants, and may also be a condition in adults. In newborns, onset of NEC is typically during the first several weeks after birth, with the age of onset inversely related to gestational age at birth. In term infants, the reported median age of onset is 1-3 days, but onset may occur as late as age 1 month or more. There is also a form of adult necrotizing enterocolitis known by different local names (for instance, 'Darmbrand' in Germany and 'pigbel' in Papua New Guinea).

B. Infectious Colitis.

Infectious colitis refers to when inflammation of the intestines is caused by infection of a pathogen (bacterial, parasitic, or viral). Infectious colitis is a common form of pediatric colitis and occurs in adults. Pathogens induce degeneration of the epithelium and inflammation of the lamina propria, even when the pathogenic organisms themselves do not penetrate to the lamina propria region. In one embodiment, biopsies are contemplated as sources of these cells for use with the microfluidic devices described herein.

1. Bacterial Colitis

Bacterial colitis refers to colitis induced by bacteria. Examples of such bacteria include but are not limited to *Escherichia coli* (including both enterohemorrhagic *E coli* [EHEC] and enteroinvasive *E coli* [EIEC]) and species of *Shigella, Salmonella, Campylobacter, Clostridium, Yersinia*, including *Yersinia enterocolitica*, etc.

As an example, *Salmonella* infections can cause typhoid (enteric) fever or non-typhoid infections which induce a significant proportion of food poisoning. *Salmonella* infections are typically spread via the fecal-oral route with outbreaks commonly associated with contaminated eggs, dairy products, and meats. Gastric acid is usually lethal to this bacteria, but susceptibility to infection is increased with decreased G1 motility, rapid emptying of the stomach after gastrectomy, ingesting a large quantity of *Salmonella* bacteria, malnutrition, antibiotic use, and achlorhydria (lower levels of hydrochloric acid in gastric secretions). Salmonellae can penetrate the epithelial layer to the level of the lamina propria and evoke a leukocyte response in addition to producing several toxins.

*Shigella* species attach to binding sites on the surface of the intestinal mucosal cells. This organism may penetrate and proliferate inside of epithelial cells, which may led to cell destruction, producing mucosal ulcerations, and bleeding. *Shigellae* also shed exotoxins that induce diarrhea.

*E coli* may include diarrhea in several different ways, depending on their specific pathologic characteristics. Pathologic strains of *E. coli* are classified as follows: Enteropathogenic; Enterotoxic; Enteroinvasive; Enteroaggregative; Enteroadherent; Enterohemorrhagic; and EHEC, including O157:H7 and O26:H11, which causes hemorrhagic colitis and systemic complications (e.g., hemolytic uremic syndrome [HUS]). The risk of developing HUS after infection with *E. coli* O157 is estimated to be 10-15% in children. In typical infectious colitis, the lamina propria of the large intestine is infiltrated by PMNs. EIEC, on the other hand, exhibits almost exactly the same pathogenetic mechanisms as *Shigella*.

2. *Clostridium difficile* Colitis

A subtype of infectious bacterial colitis is *Clostridium difficile* colitis. *C. difficile* Colitis refers to inflammation of the colon associated with an overgrowth of the bacterium *Clostridium difficile* (*C. diff*). This overgrowth of *C. difficile* is most often related to recent antibiotic use but may be a result of other causes. *C. difficile* is typically associated with the presence of pseudomembranes and may also be referred to as 3. Viral Colitis Viral colitis refers to virally induced colitis. As an example, colitis may be caused by cytomegalovirus (CMV) infection, typically found in immunocompromised patients (e.g., organ recipients who are receiving immunosuppressive treatment). Viral colitis results in deep round ulcerations that have a tendency to bleed easily and profusely. Adenovirus infection can also cause a severe colitis in immunocompromised patients, especially those with AIDS. In addition to patients having solid organ and bone marrow transplants. Viruses include but are not limited to (Norwalk agent, Rotaviruses, cytomegalovirus [CMV], etc), As one example, *Escherichia Coli* (EC) induced inflammatory gastroenteritis. The common *Escherichia coli* strains carried in the human intestine have minimal or no invasive ability. HEC strains have acquired the genes to express Shiga-toxins. These toxins causes cell death, edema and hemorrhage in the lamina propria. The enteroinvasive *E. coli* (EIEC) has acquired certain genetic traits from *Shigella* sp. that allow it the same invasive capabilities that certain

*Shigella* sp. possess, EHEC, the majority of the pathology occurs in the ascending and transverse colon lamina propria. Colonic biopsy specimens show focal necrosis and infiltration of neutrophils.

4. Parasitic Colitis

Parasitic colitis refers to parasite-induced colitis. Including but not limited to protozoan and non-protozoan parasites such as *Giardia, Entamoeba, Balanildium coli, Cyptosporidium, Ascaris*, etc. Chronic parasite-induced colitis may lead to UC. Moreover parasite infections, thus inflammation, may be further found in the stomach and lungs.

As an example, *Giardia lamblia*, a flagellate, may colonize the small intestinal duodenum and jejunum where they adhere to the epithelium of the microvillus and induce mild pathologic changes. Shortening and thickening of the villi is associated with acute focal inflammatory changes in the mucosal epithelium and chronic inflammatory infiltrates in the lamina propria. Another example is amebiasis referring to a parasitic infection of the intestines caused by any of the amoebas of the *Entamoeba* group, including *Entamoeba histolytica*, or *E. histolytica* which is a common cause of parasitic colitis throughout the world. Transmission of *Entamoeba* spp. takes place through ingestion of trophozoites (referring to a growing stage in the life cycle capable of absorbing nutrients from a host), usually from water contamination, and person-to-person transmission (typically because of poor sanitation). Another example is *Balantidiuns coli*, a large ciliated protozoan that may cause colitis. Balantidiasis symptoms are similar to amebiasis.

As another example, common features in an intestinal *Cryptosporidium* infection include immune cell infiltration of the lamina propria, villus atrophy, crypt hyperplasia, a reduced barrier function (increased paracellular permeability), etc. *Cryptosporidium* frequently causes diarrhea due to inflammatory damage of the microvilli. The majority of human infections by *Cryptosporidium* are due to either *Cryptosporidium hominis* (*C. hominis*) and/or *Cryptosporidium parvum* (*C. parvum*).

C. Pseudomembranous Colitis.

Pseudomembranous colitis refers to a form of inflammatory colitis characterized by the pathologic presence of pseudomembranes comprising of mucin, fibrin, necrotic cells, and polymorphonuclear leukocytes (PMNs). Thus Pseudomembranous colitis generally refers to a non-specific histomorphologic description, Pseudomembranous colitis may also refer to colitis induced as antibiotic-associated colitis or *Clostridium difficile* colitis when these types of colitis further involve a pseudomembrane.

Factors that may increase risk of pseudomembranous include: taking antibiotics; staying in the hospital or a nursing home; increasing risk along with an increase in age, and a higher risk in people over 65 years of age; having a weakened immune system; having a colon disease, such as inflammatory bowel disease or colorectal cancer; undergoing intestinal surgery; receiving chemotherapy treatment for cancer, etc. Pseudomembranous colitis may sometimes return, days or even weeks after apparently successful treatment for reducing inflammation. In relation to onset of antibiotic-associated pseudomembranous colitis, symptoms may begin as soon as one to two days after initiating an antibiotic treatment, or might take as long as several weeks after completing a course of antibiotic treatment. In one embodiment, biopsies are contemplated as sources of these cells for use with the microfluidic devices described herein.

D. Ischemic Colitis.

Ischemic colitis (ischaemic colitis) refers to when inflammation and injury of the large intestine (ischemia) is triggered by inadequate blood supply or to a loss of blood supply to the colon (ischemia). Ischemia leads to mediator release. Inflammation, and ultimately infarction. If a blood clot interrupts the flow of blood to a segment of the colon, the result is inflammation of that segment and, sometimes, even death [gangrene] of the segment). Although uncommon in the general population, ischemic colitis occurs with greater frequency in the elderly, and is the most common form of bowel ischemia.

Causes of the reduced blood flow can include changes in the systemic circulation (e.g. low blood pressure) or local factors such as constriction of blood vessels or a blood clot. However. In most cases, no specific cause can be identified.

Ischemic colitis is also a form of vasculitis that results from inflammation and ischemia of colonic mucosa, resulting in rectal bleeding and abdominal pain. This form of colitis is common in Henoch-Schönlein purpura (HSP), which is considered one of the collagen-vascular diseases.

E. Allergic Colitis.

Allergic (response) colitis refers to an exaggerated response of the immune system, often to common substances such as foods causing inflammation of the intestine.

Allergic colitis refers to colitis resulting from an immune response to an allergen, for example, a hypersensitivity reaction to an allergen. One example of allergic colitis is a hypersensitive response to allergens in cow's milk or soymilk, as examples. Breast milk allergy refers to a food allergy induced in breastfed babies by heterologous proteins (typically cow's milk proteins) ingested by their mothers and appearing in their breast milk.

Immunologic responses including immune cells in the lamina propria, may range from allergic mast cell activation to more involved immune responses including mononuclear cells, leukocytes, lymphocytes, etc.

Thus, in some embodiments, a potential allergen is tested on healthy, pre-inflammatory and inflammatory gastrointestinal tissue with devices of the present inventions.

F. Diversion Colitis.

Diversion colitis refers to an inflammation of the colon, which can occur as a complication of ileostomy or colostomy, often occurring within the year following the surgery. Ileostomy refers to a surgical operation in which a piece of the ileum is diverted to an artificial opening in the abdominal wall so-as-to bypass a damaged part of the small intestine. Colostomy refers to a surgical operation in which a piece of the colon is diverted to an artificial opening in the abdominal wall so-as-to bypass a damaged part of the colon. Diversion colitis frequently occurs when a neovagina is created by colovaginoplasty, with a varying delay in onset time after the original procedure. Colovaginoplasty, also known as a colon section, refers to an operation for creating a vagina by cutting away a section of the sigmoid (descending) or ascending colon and then using it to form a vaginal lining. Diversion proctitis colitis may also be induced by these types of surgery.

Despite the presence of a variable degree of inflammation in diversion colitis, which may include a diffuse increase in lymphocytes and plasma cells in the lamina propria, prominent lymphoid aggregates are observed histologically in biopsies of inflamed tissue. Inflamed areas may occur in remaining in-stream colon and/or in by-passed sections. In milder cases after ileostomy or colostomy, diversion colitis left untreated disappears naturally. In more severe cases, treatment is initiated, including but not limited to short-chain fatty acid irrigation, steroid enemas and mesalazine. Moreover, diversion colitis may trigger ulcerative colitis. Lim, et al., "Diversion colitis: a trigger for ulcerative colitis in the in-stream colon?" Gut 44:279-282 1999. Therefore, diversion colitis may be a risk factor for ulcerative colitis in predisposed individuals and that ulcerative colitis can be triggered by anatomically discontinuous inflammation elsewhere in the large intestine. Thus, modeling of the in-stream vs. bypassed stream tissue is contemplated for use with the microfluidic devices of the present invention. Further, comparisons to tissue from comparative areas of healthy individuals or compared to modeling using cells harvested from healthy individuals are contemplated for comparison.

G. Chemical Colitis.

Chemical colitis is a type of colitis, an inflammation of the large intestine or colon, caused by the introduction of chemicals to the colon. Chemical exposure may occur by an enema or other procedure, such as exposure to endoscope or colonoscopies cleaning solutions sometimes accidentally introduced into the colon during colonoscopy or other procedures. Endoscopically, chemical colitis can resemble ulcerative colitis, infectious colitis and/or pseudomembranous colitis, among others. Specific chemical exposure, such as during hydrogen peroxide enemas, common prior to 1950, soap enemas, glutaraldehyde, alcohol, radiocontrast dyes, etc. may result in chemical colitis.

Chemical colitis may trigger a flare of ulcerative colitis or Crohn's colitis. In one embodiment, biopsies are contemplated as sources of these cells for use with the microfluidic devices described herein. In some embodiments, a potentially harmful chemical is tested on healthy, pre-inflammatory and inflammatory gastrointestinal tissue with devices of the present inventions.

H. Microscopic Colitis.

Microscopic colitis refers to inflammation of the colon that is only visible when the colon's lining is examined under a microscope. The appearance of the inner colon lining in microscopic colitis is normal by visual inspection during colonoscopy or flexible sigmoidoscopy. The diagnosis of microscopic colitis is made when a doctor, while performing colonoscopy or flexible sigmoidoscopy, takes biopsies (small samples of tissue) of the normal-appearing lining from different regions of the colon during colonoscopy and then examines the biopsies under a microscope. The abnormalities of the colon's lining in microscopic colitis occur in a patchy distribution (areas of normal lining may coexist adjacent to areas of abnormal lining). For this reason, multiple biopsies should be taken from several different regions of the colon in order to accurately make a diaposis.

Therefore these biopsies are contemplated as sources of cells for use with devices described herein. Thus, in some embodiments, long term modeling of microscopic colitis using a device described herein is contemplated as a method for identifying a cause of microscopic colitis and/or treatments.

The primary symptom of microscopic colitis is chronic, watery diarrhea likely caused by inflammation. There are two types of microscopic colitis: 1) lymphocytic colitis and 2) collagenous colitis. In lymphocytic colitis, there is an accumulation of lymphocytes (a type of white blood cell) within the lining of the colon. In collagenous colitis, there is an additional layer of collagen (sear tissue) just below the lining.

Lymphocytic colitis and collagenous colitis are contemplated to represent an autoimmune disorder similar to the autoimmune disorders that cause chronic ulcerative colitis and Crohn's disease. However, a previous study implicated long term (longer than 6 months) use of nonsteroidal anti-inflammatory drugs (NSAIDs) as a cause of microscopic colitis. In fact, some individuals' diarrhea improves after stopping the NSAIDs. Several other drugs have also been incriminated as a cause of microscopic colitis. The most common are proton pump inhibitors (APIs) such as lansoprazole (Prevacid, Prevacid SoluTab), omeprazole (Prilosec, Zegerid), and esomeprazole (Nexium): the Statin simvastatin (Zocor); H2 blocker ranitidine (Zantac); SSRI sertraline Zoloft); and P2Y12 inhibitor ticlopidine (Tilcid).

Individuals with microscopic colitis can have diarrhea for months or years before the diagnosis is made. Typically, the symptoms begin very gradually and are intermittent in nature with periods when the person feels well, followed by bouts of chronic diarrhea. This chronic diarrhea of microscopic colitis is different from the acute diarrhea of infectious colitis, which typically lasts only days to weeks.

The patchy nature of microscopic colitis may be a reason why flexible sigmoidoscopy often is inadequate in diagnosing the condition because the abnormalities of microscopic colitis may be absent from the sigmoid colon (the colonic segment that is closest to the rectum and is within the reach of a sigmoidoscope) in some of the patients with microscopic colitis. Thus, biopsies of other regions of the colon accessible only with colonoscopy may be necessary for diagnosing microscopic colitis. Therefore, these biopsies are contemplated as sources of cells for use with devices described herein.

The long-term prognosis (course) of microscopic colitis is not clear. In approximately two-thirds of the patients with microscopic colitis, the diarrhea resolves spontaneously after several years. The remaining one-third of the patients with microscopic colitis experience persistent or intermittent diarrhea and/or abdominal pain for many years (possibly indefinitely) as there is no cure for the condition. This information came from: Microscopic Colitis (Lymphocytic Colitis and Collagenous Colitis) Medically Reviewed by a Doctor on Aug. 8, 2016 Medical Author: Bhupinder Anand, Md.; Medical Editor: Jay W. Marks, MD. Thus. In some embodiments, long term modeling of microscopic colitis using a device described herein is contemplated as a method for identifying a cause of microscopic colitis and/or treatments.

Injury to the intestines can occur following radiation therapy for cancer. It can affect both the large and small intestines, is often progressive, and may lead to a variety of clinical consequences depending upon the extent of the injury. It usually develops three or more months after radiation therapy. Chronic radiation enteritis is due to an obliterative arteritis that leads to intestinal ischemia, which can result in stricture, ulceration, fibrosis, and occasionally fistula formation.

I. Proctitis Colitis.

Proctitis colitis generally refers to chronic inflammation of the rectum. Proctitis has an acute (early) and chronic (late or slower) manifestation. In one embodiment, biopsies are contemplated as sources of these cells for use with the microfluidic devices described herein.

J. Radiation Induced Colitis.

Adverse effects of radiation therapy is the development of inflammatory radiation colitis, radiation enteritis and radiation proctitis. Radiation colitis refers to colitis that develops after radiation, such as following treatment with radiation for prostate cancer. Radiation enteritis refers to irritation and inflammation of the large and small intestines. Radiation proctitis refers to inflammation and damage to the lower parts of the colon after exposure to x-rays or other ionizing radiation as a part of radiation therapy. Radiation enteritis has an acute (early) and chronic (later or slower) manifestation.

K. Irritable Bowel Syndrome (IBS)

Irritable bowel syndrome (IBS), sometimes referred to as having "spastic colitis" may represent a mild inflammatory condition due to the presence of an inflammatory infiltrate in the lamina propria of the colonic mucosa, represented by increased numbers of T lymphocytes and mast cells compared with healthy subjects. Sinagra, et al., "Inflammation in irritable bowel syndrome: Myth or new treatment target?" World J Gastroenterol. 2(7) 2242-2255 2016. Infiltrates appear to be more predominant in the right than in the left colon (Salzmann, et at, "Morphometric study of colonic biopsies: a new method of estimating inflammatory diseases." Lab Invest. 1989; 60:847-851). Also, individuals may have symptoms that mimic colitis such as diarrhea, abdominal pain, and mucus in stool. Nevertheless, the cause of symptoms in IBS is not clearly known. Thus, in some embodiments, a microfluidic device described herein is contemplated for use with tissue from patients having IBS.

III. Inflammatory Bowel Diseases (IBD).

Inflammatory bowel disease (IBD) refers to chronic inflammation in human intestines causing swelling and irritation that may further involve other locations in the gastrointestinal tract, lungs and other parts of the body, such as joints, skin, etc. IBD symptoms are painful and lifelong as there is no cure for the majority of IBDs where current treatments might help to temporarily reduce symptoms. However, while IBD symptoms may be reduced for a time period, symptoms will arise again with flare-ups of inflammation. In one embodiment, biopsies are contemplated as sources of these cells for use with the microfluidic devices described herein.

Around 1.6 million residents in the USA are estimated to have IBD as reported in 2014 (THE FACTS ABOUT Inflammatory Bowel Disease, Crohn's & Colitis Foundation of America, 2014, www.ccfa.org). 2.5 million people in Europe are estimated to have IBD. With the corresponding lifelong need for medical care there is a substantial cost for current IBD patient health care. These estimates do not factor in the 'real' price of IBD, which can impede career aspirations. Instill social stigma and impair quality of life in patients. Further, the majority of IBD patients are diaposed early in life and the incidence continues to rise; therefore, the effect of IBD on health-care systems will rise exponentially. Moreover, IBD has emerged in newly industrialized countries in Asia, South America and Middle East and has evolved into a global disease with rising prevalence in every continent, Kaplan, "The global burden of IBD: from 2015 to 2025." Nature Reviews Gastroenterology & Hepatology 12:720-727, 2015.

The cause of IBD remains unknown in human patients but generally considered to be caused by environmental factors interacting with a genetically susceptible or physiologically susceptable human subject. Current research indicates that a human subject at risk of developing IBD likely involves a complex interaction of factors, including but not limited to antigens from the environment such as bacterial/pathogen exposure from food/water. In addition to the subject's susceptibility including a genetic predisposition to IBD (i.e. heredity, since IBD is familial), and physiological susceptibility which includes any one or more of the status of the person's immune system (because IBD involves abnormal immune regulation), damage to epithelium from pathogens, and constitution of resident gut bacteria, i.e. types and strains. While IBD can affect anyone, equally affecting males and females, a genetic predisposition to IBD is supported by the increased rates of IBD in northern European-Caucasians along with Jews of European descent (Ashkenazi Jews) which are currently more likely than other ethnic groups to have 180. However, increasing rates of 180 are involving African Americans and Hispanics in the United States.

Studies have shown that 5% to 20% of affected individuals have a first—degree relative (parents, child, or sibling) with one of the diseases. A familial (hereditary) risk is greater with Crohn's disease than ulcerative colitis. The risk is also substantially higher when both parents have an IBD.

A genetic predisposition to IBD includes genetic effects on the immune system, etc. The lack of total concordance of disease among monozygotic twins, along with other differences, supports a role for environmental cofactors in the development of IBD.

What is known is that an inflammatory response, triggered in an area of the gastrointestinal tract is initiated by epithelial damage or by local immune cells, signals additional immune cells to migrate into the area as capillaries in the lamina propria expand, resulting in swelling and inflamed tissue. But instead of subsiding, as typical immune responses shut down over time while the area heals, the inflammatory condition of the inflamed area continues or increases over longer time periods, which causes a chronic long-term inflammation. Chronic inflammation may in turn cause thickening of the intestinal wall, ulceration, etc., and symptoms of an IBD patient. Including pain and diarrhea.

One scenario-describing onset of IBD indicates that an intestinal inflammatory response is triggered by a foreign pathogen, i.e. bacteria, amoebae, or virus, via a toxin, contact with intestinal tissue or infection. This inflammatory response. Instead of removing the pathogen or toxin while allowing healing of intestinal tissue then turning off, remains active which causes or allows additional damage to the local tissue. It is further contemplated that the immune cells stay active after the pathogen is removed because they begin reacting to normal gut bacteria, and/or local gastrointestinal cells, thus continuing and often spreading inflammation to larger areas of the gut. The immune cells are contemplated to remain abnormally active in part due to an underlying autoimmune genetic or physiological condition of the patient.

IBD symptoms may be constant or occur during flare-ups. General symptoms associated with IBD include an urgent need to move bowels; diarrhea; bloody diarrhea; or when areas of the intestine begin to block passage of their contents, constipation (leading to bowel obstruction); abdominal pain and cramping; a sensation of incomplete evacuation; weight loss; loss of appetite; nausea and vomiting; fatigue; etc. IBD symptoms may be reduced to some extent with simple dietary changes, such as switching to a diet that is low in fat; rich in fruits and vegetables; low in fiber and dairy products, and lifestyle changes such as reducing stress and resting, however as stated herein, there is no cure and symptoms will flare throughout the life of a patient.

Medications for IBD focus on reducing the swelling and/or irritation of the intestine. Medications include anti-inflammatory drugs; corticosteroids; immune system suppressors; antibiotics to kill germs in the intestinal tract; anti-diarrhea medication; laxatives; and pain relievers. Anti-inflammatories, such as sulfasalazine (Azulfidine©), Mesalamine (e.g. Asacol© or Rowasa©), Olsalazine (Dipentum©), and Balsalazide (Colazali©), help reduce inflammation, Corticosteroids, such as prednisone (Deitasone©), have been shown to effectively reduce inflammation of the gastrointestinal tract in IBD patients. Medications, called immunosuppressant, have been used to treat IBD. Examples include Azathioprine (Imuran©), Mercaptopurine (Purinethol©), cyclosporine (e.g. Neoral© or Sandimmune©) and Infliximab (Remicade©). A fiber supplement, such as psyllium powder (Metamucil©) or methylcellulose (Citrucel©), may help relieve symptoms of mild to moderate diarrhea. Because inflammation may cause the intestines to narrow, resulting in constipation, as described herein, laxatives may be taken to relieve symptoms of constipation. Oral laxatives such as Correctol© have been used. Acetaminophen (Tylenol©) may relieve mild pain. However, researchers have found a strong relationship between ingesting NSAIDs (nonsteroidal anti-inflammatory drugs), such as ibuprofen (Advil© or Motrin©) or naproxen (Aleve©), with IBD flare-ups.

While two common major types of IBD are well known, Crohn's disease and Ulcerative colitis, described below, IBD actually covers a range of gastrointestinal inflammatory diseases including Celiac disease, proctitis, ulcerative proctosigmoiditis; pancolitis and stomach ulcers. In fact, IBD may be associated with several different types of IBD and other autoimmune disorders such as celiac disease associated ulcerative colitis; dermatitis hepetiformis associated ulcerative colitis; systemic and discoid lupus associated ulcerative colitis; rheumatoid arforitis associated ulcerative colitis; ankylosing spondylitis associated ulcerative colitis; scleroderma associated ulcerative colitis; Sjogren's disease associated ulcerative colitis; porphyrinogenic drug induced ulcerative colitis, such as sulfasalazine; SLE associated with Crohn's disease; Crohn's disease of oral cavity; Crohn's disease of the hypopharynx; etc. In one embodiment, biopsies are contemplated as sources of these cells for use with the microfluidic devices described herein.

In some cases, IBD may be cured if detected early, such as for ulcerative colitis, early onset Crohn's disease, proctitis, and left sided colitis. However, typically there is no cure for IBDs.

The two major types of inflammatory bowel disease: ulcerative colitis (UC) and Crohn disease (CD), which are described in more detail below. The symptoms of these two illnesses may overlap. However whereas Crohn's related inflammation typically starts in the small intestine and may spread to any area of the gastrointestinal tract (GI tract) as "skip lesions" where patches of diseased areas are separated by normal areas, UC is limited to inflammation in the colon, Crohn's disease can also affect the entire thickness of the bowel wall, from the mucosa to the adveritia, unlike ulcerative colitis that mainly involves the innermost lining of the colon, the mucosa. When medical practitioners are not able to diagnose the specific type of IBD due to overlapping symptoms, the condition is called indeterminate colitis.

A. Crohn's Disease.

Crohn's disease (CD) refers to a life long chronic inflammatory bowel disease of the gastrointestinal tract that arises in the small intestine that may progress to affect any part of the gastrointestinal system from the mouth to the anus. Crohn's is a chronic disease with patients experiencing time periods when the disease flares up and causes symptoms, followed by periods of remission when patients may not experience symptoms.

CD results in inflammation, ulcers, and bleeding in the digestive tract. It usually affects the end portion of the small intestine called the ileum. However, any part of the digestive tract can be affected, from the mouth to the anus. Crohn's associated inflammation most commonly affects the lower part of the small intestine (ileum) then may spread to or further involve the beginning of the colon. Crohn's related inflammation may further occur in any part of the large intestine, small intestine, or stomach. In fact patches or lesions of CD related inflammation might occur anywhere in the GI system, including as ulcers or lesions in the oral cavity (mouth). In one embodiment, biopsies are contemplated as sources of these cells for use with the microfluidic devices described herein.

Further, CD inflammation may cause joint pain and swelling. Inflammation and irritation of the eyes in addition to areas of painful, red and swollen skin, most often the legs. People with Crohn's disease often go through periods of flare-ups where they have severe symptoms and periods where their symptoms are more mild or non-existent. Someone with the disease who isn't displaying any symptoms is known to be in remission.

Crohn's disease may affect as many as 700,000 Americans. Men and Women are equally likely to be affected, and while the disease can occur at any age, Crohn's is more prevalent among adolescents and young adults between the ages of 15 and 35. People of Jewish heritage are more likely to get Crohn's disease. Risk may also be increased if you have family members with inflammatory bowel disease or other autoimmune diseases.

The cause of Crohn's disease is not known and there is no known cure for Crohn's disease. The environment also appears to play a role as Crohn's is more common in developed countries than in undeveloped countries, and occurs in more people in urban rather than in rural areas, and occurs in more people of northern rather than southern climates. Diet and stress may aggravate Crohn's Disease, but they do not cause the disease on their own. People suffering from Crohn's often experience loss of appetite, may lose weight, and have a feeling of low energy and fatigue. Among younger children, CD may delay growth and development.

Chronic Crohn's disease inflammation in the intestines can cause the walls of digestive organs to thicken or form scar tissue. This wall thickening from inflammation can narrow a section of intestine, i.e, stricture, which may lead to an intestinal blockage. A stricture refers to a narrowing of a section of intestine that, in turn, causes problems by slowing or blocking the movement of food through the area. Nausea and vomiting or constipation may be signs of a stricture, which may lead to hospitalization and also to surgery to correct it. Crohn's disease can disrupt the normal function of the bowel in a number of ways such as when the bowel tissue may: swell, thicken, or form scar tissue, leading to blockage of the passageway inside the bowel; develop ulcers that can involve the deep layers of the bowel wall; lose its ability to absorb nutrients from digested foods, a condition called malabsorption; develop abnormal passageways known as fistulas from one part of the bowel to another part of the bowel, or from the bowel to nearby tissues such as the bladder or vagina. In severe cases, Crohn's can lead to tears (fissures) in the lining of the anus, which may cause pain and bleeding, especially during bowel movements. Inflammation may also cause a fistula to develop. A fistula is a tunnel that leads from one loop of intestine to another, or that connects the intestine to the bladder, vagina, or skin. This is a serious condition that requires immediate medical attention.

Symptoms include but are not limited to: diarrhea; abdominal cramps and pain; rectal bleeding; weight loss; fatigue, weakness; nausea; fever; mouth sores; sores, abscesses in the anal area, Complications of untreated Crohn's disease may lead to: Fistulas, i.e. abnormal connections between the intestine and other organs or tissues, such as the bladder, vagina, or skin; intestinal obstruction; liver disease; bowel perforation; bleeding; kidney stones; gallstones; osteoporosis, etc. Extraintestinal manifestations, which are slightly more common in CD than in UC, result from bacterial products and inflammatory mediators (e.g., cytokines, prostaglandins, and reactive oxygen metabolites) entering and subsequently being deposited in various tissues and organs, such as the eyes (uveitis), skin (erythema nodosum), liver (cholangitis, hepatitis), and joints (arforitis).

Treatment may include dietary changes and; medications to reduce symptoms. Dietary changes include avoid foods that trigger symptoms, which may be dairy foods if the patient also has lactose intolerance; highly seasoned foods; and high-fiber foods. However these foods are different for each person. There are many types of medications that are used to treat Crohn's disease however many of the treated patients continue to experience symptoms. Examples of these medications include: Aminosalicylate medications, such as sulfasalazine, mesalamine, and olsalazine; Anti-inflammatory medications, such as prednisone, methylprednisolone, and budesonide; Immune modifiers, such as azathioprine, 6-mercaptopurine, and methotrexate; TNF inhibitors, such as infliximab, adalimumab, and certolizumab; and antibiotics, such as metronidazole, ampicillin, and ciprofloxacin.

Severe Crohn's may not improve with medications such that for certain patients the diseased section of the intestine removed. The two remaining healthier ends of the intestine are then joined together, i.e. re-sectioned. However, there remains a high risk for the disease occurring in the remaining "healthy" tissue. Surgery may also be done to remove obstructions or repair/close fistulas. Approximately 70% of children with CD require surgery within 10-20 years after the diagnosis.

There are at least six types of Crohn's disease. The following are brief descriptions of types located in the small intestine, large intestine and a part of the stomach.

1. Crotan's Ileitis

Human patients with fields in general have inflammation of the ileum, Crohn's Ileitis is a chronic ileitis inflammation affecting the ileum, the third portion of the small intestine, between the jejunum and the cecum. In one embodiment, biopsies are contemplated as sources of these cells for use with the microfluidic devices described herein.

Patients experience considerable weight loss, diarrhea, and cramping or pain in the middle or lower right part of the abdomen, similar to symptoms of ileocolitis, see below, which further involves the beginning of the colon. In addition to the inflammatory intestines, fistulas (an abnormal connection between two hollow spaces (i.e., two epithelialized surfaces), such as intestines, blood vessels, or other hollow organs), or inflammatory abscesses (a collection of pus that accumulates within the tissue due to an inflammatory reaction) may also form in the lower right section of the abdomen where the ileum is located.

2. Crohn Enteraeolitis (or Ileocolitis)

Ileocolitis is a common type of Crohn's disease. It affects the small intestine in the area of the ileum, at the end of the small intestine, and the beginning of colon (in the area of the cecum-appendix/ascending colon). Human patients who have ileocolitis experience considerable weight loss, diarrhea, and cramping or pain in the middle or lower right part of the abdomen. In one embodiment, biopsies are contemplated as sources of these cells for use with the microfluidic devices described herein.

3. Gastroduodenal Crohn's Disease

This form of Crohn's disease involves both the stomach (typically the pyloric area) and duodenum of the small intestine, which is the first part of the small intestine located after the pyloric area of the stomach. People with this type of Crohn's disease suffer nausea, weight loss, and loss of appetite. In addition, if the narrow segments of bowel are obstructed, they experience vomiting. In one embodiment, biopsies are contemplated as sources of these cells for use with the microfluidic devices described herein.

4. Crohn's Jejunoilitis

This form of the disease affects the upper half of the small intestine, i.e. jejunum. It causes areas of inflammation. Symptoms include cramps after meals, the formation of fistulas, diarrhea, and abdominal pain that can become intense. In one embodiment, biopsies are contemplated as sources of these cells for use with the microfluidic devices described herein.

5. Crohn's (Granulomatous) Colitis

This form of Crohn's disease involves merely any area of the colon, rectum or anus. Symptoms include skin lesions, joint pains, diarrhea, rectal bleeding, and around the anus, the formation of ulcers, fistulas, and abscesses. Skin lesions and joint pains are more common in this form of Crohn's than in others. In one embodiment, biopsies are contemplated as sources of these cells for use with the microfluidic devices described herein.

6. Perianal Crohn's

Perianal Crohn's refers to inflammation around the anus. In one embodiment, biopsies are contemplated as sources of these cells for use with the microfluidic devices described herein.

B. Ulcerative Colitis.

Ulcerative colitis (UC) refers to a long-term form of a chronic inflammatory bowel disease arising in the colon and confined (limited) to the mucosa. Thus ulceration is generally shallow and does not extend into muscularis propria unlike Crohn's disease. UC disease limited to the rectum refers to ulcerative proctitis (colitis). UC beginning in the rectum may spread proximally through the large intestine, typically without skipping Haustra sections (segments).

Ulcerative colitis symptoms may come and go. Remission can last for months or years, but the symptoms eventually return. Not knowing when symptoms will flare can add to the stress of the disease and make it difficult to come up with an effective treatment plan.

Ulcerative colitis sometimes causes complications that require hospitalization. These may include an ulcer that is bleeding profusely or severe diarrhea that causes dehydration. If there is a tear in the colon, it may need to be surgically repaired. For people with severe ulcerative colitis, a surgery to remove the colon may be done. The symptoms of ulcerative colitis may include: Diarrhea or rectal urgency. Some people may have diarrhea 10 to 20 times a day. The disease usually causes bloody diarrhea and mucus.

With UC, small ulcers can develop on the colon's lining (mucosa) producing pus and mucus. This can cause abdominal discomfort and frequent emptying of the colon (diarrhea). Around 50% of people with UC are diagnosed with ulcerative proctitis or proctosigmoiditis.

UC is referred to as an autoimmune disorder. There is no known cure for UC. Some people have surgery to remove parts of their colon and rectum that are affected but inflammation may arise if any of the colon, rectum or anus are left in the patient. Often surgery doesn't remove symptoms and complications of IBD. In one embodiment, biopsies are contemplated as sources of these cells for use with the microfluidic devices described herein.

1. Pancolitis/Pan-Ulcerative Colitis/Universal Colitis

Pancolitis/Pan-ulcerative colitis/Universal Colitis refers to a severe form of a life-long duration ulcerative colitis that spreads through the entire large intestine, normally stops abruptly at the ileocecal valve, however in some cases distal ileitis may occur. The appendix and appendiceal orifice may also be involved.

This form of ulcerative colitis is spread throughout the entire large intestine including extending proximally to the splenic flexure, the cecum, right colon, the left colon, the transverse colon and the rectum. Twenty percent of people start with another form of UC, such as proctitis, proctosigmoiditis or left-sided colitis, however over time the inflammation spreads throughout their colon resulting in pan-ulcerative colitis. Symptoms of pancolitis include bloody diarrhea, abdominal pain and cramps, weight loss, fatigue, fever, and night sweats. There is no known cause of UC.

UC may also lead to cancer, where risk factors for developing adenocarcinoma UC are the duration and extent of disease. After the first decade of disease, the risk of development of colon cancer increases rapidly. Colectomy may be performed if there is finding of high-grade dysplasia viewed by colonoscopy or in a biopsy.

The course of UC is marked by remissions and exacerbations. Most patients respond initially to medical treatment, and many children with mild manifestations stay in remission on prophylactic therapy, for example with 5-amiosalicylic acid (5-ASA). About 70% children with UC enter remission within 3 months of initial therapy with 50% remaining in remission over the next year. Colectomy within 5 years may be required in as many as 26% of children who present with severe disease compared with less than 10% of those who present with mild disease.

In biopsies of inflamed areas, an inflammatory infiltrate may be observed, indicative of chronic inflammation. In the lamina propria and submucosa, comprising lymphocytes, plasma cells, eosinophils; basal lymphoid aggregates may be present with few granulomas. A neutrophilic infiltrate is typically present when disease inflammation is active, involving epithelium of surface and crypts with frequently observed crypt abscesses. Lamina propria fibrosis may be present.

2. Proctosigmoiditis

Proctosigmoiditis refers to a form of ulcerative colitis that affects the rectum and sigmoid colon (the S-shaped last part of the large intestine, leading into the rectum). Treatments currently include medication and surgery. Some people have severely inflamed or damaged parts of their colon surgically removed. This can reduce or eliminate the symptoms of proctosigmoiditis, however it does not get rid of the disease and there is a risk that it will return to another area of the colon in the future.

3. Left-Sided Colitis

Left-sided colitis (also known as distal colitis) refers to inflammation that begins at the rectum and extends as far as a bend in the colon near the spleen called the splenic flexure.

C. Indeterminate Colitis.

Indeterminate colitis is a general term referring to a chronic idiopathic (i.e. unknown cause) type of colitis that cannot be separated as either Crohn colitis or ulcerative colitis by a medical practitionioner using conventional diagnostic modalities. Thus, in one embodiment, cells derived from a biopsy(ies) of a patient identified as having indeterminate colitis are contemplated for use in modeling inflammation for use in identifying a drug for use in treating that individual patient's inflammation. In some embodiments a drug for use in treating any patient with indeterminate colitis is contemplated.

IV. Immunology of the Mucosa and Gut.

Mucosa associated lymphoid tissue (MALT) refers to lymphoid tissue and lymphocytes located in the mucosal epithelial cell layer and lamina propria throughout the body. According to their location, lymphocytes are subdivided into intraepithelial lymphocytes (IEL), lamina propria lymphocytes and lymphocytes organized in follicles in association with epithelial cells (e.g. subepithelial lymphoid follicles). The latter may extend into the muscularis mucosae layer. MALT is present in the gastrointestinal system. In one embodiment, biopsies are contemplated as sources of these cells for use with the microfluidic devices described herein.

Intraepithelial lymphocytes (IEL) refer to lymphocytes found in the epithelial layer and are present in-between the epithelial cells lining the surface, e.g. CD8+ T lymphocytes.

Mucosal lymphoid follicles, which in aggregates of on average 30-50 follicles are called Peyer's patches, contain mononuclear cells, T cells. Including CD43+, CD8, γδ+ T cell receptor, B cells, plasma cells, etc. In other words, isolated or aggregated lymphoid follicles forming Peyer's patches (PPs) may be found in areas of the intestine. PPs are considered immune sensors of the intestine by their ability to transport luminal antigens and bacteria and induction of immune tolerance or defense against pathogens resulting from a complex interplay between immune cells located in the lymphoid follicles and the follicle-associated epithelium. The M cell refers to a specialized epithelial cell that transports luminal antigens, thus allowing access to immunocompetent cells. It plays a role in mucosal-based immunity and antigen tolerance.

In healthy gastrointestinal tissues, T lymphocytes are found at mucosal surfaces, primarily in the epithelium, the lamina propria cores of the villa, Peyer's patches and lymphoid follicles. Less common in normal colon epithelium and lamina propria but abundant in isolated colonic lymphoid follicles. When present, lymphoid follicles might be visible at microscopic examination of biopsies, such as a biopsy of the ileum.

Follicle-associated epithelium (FAE) refers to areas covering the Peyer's patches, The specialized epithelium overlying lymphoid aggregates, i.e. FAE, is distinct from the surrounding villous epithelial surfaces. It characteristically has fewer goblet cells and contains membranous cells or M cells.

Gut associated lymphoid tissue (GALT) specifically refers to mucosal lymphoid tissue and lymphocytes located in the gastrointestinal system. GALT tissue includes lamina propria lymphocytes (LPL). Intraepithelial lymphocytes (IEL), Peyer's patches and scattered follicles.

GALT is especially prominent in the appendix and terminal ileum where it forms Peyer's patches along the anti-mesenteric border. Four compartments are distinguished in Peyer's patches, which refer to small masses of lymphatic tissue found throughout the ileum region of the small intestine. Peyer's patches appear histologically as oval or round lymphoid follicles or nodules (similar to lymph nodes) located in the lamina propria layer of the mucosa and may extend into the submucosa of the ileum. Smaller lymphoid nodules can be found throughout the intestinal tract.

V. Lamina Proprin of the Gastrointestinal System.

Lamina propria refers to a layer of loose connective tissue that extends from the subepithelial basement membrane complex (underneath epithelial cells) to the muscularis mucosae in tubes found in humans, e.g. gastrointestinal. For example, in the gastrointestinal tract, LP is found between villi of the stomach, small intestine and large intestine, typically separated from the epithelial cells by a basement membrane.

Healthy lamina propria in vivo (e.g. non-inflamed in humans without an inflammatory disorder) provides immunological cells, nutritional support for the epithelium, e.g. from capillaries, and structural support for the epithelium e.g. by connective tissue secreting cells. Thus, lamina propria contains a variety of cell types including lymphocytes and other immune cells of MALT/GALT. In particular, healthy lamina propria generally comprises stromal calls, extracellular matrix, fibroblast cells, immune cells including various types of leukocytes, such as mononuclear cells, lymphocytes, B cells, T cells, natural killer cells, plasma cells, macrophages, eosinophils, and mast cells, along with capillary endothelium, etc. In one embodiment, biopsies are contemplated as sources of these cells for use with the microfluidic devices described herein.

Lamina propria includes capillary beds, wherein the healthy (non-inflamed) capillaries are lined with a single layer of endothelial cells. In the small intestine, lamina propria of villi includes lacteals (i.e. lymphatic capillaries) in addition to smooth muscle fiber cells. Where epithelial invaginations are densely packed (e.g., gastric glands of stomach), lamina propria can be relatively inconspicuous, i.e. by histology observation and thus contains few cells. Where the mucosal epithelium is extensively evaginated (e.g., intestinal invaginated (intestinal crypts), the location of lamina propria "beneath" the epithelium amounts to filling-in the spaces between nearby epithelial surfaces (i.e., surrounding each crypt, within each villus).

The lamina propria that surrounds crypts in healthy colon tissue contains eosinophils, lymphocytes, plasma cells, and some histiocytes. Relative to the left colon and rectum, the right colon contains greater numbers of immune cells in the lamina propria. Including more plasma cells and eosinophils. In fact, areas around the ileocecal valve appears to have inflamed the lamina propria in healthy tissue merely because of the number of cells present. The left side of the colon contains significantly fewer cells within the lamina propria, and the surface epithelium contains more goblet cells and fewer absorptive cells relative to the right colon, Cerilli and Greenson, (2012) The Differential Diagnosis of Colitis in Endoscopic Biopsy Specimens: A Review Article. Archives of Pathology & Laboratory Medicine: Vol. 136, No. 8, pp. 854-864.

A subtype of leukocytes in the lamina propria are the cells of the monocyte/macrophage lineage. In the colon they are diffusely present in the subepithelial part of the lamina propria. They are a heterogeneous group composed of cells having more phagocytic properties and cells equipped for antigen presentation. They appear often as foamy histiocytes. Other myeloid cells that normally reside in the lamina propria are eosinophils and mast cells. Neutrophils are not typically present in healthy lamina propria. Fibroblasts are located randomly, distributed throughout the lamina propria and in the most superficial portion and the pericryptal fibroblast sheet, tightly apposed to the subepithelial basement membrane complex.

Mesenchymal derived cells are also found in intestinal lamina propria including intestinal stromal cells (e.g. myofibroblasts and fibroblasts), mural cells (pericytes) of the vasculature (also part of the intestinal stromal cells), bone marrow-derived stromal stem cells, smooth muscle of the muscularis mucosae, and the smooth muscle of the small intestinal villus core surrounding the lymphatic lacteals. In fact, myofibroblasts are considered nonprofessional immune cells that may be important as an alarm system for the gut and as a participant in peripheral immune tolerance (Powell, et al., "Mesenchymal Cells of the Intestinal Lamina Propria." Annual Review of Physiology, Vol. 73: 213-237 (Volume publication date March 2011). First published online as a Review in Advance on Nov. 3, 2010).

DETAILED DESCRIPTION OF THE INVENTION

Gut-On-A-Chip (Intestine-On-Chip) with Lamina Propria-Derived Cells.

As described and shown herein, chips containing co-cultures of epithelial cells (e.g. Caco-2, human primary colonic epithelial cells, etc.) and vascular endothelial cells (e.g. HUVECs) in the presence of lamina propria (LP) derived cells (LPDCs) are provided. Out-On-A-Chip cultures of primary (healthy) leukocytes (LPDCs) were maintained up to 9 days. Further, cultures of leukocytes (diseased) from inflamed ulcerative colitis (UC) tissue retained their inflammatory phenotype.

These Gut-On-A-Chip (or Gut-On-Chip) cultures demonstrated physiological and morphological changes in epithelial cell layers directly related to the source of LP derived cells. In particular, resident immune cells, i.e. lamina propria-derived cells (including but not limited to B cells, T cells, dendritic cells, monocytes, macrophages, and innate lymphoid cells) were isolated from healthy and Ulcerative Colitis (UC) patients (including inflamed and non-inflamed regions of patient tissue) were used in this chip based co-culture system. Specifically, comparisons of these co-cultures showed changes in secreted cytokines and barrier function measurements, described herein.

Thus additional features related to embodiments of the present inventions to providing co-cultures of epithelial cells, vascular endothelial cells and resident immune cells (i.e. lamina propria-derived cells) include but are not limited to providing a capability for measuring amounts of secreted cytokines; epithelial cell bather function measurements; determining effects of bacterial antigens, such as in a toss-of-barrier-function bioassay. Including with bacterial antigen treatments; and establishing a model for the study of IL-9 mediated colitis.

Results described herein show that by using the chip based co-culture system the inventors discovered that IL9 production is LP dependent, i.e. induced by resident immune cells isolated from inflammatory intestinal tissues (i.e. biopsies); and that a loss of barrier function is LP cell density dependent, such that more than 2 mil/ml of cells, for example 4 mil/ml of UC LP cells, induce this loss of barrier function.

Accordingly, some embodiments described herein relate to devices for simulating a function of gastrointestinal tissue (also referred to as "gut-on-a-chip device"). The gut-on-a-chip microfluidic devices described herein can be used to simulate at least one or more (e.g., 1, 2, 3, 4, 5 or more) phenotypes and/or functions of a variety of gastrointestinal tissues.

In one embodiment, the present invention contemplates incorporating lamina propria derived cells (such as resident immune cells, e.g. leukocytes, (i.e. white blood cells), mononuclear cells, resident fibroblasts, etc.) in the chip embodiments described herein. Thus, in one embodiment, LPDCs are incorporated into an embodiment of the gut-on-chip. This can be done in a variety of combinations. In one embodiment, the LPDCs are deposited underneath intestinal epithelial cells and on top of an extracellular matrix (ECM) composition coated membrane (e.g. with a gel overlay or simply underneath the epithelial cells, i.e. without a gel overlay). In one embodiment, the LPDCs are further overlaid with a layer of ECM, i.e. ECM overlay, before depositing the epithelial layer. In one embodiment, however, the LPDCs are overlaid with an actual gel. In one embodiment, the LPDCs are deposited within a gel layer. The same or similar approaches can be used to incorporate other tissue-specific or resident cells (whether immune cells, fibroblasts, mixtures, etc.). FIGS. 61A-G shows exemplary embodiments of epithelial channels and vascular channels, with or without a gel, in a gut-on-chip with symbol information provided in FIG. 61H, FIG. 61A shows LPDCs located under epithelial cells. FIG. 61B shows LPDCs located under gel. FIG. 61C shows LPDCs located over get. FIG. 61D shows LPDCs located in gel. FIG. 61E shows LPDCs located in bottom channel. FIG. 61F shows LPDCs located in gel in bottom channel. FIG. 61G shows LPDCs located over epithelial cells. FIG. 61H shows symbols representing: Membrane, Gel, Endothelial Cells, e.g. HUVEC, Intestinal Epithelial Cells (epis) and lamina Propria (LP) Derived Cells (LPDC).

The lamina propria-derived cells can be used for different degrees of purification or cell isolation: used wholesale, used with the cells isolated from ECM components, and isolated for specific cell types. Thus, in one embodiment, a full milieu of cell types was isolated and used in microfluidic devices described herein. An example of a full milieu of cell types used as a lamina propria derived cell population. Include but are not limited to stromal cells, fibroblasts, and resident immune cells. Examples of stromal cells include but are not limited to connective tissue cells, e.g. fibroblasts, myofibroblasts, etc., located in the mucosa, submucosa, etc. In fact, cells comprising LP-derived cells may not be limited to the mucosa. In some embodiments, Examples of resident immune cells including but are not limited to innate immune cells such as natural killer cells, γδ+ T cell receptor cells, adaptive immune cells, such as mononuclear cells. Including monocytes, macrophages, basal cells, eosinophils, plasma cells, T cells, such as CD8+ CD4+, double positive, and dendritic cells, immature through mature, are found here. As another example, purified isolated LP-derived cell populations were used in microfluidic devices described herein. In some embodiments LP-derived cells may be used directly after isolation. In some embodiments, LP-derived cells are expanded in cultures before adding to a microfluidic chip of the present inventions.

Thus, in other embodiments, other types of purifications or isolations are possible, including cells extracted from or isolated from lamina propria (as lamina propria derived cells, or LPDCs). In a preferred embodiment, resident immune cells are extracted and purified. In one embodiment, lymphoid follicles are not included. In one embodiment, lymphoid follicles are included. In one embodiment. Payers patches are not included. In one embodiment, Payers patches are included. Such that the presence of a lymphoid follicle or Payers patch in tissue used for isolation or extraction of cells may be determined by observation of the lamina propria tissue by optical microscopy prior to removal of cells. In one embodiment, capillary endothelial cells are extracted and purified.

In one embodiment stromal tissue is used for isolation of stromal cells, LP derived cells, etc.

Model of Inflammatory Bowel Disease: In Vitro Activation and Differentiation of T-Cell Effector Subsets Derived From Blood.

Other embodiments contemplated for mimicking disease is by manipulating differentiation and/or activation stages of T cells. Thus. In addition to obtaining resident intestinal immune cells from lamina propria, immune cells may be obtained from peripheral blood, either directly from a patient or donor for matching tissue haplotypes, or obtained from a blood hank in experiments where matching is not desired. One advantage of using peripheral blood as a source of a relatively large number of T cells overcomes the limitation of low numbers of immune cells obtained from biopsies for matched tissues and overcomes donor-to-donor variation in low numbers of immune cells in any of these types of experiments. Further, PBMCs are easier to obtain over biopsy derived immune cells in part because a physician/ surgical procedure is not needed, and PBMCs and immune cells may also be purchased from commercial suppliers. Thus, using peripheral blood as a source of immune cells allows the development of a larger scale and more reproducible model of Crohn's Disease and Ulcerative Colitis as a microfluidic Intestine On-Chip for use in investigations of host-immune interactions in a patient-specific fashion.

Thus, in yet another embodiment, pre-differentiated T-cells are added to a chip of the present inventions. In one embodiment, the present invention contemplates the use of published protocols to differentiate naïve T-cells from peripheral blood mononuclear cells (PBMCs) isolated from blood samples towards a $T_H9$ T-helper cell fate comprising the use of TGFb (TGFbeta) and IL4. With this approach, T-helper profiles can be generated that mimic different types of autoimmune diseases. Including asthma and gastrointestinal diseases described herein.

Therefore, the development of methods for obtaining, purifying, isolating then activating, and differentiating disease-type associated effector T-cells from peripheral blood as described herein.

As one example, one embodiment for isolating and differentiating disease type associated effector T-cells was to use PBMCs (whole blood) in differential centrifugation methods, for providing a lymphocyte layer (buffy coat) that is pipetted out, by inserting a pipette tip in or at the side of the lymphocyte layer, then sucking out the lymphocytes leaving the other layers relatively intact. These isolated lymphocytes then underwent purification to provide a population of CD4+ T cells including mature, i.e, naïve CD4+ T cells. This purified CD4+ population of T cells may be used to produce larger quantities of a specific $T_H$ subset, or divided into smaller samples for use in providing two or more T cell subsets as described herein.

FIGS. 25A-C shows an exemplary schematic model for translating in vivo T cell activation and differentiation of T-Cell effector subsets derived from blood to an in vitro method for providing human activated immune cells simulating CD as $T_H1$ subsets and simulating UC as $T_H9$ subsets. FIG. 25A shows one embodiment as an exemplary schematic of T cell activation in vivo (nature) where antigen presentation in the context of cell bound MHCII-antigen triggers a CD3 signaling complex on a T cell, while cell bound CD80 and CD86 molecules co-activate CD28 signaling on the same cell, as compared to T cell activation in vivo (laboratory) where activation factors such as anti-CD3 and anti-CD28 antibodies are soluble (in solution) that activate the T cell bound CD3 complex bypassing recognition of TCR (T cell receptor) antigen specific MBCII molecules and the CD28 receptor. FIG. 25B shows one embodiment as an exemplary schematic for lymphocyte isolation from peripheral blood (i.e. PBMCs), including T cells, as a buffy coat layer (right) obtained after centrifugation of a mixture of whole blood, i.e. peripheral whole blood mononuclear (PBMCs) cells, in a solution comprising a gradient forming particle (left). FIG. 25C shows one embodiment as an exemplary schematic for post-activation of a population of CD4+ enriched T cells differentiated into T cell subsets depending upon differential levels of cytokine additions for inducing differentiation into the exemplary T cell subsets depicted.

For non-limiting examples, examples of $T_H1$, $T_H2$ and $T_H9$ differentiated subsets of activated CD4+ T cell populations are shown resulting from either a default subset without exposure to additional cytokines, e.g. a $T_H1$ subset, vs. exposure to IL-2 and IL4 for producing $T_H2$ CD4+ T cell populations and exposure to IL-4 and TGF-beta for producing $T_H9$ CD4+ T cell populations.

In some embodiments, each of these subsets is found in comparatively larger numbers or percentages in the lamina propria of associated diseases, e.g. $T_H1$ secreting an exemplary IFN gamma cytokine with Crohn's; $T_H2$ secreting an exemplary IL-13 cytokine with UC and asthma patients; and $T_H9$ secreting an exemplary IL-9 cytokine with UC. Thus, activated CD4+ T cells as populations of subsets may be used for modeling an exemplary inflammatory bowel disease (IBD) of UC in a microfluidic intestine on-chip.

In Vitro Activation and Differentiation of T-Cell Effector Subsets Derived from Blood Further Stimulated On-Plate.

Addition of PAM2CSK4, a bacterial agonist here used to mimic an inflammatory stimulus, causes increases in the concentration of cytokine protein signaling in both $T_H1$ (CD) and $T_H9$ (UC) Cells.

Figure 26A:
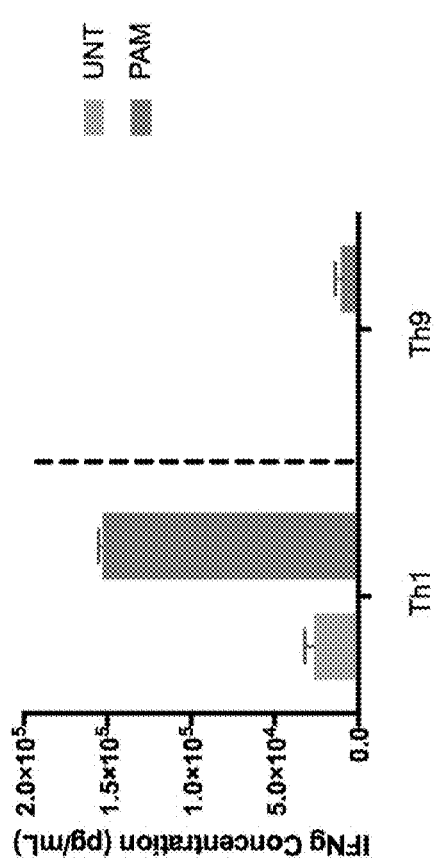
FIGS. 26A-B shows exemplary results comparing post differentiation CD4+ T cell cytokine expression from each of the differentiated CD4+ T cell subsets on plates. Further cytokine secretion is compared between subtypes after stimulation with an exemplary bacterial agonist, i.e. PAM2CSK4, for mimicking an inflammatory stimulus.
Figure 26B:
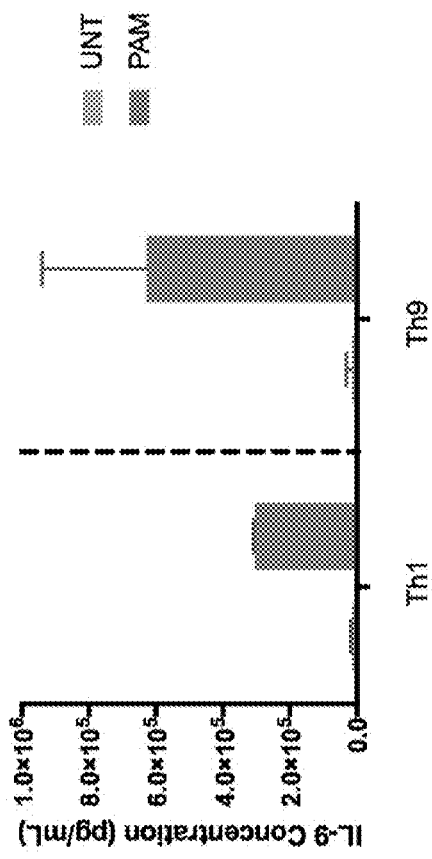

FIGS. 26A-B shows exemplary results comparing post differentiation CD4+ T cell cytokine expression from each of the differentiated CD4+ T cell subsets on-plates. Further cytokine secretion is compared between subtypes after stimulation with an exemplary bacterial agonist, i.e. PAM2CSK4, for mimicking an inflammatory stimulus. FIG. 26A shows exemplary comparative IFNgamma cytokine protein expression. FIG. 26B shows exemplary IL-9 cytokine protein expression. For each CD4+ T cell subset, the left bar represents expression without an additional stimulus whiles the right bar represents expression after exposure to soluble PAM2CSK4, PAM2CSK4 increases in the concentration of protein signaling in both $T_H1$ (CD) and $T_H9$ (UC) cells.

Figure 27A:
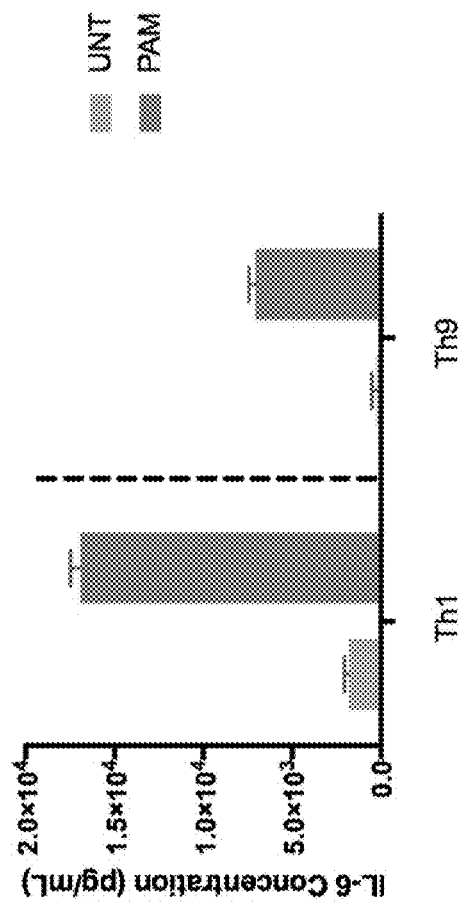
FIGS. 27A-B shows exemplary results for additional comparative cytokine production as described in FIGS. 26A-B.
Figure 27B:
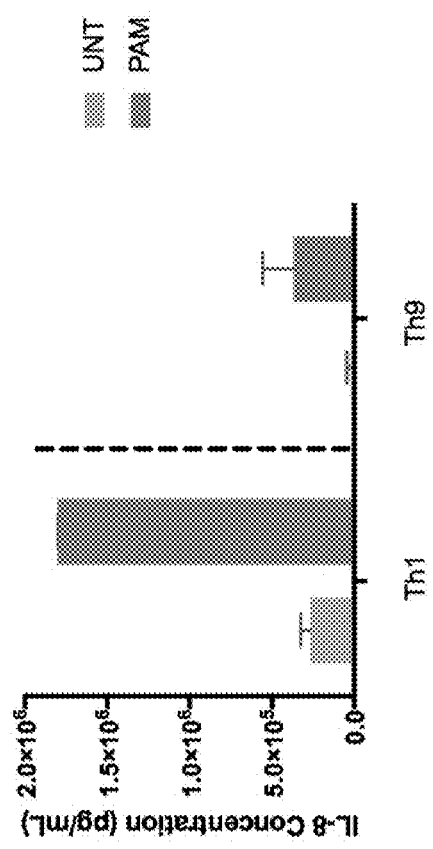

FIG. 27A-B shows exemplary results for additional comparative cytokine production as described in FIGS. 26A-B. FIG. 27A shows exemplary comparative IL-6 cytokine protein. FIG. 27B shows exemplary comparative IL-8 cytokine protein expression. For each CD4+ T cell subset, the left bar represents expression without an additional stimulus while the right bar represents expression after exposure to soluble PAM2CSK4.

FIG. 28A-C shows exemplary results of measuring cytokine expression post differentiation as described in FIGS. 26A-B. FIG. 28A shows exemplary comparative IL-13 cytokine protein expression. FIG. 28B shows exemplary comparative IL-1beta cytokine protein expression. FIG. 28C shows exemplary comparative TNF-alpha (Tumor Necrosis Factor (TNF)) cytokine protein expression.

Therefore, CD4+ T cells, obtained from peripheral blood lymphocytes, were activated and differentiated on plates using soluble antibodies then used in microfluidic chips under certain stimulation conditions.

Exemplary $T_H9$ Cell Introcellular Signaling Pathways Associated with Certain Types of Cytokine or Growth Factor Stimulation.

Figure 29:
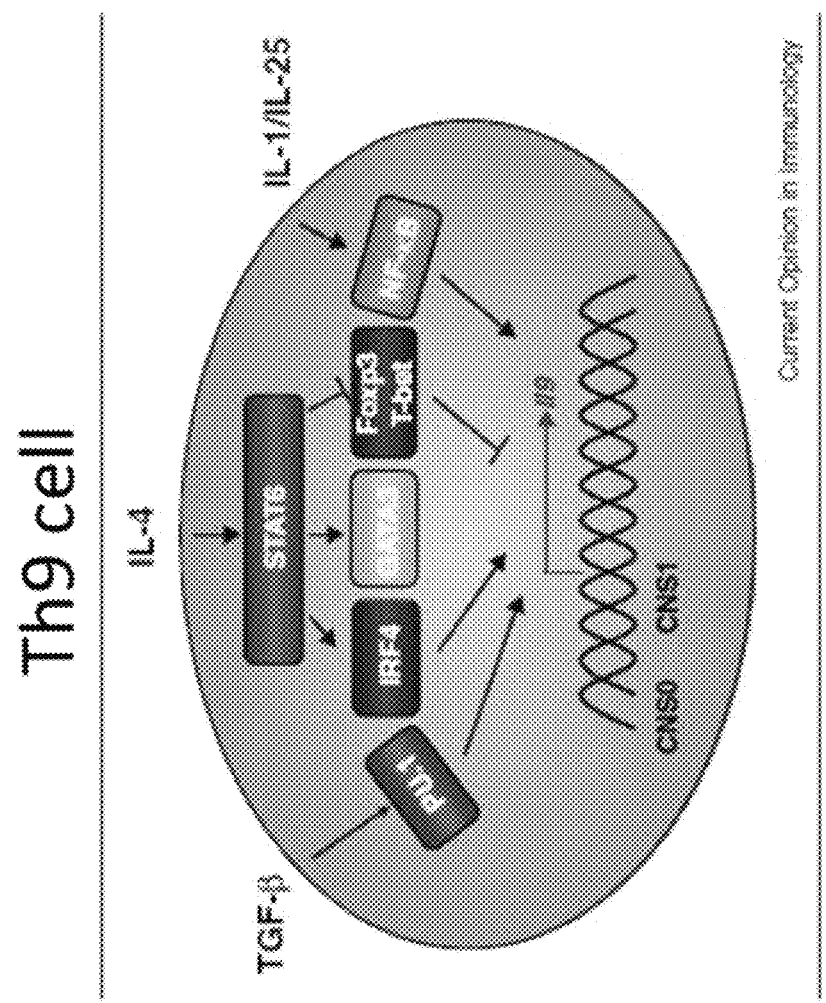
FIG. 29 shows a schematic representation demonstrating exemplary intracellular signaling pathways in an activated $T_H9$ CD4+ T cell. IL-9 production is triggered by binding of particular cytokines to membrane receptors for TGF-beta, e.g. PU.1 associated signaling pathway(s); IL-4, e.g. parts of the STAT6 associated signaling pathway; and IL-1 and IL-25 e.g. NF-kappaB associated signaling pathway(s), each contributing to the expression of IL-9.

At least three exemplary types of intracellular signaling pathways were chosen, in part, for determining whether differentiation pathways were effectively induced and to discover what effect exposure to PAM2CSK4 would have on these pathways. As depicted in FIG. 29, a schematic representation is shown demonstrating exemplary intracellular signaling pathways in an activated $T_H9$ CD4+ T cell resulting in the production of IL-9. In brief, IL-9 expression and production is triggered by binding of particular cytokines to membrane receptors for TF-beta, e.g. PU.1 associated signaling pathway; IL-4, e.g. STAT6 associated signaling pathway; and IL-1 and IL-25 e.g. NF-kappaB associated signaling pathway, each contributing to the expression of IL-9.

Thus, specific activated transcription factors, expressed as proteins, were chosen as exemplary biomarkers for disease related $T_H9$ effector populations. As nonlimiting examples, SPI1 (Spi-1 Proto-Oncogene) refers to a PU.1 protein; IRF4 (Interferon Regulatory Factor 4) and GATA3 (GATA Binding Protein 3) were chosen to represent the STAT6 associated signaling pathway; and IL-9 (Interleukin 9) itself as a comparative readout.

SPI1 (Spi-1 Proto-Oncogene) (Hematopoietic) Transcription Factor PU.1 encodes an ETS-domain transcription factor that activates gene expression during myeloid and B-lymphoid cell development. The nuclear protein binds to a purine-rich sequence known as the PU-box found near the promoters of target genes, and regulates their expression in coordination with other transcription factors and cofactors. The protein can also regulate alternative splicing of target genes. Multiple transcript variants encoding different isoforms have been found for this gene.

IRF4 (Interferon Regulatory Factor 4) refers to a transcriptional activator found in lymphocytes. The protein encoded by this gene belongs to the IRF (interferon regulatory factor) family of transcription factors, characterized by a unique tryptophan pentad repeat DNA-binding domain. IRF4 binds to the interferon-stimulated response element (ISRE) of the MHC class 1 promoter and to the immunoglobulin lambda light chain enhancer, together with PU.1. The IRFs are involved with regulation of interferons in response to infection by virus, and in the regulation of interferon-inducible genes. This family member is lymphocyte specific and negatively regulates Toll-like-receptor (TLR) signaling involved with the activation of innate and adaptive immune systems. Alternatively spliced transcript variants have been found for this gene.

GATA3 refers to GATA Binding Protein 3 within the GATA family of transcription factors. The protein contains at least two GATA-type zinc fingers and is a regulator of T-cell development and involved in endothelial cell biology. Transcriptional activator which binds to the enhancer of the T-cell receptor alpha and delta genes. Binds to the consensus sequence 5-AGATAG-3. Required for the T-helper 2 ($T_H2$) differentiation process following immune and inflammatory responses.

IL-9 (interleukin 9) refers to a cytokine associated with regulating a variety of hematopoietic cells, e.g. stimulates cell proliferation and prevents apoptosis. IL-9 binds to the interleukin 9 receptor (IL-9R), which activates different signal transducer and activator (STAT) proteins and thus connects this cytokine to various biological processes.

FIG. 29 shows a schematic representation demonstrating exemplary intracellular signaling pathways in an activated $T_H9$ CD4+ T cell. IL-9 production is triggered by binding of particular cytokines to membrane receptors for TGF-beta, e.g. PU.1 associated signaling pathway(s); IL-4, e.g. parts of the STAT6 associated signaling pathway; and IL-1 and IL-25 e.g. NF-kappaB associated signaling pathway(s), each contributing to the expression of IL-9.

FIG. 30A-D shows exemplary results comparing post differentiation CD4+ $T_H9$ T cell activation factors and IL-9 cytokine secretion from activation of CD4+ T cell subsets using soluble CD3 and CD28 antibodies, with or without stimulation by soluble PAM2CSK4, on-plates. FIG. 30A shows exemplary results for GATA3 protein production. FIG. 30B shows exemplary results for SF11 protein production. FIG. 30C shows exemplary results for IRF4 protein production. FIG. 30D shows exemplary results for IL-9 protein production.

$TH_H1$ and $T_H9$ Cells On-Chips (Previously Activated and Differentiated) Activated (Re-Stimulated) On-Chips in the Presence Antigen Using Soluble Activation Factors Did not Provide Inflammatory Reactions for Simulating CD or UC Physiology, Respectively.

Experiments were designed to evaluate whether anti-CD3 and anti-CD28 co-stimulatory activation (soluble reagents) on chip would stimulate on chip T cells (previously activated and differentiated on plates) to continue functioning as activated effector cells within the chip tissue microenvironment. Further, $T_H1$ and $T_H9$ T cell populations underwent testing for an exacerbated response (either tissue alterations or changes in the characteristics of the T cell population) to a specific antigen stimulation, e.g. PAM2CSK4 (TLR2) bacterial agonist, with or without additional co-stimulation (i.e. using soluble reagents). Stimulation on-chip was done as a treatment on Day 7 of culture.

Figure 31:
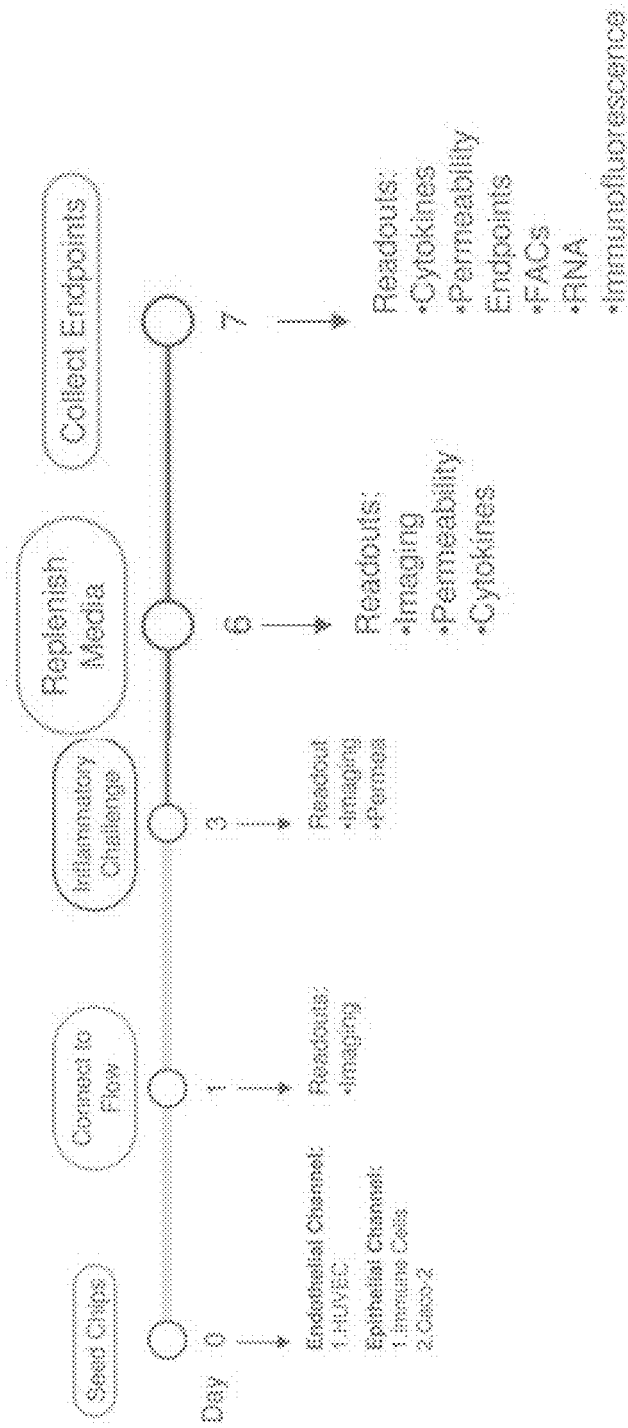
FIG. 31 shows a schematic representation demonstrating an exemplary timeline for one embodiment of a microfluidic chip, Chips are seeded at Day 0 in the Endothelial Channel: HUVECs and Epithelial Channel: 1. Immune Cells and 2. Caco-2 epithelial cells then incubated at 37° C. On Day 1 the chips are connected to flow, in some embodiments readouts on Day 1 may include imaging cells attached to the chip surfaces. On Day 3, in some embodiments, a microfluidic chip has an inflammatory challenge (i.e. treatment. Including but not limited to a treatment shown in Tables 1, 2, 4, 5, 7, 9, 10, 13, for nonlimiting examples), for one example e.g. adding PAM or IL-9 to media flowing through the chip. In some embodiments, chips are disconnected from flow. In some embodiments, readouts on Day 3 or later, may include imaging cells and permeability assays. In chips disconnected from flow, media may be replenished on Day 6. In chips with closed media flow, media may be replenished on Day 6, Day 6 readouts: may include cell imaging, permeability assays, cytokine analysis, etc. Day 7 or later: collect endpoint samples for readouts; including but not limited to cell imaging, permeability assays, cytokine analysis, etc. Endpoint sample collection (sample collection of cells from chips): including but not limited to PACs, RNA, and immunofluorescence.

In Vitro Activation and Differentiation of T-Cell Effector Subsets Derived from Blood Further Stimulated On-Chip FIG. 31 shows a schematic representation demonstrating an exemplary timeline for one embodiment of a microfluidic chip, Chips are seeded at Day 0 in the Endothelial Channel: HUVECs and Epithelial Channel: 1. Immune Cells and 2. Caco-2 epithelial cells or human primary epithelial cells, for examples, then incubated at 37° C. On Day 1 the chips are connected to flow. In some embodiments readouts on Day 1 may include imaging cells attached to the chip surfaces. On Day 3, in some embodiments, a microfluidic chip has an inflammatory challenge (i.e. treatment, including but not limited to a treatment shown in Table 1), for one example e.g. adding PAM or IL-9 to media flowing through the chip. In some embodiments, chips are disconnected from flow. In some embodiments, readouts on Day 3 or later, may include imaging cells and permeability assays. In chips disconnected from flow, media may be replenished on Day 6. In chips with closed media flow, media may be replenished on Day 6. Day 6 readouts: may include cell imaging, permeability assays, cytokine analysis, etc. Day 7 or later: collect endpoint samples for readouts: including but not limited to cell imaging, permeability assays, cytokine analysis, etc. Endpoint sample collection (sample collection of cells from chips): including but not limited to FACs, RNA, and immunofluorescence.

Stimulation conditions include but not limited to additional stimulation with PAM2CSK4 (i.e. PAM), with or without additional cytokines, e.g. IL-9, IFN-gamma. See, Table 1.

TABLE 1

Exemplary experimental conditions for stimulation of $T_H9$ populations using plate activated and differentiated CD4+ T cells (soluble reagents), obtained from peripheral blood lymphocytes.

| T-Cells | Treatment | # Chips |
|---|---|---|
| — | 1. Control | 4 |
|  | 2. +PAM (10 ug/ml) | 4 |
|  | 3. +IL-9 (30 ng/mL) | 4 |
| CD4+ | 1. Control | 4 |
|  | 2. +PAM (10 ug/mL) | 4 |
| Th9 | 1. Control | 4 |
|  | 2. +PAM (10 ug/mL) | 4 |

In this example, a $T_H1$ cell population was produced from a population of mature/naive CD4+ T cells, as described in Example 7. This population of CD4+ T cells were co-stimulated with adhered CD3 and soluble CD28 antibodies, without added cytokines, for inducing differentiation of $T_H1$ cells on plates. Unlike co-stimulation with adhered CD3 and soluble CD28 antibodies in the presence of TGFB IL-4, and IFNg cytokines which induced differentiation of $T_H9$ cells, as described herein. Thus, in this example, purified CD4+ T cell populations were plated into tissue culture plates for activation and differentiation into one selected T cell subtype, e.g. $T_H1$ in one plate, and $T_H9$ in another plate.

Figure 32B:
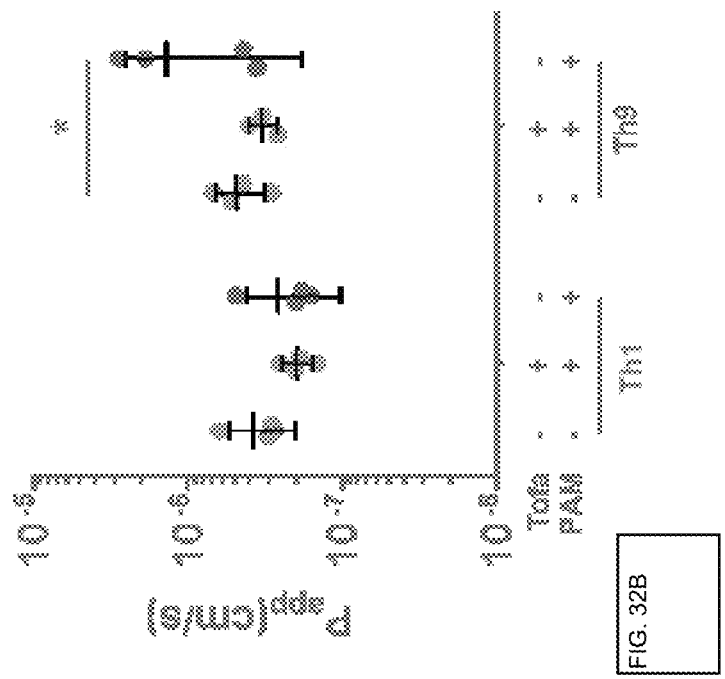
FIGS. 32A-B shows exemplary results comparing apparent permeability of untreated vs. treated epithelial layers in microfluidic chips over time, after seeding with TH1 or TH9 T-cells differentiated on plates, shown in FIG. 32A.
Figure 32A:
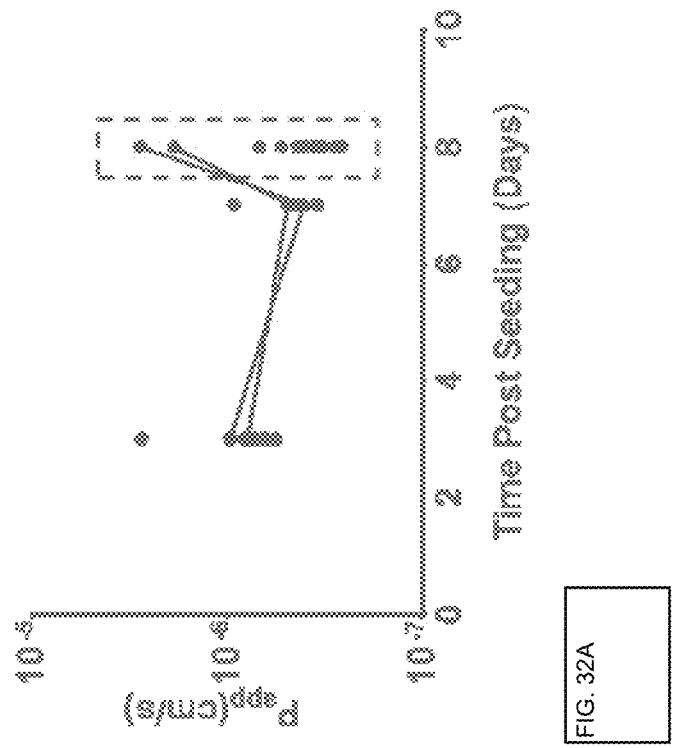

FIG. 32A-B shows exemplary results comparing apparent permeability of untreated vs. treated epithelial layers in microfluidic chips over time, after seeding with TH1 or TH9 T-cells differentiated on plates, shown in FIG. 32A. FIG. 32B shows results from Day 8 microfluidic chips treated with Tofacitinib (citrate) with or without PAM2CSK4 (PAM).

Thus, methods using plate pre-activation of mature CD4+ T-cells provided an activated and differentiated population of $T_H9$ cells added to the chip, for on-Chip stimulation with PAM (without anti-CD3 or anti-CD28 antibodies) but failed to provide a uniform stimulated $T_H9$ population on-Chip, i.e., this method provided a mixed population of T cells of which some were not capable of further activation when exposed to a soluble bacterial antigen mimic, PAM2CSK4. As this result was puzzling, the following experiment was designed for measuring permeability of the epithelial layer for comparison. Additionally, Tofacitinib (citrate), or Tofa, was tested alongside PAM2CSK4. Tofacitinib (citrate) refers to an inhibitor of the enzymes Janus kinase 1 (JAM) and Janus kinase 3 (JAK 3), which means that it interferes with the JAK-STAT signaling pathway. A JAK-STAT signaling pathway is involved with transmitting extracellular information into the cell nucleus. Influencing DNA transcription related to inflammatory mediators.

Thus, CD4+ T-cells were differentiated on plates and then seeded on chips, that were further stimulated, did not induce a definitive decrease in barrier function unlike intestine on-chips stimulated for inflammation, e.g. PAM2CSK4.

In order to further test whether PBMCs activated and differentiated with soluble factors were capable of inducing inflammation on chips, pro-inflammatory cytokine production was compared between untreated, PAM2CSK4 treated with and without Tofacitinib.

For IL-6, there were no significant differences between amounts of IL-6 protein measured between any of the experimental conditions. For IL-10, $T_H9$ populations showed no insignificant differences between unstimulated and Pam stimulated cells while a mixture of PAM2CSK4 and Tofacitinib induced significant amounts compared to unstimulated cells. However, this experiment showed that CD4+ T$_H$9 populations were not producing significant increases in pro-inflammatory cytokine production.

Figure 33A:
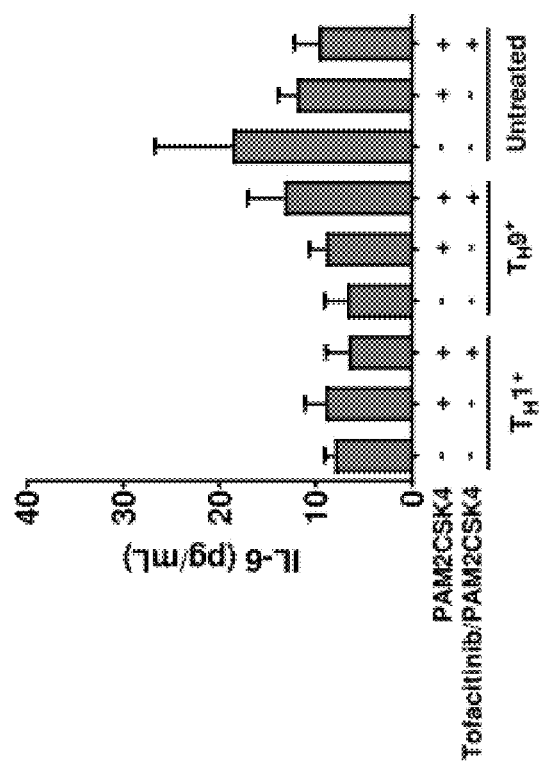
FIGS. 33A-B shows exemplary results comparing pro-inflammatory cytokine production in chips described in FIGS. 32A-B.
Figure 33B:
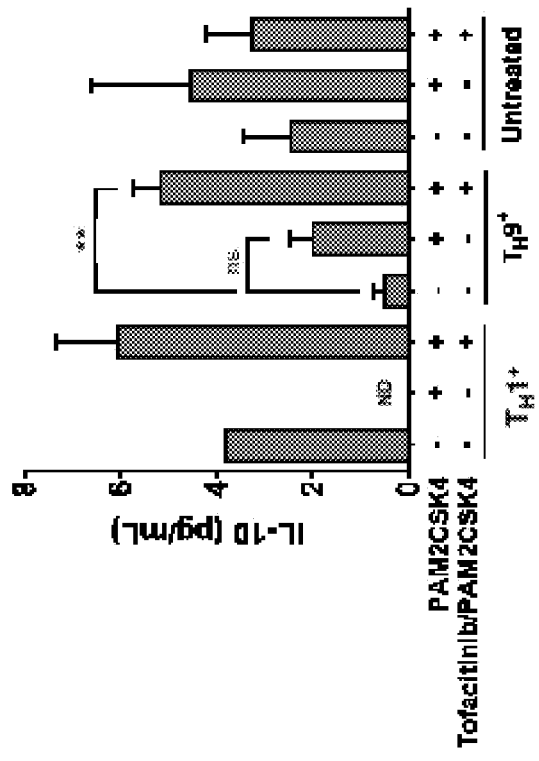

FIGS. 33A-B shows exemplary results comparing pro-inflammatory cytokine production in chips described in FIGS. 32A-B, FIG. 33A shows exemplary IL-6 secretion. FIG. 33B shows exemplary IL-10 secretion.

Despite showing production of high levels of pro-inflammatory cytokines on-plates, after adding these activated cells to chips they did not provide an activated population of immune cells on-chips capable of further activation with an antigen specific signal, i.e. PAM2CSK4. Thus, it was concluded that when immune T-cell activation and differentiation was done using soluble factors added to T cells cultured in plates, then after these cells were added to microfluidic chips they were not capable of further responding to an antigen specific signal in a significant manner desirable for disease modeling on-chip. In part, this conclusion was based upon inconsistent results in disruption in barrier function, and because proinflammatory cytokine production levels were not significantly elevated upon antigen stimulation. In fact, in general, previously activated and differentiated immune cells incorporated on chips were inactive in inflammatory induction experiments on-chips. Having a certain percentage of activated immune cells on-hip, capable of a significant response to antigen specific stimulation is desirable for modeling inflammatory induction, e.g. by a bacterial antigen.

Therefore, experiments were done by providing a second round of activation through anti-CD3 and anti-CD28 co-stimulation on-chip, using soluble activation reagents.

Activating T$_H$1 and T$_H$9 cells On-Chips Using Soluble Activation Factors Did Not Provide Inflammatory Reactions For Simulating CD or UC Physiology, Respectively.

Experiments were designed to evaluate whether anti-CD3 and anti-CD28 co-stimulatory activation (soluble reagents) on chip would stimulate on chip T cells (previously activated and differentiated on plates) to continue functioning as activated effector cells within the chip tissue microenvironment. Further, T$_H$1 and T$_H$9 T cell populations underwent testing for an exacerbated response (either tissue alterations or changes in the characteristics of the T cell population) to a specific antigen stimulation, PAM2CSK4 (TLR2) bacterial agonist, with or without additional co-stimulation (i.e. using soluble reagents). Stimulation on-chip was done as a treatment on Day 7 of culture.

Figure 34:
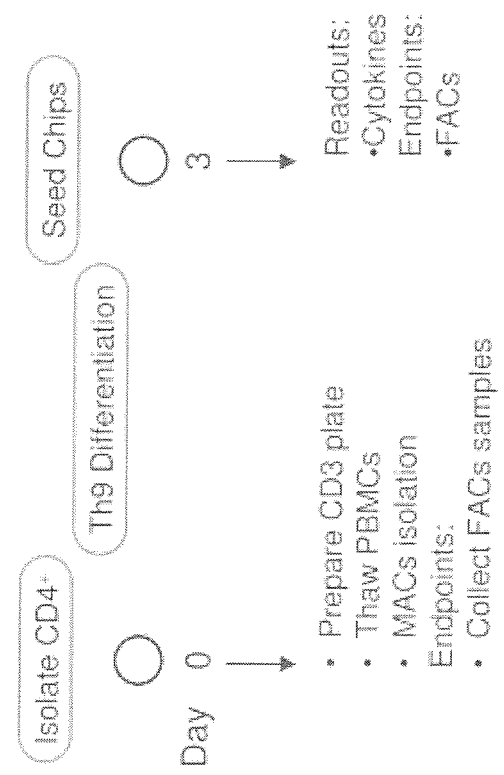
FIG. 34 shows a schematic representation demonstrating an exemplary timeline for on-plate production of TH cell subsets. Day 0 (Day-3 in relation to the microfluidic chip timeline): Prepare anti-CD3 plate; Thaw PBMCs; magnetic-activated cell sorting (MACs) isolation. The after 3 days of activation and differentiation under condition for producing a particular T cell subset, e.g. TH9, TH1, TH2, TH17, Treg (produced without adding cytokines to the CD28 antibody containing media). Endpoints: Collect FACs samples. On Day 3 CD4+ populations are activated and differentiated into subsets then used to seed microfluidic chips on Day 0. Differentiation media refers to media used for plate activation and differentiation of T cell subsets.

FIG. 34 shows a schematic representation demonstrating an exemplary timeline for on-plate production of TH cell subsets. Day 0 (Day −3 in relation to the microfluidic chip timeline): Prepare anti-CD3 plate; Thaw PBMCs; isolation. The after 3 days of activation and differentiation under condition for producing a particular T cell subset, e.g. TH9 or TH1 (produced without adding cytokines to the CD28 antibody containing media). Endpoints: Collect FACs samples. On Day 3 CD4+ populations are activated and differentiated into subsets then used to seed microfluidic chips on Day 0. Differentiation media refers to media used for plate activation and differentiation of T cell subsets.

Figure 35:
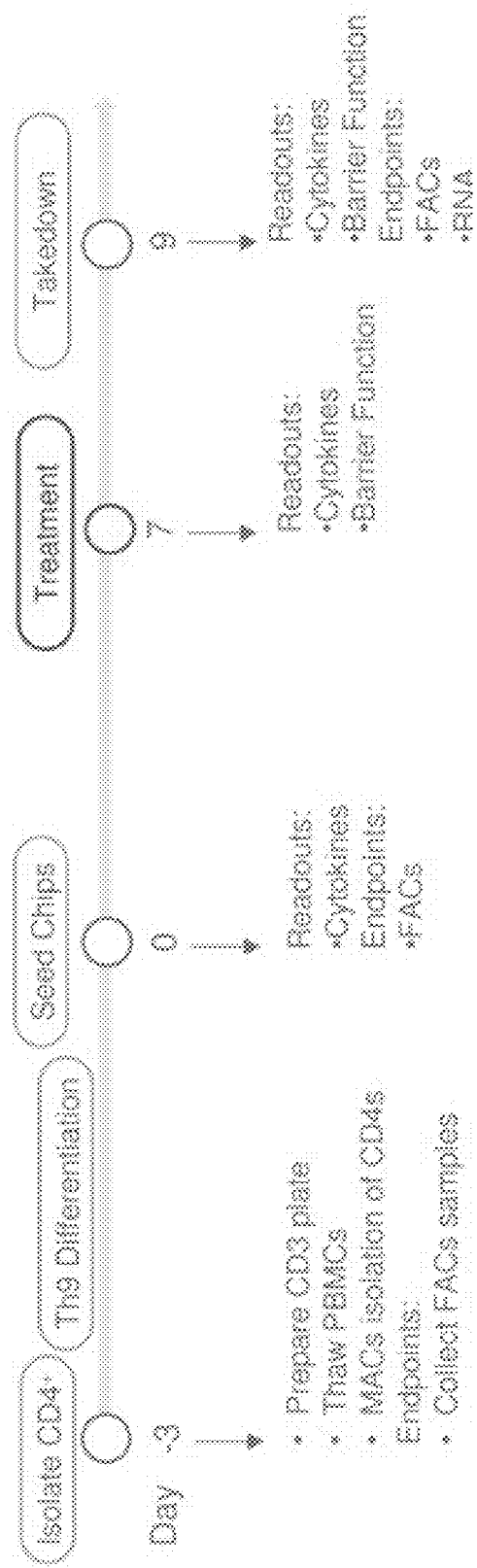
FIG. 35 shows a schematic representation demonstrating an exemplary timeline for activating immune cells on-chip where chips were seeded using $T_H1$ and $T_H9$ populations activated and differentiated into subsets using CD3 antibody coated tissue culture plates co-stimulated with soluble CD28 antibodies. In this embodiment, the method includes treatment at Day 7 with an endpoint readout at Day 9 (Takedown).

FIG. 35 shows a schematic representation demonstrating an exemplary timeline for activating immune cells on-chip where chips were seeded using T$_H$1 and T$_H$9 populations activated and differentiated into subsets using CD3 antibody coated tissue culture plates co-stimulated with soluble CD28 antibodies. In this embodiment, the method includes treatment at Day 7 with an endpoint readout at Day 9 (Takedown).

Stimulation (treatment) conditions on chips include but are not limited to additional soluble activation factors and stimulation with PAM2CSK4 (i.e. PAM), with or without additional IL-9. See, Table 2 where Top media and Bottom media describe flow through media on-chip, as opposed to differentiation media in static tissue culture plates. Exemplary Table 3 shows cell types and seeding densities on-chips. Table 4 shows exemplary treatments, while Table 5 shows exemplary on-chip reagents, exemplary amounts used and exemplary volumes of media. Table 6 shows exemplary readouts, e.g. cytokine production, barrier function and expression, such as mRNA quantitation, and amounts of samples used for analysis.

TABLE 2

Exemplary experimental conditions using CD4+ T cells that were plate activated and differentiated into T$_H$9 populations using soluble activation reagents.

| | |
|---|---|
| Flow Rate | 30 uL/hour |
| Stretch | None |
| ECM | Matrigel 100 ug/mL, Collagen I 30 ug/mL |
| Differentiation Media | CD4: DMEM, 10% FBS, Penicillin/Streptomycin, anti-CD3 bound at 3 ug/mL, anti-CD28 (3 ug/mL) Th9: DMEM, 10% FBS, Penicillin/Streptomycin, anti-CD3 bound at 3 ug/mL, anti-CD28 (3 ug/mL), anti-IFNg (10 ug/mL), rhIL-2 (20 ng/mL), rhIL-4 (20 ng/mL), rhTGFb (5 ng/mL) |
| Top Media | DMEM, 10% FBS, Penicillin/Streptomycin, Phenol Red, 4.5 g/mL Glucose, Glutamine, No Pyruvate, 20 ug/mL Lucifer Yellow |
| Bottom Media | Days 0-3: EGM-2 Complete, 2% FBS, No Gentamicin, Penicillin/Streptomycin Days 3-9: EGM-2 Complete, 0.5% FBS, No Gentamicin, Penicillin/Streptomycin |

TABLE 3

Exemplary experimental cell types and seeding densities for microfluidic chips.

| Cell Type | Donor/Passage | Viability | Total # Cells | Seeding Density |
|---|---|---|---|---|
| HUVEC | 8/7/17 p3 | 89% | 12 million | 10 mill/mL |
| CD4 | Donor 1 | 100% | 0.4 million | 1 mill/mL |
| Th9 | Donor 1 | 94% | 0.6 million | 1 mill/mL |
| Caco2 | 8/8/17 p3 | 91% | 11.25 million | 1.5 mill/mL |

TABLE 4

Exemplary experimental conditions for activating T cells on chips on Day 7, using chips seeded on Day 0 with plate activated and differentiated CD4+ T cells (Day −3 to Day 0). T cells on chips were further activated using soluble reagents. Activating on-chip refers to on-chip treatment as shown in FIG. 35 on Day 7.

| T-Cells | Treatment | #Chips |
|---|---|---|
| N/A | 1. Control | 3 |
| | 2. +PAM (10 ug/mL) | 3 |
| | 3. +IL9 + PAM | 3 |
| | 4. +IFNg + PAM | 3 |
| N/A | 1. Control | 3 |
| | 2. +PAM (10 ug/mL) | 3 |
| | 3. +CD3 + CD28 | 3 |
| | 4. +CD3 + CD28 + PAM | 3 |
| Th1 | 1. Control | 3 |
| | 2. +PAM (10 ug/mL) | 3 |
| | 3. +CD3 + CD28 | 3 |
| | 4. +CD3 + CD28 + PAM | 3 |
| Th9 | 1. Control | 3 |
| | 2. +PAM (10 ug/mL) | 3 |
| | 3. +CD3 + CD28 | 3 |
| | 4. +CD3 + CD28 + PAM | 3 |

TABLE 5

Exemplary Treatments, types of and amounts of reagents.

| Treatment | Concentration | Total Amount (ml) | Treatment Added |
|---|---|---|---|
| Control | — | 24 mL | — |
| +PAM | 10 ug/mL | 24 mL | 240 uL |
| IL9 + PAM | 20 ng/mL IL9 | 6 mL | 1.2 uL IL9 |
| | 10 ug/mL PAM | | 60 uL PAM |
| IFNg + PAM | 100 ug/mL IFNg | 6 mL | 0.3 uL IFNg |
| | 10 ug/mL PAM | | 60 uL PAM |
| CD3/CD28 | 1 ug/mL CD3 | 18 mL | 18 uL CD3 |
| | 5 ug/mL CD28 | | 90 uL CD28 |
| CD3/CD28 +PAM | 1 ug/mL CD3 | 18 mL | 18 uL CD3 |
| | 5 ug/mL CD28 | | 90 uL CD28 |
| | 10 ug/mL PAM | | 180 uL PAM |

TABLE 6

Exemplary readouts, e.g. cytokine production, barrier function and expression, such as mRNA Quantitation, with amounts of samples used for analysis.

| Readouts | Cytokines - 50 uL<br>Barrier Function - 100 uL<br>RNA - use fraction of cells fixed for FACS |
|---|---|
| Chip 1 | FACS/RNA |
| Chip 2 | FACS/RNA |
| Chip 3 | FACS/RNA |

Evaluation of the effects of T-cell activation on the Intestine On-Chip by perfusion of soluble immune activating factors (anti-CD3 and anti-CD2) to the media is shown in FIGS. 36A-B-39A-C. In particular, activated T-cell subsets were evaluated for disease-specific cytokine production.

Figures 36A, 36B:
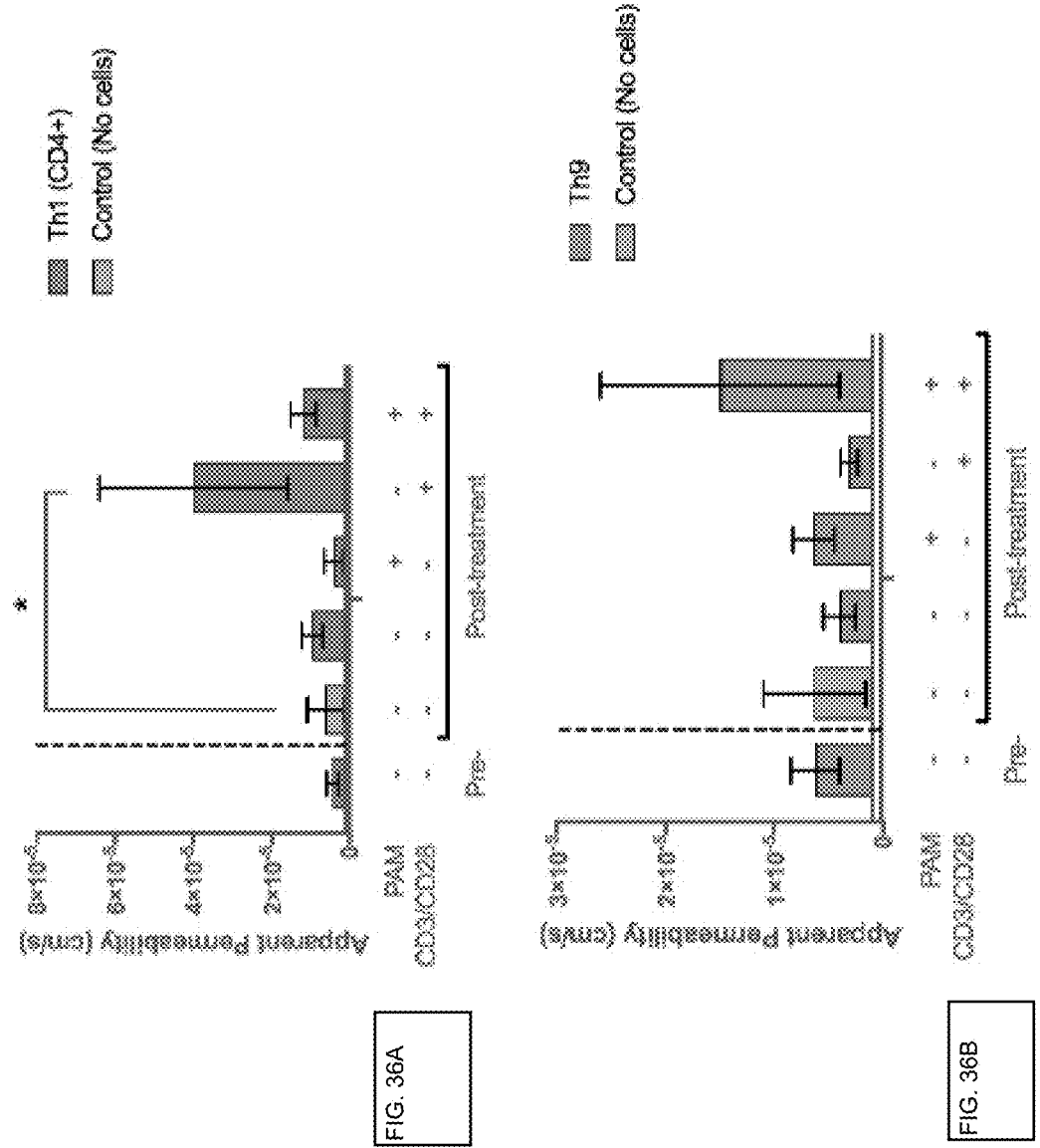
FIGS. 36A-B shows exemplary results comparing barrier function, i.e. permeability loss between $TH_1$ and $T_H9$ populations activated by soluble anti-CD3/CD28 vs. PAM on-chip.

FIGS. 36A-B shows exemplary results comparing barrier function, i.e. permeability loss between $T_H1$ and $T_H9$ populations activated by soluble CD3/CD28 vs. PAM on-chip. FIG. 36A shows exemplary apparent permeability representative of barrier function of treated Intestine-Chip with $T_H1$-Activated populations (simulating Crohn's). FIG. 36B shows exemplary apparent permeability representative of barrier function of treated Intestine-Chip with $T_H9$ Activated populations (simulating Ulcerative Colitis).

Addition of activators (anti-CD3 anti-CD2) causes increases in immune cell-driven barrier permeability characteristic of CD and UC.

Figure 37A:
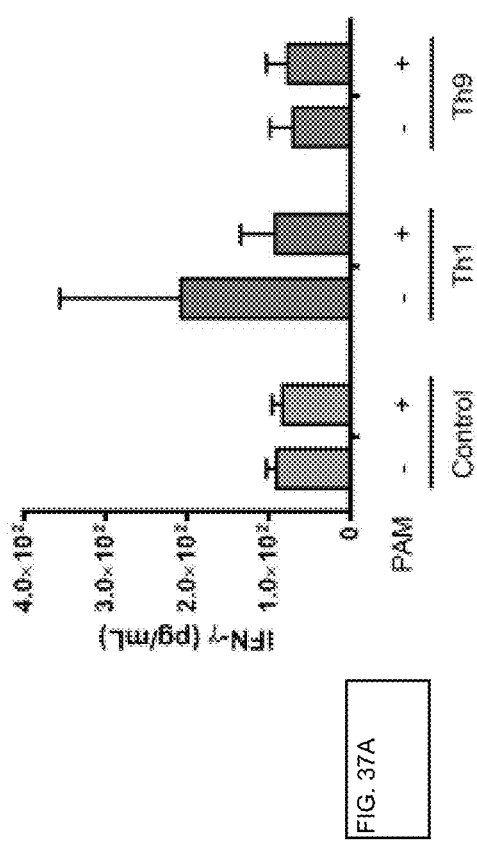
FIGS. 37A-B shows exemplary results comparing pro-inflammatory cytokine production.
Figure 37B:
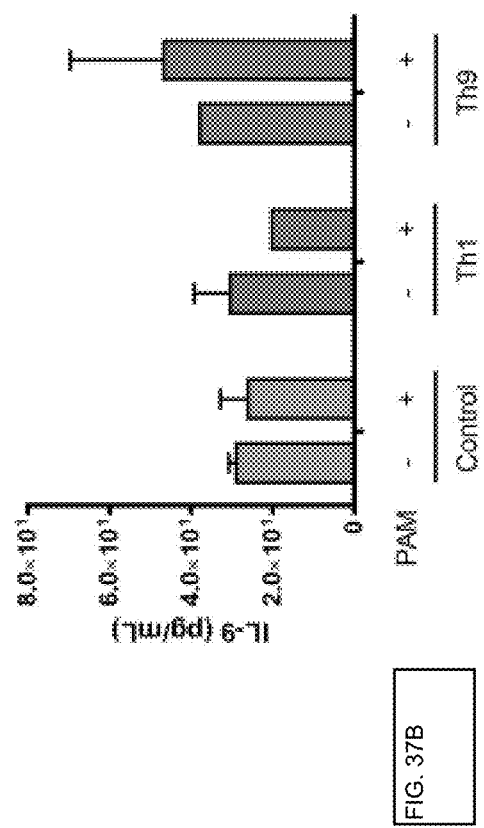

FIGS. 37A-B shows exemplary results comparing pro-inflammatory cytokine production. FIG. 37A shows exemplary IFN-gamma secretion. FIG. 37B shows exemplary IL-9 secretion.

Addition of activators (anti-CD3/anti-CD28) causes increases in pro-inflammatory cytokines associated with CD and UC.

Figures 38A, 38B:
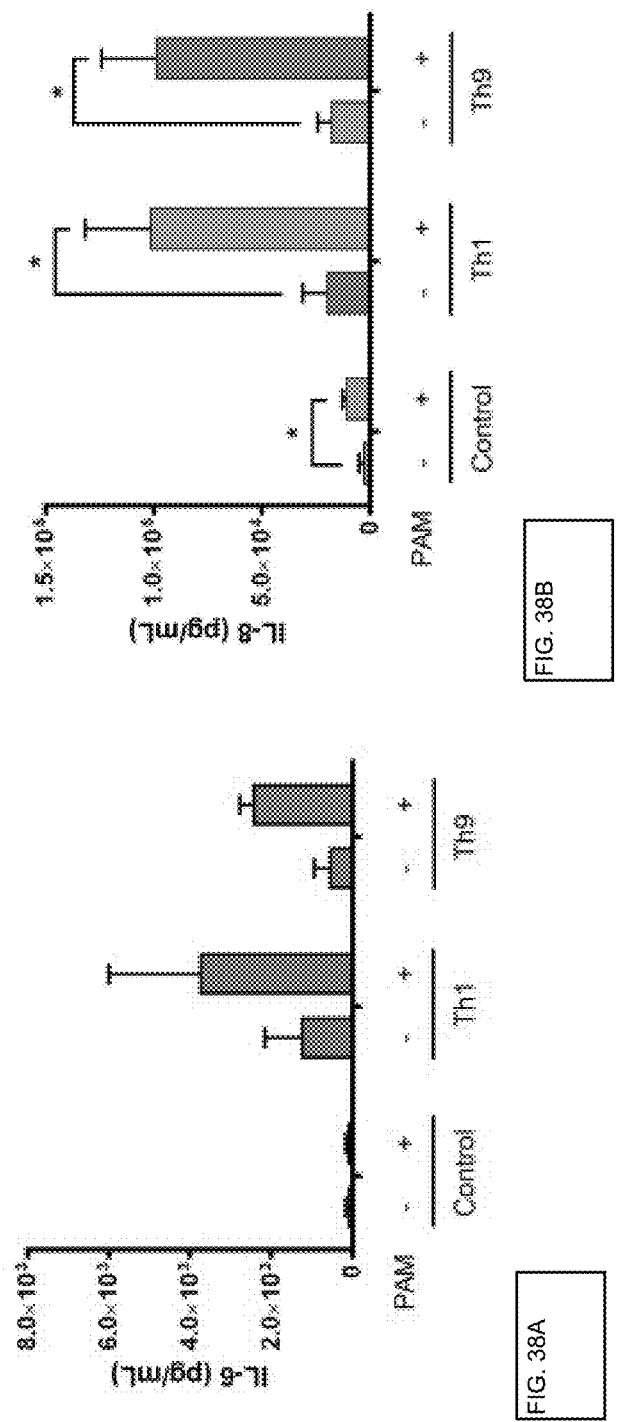
FIGS. 38A-B shows exemplary results comparing pro-inflammatory cytokine production.

FIGS. 38A-B shows exemplary results comparing pro-inflammatory cytokine production. FIG. 38A shows exemplary IL-6 secretion. FIG. 38B shows exemplary IL-8 secretion.

Figure 39B:
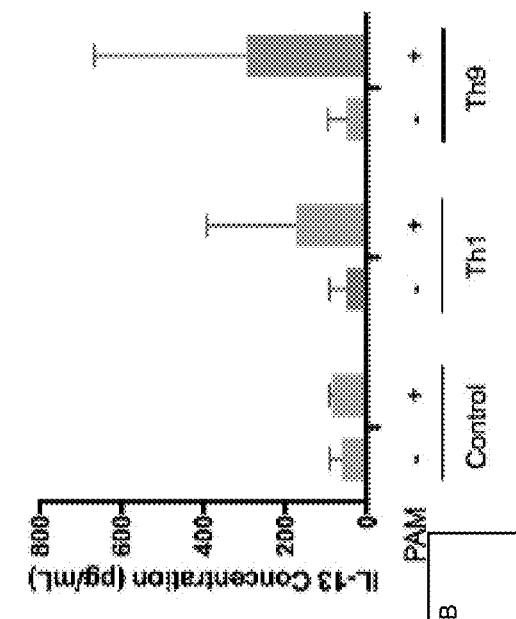
FIGS. 39A-C shows exemplary results of measuring epithelial cytokine induced by soluble anti-CD3/CD28 co-stimulation of $T_H1$ or $T_H9$ on-chip with and without an antigen, e.g. PAM, as one embodiment of a diseased immune environment.
Figure 39A:
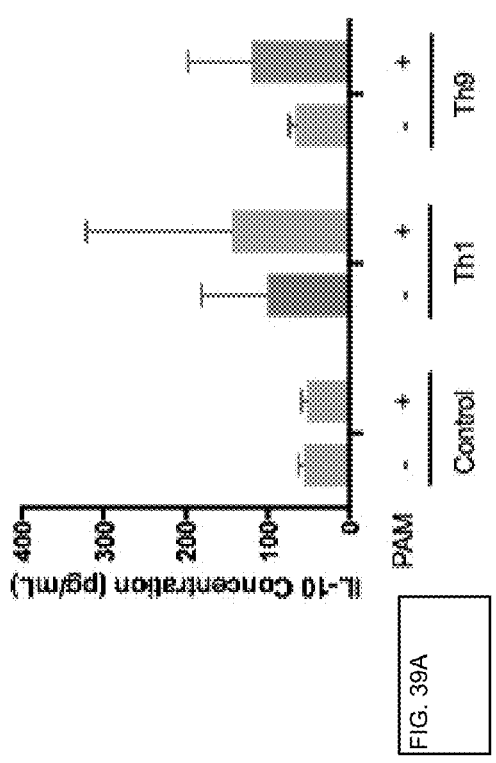
Figure 39C:
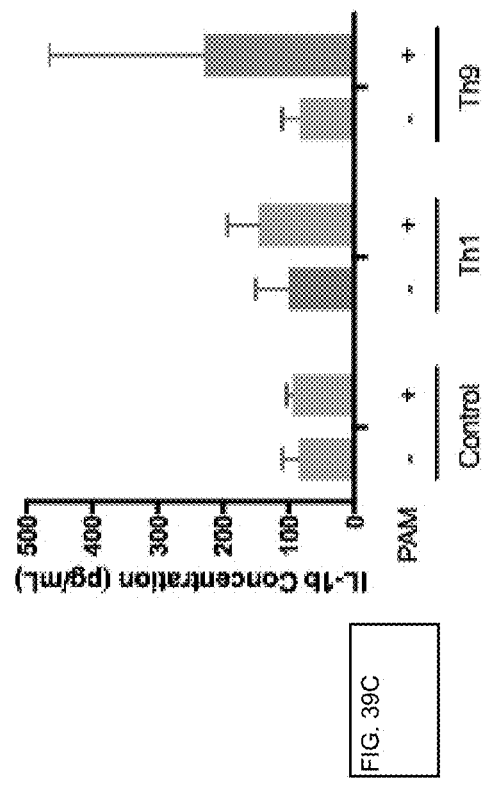

FIGS. 39A-C shows exemplary results of measuring epithelial cytokine induced by soluble anti-CD3 CD28 co-stimulation of $T_H1$ or $T_H9$ on-chip with and without and antigen, e.g. PAM, as one embodiment of a diseased immune environment. FIG. 39A IL-10 Cytokine Expression after 48 hr stimulation with soluble anti-CD3/CD28. FIG. 39B IL-13 Cytokine Expression after 48 hr stimulation with soluble anti-CD3/CD28. FIG. 39C IL-1b Cytokine Expression after 48 hr stimulation with soluble anti-CD3/CD28.

Thus, addition of soluble activators (anti-CD3 anti-CD28) on chip, as a Day 7 treatment, causes increases in pro-inflammatory cytokines associated with the epithelial inflammatory response.

However, upon additional exposure to a TLR2 agonist, PAM2CSK4, as a model antigen, there was differential regulation of the activated $T_H1$ and $T_H9$ populations. In other words, anti-CD3/CD28 stimulation on-chip induced IFN gamma and IL-6 in $T_H1$, IL-9 in $T_H9$ by picogram amounts. Furthermore, induction was not significant, nor was it augmented by co-stimulation in the presence of antigen. The cytokine IL-8 was increased by antigen specific stimulation. Furthermore, significant variability in the data, i.e. large error bars, was observed. See, FIG. 39A-C, for example.

A comparison of $\log_2$ fold change in expression of mRNA, e.g. IFNgamma, IL-9, and Occludin, from Chips showed that anti-CD3/CD28 co-stimulation induced transcription in the $T_H1$ and $T_H9$ populations relative to unstimulated control chips without immune cells. However, antigen specific stimulation did not increase IL-9 production in $T_H9$ populations, nor increased Occludin. See, FIG. 40A-C.

FIG. 40A-C shows exemplary results comparing pro-inflammatory cytokine gene expression between $T_H1$ and $T_H9$ cell populations stimulated with either soluble anti-CD3/CD28 or PAM or both. FIG. 40A shows exemplary IFN-gamma gene expression. FIG. 40B shows exemplary IL-9 gene expression. FIG. 40C shows exemplary Occludin (cell adhesion protein) gene expression.

In summary, addition of anti-CD3 and anti-CD28 antibodies to the cell media in the upper epithelial channel, i.e. by perfusing soluble activation reagents onto the cell layer, caused immune cell dependent inflammation of the Intestine-Chip that weakened the epithelial barrier relative to control (no immune cells) but did not appear to significantly damage it. The secreted cytokine profile indicated a trend toward characteristic proinflammatory cytokine production by the differentiated T-cell subsets on-Chip induced by a second stimulation using soluble anti-CD3/anti-CD28 in the flow media. While not intending to limit the invention to any particular mechanism, it is believed that exposure to an antigen did not significantly alter T cell function, supporting the idea that, in this case, the antigen is acting as a differentiation signal via the TLR2 signaling cascade and not engagement of antigen-specific TCR responses. Moreover, the error bars were large indicating a large intra-experimental variation between replicates. Thus, additional experiments were done in order to determine whether the inter-experimental variability was related to the small number of replicates, by increasing the number of biological replicates in further experiments. See, Example 16.

Figure 41A:
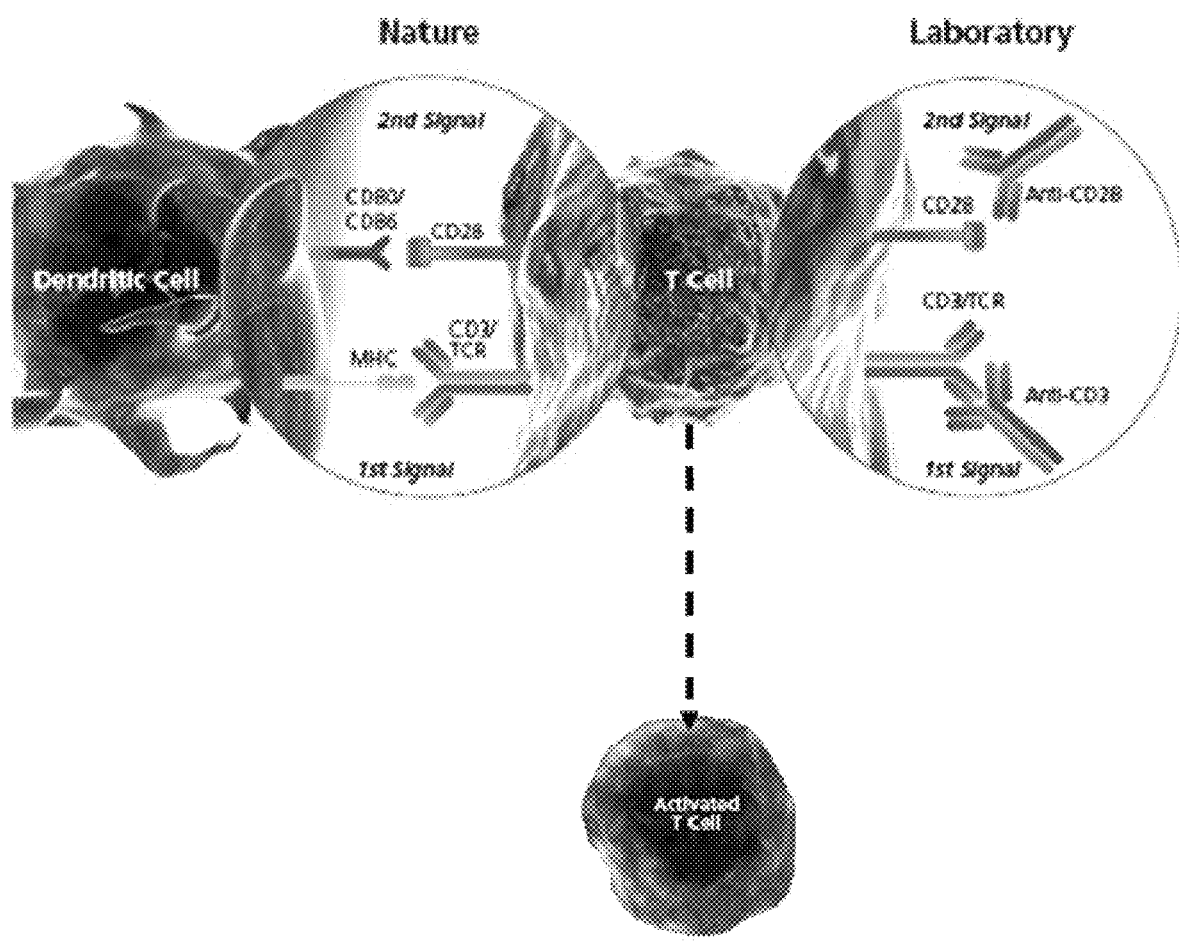
FIGS. 41A-C shows schematic representations demonstrating T cell activation, in vivo (nature) and in vitro (laboratory), compared to stimulation conditions in microfluidic chips having activation factors bound to the ECM/chip membrane.

FIG. 41A shows exemplary comparisons where dendritic cells in vivo (nature) provide membrane bound molecules, MHC in the context of antigen, for stimulating T cell antigen specific TCR complexed with CD3, a transmembrane signaling complex, along with co-stimulatory signals provided by binding of DC CD80 and CD86 to T cell CD28. Such activated T cells in the presence of exemplary cytokines, differentiated into a wide variety of subsets. Including but not limited to subsets shown in FIG. 41B, $T_H1$ (Tbet: default, no specific cytokines), $T_H2$ (IL-2, IL-4 via GATA3, IFR4, PU.1), $T_H9$ (IL-4, TGF-beta: via PU.1), $T_H17$ (IL-6, IL-21, IL-23, TGF-beta: via RORgamma t, IRF4), Treg (TGF-beta via Foxp3), Tfh (IL-21 via BCL-6), etc.

Figure 41B:
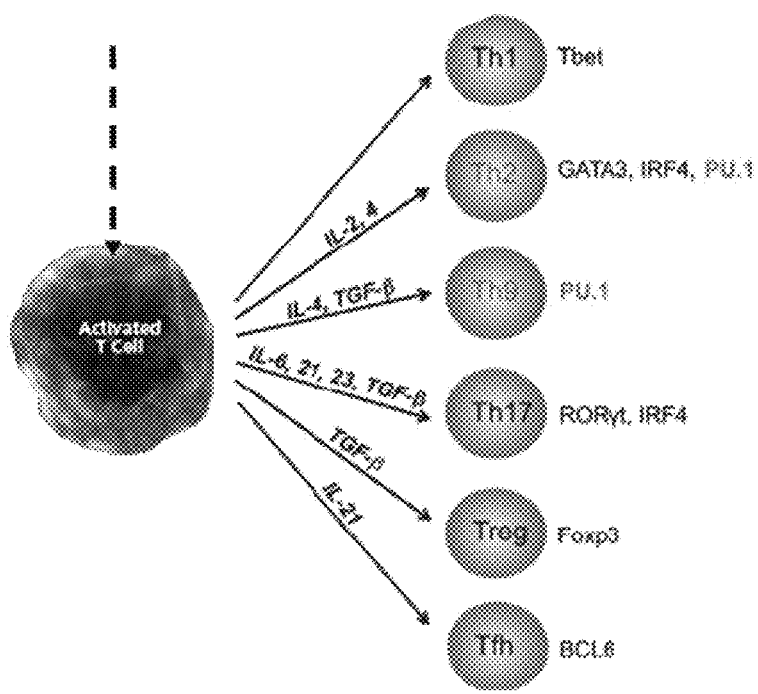
Figure 41C:
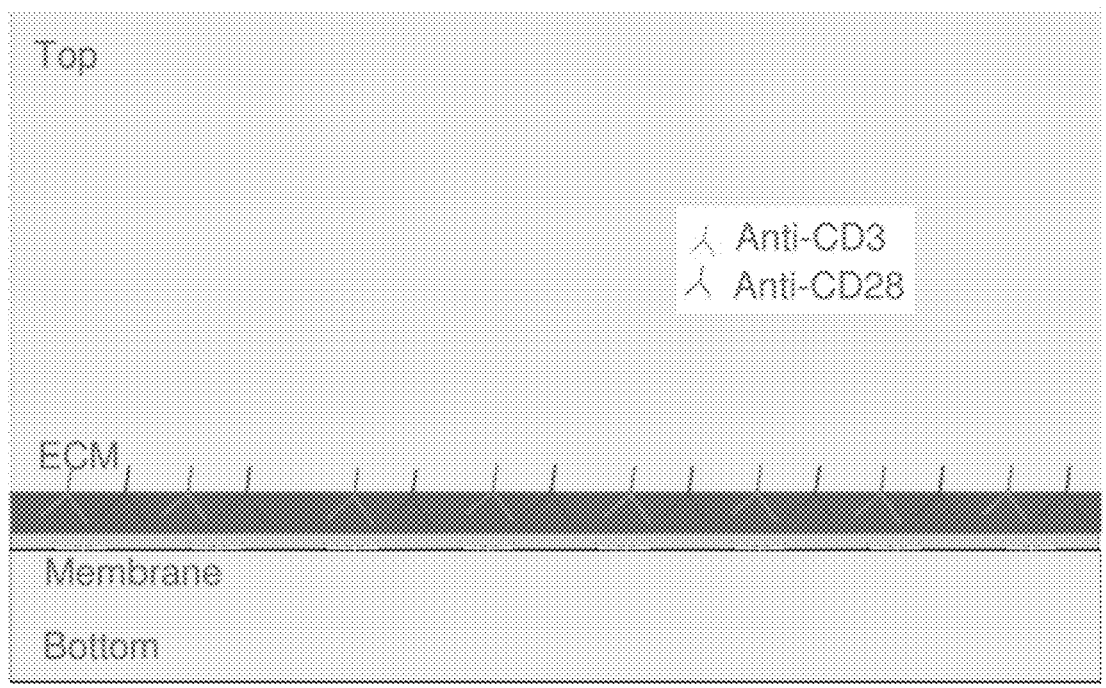

FIG. 41A-C shows schematic representations demonstrating T cell activation, in vivo (nature) and in vitro (laboratory), compared to stimulation conditions in microfluidic chips having activation factors bound to the ECM/chip membrane. FIG. 41A shows exemplary comparisons where dendritic cells in vivo activate T cells simulated by soluble activation factor induction in vitro (laboratory). The enlarged area inside of the circle highlights the 1$^{st}$ and second soluble signals used in vivo. FIG. 41B indicates the types of cytokines or growth factors present during activation (i.e. co-stimulation) that produce specific differentiated T cell subsets. FIG. 41C is a schematic representation showing immune activating factors (reagents) covalently attached to the chip membrane, alternatively trapped within or located on top of the ECM, i.e. activated ECM.

Cytokine Expression in Mucosal Biopsies from UC Patients Ranked by Severity of Inflammation.

Cytokine signaling was shown in ulcerative colitis (Nalleweg et al. "IL-9 and its receptor are predominantly involved in the pathogenesis of UC." 2015). Cytokine expression in mucosal biopsies from UC Patients was ranked by severity of inflammation. In particular, IL-9 and IL-6 were over-expressed in mucosal biopsies from severely inflamed UC patients while expression generally tracked with disease severity.

In the gut-on-chip, it was found that the presence of LDDC affects cytokine response and inflammation. Thus, studies shown herein tested exemplary cytokine production for IL-6 and IL-9 produced by microfluidic gut-on-chip models. Additionally, cytokines are contemplated for testing include but are not limited to TGF-beta, interleukin-4, interleukin-12, interleukin-17, interleukin-21, interleukin-22, interleukin-23, interleukin-27, INF-alpha, and Interferon-gamma.

Exemplary Gut-On-A-Chip (Intestine-On-Chip) Devices and Methods.

Figure 4A:
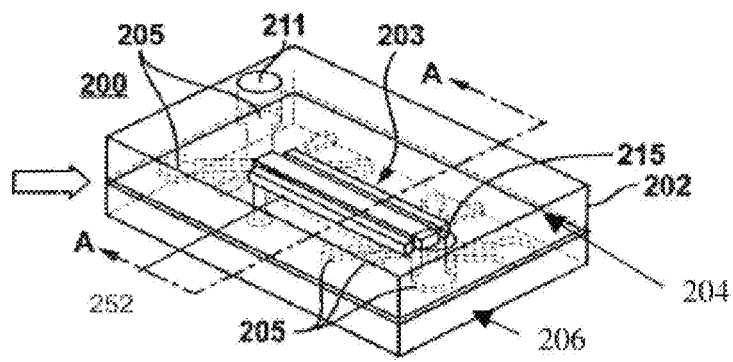
FIG. 4A illustrates a perspective view of a microfluidic device with microfluidic channels in accordance with an embodiment.
Figure 4B:
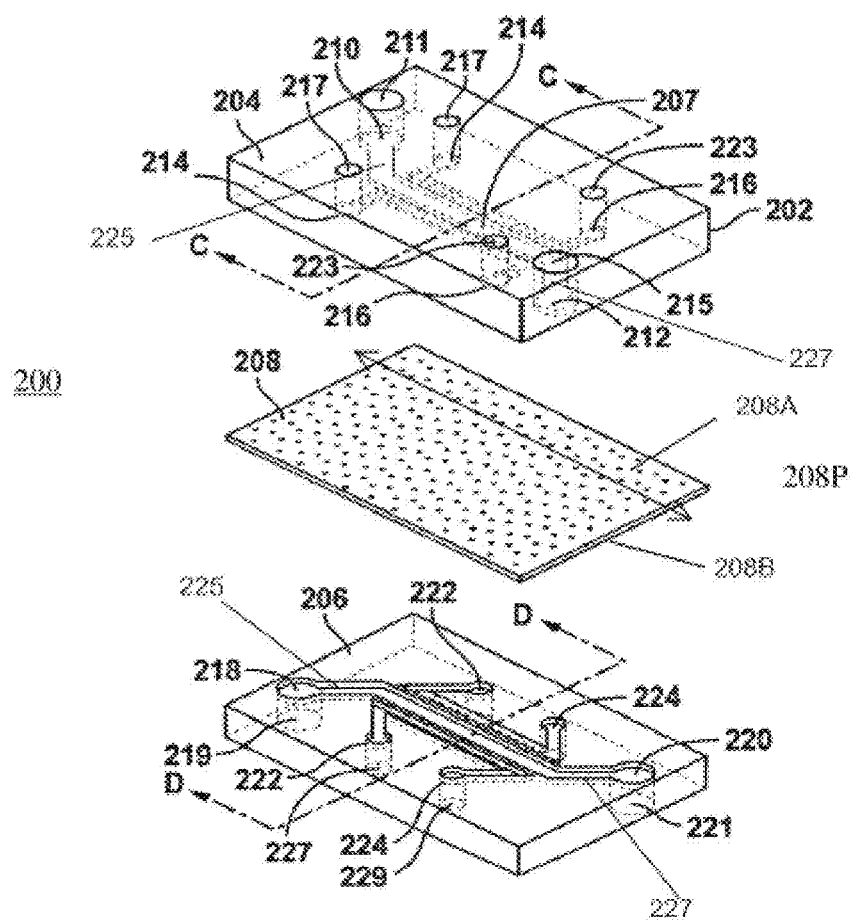
FIG. 4B illustrates an exploded view of the device in accordance with an embodiment, showing a microfluidic channel in a top piece and a microfluidic channel in a bottom piece, separated by a membrane.

FIGS. 4A-4B illustrates a perspective view of one embodiment of a microfluidic device in accordance with some embodiments described herein. For example, as shown in FIGS. 4A-4B, the device 200 can include a body 202 comprising a first structure 204 and a second structure 206 in accordance with an embodiment. The body 202 can be made of an elastomeric material, although the body can be alternatively made of a non-elastomeric material, or a combination of elastomeric and non-elastomeric materials. It should be noted that the microchannel design 203 is merely exemplary and not limited to the configuration shown in FIGS. 4A-4B. While operating channels 252 (e.g., as a pneumatics means to actuate the membrane 208, see below for information on membrane 208 and see the International Appl. No. PCT/US2009/050830, the content of which is incorporated herein by reference in its entirety, for further details of the operating channels, the content of which is incorporated herein by reference in its entirety) are shown in FIGS. 4A-4B, they are not required in all of the embodiments described herein. In some embodiments, the devices do not comprise operating channels on either side of the microchannel. In other embodiments, the devices described herein can be configured to provide other means to actuate the membrane, e.g., as described in the International Pat. Appl. No. PCT/US2014/071570, the content of which is incorporated herein by reference in its entirety.

In some embodiments, various organ chip devices described in the International Patent Application Nos. PCT/US2009/050830; PCT/US2012/026934; PCT/US2012/068725; PCT/US2012/068766; PCT/US2014/071611; and PCT/US2014/071570, the contents of each of which are incorporated herein by reference in their entireties, can be modified to form the devices described herein. For example, the organ chip devices described in those patent applications can be modified in accordance with the devices described herein.

The first structure 204 and/or second structure 206 can be fabricated from a rigid material, an elastomeric material, or a combination thereof.

As used herein, the term "rigid" refers to a material that is stiff and does not bend easily, or maintains very close to its original form after pressure has been applied to it.

The term "elastomeric" as used herein refers to a material or a composite material that is not rigid as defined herein. An elastomeric material is generally moldable and curable, and has an elastic property that enables the material to at least partially deform (e.g., stretching, expanding, contracting, retracting, compressing, twisting, and/or bending) when subjected to a mechanical force or pressure and partially or completely resume its original form or position in the absence of the mechanical force or pressure.

In some embodiments, the term "elastomeric" can also refer to a material that is flexible/stretchable but does not resume its original term or position after pressure has been applied to it and removed thereafter. The terms "elastomeric" and "flexible" are interchangeably used herein.

In some embodiments, the material used to make the first structure and/or second structure or at least the portion of the first structure 204 and/or second structure 206 that is in contact with a gaseous and/or liquid fluid can comprise a biocompatible polymer or polymer blend, including but not limited to, polydimethylsiloxane (PDMS), polyurethane, polyimide, styrene-ethylene-butylene-styrene (SEBS), polypropylene, polycarbonate, cyclic polyolefin polymer/copolymer (COP/COC), or any combinations thereof.

As used herein, the term "biocompatible" refers to any material that does not deteriorate appreciably and does not induce a significant immune response or deleterious tissue reaction, e.g., toxic reaction or significant irritation, over time when implanted into or placed adjacent to the biological tissue of a subject, or induce blood clotting or coagulation when it comes in contact with blood.

Additionally, or alternatively, at least a portion of the first structure 204 and/or second structure 206 can be made of non-flexible or rigid materials like glass, silicon, hard plastic, metal, or any combinations thereof.

The device in FIG. 4A can comprise a plurality of access ports 205. In addition, the branched configuration 203 can comprise a tissue-tissue interface simulation region or regions (such as a region on the membrane 208 in FIG. 4B) where cell behavior and/or passage of gases, chemicals, molecules, particulates and cells are monitored. FIG. 4B illustrates an exploded view of the device in accordance with an embodiment. In one embodiment, the body 202 of the device 200 comprises a first outer body portion (first structure) 204, a second outer body portion (second structure) 206 and an intermediary membrane 208 configured to be mounted between the first and second outer body portions 204 and 206 when the portions 204 and 206 are mounted onto one another to form the overall body.

The microchannel(s) in the microfluidic devices can be substantially linear or they can be non-linear. In some embodiments, the channels are not limited to straight or linear channels and can comprise curved, angled, or otherwise non-linear channels. It is to be further understood that a first portion of a channel can be straight, and a second portion of the same channel can be curved, angled, or otherwise non-linear. Without wishing to be bound by a theory, a non-linear channel can increase the ratio of culture area to device area, thereby providing a larger surface area for cells to grow. This can also allow for a higher amount or density of cells in the channel.

FIG. 4B illustrates an exploded view of the device in accordance with an embodiment. As shown in FIG. 4B, the first outer body portion or first structure 204 includes one or more inlet fluid ports 210 in communication with one or more corresponding inlet apertures 211 located on an outer surface of the first structure 204. The device 200 can be connected to a fluid source via the inlet aperture 211 in which fluid travels from the fluid source into the device 200 through the inlet fluid port 210.

Additionally, the first outer body portion or first structure 204 can include one or more outlet fluid ports 212 in communication with one or more corresponding outlet apertures 215 on the outer surface of the first structure 204. In some embodiments, a fluid passing through the device 200 can exit the device to a fluid collector or other appropriate component via the corresponding outlet aperture 215. It should be noted that the device 200 can be set up such that the fluid port 210 is an outlet and fluid port 212 is an inlet.

In some embodiments, as shown in FIG. 4B, the device 200 can comprise an inlet channel 225 connecting an inlet fluid port 210 to the first chamber 204. The inlet channels and inlet ports can be used to introduce cells, agents (e.g., but not limited to, stimulants, drug candidate, particulates), airflow, and/or cell culture media into the first chamber 204.

A Membrane Located in Between the First Structure and Second Structure.

In one embodiment, the membrane 208 is oriented along a plane between the first chamber 204 and the second chamber 206. It should be noted that although one membrane 208 is shown, more than one membrane 208 can be configured in devices which comprise more than two chambers.

The membrane separating the first chamber and the second chamber in the devices described herein can be porous (e.g., permeable or selectively permeable), non-porous (e.g., non-permeable), rigid, flexible, elastic or any combinations thereof. Accordingly, the membrane 208 can have a porosity of about 0% to about 99%. As used herein, the term "porosity" is a measure of total void space (e.g., through-holes, openings, interstitial spaces, and/or hollow conduits) in a material, and is a fraction of volume of total voids over the total volume, as a percentage between 0 and 100% (or between 0 and 1). A membrane with substantially zero porosity is non-porous or non-permeable.

As used interchangeably herein, the terms "non-porous" and "non-permeable" refer to a material that does not allow any molecule or substance to pass through.

In some embodiments, the membrane can be porous and thus allow molecules, cells, particulates, chemicals and/or media to migrate or transfer between the first chamber 204 and the second chamber 206 via the membrane 208 from the first chamber 204 to the second chamber 206 or vice versa.

As used herein, the term "porous" generally refers to a material that is permeable or selectively permeable. The teem "permeable" as used herein means a material that permits passage of fluid (e.g., liquid or gas), a molecule, a whole living cell and/or at least a portion of a whole living cell, e.g., for formation of cell-cell contacts. The term "selectively permeable" as used herein refers to a material that permits passage of one or more target group or species, but act as a barrier to non-target groups or species. For example, a selectively-permeable membrane can allow passage of a fluid (e.g., liquid and/or gas), nutrients, wastes, cytokines, and/or chemokines from one side of the membrane to another side of the membrane, but does not allow whole living cells to pass through. In some embodiments, a selectively-permeable membrane can allow certain cell types to pass through but not other cell types.

In some embodiments, a membrane can be a hydrogel or a gel comprising an extracellular matrix polymer, and/or a biopolymer or biocompatible material. In some embodiments, the hydrogel or gel can be embedded with a conduit network, e.g., to promote fluid and nor molecule transport. See, e.g., Wu et al. (2011) "Omnidirectional Printing of 3D Microvascular Networks." Advanced Materials 23: H178-H183; and Wu et al. (2010) "Direct-write assembly of biometic microvascular networks for efficient fluid transport." Soft Matter 6: 739-742, for example methods of introducing a conduit network into a gel material.

In some embodiments, a porous membrane can be a solid biocompatible material or polymer that is inherently permeable to at least one matterspecies (e.g., gas molecules) and/or permits combination of cell-cell contacts. In some embodiments, through-holes or apertures can be introduced into the solid biocompatible material or polymer, e.g., to enhance fluid molecule transport and/or cell migration. In one embodiment, through-holes or apertures can be cut or etched through the solid biocompatible material such that the through-holes or apertures extend vertically and/or laterally between the two surfaces of the membrane 208A and 208B. It should also be noted that the pores can additionally or alternatively incorporate slits or other shaped apertures along at least a portion of the membrane 208 which allow cells, particulates, chemicals and/or fluids to pass through the membrane 208 from one section of the central channel to the other.

In some embodiments, the membrane can be coated with substances such as various cell adhesion promoting substances or ECM proteins, such as fibronectin, laminin, various collagen types, glycoproteins, vitronectin, elastins, fibrin, proteoglycans, heparin sulfate, chondroitin sulfate, keratin sulfate, hyaluronic acid, fibroin, chitosan, or any combinations thereof. In some embodiments, one or more cell adhesion molecules can be coated on one surface of the membrane 208 whereas another cell adhesion molecule can be applied to the opposing surface of the membrane 208, or both surfaces can be coated with the same cell adhesion molecules. In some embodiments, the ECMs, which can be ECMs produced by cells, such as primary cells or embryonic stem cells, and other compositions of matter are produced in a serum-free environment.

In an embodiment, one can coat the membrane with a cell adhesion factor and/or a positively-charged molecule that are bound to the membrane to improve cell attachment and stabilize cell growth. The positively charged molecule can be selected from the group consisting of polylysine, chitosan, poly(ethyleneimine) or acrylics polymerized from acrylamide or methacrylamide and incorporating positively-charged groups in the form of primary, secondary or tertiary amines, or quaternary salts. The cell adhesion factor can be added to the membrane and is fibronectin, laminin, various collagen types, glycoproteins, vitronectin, elastins, fibrin, proteoglycans, heparin sulfate, chondroitin sulfate, keratin sulfate, hyaluronic acid, tenascin, antibodies, aptamers, or fragments or analogs having a cell binding domain thereof. The positively-charged molecule and/or the cell adhesion factor can be covalently bound to the membrane. In another embodiment, the positively-charged molecule and/or the cell adhesion factor are covalently bound to one another and either the positively-charged molecule or the cell adhesion factor is covalently bound to the membrane. Also, the positively-charged molecule or the cell adhesion factor or both can be provided in the form of a stable coating non-covalently bound to the membrane.

In some embodiments, cells are cultured on and/or under the membrane under flow conditions. In some embodiments, there is a steady-state perfusion of the cells. In other embodiments described herein, the devices can comprise a flowing culture medium in the first chamber and/or the second chamber, wherein the flowing culture medium generates a shear stress. Based on the viscosity of the culture medium and/or dimensions of the chambers, one of skill in the art can determine appropriate flow rates of culture medium through the chambers to achieve desired shear stress. In some embodiments, the flow rate of the culture medium through the first chamber can range from about 5 µL/hr to about 50 µL/hr. In some embodiments, the flow rate of the culture medium through the second chamber can range from about 15 µL/hr to about 150 µL/hr. Thus, in one embodiment, fluidic shear forces are generated.

Optional Vacuum Channels.

Fluidic channels in devices of the present inventions are optionally flanked by two vacuum channels that allow the pneumatically actuated stretching forces mimicking intestinal peristalsis. In some embodiments, stretching forces are for stretching an epithelial layer. In one embodiment, mechanical forces are generated.

The Use of a Cartridge with Said Device.

In some embodiments, the devices described herein can be placed in or secured to a cartridge. In accordance with some embodiments described herein, the device can be integrated into a cartridge and form a monolithic part. Some examples of a cartridge, such as a cartridge assembly for transporting fluid into or out of one or more fluidic devices, are described in the International Patent App. No. PCT/US2014/047694 (published as WO 2015013332: Microfluidic Cartridge Assembly), the content of which is incorporated herein by reference in its entirety. The cartridge can be placed into and removed from a cartridge holder that can establish fluidic connections upon or after placement and optionally seal the fluidic connections upon removal. In some embodiments, the cartridge can be incorporated or integrated with at least one sensor, which can be placed in direct or indirect contact with a fluid flowing through a specific portion of the cartridge during operation.

Exemplary Devices for Simulating a Function of a Tissue.

Some embodiments described herein relate to devices for simulating a function of a tissue, in particular a gastrointestinal tissue. In one embodiment, the device generally comprises (i) a first structure defining a first chamber; (ii) a second structure defining a second chamber; and (iii) a membrane located at an interface region between the first chamber and the second chamber to separate the first chamber from the second chamber, the membrane including a first side facing toward the first chamber and a second side facing toward the second chamber. The first side of the membrane may have an extracellular matrix composition disposed thereon, wherein the extracellular matrix (ECM) composition comprises an ECM coating layer. In some embodiments, an ECM gel layer e.g. ECM overlay, is located over the ECM coating layer.

ECM Coating.

To determine optimum conditions for cell attachment, the surface-treated material (e.g., APTES-treated or plasma-treated PDMS) can be coated with an ECM coating of different extracellular matrix molecules at varying concentrations (based on the resulting cell morphology and attachment).

ECM Overlay.

The ECM overlay is typically a "molecular coating," meaning that it is done at a concentration that does not create a bulk gel. However, in some embodiments the overlay is a gel. In some embodiments, an ECM overlay is used. In some embodiments, an ECM overlay is left in place throughout the co-culturing. In some embodiments, an ECM overlay is removed, e.g. when before seeding additional cells into a microfluidic device. In some embodiments, the ECM layer is provided by the cells seeded into the microfluidic device.

Although cells described for use in a gut-on-chip make their own ECM, it is contemplated that ECM in pre-disease and diseased states may contribute to inflammatory gastrointestinal states. Further, the protein microenvironment provided by ECM also affects cells. Thus it is contemplated that tissue-derived ECM may carry over a disease state. Therefore, in addition to the ECM described herein, ECM used in microfluidic devises of the present inventions may be gastrointestinal tissue-derived (native) ECM. In one embodiment, a device comprising tissue-derived ECM may be used as described herein, to identity contributions to healthy or disease states affected by native ECM. For example, ECM may be isolated from biopsies of healthy, non-disease and disease areas as tissue-derived ECM. Isolates for use may include cells within or attached or further processed to remove embedded cells for use in the absence of the cells.

Additional examples of ECM materials include but are not limited to Matrigel®. Cultrex®, ECM harvested from humans. It is not meant to limit ECM from humans. Indeed, ECM may be obtained from other species, including Rodentia, i.e. rodent, e.g., mouse, rat, Canidae, i.e. canine, e.g. dog, non-human primates, e.g. monkey. Insecta, i.e. insects, Reptilia, i.e. reptiles.

Matrigel® is a trade name for a solubilized basement membrane preparation extracted from the Engelbreth-Holm-Swann (EHS) mouse sarcoma, a tumor rich in such ECM proteins as laminin (a major component), collagen IV, heparin sulfate proteoglycans, entactin/nidogen, and a number of growth factors as produced and marketed by Corning Life Sciences, Matrigel® gels to form a reconstituted basement membrane. Versions of Matrigel® include BD Matrigel® (Basement Membrane) Matrix, offered as Standard, Growth Factor Reduced, Growth Factor Reduced-High Concentration (HC) and Growth Factor Reduced-Phenol Red-Free formulations, BD Matrigel® hESC-qualified Matrix, by BD Biosciences.

Trevigen, Inc. markets other ECM versions of BME harvested as a soluble form of basement membrane purified from Engelbreth-Holm-Swarm (EHS) tumor cells under the trade name Cultrex® Basement Membrane Extract (BME). Cultrex® extract gels at 37° C. to form a reconstituted basement membrane. The major components of Cultrex® BME include laminin, collagen IV, entactin, and heparin sulfate proteoglycan. Several forms Cultrex® are offered by Trevigen as: Cultrex® Reduced Growth Factor Basement Membrane Extract, Type R1. Type R1 matrix provides a proprietary formulation that has higher tensile strength when compared to other Cultrex® products, i.e. Cultrex® BME, Cultrex® BME Type 2 and Cultrex® BME Type 3. Type R1 has a higher concentration of entactin, one of the BME components that connects laminins and collagens reinforcing the hydrogel structure, Cultrex® BME Type R1 has been specifically designed to culture tissue organoids. BME type R1 supports culture of human gastric or small intestine organoids. In a Tube formation assay—BME type R1 promotes formation of capillary-like structures by human (HBMVEC; HUVEC); Barker, et al., Lgr5+ve Stem Cells Drive Self-Renewal in the Stomach and Build Long-Lived Gastric Units In Vitro. Cell Stem Cell, 2010. 6(1): p. 25-36; Sato, T., et al., Single Lgr5 stem cells build crypt-villus structures in vitro without a mesenchymal niche. Nature, 2009. 459(7244): p, 262-26; Sato, T. and H. Clevers, Growing Self-Organizing Mini-Guts from a Single Intestinal Stem Cell: Mechanism and Applications. Science, 2013. 340 (6137): p. 1190-1194; Jung, P., et al., Isolation and in vitro expansion of human colonic stem cells. Nat Med, 2011. 17(10): p. 1225-7.). Under a Cultrex® Organoid Qualified BME, Type 2 designation, several formulations of Cultrex® BME are described for organoid culture including Cultrex® Basement Membrane Extract, Type 2, PathClear® (provided as part of a protocol for subculturing normal human gastric organoids which was derived from the submerged method as described in Barker, et al., Lgr5+ve Stem Cells Drive Self-Renewal in the Stomach and Build Long-Lived Gastric Units In Vitro. Cell Stem Cell, 2010. 6(1): p. 25-36)) and Cultrex® Reduced Growth Factor Basement Membrane Extract, Type 2, PathClear® (Human Colorectal Cancer (CRC) organoids grown from single cells on Cultrex® BME Type 2 Reduced Growth Factor). Additional products that might find use include but are not limited to Cultrex® 3-D Culture Matrix® Reduced Growth Factor Basement Membrane Extract, PathClear® (allowing for the formation of acinar and other hollow unnamed structures in vitro); Cultrex® Basement Membrane Extract, PathClear®; Cultrex® Stem Cell Qualified Reduced Growth Factor Basement Membrane Extract, PathClear®; Cultrex® Basement Membrane Extract, Type 3, PathClear®. The PathClear® designation means that in addition to standard sterility, endotoxin and MAP testing, the basement membrane extract is tested by PCR and is clear of 31 pathogens and viruses. Including lactate dehydrogenase elevating virus (LDEV). Cultrex® BME Type 2 provides a formulation with a higher in tensile strength when compared to the original BME, while Cultrex® BME Type 3 is physiologically aligned with the in vivo solid tumors environment and is recommended for xenografts and other in vivo applications.

In some embodiments, ECM is activated ECM. Activating ECM prior to seeding epithelial cells may be done by several methods, as described herein.

Binding Immune Activating Factors, i.e. reagents, in the Intestine On-Chip for providing an activated ECM.

FIG. 41C is a schematic representation showing immune activating factors (reagents) covalently attached to the chip membrane, within or on top of the ECM, i.e. activated ECM.

Contemplated lymphocyte activation with IBD includes having an activated T cell population under acute or chronic inflammatory conditions, where antigen specific stimulation may exacerbate immune responses, in part which induces an increase in proinflammatory cytokines over the activated cells further intensifying tissue damage, i.e. permeability, etc.

Therefore, because soluble co-stimulatory factors on-chip generated large intra-experimental errors, testing was done using insoluble, i.e. bound, activation co-stimulatory molecules, e.g. anti-CD3 and anti-CD28, simulating cell membrane bound co-stimulatory interactions, for a second co-stimulation (alter the first plate co-stimulation) in the presence of antigen within the IBD Intestine On-Chip.

The following examples show the development of an immune activating ECM composition in Intestine-on-Chips, that provides persistent (continuous) stimulation of T cells such that in the presence of nonMHC-restricted antigen results in production of significant amounts of prostimulatory cytokines. See, FIG. 35 for a schematic representation demonstrating an exemplary timeline for experiments on chips seeded (Day 0) using $T_H1$ or $T_H9$ populations that were activated and differentiated into subsets using CD3 antibody coated tissue culture plates, co-stimulated with soluble CD28 antibodies.

Stimulation (treatment) conditions on-chips include but are not limited to adding soluble CD3 antibodies, soluble CD28 antibodies, and a combination of soluble CD3 and CD28 antibodies, etc. In some preferred embodiments, soluble activation factors include stimulatory CD28 antibodies. In some embodiments, soluble activation factors include an antigen for T-cell stimulation that bypasses the MHC-antigen complex (nonMHC-restricted antigen). Including but not limited to TLR, Toll-like receptors expressed on T cells. In some embodiments, soluble activation factors include antigen recognition by cells in an epithelial layer expressing TLR receptor molecules. Thus, in some embodiments, soluble antigen, e.g. PAM2CSK4 (i.e. PAM) is added to microfluidic chips, with or without additional IL-9. In some embodiments, soluble activation factors include MHC-restricted antigen. Wherein, in some embodiments, activated ECM comprises anti-CD3 antibodies capable of binding to and activating human CD3 T cells. In such conditions, CD28 co-stimulatory antibodies are added as a soluble reagent in the upper epithelial channel.

There are several methods for adding stimulatory antibodies to ECM on-chip. In one embodiment, antibodies in solution are added to chips in the epithelial channel prior to coating the chip's PDMS membrane with ECM. Thus, after antibodies attach to the chip membrane, see incubation times and solutions for coating plastic tissue culture plates for example, unattached antibodies are washed out, then chip membranes are coated with ECM, as described herein. In some embodiments, antibodies in solution are added to ECM solution prior to coating the chip membrane with the ECM mixture, for creating an activated ECM comprising bound antibodies. In one embodiment, antibodies in solution are added to and incubated on top of ECM coated chip membranes, i.e. preECM coated membranes, after which the unbound antibodies are washed off the ECM prior to adding epithelial cells, for creating an activated ECM comprising bound antibodies. Such activated ECM may be considered "doped", wherein to "dope" the ECM refers to adding a T cell stimulatory reagent to the ECM. In preferred embodiments, CD3 antibodies and CD28 antibodies are capable of binding to and activating human CD4+ T-cells. Examples of anti-human CD3 antibodies (i.e. CD3 antibodies) include but are not limited to mouse-anti-human OKT3, soluble anti-CD28 Abs. Nonlimiting examples of anti-CD3 antibodies include anti-human CD3 antibody OKT 3, Anti-CD3 (OKT3) MoAb Caltag Corporation (Burlingame, Calif.); Bioscience #555336; anti-human CD3 mAb (PharMingen)).

Simulating in Vivo Co-Stimulation (Activation) of TH1 Cell Subsets On-Chip in the Presence of Antigen Using Activated ECM.

Stimulation conditions include but not limited to comparing stimulation effects on barrier function, i.e. apparent permeability, and cytokine expression, as shown in Table 7, with results described below. T cell subsets were purified from PBMCs as described herein, then stimulated in tissue culture plates using plate bound CD3 and soluble CD28 antibodies.

Figure 42:
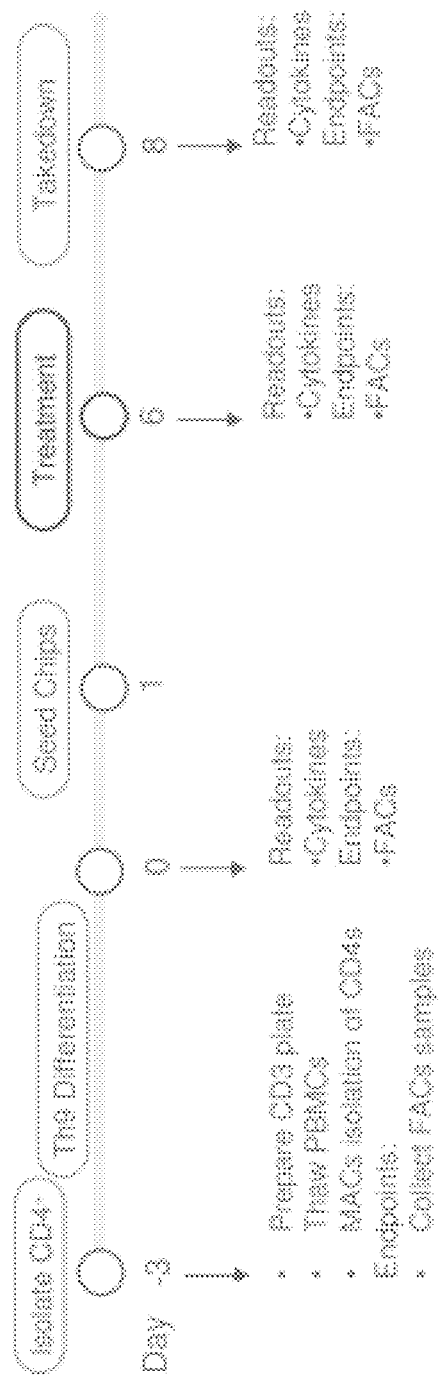
FIG. 42 shows a schematic representation demonstrating an exemplary timeline for activating immune cells on-chip comprising an activated ECM, where chips were seeded using $T_H1$ or $T_H9$ populations activated and differentiated into subsets using CD3 antibody coated tissue culture plates co-stimulated with soluble CD28 antibodies. In this embodiment, the method includes treatment at Day 6 with an endpoint readout at Day 8 (Takedown).

FIG. 42 shows a schematic representation demonstrating an exemplary timeline for activating immune cells on-chip comprising an activated ECM, where chips were seeded using $T_H1$ or $T_H9$ populations activated and differentiated into subsets using CD3 antibody coated tissue culture plates co-stimulated with soluble CD28 antibodies. In this embodiment, the method includes treatment at Day 6 with an endpoint readout at Day 8 (Takedown). See the following Tables for additional embodiments.

TABLE 7

Exemplary experimental conditions using CR4+ T cells that were plate activated and differentiated into TH9 populations. After seeding into chips, immune cells were further stimulated using activated ECM, in one embodiment comprising bound CD3 antibodies, and in another embodiment using activated ECM with both CD3 and CD28 antibodies.

| | |
|---|---|
| Flow Rate | 30 uL/hr |
| Stretch | None |
| ECM | Matrigel 100 ug/mL, Collagen I 30 ug/mL, CD3 20 ug/mL, +/−CD28 20 ug/mL |
| Differentiation Media | CD4: DMEM, 10% FBS, Penicillin/Streptomycin, anti-CD3 bound at 3 ug/mL, anti-CD28 (3 ug/mL) Th9: DMEM, 10% FBS, Penicillin/Streptomycin, anti-CD3 bound at 3 ug/mL, anti-CD28 (3 ug/mL), anti-IFNg (10 ug/mL), rhIL-2 (20 ng/mL), rhIL-4 (20 ng/mL), rhTGFb (5 ng/mL), PAM (10 ug/mL) |
| Top Media | DMEM, 10% FBS, Penicillin/Streptomycin, Phenol Red, 4.5 g/mL Glucose, Glutamine, No Pyruvate, 20 ug/mL Lucifer Yellow |
| Bottom Media | Days 0-3: EGM-2 Complete, 2% FBS, No Gentamicin, Penicillin/Streptomycin Days 3-9: EGM-2 Complete, 0.5% FBS, No Gntamicin, Penicillin/Streptomycin |

TABLE 8

Exemplary experimental cell types and seeding densities for microfluidic chips.

| Cell Type | Donor/Passage | Viability | Total # Cells | Seeding Density |
|---|---|---|---|---|
| HUVEC | — | 91% | 7.4 mill | 10 mill/mL |
| CD4 | 7/27 PBMC | — | 0.8325 mill | 0.55 mill/mL |
| Th9 | 7/27 PBMC | — | 0.198 mill | 0.55 mill/mL |
| Caco2 | — | 90% | 2 million | 1 mill/mL |

TABLE 9

Exemplary experimental conditions on chips comprising bound (insoluble) CD3 antibodies as part of the ECM for another co-stimulation of T cells seeded onto chips as plate activated and differentiated CD4+ T cells, obtained from peripheral blood lymphocytes. In some embodiments, chips comprise both C3 and CD28 as bound co-stimulatory reagents for $T_H1$ subsets.

| T-Cells | Factors | Treatment | #Chips |
|---|---|---|---|
| N/A | 1. +CD3/−CD28 | 1. Control | 6 |
| | 2. +CD3/−CD28 | 2. +PAM (10 ug/mL) | 6 |
| CD4+ | 1. +CD3/−CD28 | 1. Control | 6 |
| | 2. +CD3/−CD28 | 2. +PAM (10 ug/mL) | 6 |
| Th9 | 1. +CD3/−CD28 | 1. Control | 6 |
| | 2. +CD3/−CD28 | 2. +PAM (10 ug/mL) | 6 |
| CD4+ | 1. +CD3/+soluble CD28 | 1. +PAM (10 ug/mL) | 4 |
| | 2. +CD3/+bound CD28 | 2. +PAM (10 ug/mL) | 4 |
| | 3. −CD3/−CD28 | 3. +PAM (10 ug/mL) | 4 |

TABLE 10

Exemplary experimental conditions on chips comprising bound (insoluble) CD3 antibodies and CD28 antibodies as part of the ECM.

| Treatment | Concentration | Total Volume (ml) | Treatment Added |
|---|---|---|---|
| Control | — | 36 mL | — |
| +PAM | 10 ug/mL | 60 mL | 600 ug = 600 uL |
| ECM: +CD3 | 20 ug/mL | 2 mL | 40 uL |
| ECM: +CD3 | 20 ug/mL | 200 uL | 4 uL |
| +CD28 | 20 ug/mL | | 4 uL |

TABLE 11

Exemplary readouts, e.g. cytokine production, barrier function and expression, such as mRNA Quantitation, with amounts of samples used for analysis.

| Readouts | Cytokines - 50 uL<br>Barrier Function - 100 uL<br>RNA - use fraction of cells fixed for FACS |
|---|---|
| Chip 1 | FACS/RNA |
| Chip 2 | FACS/RNA |
| Chip 3 | FACS/RNA |
| Chip 4 | Fix for imaging |
| Chip 5 | Fix for imaging |
| Chip 6 | Fix for imaging |

These experiments showed that chips having bound CD3 and hound CD28 (one embodiment of activated ECM) in combination with the presence of a soluble antigen, PAM, causes a significant increase in the apparent permeability of the $T_H1$ Intestine On-Chip epithelial barrier over embodiments of intestine on-chip without an activated ECM embodiment, i.e. no bound CD3 or bound CD28. This embodiment of activated ECM in one embodiment of an intestine on-chip having ECM bound CD3 and bound CD28, mimics the induction of a weaker barrier function, where a weaker barrier function is one symptom (component) of both IBD subtypes, CD and UC.

Figure 43:
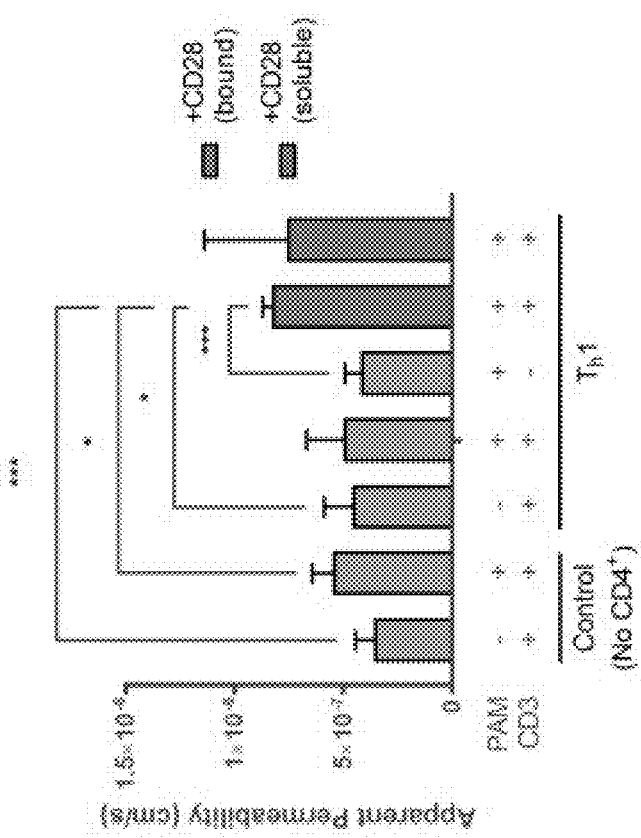
FIG. 43 shows exemplary results of measuring barrier function after the addition of bound activation reagents on-chip with exposure to antigen. The graph demonstrates that bound antiCD3, with soluble or bound anti-CD28, for co-stimulation of $T_H1$ cells in the presence of antigen has a significant impact on decreasing the barrier function of the intestine On-Chip. The decreasing barrier function is represented as an increase in permeability.

FIG. 43 shows exemplary results of measuring barrier function after the addition of bound activation reagents on-chip with exposure to antigen. The graph demonstrates that bound CD3, with soluble or bound CD28, for co-stimulation of $T_H1$ cells in the presence of antigen has a significant impact on decreasing the barrier function of the Intestine On-Chip. The decreasing barrier function is represented as an increase in permeability.

Further, these experiments showed that $T_H1$ Intestine On-Chip having bound CD3 and bound CD28 (one embodiment of activated ECM) in combination with the presence of a soluble antigen, PAM, causes a significant increase (up-regulation) of inflammatory cytokine production, e.g. IFN-gamma and IL-10, in Intestine On-Chip, in vitro. In vivo, IFNgamma and IL-10 production are associated with the Th1 T-cell subset and CD. This upregulation is in contrast to insignificant increases of IL-9, IL-13, IL-6 and IL-8 production from TH1 cells in Intestine On-Chip, see, FIGS. 44A-D and 45A-B.

FIGS. 44A-D shows exemplary results of measuring immune cytokine expression after the addition of bound activation reagents on-chip with exposure to antigen. The graphs demonstrate that bound CD3 with soluble or bound CD28 for co-stimulation of $T_H1$ cells in the presence of antigen show a significant increased in IFN-gamma but not IL-9 using bound CD3 and CD28 in the presence of soluble antigen. Thus, binding both CD3 and CD28 to the membrane causes a significant upregulation in inflammatory cytokine production on the Intestine On-Chip for $T_H1$ cells. FIG. 44A shows IFN-gamma production. FIG. 44B shows IL-9 production. FIG. 44C shows IL-10 production. FIG. 44D shows IL-13 production.

Figure 45B:
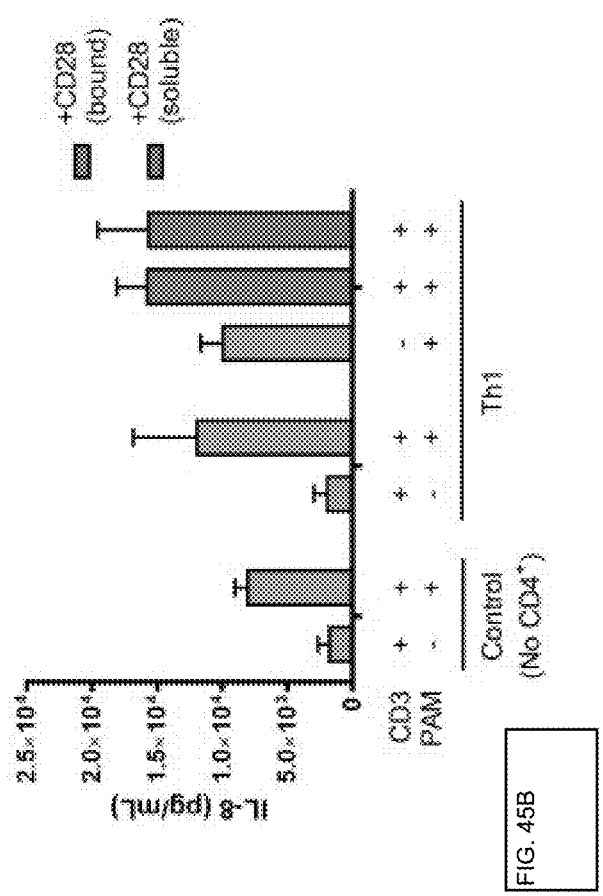
FIGS. 45A-B shows exemplary results of measuring epithelial cytokine expression using activated ECM as hound anti-CD3 with soluble or bound CD28 for co-stimulation of TH1 cells in the presence of antigen.
Figure 45A:
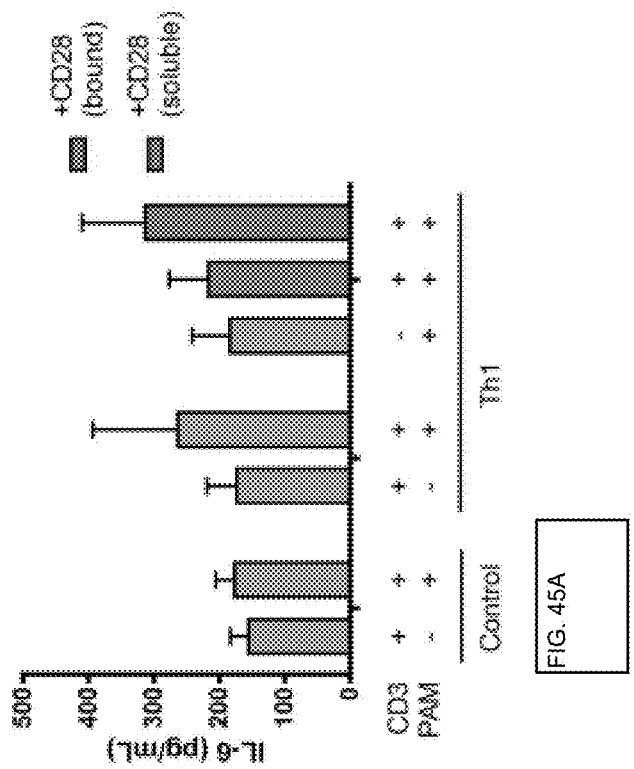

FIGS. 45A-B shows exemplary results of measuring epithelial cytokine expression using activated ECM as bound CD3 with soluble or bound CD28 for co-stimulation of TH1 cells in the presence of antigen. FIG. 45A shows IL-6 production. FIG. 45B IL-8 production.

FIGS. 46A-C shows exemplary results of measuring epithelial cytokine expression in the presence of T cells and activated ECM. In this embodiment as intestine on-chips having bound CD3 antibodies. In combination with bound CD28 or soluble CD28 co-stimulation of $T_H1$ cells. FIG. 46A TNF alpha cytokine expression. FIG. 46B IL-1b cytokine expression FIG. 46C shows an exemplary key for experimental conditions: control, antigen stimulation (PAM). In the presence of soluble CD28, bound CD28 and T cells without activated ECM (i.e. inactivated).

Thus, Inflammatory cytokine production by immune cell populations differentiated into a $T_H1$ subsets in Intestine On-Chips treated with soluble CD28 mimics elevated cytokine levels found in the mucosa of CD patients. Addition of bound CD3 and CD28 causes a significant increase in permeability of the epithelial layer, resulting in a weaker barrier function. A weaker barrier function in the intestine is a major component of both IBD subtypes.

Double-Bound (CD3 and CD28) Membrane in Intestine On-Chips Comprising $T_H1$ or $T_H9$ Immune Cells.

In one embodiment, an activated ECM is a double-bound (CD3 and CD28) membrane On-Chip. This embodiment was evaluated for its effect of continuous activation of a T cell subset over time. A CD4+ T cell subset was purified from PBMCs, activated by tissue culture plate bound CD3 antibodies and differentiated into a desired T cell subset over 3 days of incubation at 37° C., without cytokines for producing predominantly a CD4+ $T_H1$ cell population, or with cytokines for producing a predominantly CD4+ $T_H9$ cell population. On Day 3 of stimulation, a desired CD4+ T cell subpopulation was seeded into microfluidic intestine on-chips. On Day 7, the chips were treated using exemplary factors and one of the treatments as shown in exemplary Table 12.

Figure 47:
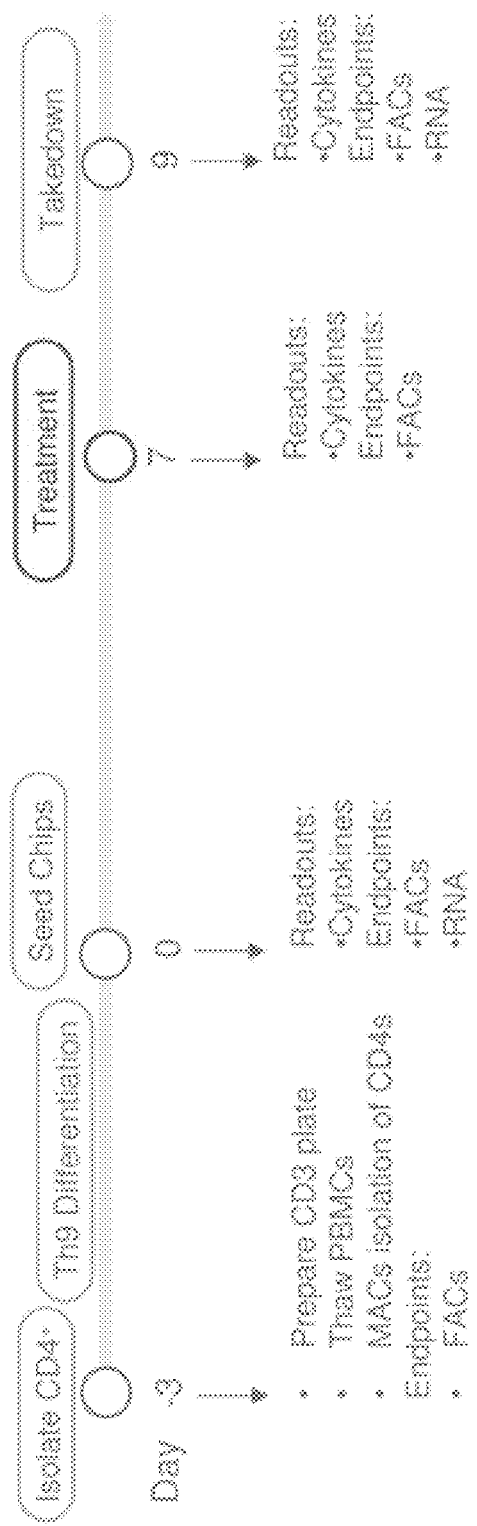
FIG. 47 shows a schematic representation demonstrating an exemplary timeline for experiments on chips comprising both anti-CD3 and anti-CD28, i.e. a double-bound chip, seeded with $T_H1$ (CD4+) or $T_H9$ populations in the presence of antigen, e.g. PAM. These T cell populations were activated and differentiated into subsets using CD3 antibody coated tissue culture plates co-stimulated with soluble CD28 antibodies (Day −3 to Day 0). See, FIG. 34 for additional details for the exemplary timeline of providing on-plate activated and differentiated T cell subsets. Treatment of immune cells on-chip was on Day 7 with Takedown on Day 9.

FIG. 47 shows a schematic representation demonstrating an exemplary timeline for experiments on chips comprising both CD3 and CD28, i.e. a double-bound chip, seeded with $T_H1$ (CD4+) or $T_H9$ populations in the presence of antigen, e.g. PAM. These T cell populations were activated and differentiated into subsets using CD3 antibody coated tissue culture plates co-stimulated with soluble CD28 antibodies (Day −3 to Day 0). See, FIG. 34 for additional details for the exemplary timeline of providing on-plate activated and differentiated T cell subsets. Treatment of immune cells on-chip was on Day 7 with Takedown on Day 9.

TABLE 12

Exemplary experimental conditions on-chips comprising one activated ECM embodiment comprising bound (insoluble) CD3 antibodies and bound (insoluble) CD28 antibodies (i.e. double bound chip) for co-stimulation of T cells in the presence of antigen (PAM). Exemplary factors and treatments for T cells on-chips on Day 7 are shown, in addition to an exemplary number of chips. Chips are seeded on Day 0 with plate activated and differentiated CD4+ T cells (Day −3 to Day 0). T cells on chips were exposed to soluble antigen.

| T-cells | Factors | Treatment | # Chips |
|---------|---------|-----------|---------|
| N/A | 1. +CD3/+bound CD28 | 1. Control | 6 |
|  | 2. +CD3/+bound CD28 | 2. +PAM (10 ug/mL) | 6 |
| CD4+ | 1. +CD3/+bound CD28 | 1. Control | 6 |
|  | 2. +CD3/+bound CD28 | 2. +PAM (10 ug/mL) | 6 |
| TH9 | 1. +CD3/+bound CD28 | 1. Control | 6 |
|  | 2. +CD3/+bound CD28 | 2. +PAM (10 ug/mL) | 6 |

Thus, in some embodiments, CD4+ $T_H1$ populations' on-chips were compared to $T_H9$ populations' on-chips, where the chips comprised activated ECM having both CD3 and CD28. In some contemplated embodiments, intestine on-chips comprising activated ECM having both CD3 and CD28 are contemplated to mimic immune microenvironment of IBDs. In some contemplated embodiments. Inflammatory responses by activated T cells are measured when treated with soluble antigen.

Evaluating Effect of Double-Bound (CD3 and CD28) Membrane on Intestine-Chips with $T_H1$ and $T_H9$ Immune Cells.

This example describes experiments using activated ECM comprising both CD3 and CD28 antibodies in the presence of soluble antigen for $T_H1$ compared to $T_H9$ immune cells. Soluble antigen was added as treatment on Day 7.

FIG. 47 shows a schematic representation demonstrating an exemplary timeline for experiments on chips seeded with $T_H1$ or $T_H9$ populations, activated and differentiated into subsets using CD3 antibody coated tissue culture plates co-stimulated with soluble CD28 antibodies (Day −3 to Day 0). See, FIG. 34 for additional details for the exemplary timeline of providing plate activated and differentiated T cell subsets, i.e. Day −3 to Day 0 of chip seeding. Treatment of immune cells on-chip includes an additional stimulation using bound activation reagents, CD3 antibodies and CD28 antibodies in the presence of antigen.

Figure 48:
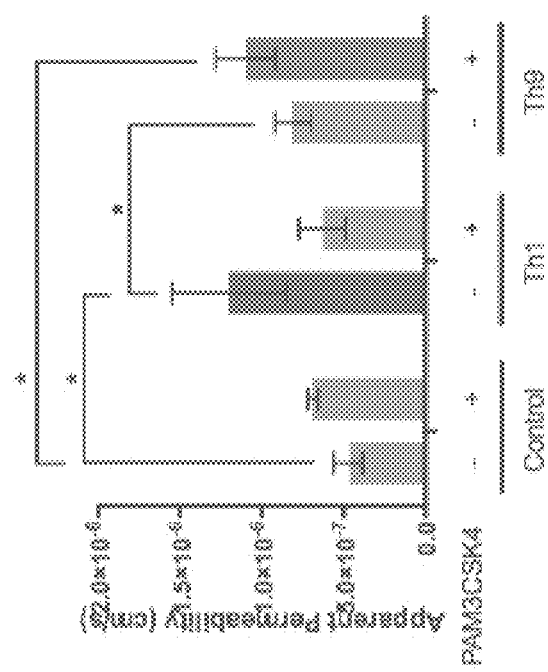
FIG. 48 shows exemplary results of measuring apparent permeability using a double bound activated ECM, with or without antigen, comparing $T_H1$ and $T_H9$ populations.

FIG. 48 shows exemplary results of measuring apparent permeability using a double bound activated ECM, with or without antigen, comparing $T_H1$ and $T_H9$ populations.

The addition of bound CD3 and CD28 has a significant affect on the barrier function of the Intestine-Chip in the presence of $T_H1$ or $T_H9$ cells.

When bound to the Intestine-Chip membrane, CD3 and CD28 were able to activate the $T_H1$ and $T_H9$ immune response, simulating Crohn's and Ulcerative Colitis diseased states, respectively.

Thus, culturing T cell subpopulations, e.g. $T_H1$ and $T_H9$, in the presence of ECM bound CD3 and CD28, in an intestine on-chip caused a significant increase in the apparent permeability of the epithelial barriers in both $T_H1$ and $T_H9$ Intestine On-Chips.

Therefore, exacerbation of antigen induced inflammatory reactions in TH populations in an Intestine On-Chip was caused by cell receptor signal activation, i.e. insoluble co-stimulatory molecules. This type of in vitro on-chip exacerbated inflammation response is contemplated to characterize the type of exacerbated inflammation observed in biopsies of inflammatory regions of in vivo IBDs.

II. Closed Top Chips.

The present disclosure relates to gut-on-chips, such as fluidic devices comprising one or more cells types for the simulation one or more of the function of gastrointestinal tract components. Accordingly, the present disclosure additionally describes closed-top intestine-on-chips, see, e.g. schematic in FIG. 5A-B.

A. Closed Top Microfluidic Chips without Gels.

In one embodiment, closed top gut-on-chips do not contain gels, either as a bulk gel or a gel layer. Thus, in one embodiment, the device generally comprises (i) a first structure defining a first chamber; (ii) a second structure defining a second chamber; and (iii) a membrane located at an interface region between the first chamber and the second chamber to separate the first chamber from the second chamber, the membrane including a first side facing toward the first chamber and a second side facing toward the second chamber, wherein the first and second chambers are enclosed. The first side of the membrane may have an extracellular matrix composition disposed thereon, wherein the extracellular matrix (ECM) composition comprises an ECM coating layer. In some embodiments, an ECM gel layer e.g. ECM overlay, is located over the ECM coating layer.

Additional embodiments are described herein that may be incorporated into closed top chips without gels.

B. Closed Top Microfluidic Chips with Gels.

In one embodiment, closed top gut-on-chips do contain gels, such as a gel layer, or bulk gel. Including but not limited to a gel matrix, hydrogel, etc. Thus, in one embodiment, the device generally comprises (i) a first structure defining a first chamber; (ii) a second structure defining a second chamber; and (iii) a membrane located at an interface region between the first chamber and the second chamber to separate the first chamber from the second chamber, the membrane including a first side facing toward the first chamber and a second side facing toward the second chamber, wherein the first and second chambers are enclosed. In some embodiments, the device further comprises a gel. In some embodiments, the gel is a continuous layer. In some embodiments, the gel is a layer of approximately the same thickness across the layer. In some embodiments, the gel is a discontinuous layer. In some embodiments, the gel has different thicknesses across the layer. In some embodiments, the first side of the membrane may have a gel layer. In some embodiments, a gel is added to the first side of the membrane without an ECM layer. The first side of the membrane may have an extracellular matrix composition disposed thereon, wherein the extracellular matrix (ECM) composition comprises an ECM coating layer. In some embodiments, an ECM gel layer e.g. ECM overlay, is located over the ECM coating layer. In some embodiments, the gel layer is above the ECM coating layer. In some embodiments, the ECM coating layer may have a gel layer on the bottom, i.e. the side facing the membrane. In some embodiments, the gel overlays the ECM gel layer.

Additional embodiments are described herein that may be incorporated into closed top chips with gels.

C. Closed Top Microfluidic Chips with Simulated Lumens.

A closed top gut-on-chip comprising a gel-lined simulated lumen may be used for generating a more physiological relevant model of gastrointestinal tissue. In some embodiments, closed top gut-on-chips further comprise a gel simulated three-dimensional (3-D) lumen. In other words, a 3-D lumen may be formed using gels by providing simulated intestinal villi (e.g. viscous fingers) and/or mimicking intestinal folds. In a preferred embodiment, the gel forms a lumen, i.e. by viscous fingering patterning.

Using viscous fingering techniques, e.g. viscous fingering patterning, a simulated intestinal lumen may be formed by numerous simulated intestinal villi structures. Intestinal villi (singular: villus) refer to small, finger-like projections that extend into the lumen of the small intestine. For example, healthy small intestine mucosa contains these small finger-like projections of tissue that are present along the lumen as folds of circular plica finger-like structures, see, FIG. 4A-B. A villus is lined on the luminal side by an epithelial cell layer, where the microvillus of the epithelial cells (enterocytes) faces the lumen (i.e. apical side). Viscous fingers may be long and broad, for mimicking villi in the duodenum of the small intestine, while thinner or shorter viscous fingers may be used for mimicking villi in other parts of the gastrointestinal tract. As one example, viscous fingers may be formed and used to mimic epithelial projections in the colon.

Methods to create three-dimensional (3-D) lumen structures in permeable matrices are known in the art. One example of a 3-D structure forming at least one lumen is referred to as "viscous fingering". One example of viscous fingering methods that may be used to for form lumens, e.g. patterning lumens, is described by Bischel, et al. "A Practical Method for Patterning Lumens through ECM Hydrogels via Viscous Finger Patterning," J Lab Autom, 2012 April; 17(2) 96-101 Author manuscript; available in PMC 2012 Jul. 16, herein incorporated by reference in its entirety. In one example of a viscous finger patterning method for use with microfluidic gut-on-chips, lumen structures are patterned with an ECM hydrogel.

"Viscous" generally refers to a substance in between a liquid and a solid, i.e. having a thick consistency. A "viscosity" of a fluid refers to a measure of its resistance to gradual deformation by shear stress or tensile stress. For liquids, it corresponds to an informal concept of "thickness"; for example, honey has a much higher viscosity than water.

"Viscous fingering" refers in general to the formation of patterns in "a morphologically unstable interface between two fluids in a porous medium.

A "viscous finger" generally refers to the extension of one fluid into another fluid. Merely as an example, a flowable gel or partially solidified gel may be forced, by viscous fingering techniques, into another fluid, into another viscous fluid in order to form a viscous finger, i.e. simulated intestinal villus.

In some embodiments, the lumen can be formed by a process comprising (i) providing the first chamber filled with a viscous solution of the first matrix molecules; (ii) flowing at least one or more pressure-driven fluid(s) with low viscosity through the viscous solution to create one or more lumens each extending through the viscous solution; and (iii) gelling, polymerizing, and/or cross linking the viscous solution. Thus, one or a plurality of lumens each extending through the first permeable matrix can be created.

In another embodiment, gel is added to a channel for making a lumen.

In some embodiments as described herein, the first and second permeable matrices can each independently comprise a hydrogel, an extracellular matrix gel, a polymer matrix, a monomer gel that can polymerize, a peptide gel, or a combination of two or more thereof. In one embodiment, the first permeable matrix can comprise an extracellular matrix gel, (e.g. collagen). In one embodiment, the second permeable matrix can comprise an extracellular matrix gel and/or protein mixture gel representing an extracellular miroenviroment, (e.g. MATRIGEL®. In some embodiments, the first and second permeable matrixes can each independently comprise a polymer matrix. Methods to create a permeable polymer matrix are known in the art, including, e.g., but not limited to, particle leaching from suspensions in a polymer solution, solvent evaporation from a polymer solution, sold-liquid phase separation, liquid—liquid phase separation, etching of specific "block domains" in block co-polymers, phase separation to block-co-polymers, chemically cross-linked polymer networks with defined permabilities, and a combination of two or more thereof.

Another example for making branched structures using fluids with differing viscosities is described in "Method And System For integrating Branched Structures In Materials" to Katrycz, Publication number US20160243738, herein incorporated by reference in its entirety.

Regardless of the type of lumen formed by a gel and/or structure, cells can be attached to theses structures either to lumen side of the gel and/or within the gel and/or the side of the gel opposite the lumen. Thus, three-dimensional (3-D) lumen gel structures may be used in several types of embodiments for closed top microfluidic chips, e.g. epithelial cells can be attached to outside of the gel, or within the gel. In some embodiments, LPDCs may be added within the gel, or below the gel, on the opposite side of the lumen. In some embodiments, stoma cells are added within the gel. In some embodiments, stomal cells are attached to the side of the gel opposite from the lumen. In some embodiments, endothelial cells are located below the gel on the side opposite the lumen. In some embodiments, endothelial cells may be present within the gel.

Additional embodiments are described herein that may be incorporated into closed top chips with simulated 3D lumens containing a gel.

III. Open Top Micrufluidic Chips.

Figure 24:
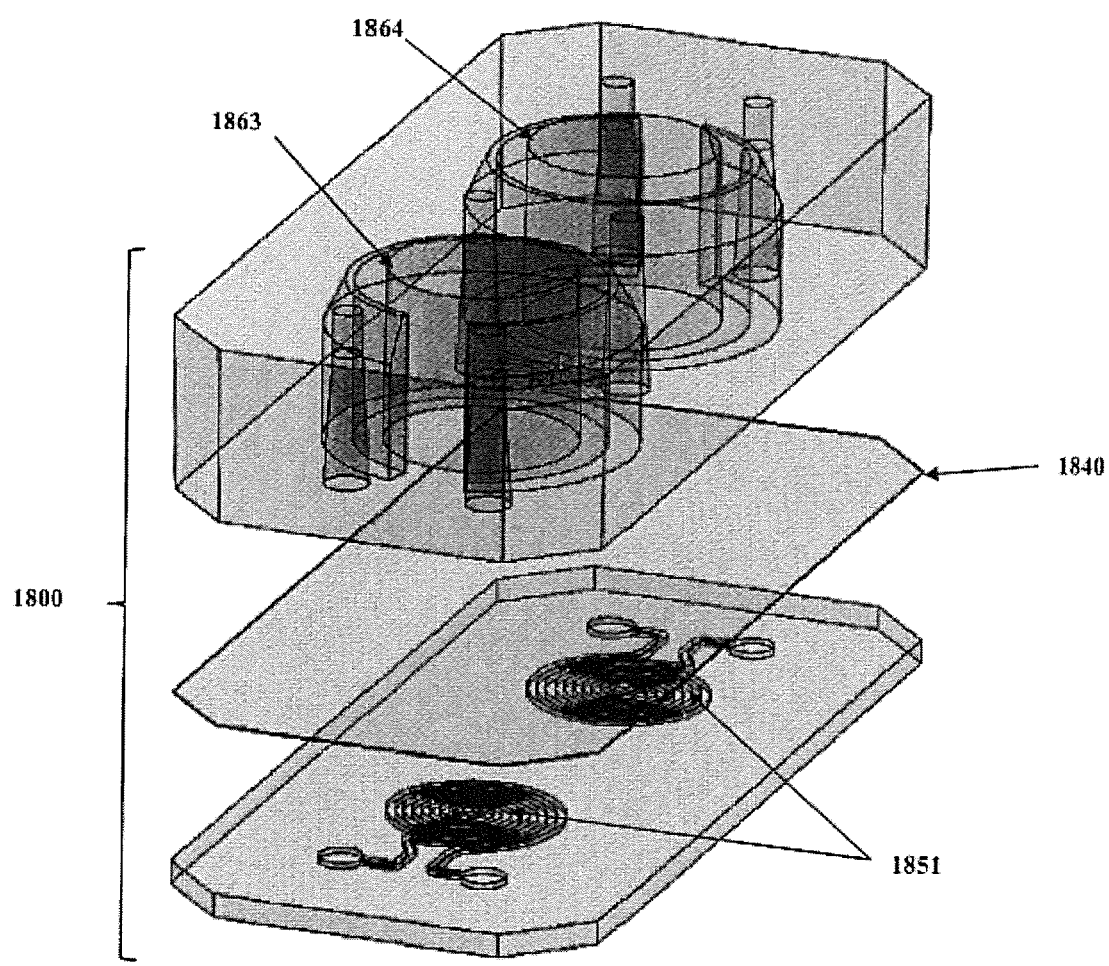
FIG. 24 shows an exemplary schematic of an open top microfluidic chip.

The present disclosure relates to gut-on-chips, such as fluidic devices comprising one or more cells types for the simulation one or more of the function of gastrointestinal tract components. Accordingly, the present disclosure additionally describes open-top gut-on-chips, see, e.g. schematic in FIG. 24, FIG. 24 shows an exemplary exploded view of one embodiment of an open-top chip device 1800, wherein a membrane 1840 resides between the bottom surface of the first chamber 1863 and the second chamber 1864 and the at least two spiral microchannels 1851. Open top microfluidic chips include but are not limited to chips having removable covers, such as removable plastic covers, paraffin covers, tape covers, etc.

Many of the problems associated with earlier systems can be solved by providing an open-top style microfluidic device that allows topical access to one or more parts of the device or cells that it comprises. For example, the microfluidic device can include a removable cover, that when removed, provides access to the cells of interest in the microfluidic device. In some aspects, the microfluidic devices include systems that constrain fluids, cells, or biological components to desired area(s). The improved systems provide for more versatile experimentation when using microfluidic devices. Including improved application of treatments being tested, improved seeding of additional cells, and/or improved aerosol delivery for select tissue types.

It is also desirable in some aspects to provide access to regions of a cell-culture device. For example, it can be desirable to provide topical access to cells to (i) apply topical treatments with liquid, gaseous, solid, semi-solid, or aerosolized reagents, (ii) obtain samples and biopsies, or (iii) add additional cells or biological/chemical components.

Therefore, the present disclosure relates to fluidic systems that include a fluidic device, such as a microfluidic device with an opening that provides direct access to device regions or components (e.g. access to the gel region, access to one or more cellular components, etc.). Although the present disclosure provides an embodiment wherein the opening is at the top of the device (referred to herein with the term "open top"), the present invention contemplates other embodiments where the opening is in another position on the device. For example, in one embodiment, the opening is on the bottom of the device. In another embodiment, the opening is on one or more of the sides of the device. In another embodiment, there is a combination of openings (e.g. top and sides, top and bottom, bottom and side, etc.).

While detailed discussion of the "open top" embodiment is provided herein, those of ordinary skill in the art will appreciate that many aspects of the "open top" embodiment apply similarly to open bottom embodiments, as well as open side embodiments or embodiments with openings in any other regions or directions, or combinations thereof. Similarly, the device need not remain "open" throughout its use; rather, as several embodiments described herein illustrate, the device may further comprise a cover or seal, which may be affixed reversibly or irreversibly. For example, removal of a removable cover creates an opening, while placement of the cover back on the device closes the device. The opening, and in particular the opening at the top, provides a number of advantages, for example, allowing (i) the creation of one or more gel layers for simulating the application of topical treatments on the cells, tissues, or organs, or (ii) the addition of chemical or biological components such as the seeding of additional cell types for simulated tissue and organ systems. The present disclosure further relates to improvement in fluidic system(s) that improve the delivery of aerosols to simulated tissue and organ systems, such as simulated gastrointestinal tissues.

The present invention contemplates a variety of uses for these open top microfluidic devices and methods described herein. In one embodiment, the present invention contemplates a method of topically testing an agent (whether a drug, food, gas, or other substance) comprising 1) providing a) an agent and b) microfluidic device comprising i) a chamber, said chamber comprising a lumen and projections into the lumen, said lumen comprising ii) a gel matrix anchored by said projections and comprising cell in, on or under said gel matrix, said gel matrix positioned above iii) a porous membrane and under iv) a removable cover, said membrane in contact with v) fluidic channels; 2) removing said removable cover; and 3) topically contacting said cells in, on or under said gel matrix with said agent. In, one embodiment, said agent is in an aerosol. In one embodiment, agent is in a liquid, gas, gel, semi-solid, solid, or particulate form. These uses may apply to the open top microfluidic chips described below and herein.

A. Open Top Microfluidic Chips without Gels.

In one embodiment, open top gut-on-chips do not contain gels, either as a bulk gel or a gel layer. Thus, the present invention also contemplates, in one embodiment, a layered structure comprising i) fluidic channels covered by ii) a porous membrane, said membrane comprising iii) a layer of cells and said membrane positioned below said cells. In one embodiment, there is a removable cover over the cells.

Additional embodiments are described herein that may be incorporated into open top chips without gels.

B. Open Top Microfluidic Chips with Gels.

Furthermore, the present disclosure contemplates improvements to fluidic systems that include a fluidic device, such as a microfluidic device with an open-top region that reduces the impact of stress that can cause the delamination of tissue or related component(s) (e.g., such as a gel layer). Thus, in a preferred embodiment, the open-top microfluidic device comprises a gel matrix. In one embodiment, the open-top microfluidic device does not contain a bulk gel.

The present invention also contemplates, in one embodiment, a layered structure comprising i) fluidic channels covered by ii) a porous membrane, said membrane comprising iii) a layer of cells and said membrane positioned below iv) a gel matrix. In one embodiment, there is a removable cover over the gel matrix (and/or cells). It is not intended that the present invention be limited to embodiments with only one gel or gel layer. In one embodiment, the layered structure further comprises a second gel matrix (e.g. positioned under said membrane). The gel(s) or coatings can be patterned or not patterned. Moreover, when patterned, the pattern need not extend to the entire surface. For example, in one embodiment, at least a portion of said gel matrix is patterned. It is not intended that the present invention be limited by the nature or components of the gel matrix or gel coating. In one embodiment, gel matrix comprises collagen. A variety of thickness is contemplated. In one embodiment of the layered structure, said gel matrix is between 0.2 and 6 mm in thickness.

Also described is a simulated lumen further comprising gel projections into the simulated lumen. Thus, in yet another embodiment, the present invention contemplates a microfluidic device comprising i) a chamber, said chamber comprising a lumen and projections in the lumen, said lumen comprising ii) a gel matrix anchored by said projections, said gel matrix positioned above iii) a porous membrane, said membrane in contact with iv) fluidic channels. In one embodiment, said membrane comprises cells. The projections serve as anchors for the gel. The projections, in one embodiment, project outward from the sidewalls. The projections, in another embodiment, project upward. The projects, in another embodiment, project downward. The projections can take a number of forms (e.g. a T structure, a Y structure, a structure with straight or curving edges, etc). In some embodiments, there are two or more projections; in other embodiments, there are four or more projections to anchor the gel matrix. In one embodiment, the membrane is above said fluidic channels.

In other embodiments, open top microfluidic chips comprise partial lumens as described herein for closed top chips. Thus, in some embodiments, open top microfluidic, chips comprise lumens formed by viscous fingering described herein for closed top chips.

Lumen gel structures may be used in several types of embodiments for open top microfluidic chips, e.g. epithelial cells or parenchymal cells can be attached to outside of the gel, or within the gel. In some embodiments, LPDCs may be added within the gel, below the gel, or above the gel. In some embodiments, stomal cells are added within the gel. In some embodiments, stomal cells are attached to the side of the gel opposite from the lumen. In some embodiments, endothelial cells are located below the gel on the side opposite the lumen. In some embodiments, endothelial cells may be present within the gel.

Additional embodiments are described herein that may be incorporated into open top chips with gels, with or without gels.

IV. Exemplary Gut-On-Chips.
Modeling Immune Activation with Primary Resident Immune Cells.

As described herein, Primary Resident Immune Cells were Isolated from Donor Intestinal Lamina Propria.

Figure 50B:
FIG. 50B shows a micrograph of a hematoxylin and eosin stained intestinal biopsy. 1. Crypt. 2. Lamina Propria.
Figure 50A:
FIG. 50A shows a representation of an intestinal cell layer on top of a basement membrane, endothelial cells (surrounding capillaries) in the underlying lamina propria involved with inflammatory bowel disease (IBD).

FIG. 50A shows a representation of an intestinal cell layer on top of a basement membrane, endothelial cells (surrounding capillaries) in the underlying lamina propria involved with inflammatory bowel disease (IBD).

FIG. 50B shows a micrograph of a hematoxylin and eosin stained intestinal biopsy. 1. Crypt. 2. Lamina Propria.

Figure 51:
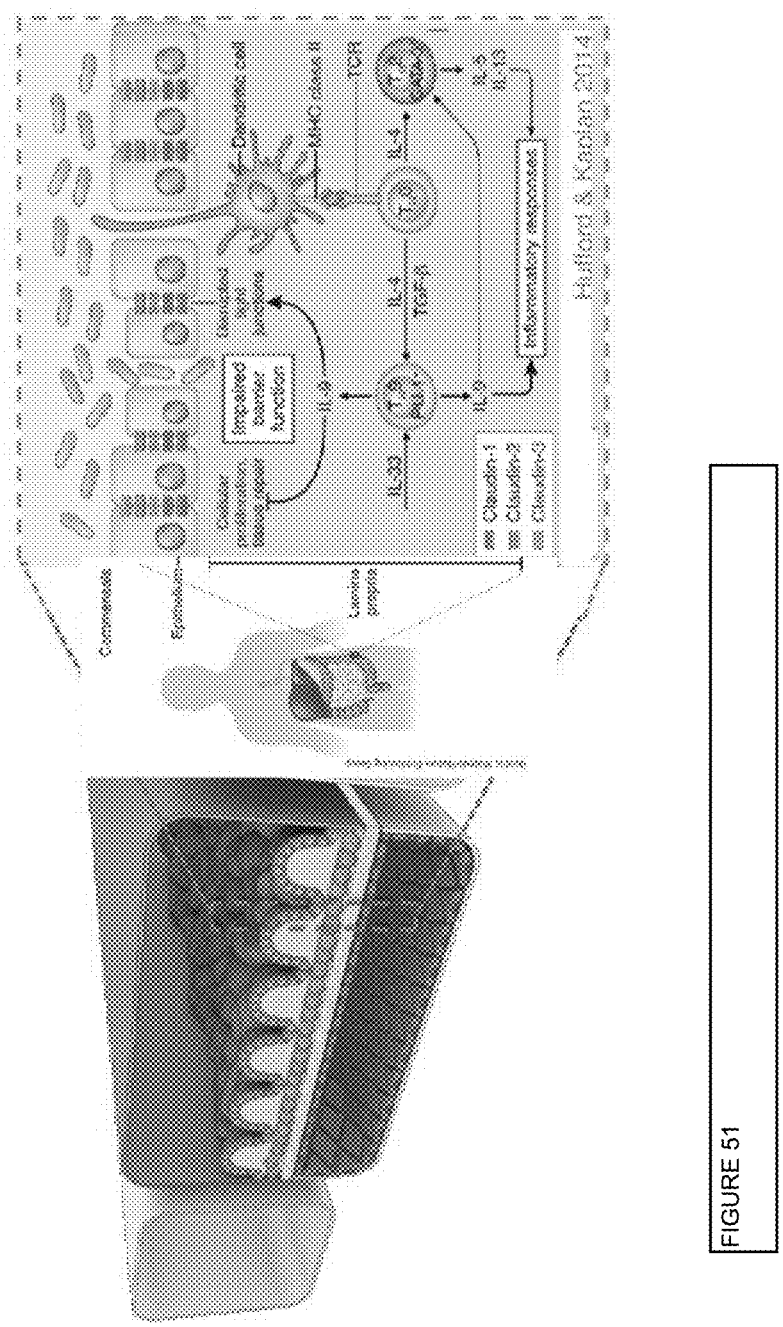
FIG. 51A shows one embodiment of primary resident immune cells in an Intestine On-Chip compared to FIG. 51B a schematic showing contemplated immune cell interactions in the presence of commensal bacteria. A schematic of IL-9 action, which weakens the epithelium and induces inflammatory responses, is depicted in FIG. 51B.

FIGS. 51A-shows one embodiment of primary resident immune cells in an Intestine On-Chip compared to FIG. 51B a schematic showing contemplated immune cell interactions in the presence of commensal bacteria. A schematic of IL-9 action, which weakens the epithelium and induces inflammatory responses, is also depicted in FIG. 51B.

Thus, in vivo, antigen-presenting cells, expressing cell-bound activation molecules, activate cells that are part of the adaptive immune response in the lamina propria. Such cells may include pre-activated and differentiated T cell subsets. Such pre-activated and differentiated T cell subsets may be simulated by methods of plate-activation and differentiation as described herein. Therefore, membrane-bound immune activating factor(s) on chip, i.e. activated ECM, may more accurately simulate immune activation in vivo, i.e. restimulation of activated T cell subsets in the presence of antigen.

A. Chip Culture Timeline and Example of a Gut-On-Clip.

Figure 6:
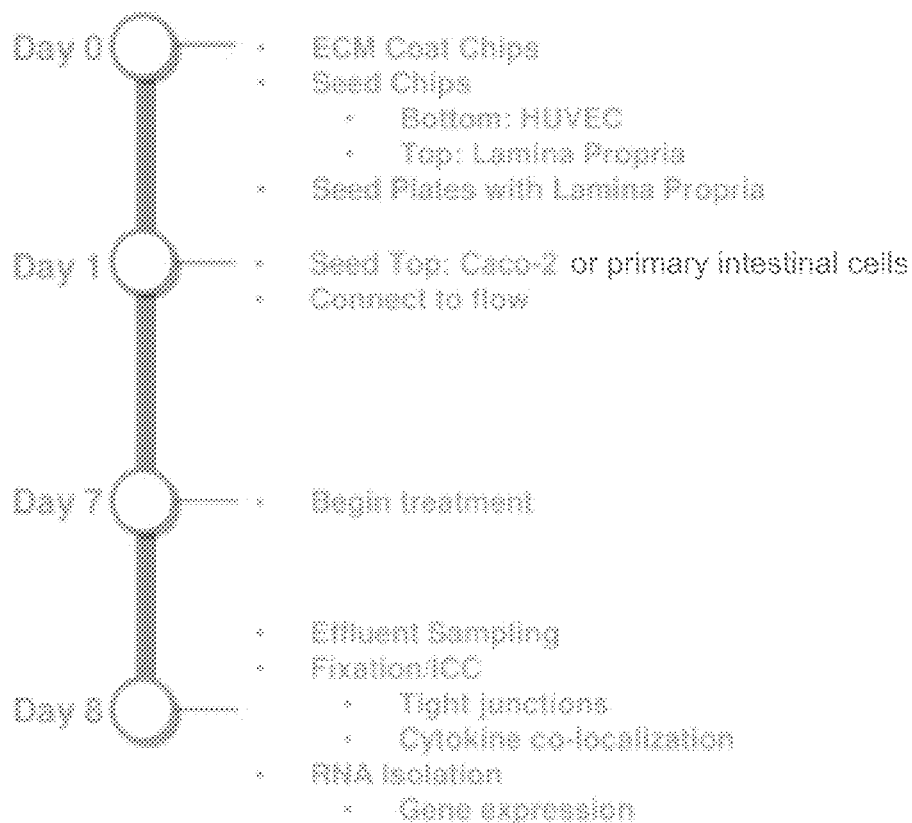
FIG. 6 shows an exemplary experimental timeline from Day 0 (seeding chips) adding HUVEC cells and lamina propria derived cells; Day 1 seeding a top layer of epithelial cells and connecting to flow; Day 7 beginning treatment; and by Day 8 testing layers and or removing samples for further analysis.

An exemplary experimental chip culture schedule is presented as a timeline starting from Day 0 (seeding chips) by adding HUVEC cells and lamina propria-derived cells; Day 1 was seeding a top layer of epithelial cells and connecting to a flow system; by Day 7 treatments, such as adding PAM2CSK4; and starting Day 8 testing layers and/or removing samples for further analysis. A sample such as effluent was tested for cytokine section from cells. Other samples removed were histological samples for fixation and ICC (immunocytochemistry) such as for determining cellular appearance, determination of tight junction integrity, such as by staining for actin, ZO-1, intracellular cytokine co-localization, etc, and physiological testing, such as migration of particles through the extracellular regions of the epidermal layer. Additional tests may include RNA isolation for determining gene expression levels, such as for proteins involved with tight junction formation, cytokine expression, etc. An exemplary timeline is shown in FIG. 6.

An exemplary gut-on-chip was assembled using the protocol described in Example 1 and the chip culture schedule described above. Samples were removed, fixed then immunoflorescently stained as described herein. DAPI was used in solution to identify nuclear DNA. FIG. 5A-B shows exemplary immunofluorescently stained histological micrographs of three layers in a cross section of for one embodiment of Intestine-On-Chip. Top layer (right) is an epithelial channel of Caco-2 cells which is shown in the top (left) micrograph as cells outlined in red ZO-1 (Zonula occludens-1, also known as Tight junction protein-1) outlining cells with nuclei stained by DAN (4',6-diamidino-2-phenylindole) fluorescent stain in blue. Note that the apical microvilli are depicted facing away from the other cells in the chip. Underneath the epithelium (right), on the basal side, is the layer of resident immune cells (* lamina propria-derived cells), which in the middle (left) micrograph shows CD45+ (a lymphocyte common antigen expressed on leucocytes) cells in pink, with intracellular green actin fibers and nuclei stained by DAPI in blue. The lower vascular channel (right) shows a channel formed by HUVECs which in the lower (right) micrograph shows red VE-Cadherin (vascular endothelial cadherin) outlining the cells. Intracellular green actin fibers, and nuclei stained by DAPI in blue.

Figure 8:
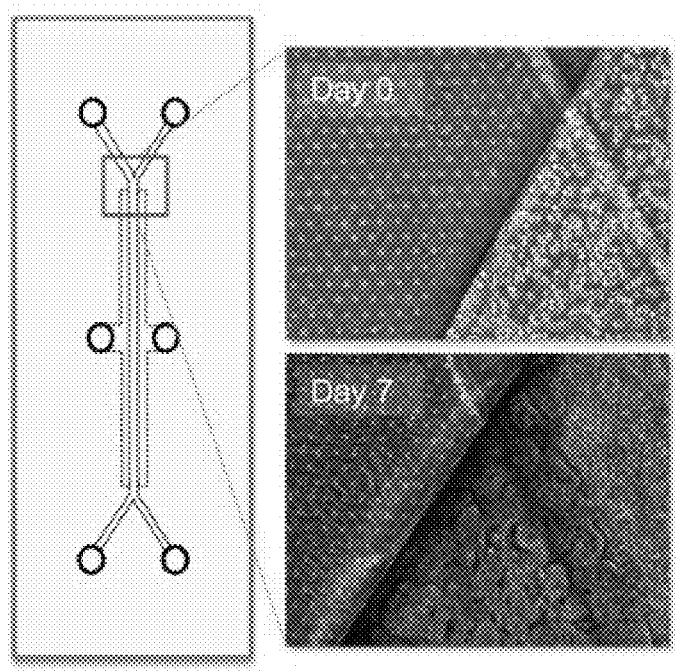
FIG. 8 shows an exemplary morphology of an Intestine-On-Chip (left schematic) along with a timeline: Day 0 (chips seeded) top micrograph of the area identified on the chip channels by a box; Day 1 connecting to flow; Day 2 monolayer developed; Day 7 'Villus' developed (bottom micrograph of the area identified on the chip channels by a box).

An exemplary morphology timeline was determined based upon appearance of the cells over time in the device and configuration described above. FIG. 8 shows an exemplary morphology of an Intestine-On-Chip (left schematic) along with a morphology timeline based upon appearance of the cells in the device over time: Day 0 (chips seeded) top micrograph of the area identified on the chip channels by a box; Day 1 connecting to flow; Day 2 monolayer developed; Day 7 'Villus' developed (bottom micrograph of the area identified on the chip channels by a box).

Thus, the inventors designed a Quality Control method for identifying a gut-on-chip that passes minimum requirements for use in embodiments described herein. FIG. 9A-B shows an exemplary embodiment for Intestine-on-Chip: Quality Control. FIG. 9A) permeability ($P_{app}$ (cm/s)) and FIG. 9B) viability (LDH release as a percent of lysis control) of cells over time. This permeability assay method for adsorption across a gut wall, i.e. caco-2 cells in a gut-on-chip, or human primary epithelial cells in a gut-on-chip, measures the rate of transport of a test compound added to the basal side of the membrane, for example, inulin-FITC, across to the apical side.

Conversely, adding a test compound to the apical side may also be used to measure transport to the basal side. This viability assay method is based on the leakage of a cytoplasmic enzyme, lactate dehydrogenase (LDH) from dying cells.

The use of this inventive gut-on-chip showed that a culture of primary (healthy) leukocytes (LPDCs) was maintained up to 9 days.

B. Use of a Gut-On-Chip for Modeling Ulcerative Colitis (UC).

Resident immune cells (B cells, T cells, dendritic cells, macrophages, and innate lymphoid cells) were isolated from contrail and Ulcerative Colitis (UC) patients including inflamed and non-inflamed regions of patient tissue. These cells were used as lamina propria-derived resident immune cells in a Gut-On-Chip as described above.

UC Lamina Propria-Derived Cells Disrupt Epithelial Barrier Function.

Inflamed UC LP resident immune cells increases permeability of epithelial cells when co-cultured in a device of the present inventions.

FIG. 10 shows an exemplary disrupted barrier function of around $0.5 \times 10^{-7}$ $P_{app}$ (cm/s) (apparent permeability) by co-culturing caco-2 epithelial cells and HUVECs with leukocytes isolated from inflamed UC tissue. Untreated controls for comparison use healthy LP derived cells and no LP cells in Gut-On-Chips for comparisons. Treated samples used leukocytes isolated from non-inflamed UC LP compared to inflamed UC LP, which induce a weakened barrier function in the co-cultured epithelial cells.

C. Toll Like Receptor 2 (TLR2) Activation Stimulates an Ulcerative Colitis-Like Responses.

Figure 7:
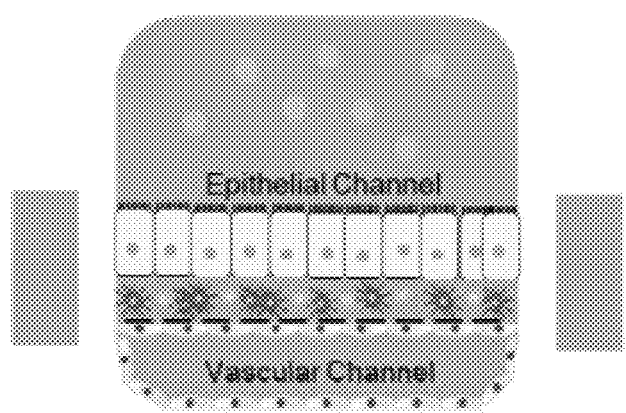
FIG. 7 shows an exemplary Gut-On-Chip Culture Schematic, where the microfluidic areas are shown in grey. An epithelial channel, containing a monolayer of epithelial cells with the microvillus on the upper side of the cells, is located above a vascular channel, containing HUVAC cells, with lamina propria-derived cells located in between these layers, along with a test agent, PAM2CSK4 represented as large spots located above the epithelial cells.

The Gut-On-Chip modeling of inflammation was used for testing bacterial antigen effects on barrier function and cytokine production. An exemplary bacteria antigen used was PAM2CSK4. FIG. 7 shows an exemplary Chip Culture Schematic used for testing effects of a representative bacterial antigen as a synthetic TLR2 agonist, PAM2CSK4, on cytokine production and barrier function. PAM2CSK4 refers to a synthetic diacylated lipopeptide (LP).

1. Cytokine Production Induced by a Synthetic TLR2 Agonist, PAM2CSK4

Figure 11A:
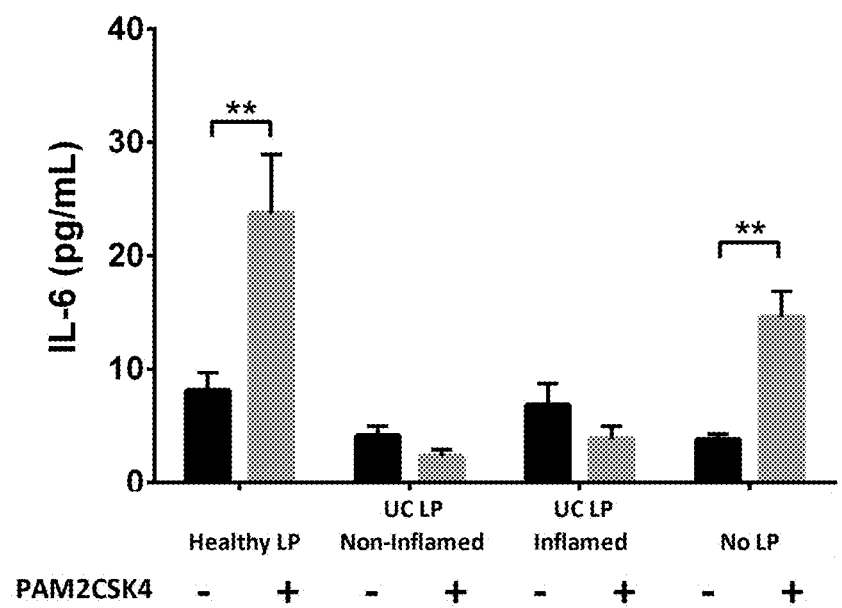
FIGS. 11A-B shows an exemplary TLR2 activation that stimulates an ulcerative colitis-like response.
Figure 11B:
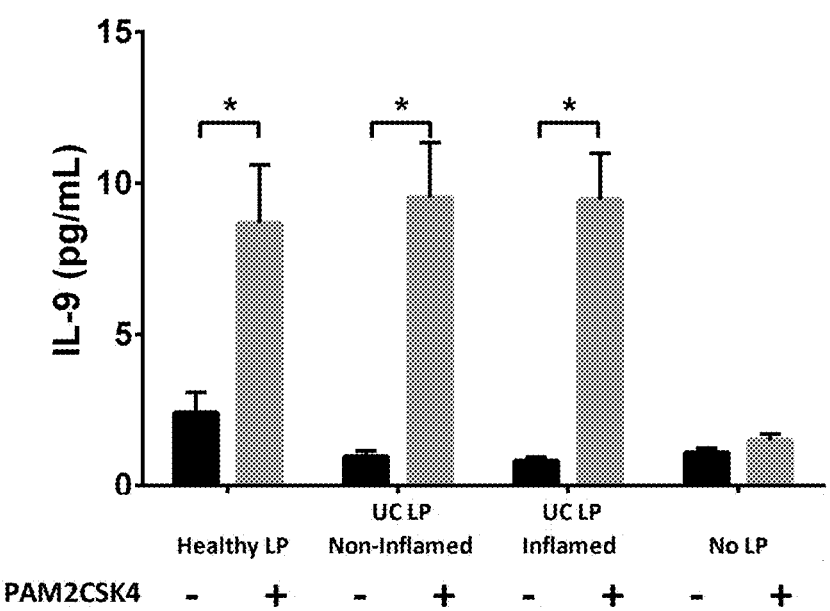

FIGS. 11A-B shows an exemplary TLR2 activation that stimulates an ulcerative colitis-like response using a co-culture as shown in a schematic in FIG. 7, PAM2CSK4 induce an IL6 response in healthy LP leukocyte co-cultures and in epithelial cells without LP, while PAM2CSK4 induce IL-9 in LP leukocyte co-cultures for each source but not in epithelial cells without LP cells, FIG. 11A) Comparison of IL-6 (pg/ml) production between chips containing healthy LP, UC LP non-inflamed, UC, LP inflamed and no LP with plus or minus PAM2CSK4. FIG. 11E) Comparison of IL-9 (pg/ml) production between chips containing healthy LP, UC LP non-inflamed, UC LP inflamed and no LP with plus or minus PAM2CSK4. IL-6 production threshold for chips with UC LP tissue is different (lower) than in control LP and no LP chips; TLR2 activation of IL-9 production is LP dependent; and no priming for IL-9 production is observed for UC LP tissue. Thus, IL-9 production is LP dependent.

2. Loss of Barrier Function is LP Cell Density Dependent in a Bioassay of Immune Activation A co-culture configured as described herein was incubated in a device of the present inventions as described in FIG. 7. Effects of resident leukocytes isolated from LP.

Figure 13:
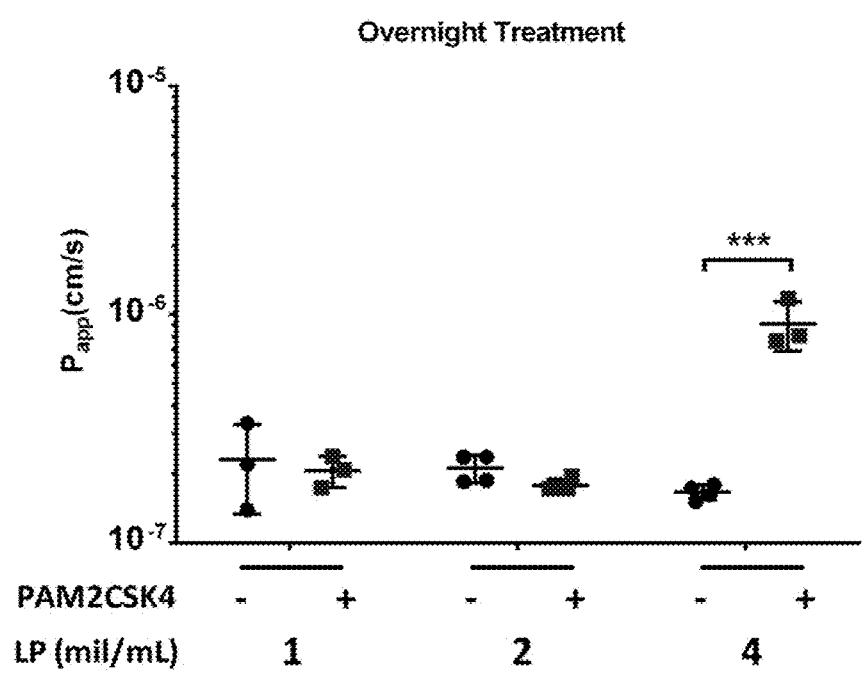
FIG. 13 shows an exemplary lamina propria-derived cells dose dependent bioassay (overnight incubation) of immune activation. Loss of barrier function is shown upon treatment with a PAM2CSK4 at LP 4 (mil/ml) but not at LP 1 mil/ml or LP 2 mil/ml.

FIG. 13 shows an exemplary lamina propria-derived cell dose dependent bioassay (overnight incubation) of immune activation. Disrupting Barrier Function, Loss of barrier function is shown upon treatment with a PAM2CSK4 at 4 LP mil/ml but not at LP 1 mil/ml or LP 2 mil/ml. There is little loss of barrier function in duplicate samples lacking PAM2CSK4 treatment even at 4 LP mil/ml.

3. Reduced 'Villus' Height in 'Infected' Chips Correlates with a Reduced Barrier Function The chips treated with PAM2CSK4 as a model bacterial antigen are considered infected chips. FIG. 14A-B shows an exemplary reduced 'Villos' Height in infected Chips as representative immunofluorescent micrograph cross-sections of one embodiment of Intestine On-Chip indicating changes in exemplary heights of the Caco-2 epithelial layer as a readout for barrier function, FIG. 14A) Untreated Control Caco-2 epithelial layer (Avg, Z Height (z arrow) 157+/−1.5 um) and FIG. 14B) Caco-2 epithelial layer+ Bacterial Challenge–PAM2CSK4 Treated (Avg. Z Height (z-arrow) 84 um+/−um). The epithelial boundary is marked by a think yellow line. Immunohistochemistry shows ZO-1 (red) outlining cells, E-cadherin (green) and nuclei (blue: DAPI stained). A decrease in barrier function in infected chips correlates with reduced 'villus' heights on the chip.

Therefore, Inflamed Intestine On-Chip has weakened barrier function and a reduction in epithelial 'villus' heights. Thus, in one embodiment, the height of the intestinal cell layer was contemplated as a faster readout of intestinal permeability. In one embodiment, the height of the intestinal cell layer was contemplated as a location specific readout of intestinal permeability.

4. IL-6 is Induced By Model Bacteria Antigen PAM2CSK4 which Activates TLR2

Treatment of co-cultures as described in FIG. 7 with PAM2CSK4 at 1, 2 and 4 LP mil/ml showed that PAM2CSK4 induced a higher level of IL-6 production than co-cultures with no PAM2CSK4. This TLR2 activation induced production was observed event at 4 LP mil/ml which showed a higher level of IL-6 production over untreated 1 and 2 mil/ml LP densities. This IL-6 (pg/ml) trend of increased production correlates with disrupted barrier function.

Figure 15:
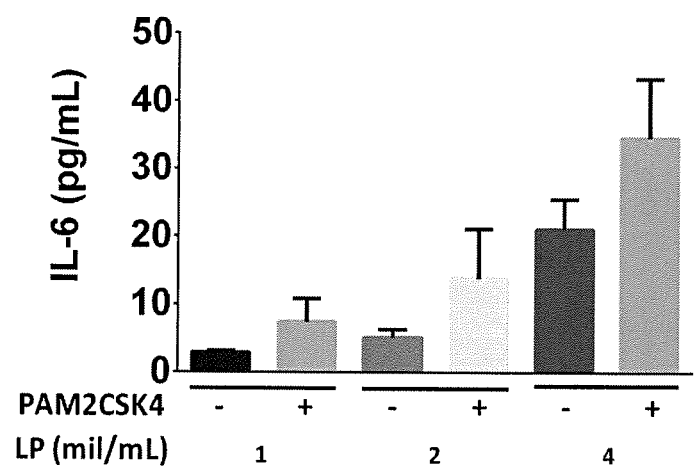
FIG. 15 shows an exemplary TLR2 activation stimulates an ulcerative colitis-like response. IL-6 (pg/ml) trend correlates with disrupted barrier function at 1, 2 or 4 LP (mil/ml).

FIG. 15 shows an exemplary TLR2 activation stimulates an ulcerative colitis-like response. IL-6 (pg/ml) trend correlates with disrupted barrier function at 1, 2 or 4 LP (mil/ml). Treatment of co-cultures as described in FIG. 7 with PAM2CSK4 at 1, 2 and 4 LP mil/ml showed that PAM2CSK4 induced a higher level of IL-6 production than co-cultures with no PAM2CSK4. This TLR2 activation induced production was observed event at 4 LP mil/ml which showed a higher level of IL-6 production over untreated 1 and 2 mil/ml LP densities.

5. IL-9 is Induced by TLR2 Activation and Alters Barrier Function and Stimulates an Ulcerative Colitis-Like IL-9 (pg/ml) Response.

Figure 16A:
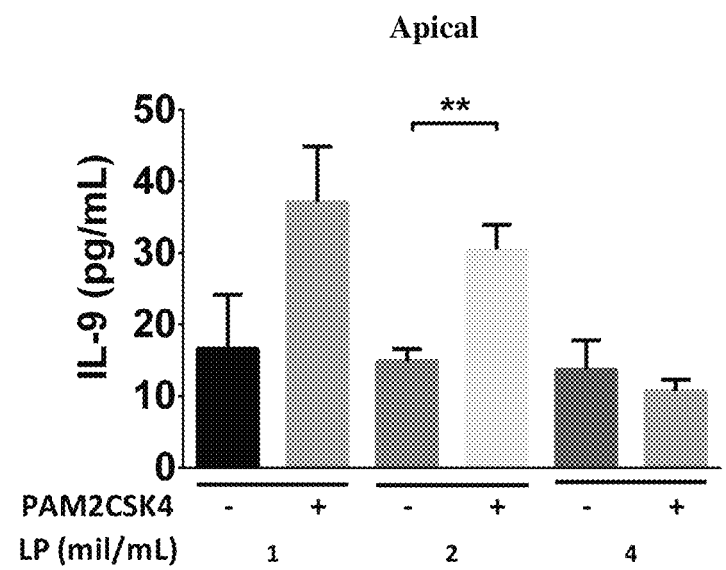
FIGS. 16A-B shows an exemplary TLR2 Activation Stimulates an Ulcerative Colitis-like IL-9 (pg/ml) response.
Figure 16B:
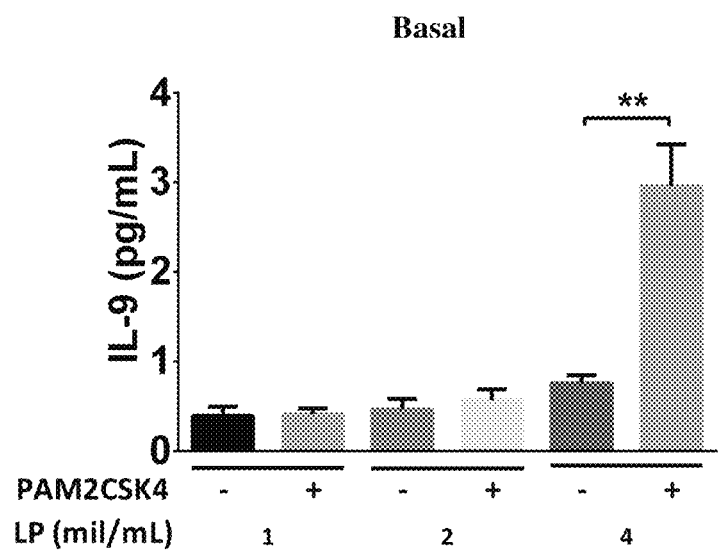

Treatment of co-cultures as described in FIG. 7 with PAM2CSK4 at 1, 2 and 4 LP mil/ml showed that PAM2CSK4 induced a higher level of IL-9 production at 4 LP mil/ml in basal areas (FIG. 16B). However, in apical regions of the epithelial cell layer IL-9 is produced at higher levels without PAM2CSK4 treatment that are increased with PAM2CSK4 treatment at 1 and 2 LP mil/ml but not at 4 LP mil/ml (FIG. 16A). Loss of barrier function correlates with presence of IL-9 in the basal channel.

FIG. 16A-B shows an exemplary TLR2 Activation Stimulates an Ulcerative Colitis-like IL-9 (pg/ml) response. FIG. 16A) Apical IL-9 (pg/ml) cytokine secretion at 1, 2 or 4 LP (mil/ml), FIG. 16B) Basal IL-9 (pg/ml) cytokine secretion at 1, 2 or 4 LP (mil/ml). Loss of barrier function correlates with presence of IL-9 in the basal channel.

Thus, inflamed UC LP resident immune cells increases permeability of epithelial cells when co-cultured in a device of the present inventions. In one embodiment, a co-culture as described herein is used for testing effects of drug treatments for reducing loss of barrier function, including hut not limited to reducing cytokine effects, such as IL-6 and IL-9.

Immune Cell Inflammatory Profile of CD45+ Resident Immune Cells On-Chip.

Lamina propria derived, resident intestinal CD45+ immune cells were labeled with Cell Tracker, seeded onto Chips with HUVEC endothelial cells, and imaged over 8 hours as time-lapse photographs. The time-lapse images indicate that the heterogeneous CD45+ resident immune cell population binds to and stably adhered to the Chip membrane.

Figure 52C:
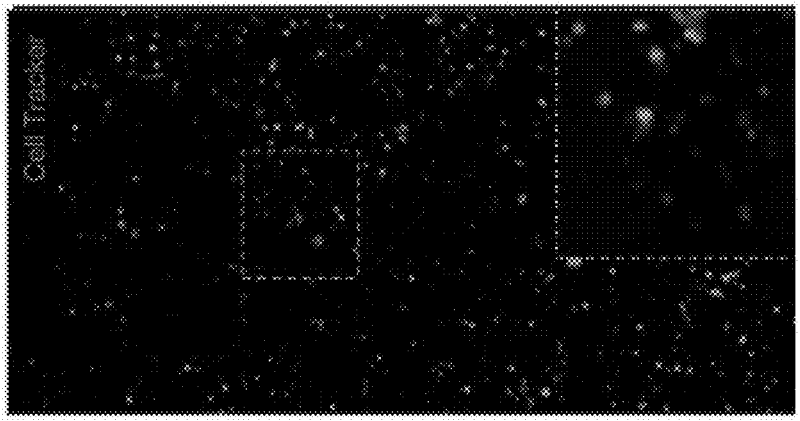
In FIG. 52C, from 8 hours of time-lapse photography of intestinal resident immune cells. Lamina propria derived, resident intestinal immune cells were labeled with Cell Tracker, seeded onto Chips with HUVEC endothelial cells. CD45+ resident immune cells are a heterogeneous population that binds and stably adheres to the Chip membrane.
Figure 52B:
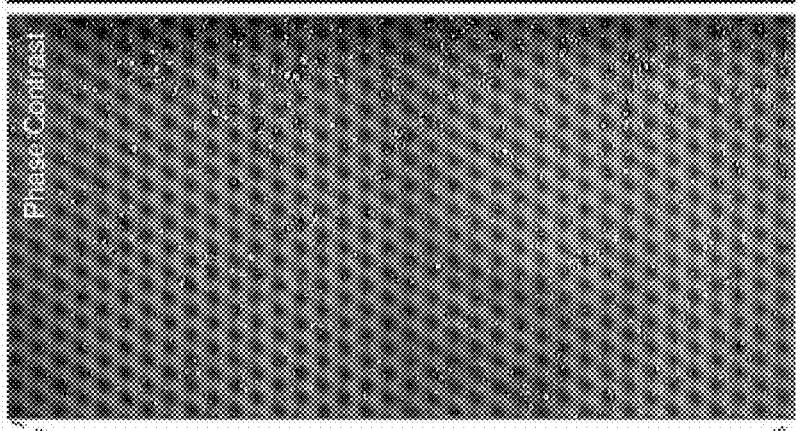
FIG. 52B shows an exemplary phase contrast image of the chip where white dots represent immune cells.
Figure 52A:
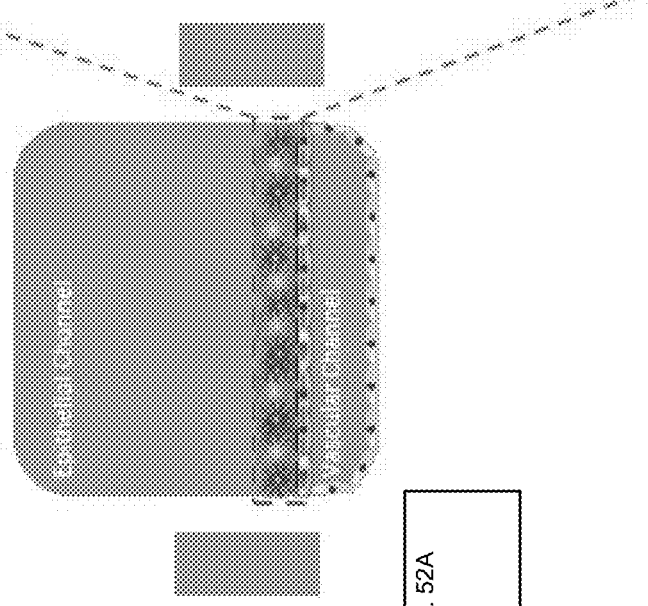
FIG. 52A shows an exemplary schematic of one embodiment of an intestine on-chip seeded with CD45+ primary resident immune cells from a patient, FIG. 52B, as one overlapping image.

FIG. 52A shows an exemplary schematic of one embodiment of an intestine on-chip seeded with C45+ primary resident immune cells from a patient, FIG. 52B, as one overlapping image, in FIG. 52C, from 8 hours of time-lapse photography of intestinal resident immune cells, Lamina propria derived, resident intestinal immune cells were labeled with Cell Tracker, seeded onto Chips with HUVEC endothelial cells. CD45+ resident immune cells are a heterogeneous population that binds and stably adheres to the Chip membrane. FIG. 52A shows an exemplary schematic of one embodiment of an intestine on-chip with an upper epithelial channel seeded with CD45+ resident immune cells and a lower vascular channel seeded with endothelial cells. FIG. 52B shows an exemplary phase contrast image of the chip where white dots represent immune cells. FIG. 52C shows an exemplary fluorescent microzraph image of the chip where green dots represent immune cells labeled with Cell Tracker.

Figure 12:
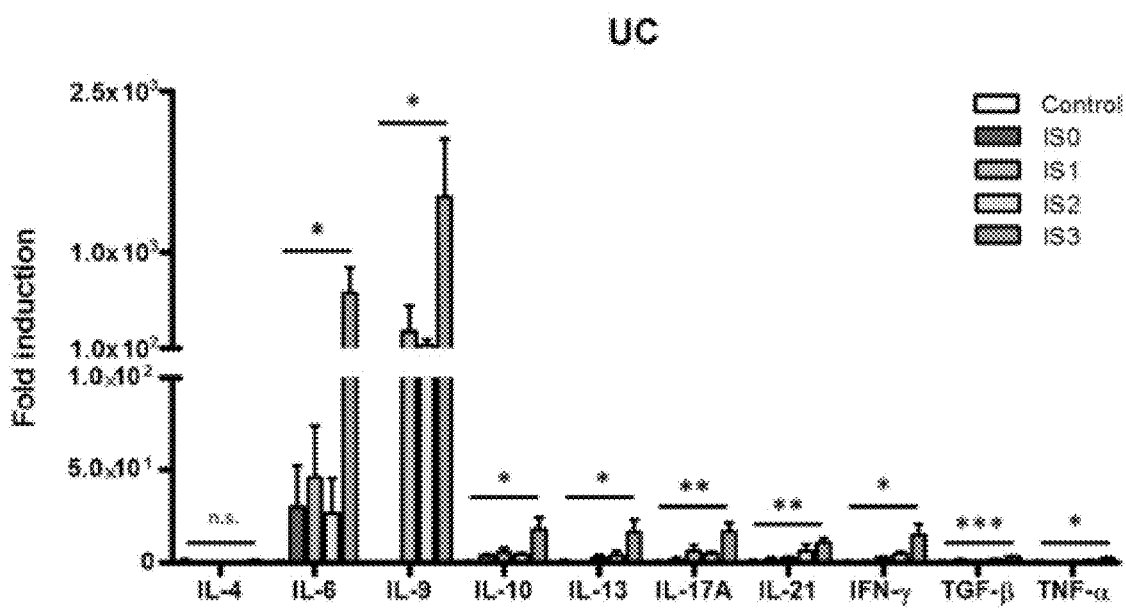
FIG. 12 Cytokine signaling was shown in ulcerative colitis (Nalleweg et al. "IL-9 and its receptor are predominantly involved in the pathogenesis of UC." 2015).

Secreted cytokine levels are an exemplary readout of inflammation and were measured for primary derived, resident intestinal immune cells (LP) in static culture, see FIG. 12. Therefore, secreted cytokine levels were measured in effluent media after seeding CD45+ resident immune cells on-chip.

FIGS. 53A-C shows exemplary results of measuring an inflammatory response (secreted cytokines) of CD45+ resident immune cells on-chip. FIG. 53A shows exemplary IL-6 protein secretion. FIG. 53B shows exemplary IL-10 protein secretion. FIG. 53C shows exemplary IL-8 protein secretion. FIG. 53D shows a key for experimental conditions, Ctrl LP, Non-Infl LP (Ulcerative Colitis) and Intl LP (Ulcerative Colitis).

Thus, it was summarized that primary resident immune cells retain their in vivo phenotype enabling a model of the mucosal microenvironment in the Intestine On-Chip in a patient-specific fashion, including for e.g., for use in personalized medicine.

LP Derived CD45+ Cells from Additional Donors.

Due to the large range in error bars after statistical analysis of some experiments, it was contemplated that more representative statistics having smaller error bars might be obtained using larger numbers of individuals as tissue donors. Thus, effects on in vitro epithelial barrier function, cytokine profile of immune cells, secreted cytokine production, and antigen activation using PAM were done after adding in vivo activated T cells to an intestine on-chip. These measurements were made across multiple donors of intestinal inflamed UC LP. Thus, it was contemplated to mimic an UC "flare up" inflammatory cell response by adding such in vivo activated T cells from inflamed intestinal regions of UC LP.

Donors included but were not limited to Control (Ctrl LP) and Ulcerative colitis (UC LP). Immune cells were isolated from different regions of Donor 2's LP tissue: Non-Inflamed (Non-Infl. UC LP) and Inflamed (Infl. UC LP).

Immune Cell Inflammatory Profile.

A cytokine profile of inflamed relative to non-inflamed immune cells was evaluated for on plate expression.

Figure 54:
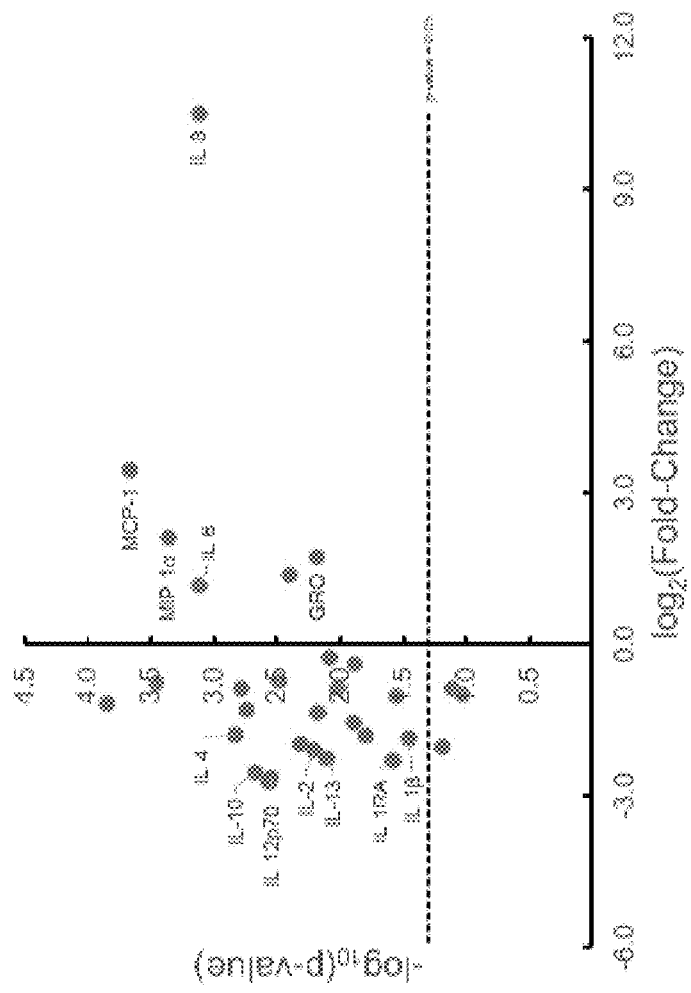
FIG. 54 shows exemplary results of measuring cytokine profile of immune cells isolated from a biopsy of inflamed colon tissues, i.e. inflamed, relative to immune cells isolated from a biopsy of non-inflamed immune cells. These experiments were done with immune cells on-plates and includes data from FIGS. 53A-C.

FIG. 54 shows exemplary results of measuring cytokine profile of immune cells isolated from a biopsy of inflamed colon tissues, i.e. inflamed, relative to immune cells isolated from a biopsy of non-inflamed immune cells. These experiments were done with immune cells on-plates.

It was found that immune cells isolated from inflamed colon tissues have a significantly higher baseline inflammatory state than non-immune cells from non-inflamed colon tissue. Therefore, the inflammatory state of resident intestinal immune cells is highly location dependent.

Bacterial Challenge of Resident Immune Cells.

Figure 55C:
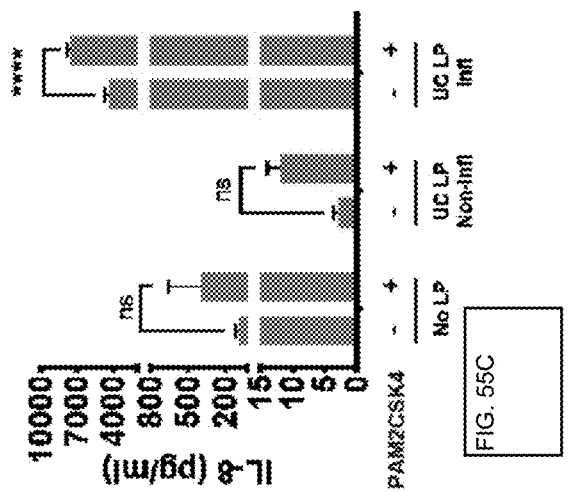
FIGS. 55A-C shows exemplary results of measuring secreted cytokine production from a UC patient's resident immune cells cultured on-plates, in response to 24 hour bacterial challenge as represented by exposure to PAM2CSK4.
Figure 55B:
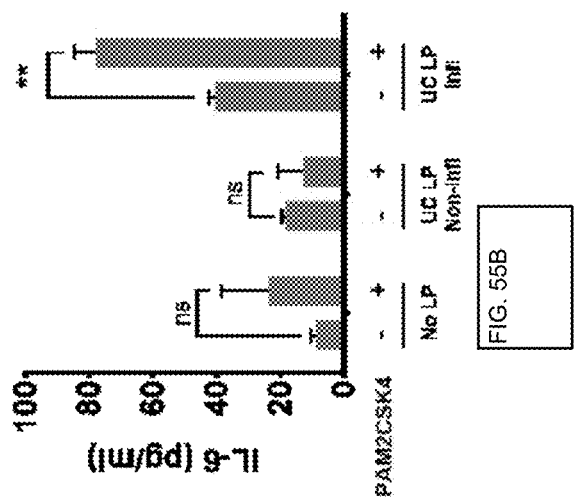
Figure 55A:
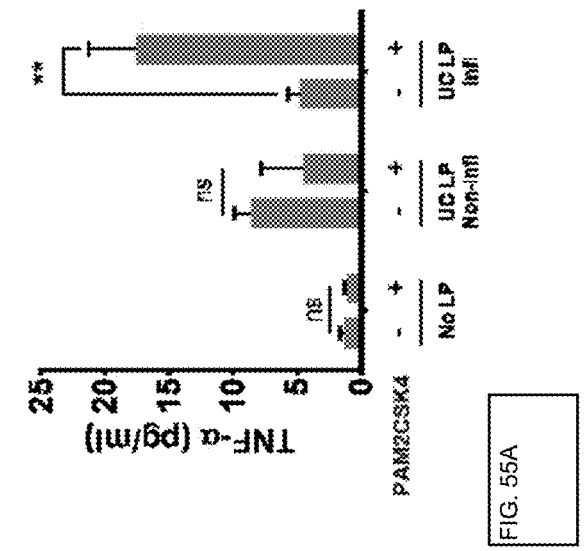

FIGS. 55A-C shows exemplary results of measuring secreted cytokine production from a UC patient's resident immune cells cultured on-plates. In response to 24 hour bacterial challenge as represented by exposure to PAM2CSK4. FIG. 55A shows exemplary TNF alpha protein secretion. FIG. 55B shows exemplary IL-6 protein secretion. FIG. 55C shows exemplary IL-8 protein secretion.

Thus, immune cells from inflamed, UC tissue have a higher baseline inflammatory state and stronger response to PAM2CSK4 treatment, as a TLR2 agonist.

In Vivo Like Immune Cells Responses to Bacterial Challenge.

Figure 56:
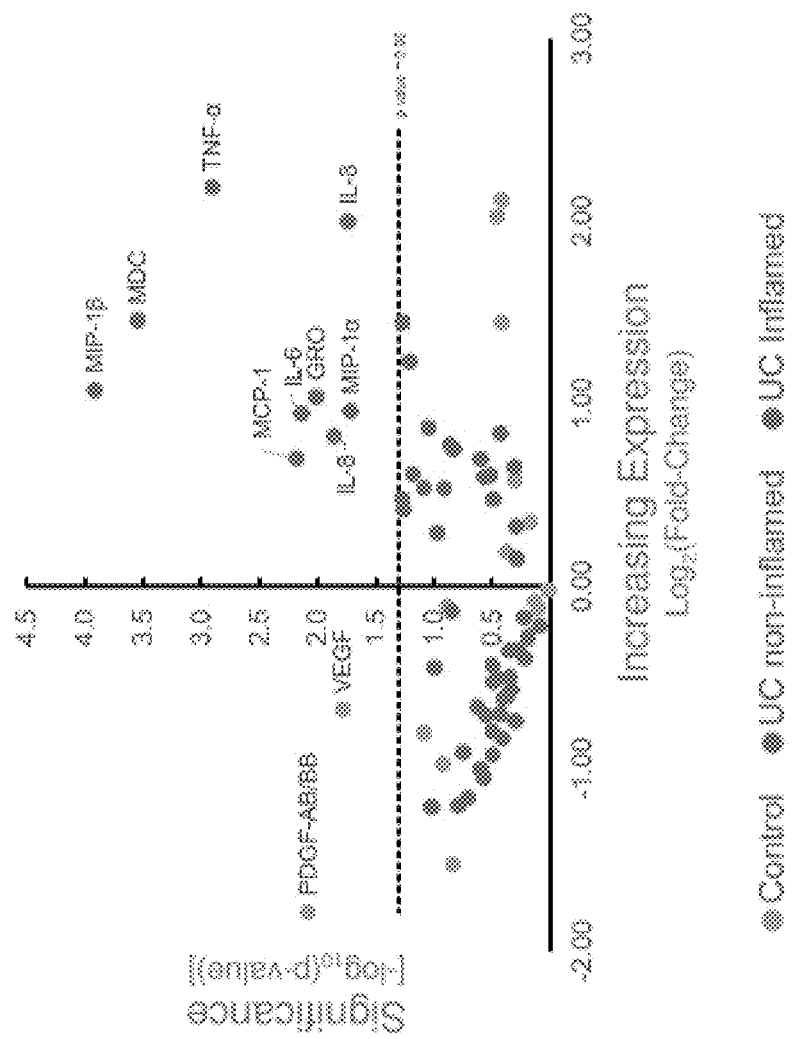
FIG. 56 shows exemplary results of measuring secreted cytokine production from a UC patient's isolated resident immune cells, cultured on plates. In response to 24 hour bacterial challenge as represented by exposure to PAM2CSK4. Includes data from FIGS. 55A-C.

FIG. 56 shows exemplary results of measuring secreted cytokine production from a UC patient's isolated resident immune cells, cultured on plates, in response to 24 hour bacterial challenge as represented by exposure to PAM2CSK4. Cytokines expressed by control, healthy patient's resident immune cells are shown in grey dots, while blue dots represent results from UC non-inflamed resident immune cells and red dots represent results from UC inflamed resident immune cells. Significance [−log 10 (p-value)] Increasing Expression Log2 (Fold-Change).

Thus, immune cells from a healthy patient are not activated by bacterial challenge. Non-inflamed immune cells from the Ulcerative Colitis patient are not significantly activated by bacterial challenge while Inflamed immune cells from the UC patient are significantly activated and primed to respond to bacterial stimuli.

Effects of Incorporated Resident Immune Cells in the Intestine-Chip.

Figure 57C:
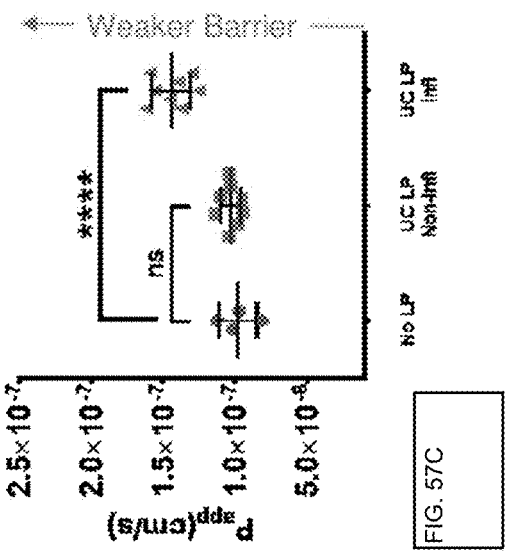
FIGS. 57A-C shows exemplary results of measuring secreted cytokines after incorporation of CD45+ resident immune cells in one embodiment of an intestine on-chip.
Figure 57B:
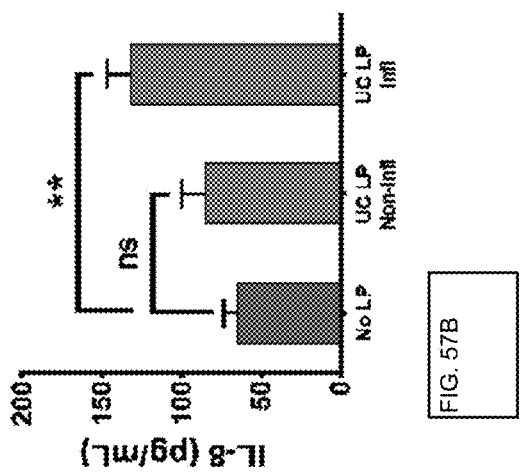
Figure 57A:
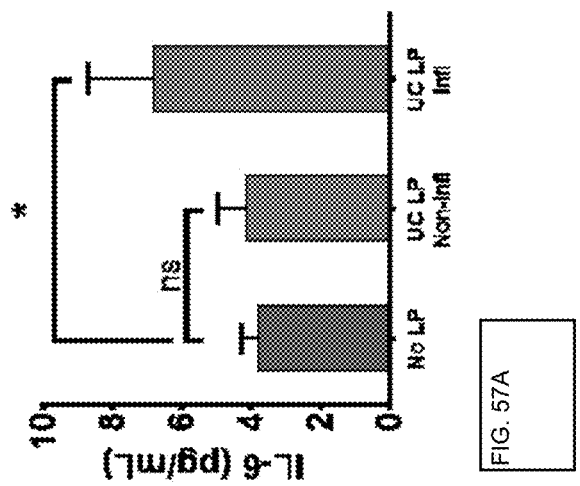

FIGS. 57A-C shows exemplary results of measuring secreted cytokines after incorporation of CD45+ resident immune cells in one embodiment of an intestine on-chip. FIG. 57A shows exemplary IL-6 protein secretion. FIG. 57B shows exemplary IL-8 protein secretion. FIG. 57C shows exemplary apparent permeability increase after CD45+ resident immune cells from an inflammatory region of UC LP.

Thus, Primary immune cells from inflamed tissues incorporated in the Intestine-Chip recapitulate relevant pro-inflammatory characteristics as shown by cytokine secretion and weakened intestinal barrier function.

Steroidal Treatment of Intestinal Inflammation.

During the development of the present invention, it was contemplated that immune cells from normal and inflamed regions would respond differently to the same treatment, in part supported by results obtained herein. Prednisone is an exemplary Standard-of-Care treatment for Ulcerative Colitis. However, Prednisone has undesirable Side Effects such as increased Risk of infection, Weight gain, Hyperglycemia, Hypertension, Bone loss. Further, the Efficacy of Prednisone is variable such that around 16% of treated patients are non-responsive, 30% have partial remission and 54% have full remission (Lichtenstein, et al. 2006).

Figure 58A:
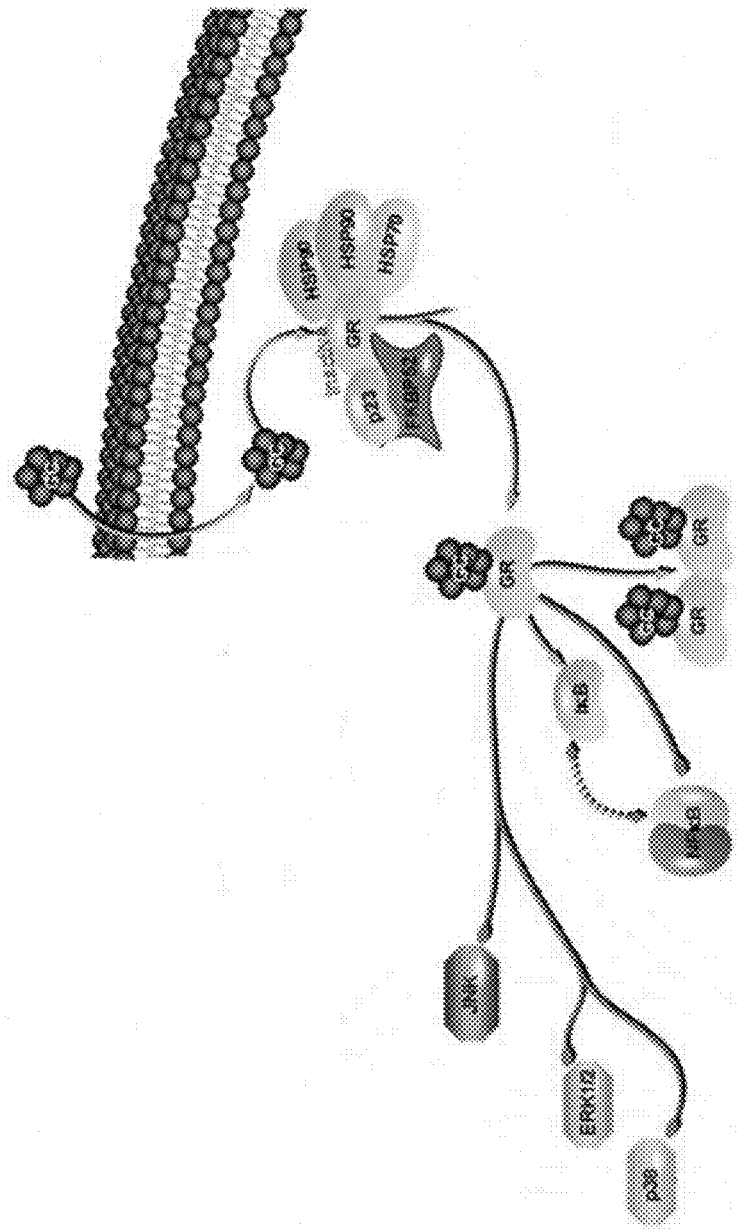
FIGS. 58A-B shows representative schematics as FIG. 58A anti-inflammatory pathways involving glucocorticoid compound (as a red flower) entry through a cell membrane (upper right representation of a lipid bilayer) and FIG. 58B an exemplary Prednisone chemical structure.
Figure 58B:
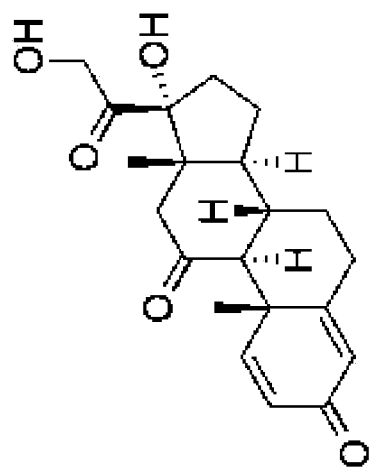

FIGS. 58A-B shows representative schematics as FIG. 58A anti-inflammatory pathways involving glucocorticoid compound (as a red flower) entry through a cell membrane (upper right representation of a lipid bilayer) and FIG. 58B an exemplary Prednisone chemical structure.

When evaluating secreted cytokine production from one embodiment of an Intestine on Chip cultured with a UC patient's resident immune cells in response to bacterial challenge and prophylactic treatment with prednisone, there was no difference in the response of noninflamed vs. Inflamed resident immune cells on-chip. In other words, Prednisone treatment on-chip suppresses the inflammatory responses of both noninflamed and inflamed tissues to treatment with PAM2CSK4.

Figure 59B:
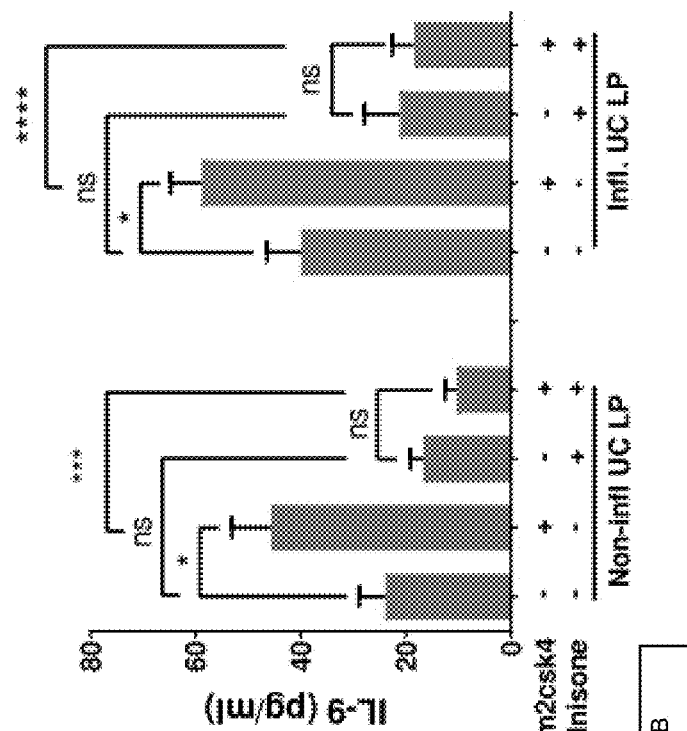
FIGS. 59A-B shows secreted cytokine production from Intestine-Chip cultured with a UC patient's resident immune cells in response to bacterial challenge and prophylactic treatment with prednisone.
Figure 59A:
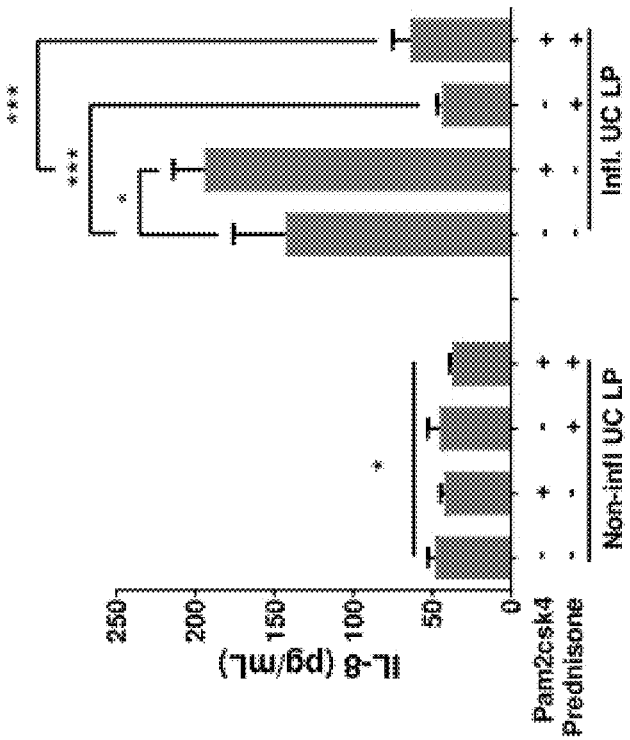

FIGS. 59A-B shows secreted cytokine production from Intestine-Chip cultured with a UC patient's resident immune cells in response to bacterial challenge and prophylactic treatment with prednisone. FIG. 59A shows exemplary IL-8 protein secretion. FIG. 59B shows exemplary IL-9 protein secretion.

Interleukin 9 (IL-9) Production in the Pathogenesis of Ulcerative Colitis (UC).

While IL-9 promotes the development of allergic and autoimmune diseases (asthma/UC), IL-9 expression correlates with UC disease severity, but is not correlated with CD severity (Gerlach, et al., 2014). Further, Intestinal epithelial cells of UC patients express more IL-9R than in healthy patients (Nalleweg, et al., 2015) and IL-9 was shown to have a direct effect on the epithelium and promotes pathogenic immune responses in UC (Gerlach, et al., 2015). See, exemplary FIG. 51B showing a schematic representation of immune stimulation in relation to IL9. In particular, IL-9 and IL-6 are overexpressed in mucosal biopsies from severely inflamed UC patients. See, FIG. 12, Overexpression of IL-9 and IL-6 generally tracks with disease severity.

Resident Immunity in the Pathogenesis of Ulcerative Colitis $T_H9$ Mediated Ulcerative Colitis.

As demonstrated herein, intestine on-chip comprising immune cells isolated from primary LP tissue samples from patients, show that the presence of IL-9 protein and IL-9 receptors in the intestinal epithelial layer is associated with weakening the epithelial barrier and induces inflammatory responses.

Figure 60B:
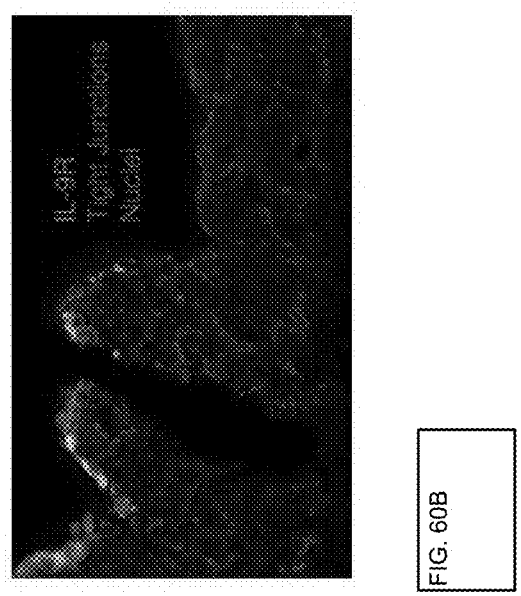
FIG. 60A-B shows an exemplary comparison of IL-9 production in response to PAM stimulation as an exemplary bacterial agonist, FIG. 60A, and an immunofluorescent microgaph showing IL-9R (receptor) expression in the epithelial layer of one embodiment of an Intestine On-Chip, FIG. 60B. IL-9R is shown in green, tight junctions shown in red and nuclei stained with DAPI are colored blue.
Figure 60A:
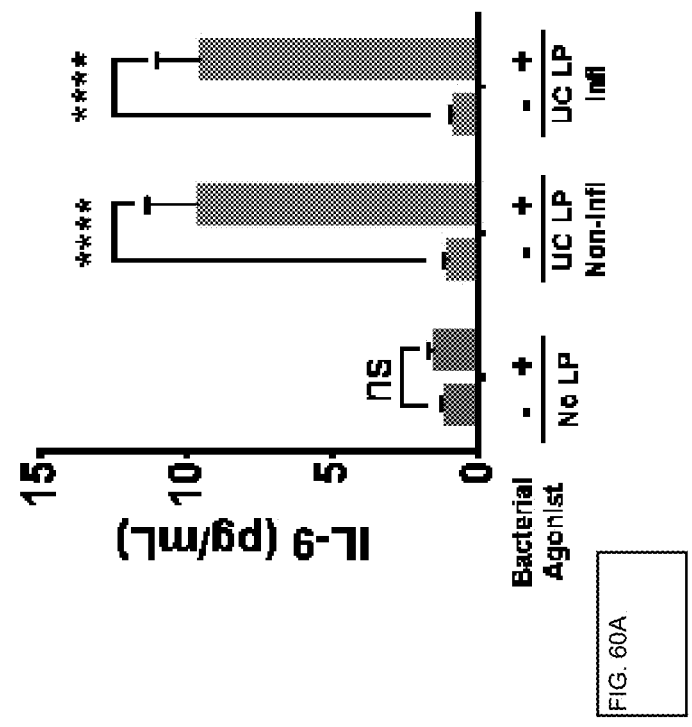
Figure 62:
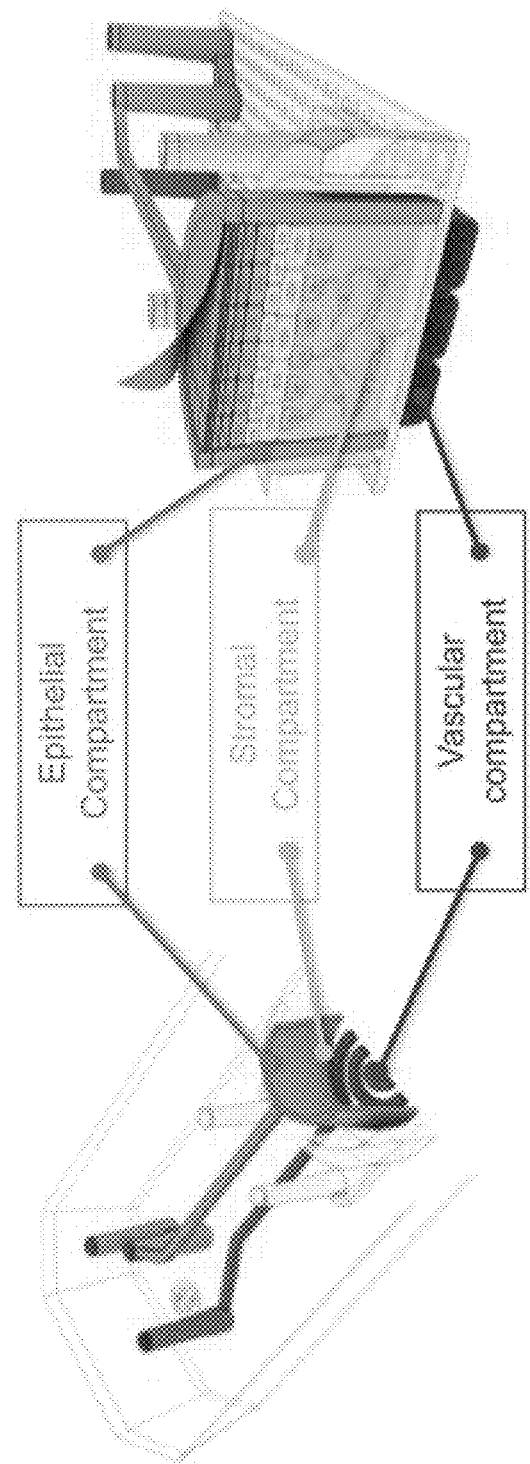
FIG. 62 shows two exemplary embodiments of an Intestinal Mucosa On-Chip (enteroids'-derived cells) modeling a simulated intestine comprising intestinal epithelium from up to four areas of the intestine. One embodiment as a schematic of a partial open top chip demonstrating channels and open area in relation to compartments in the chip (left). One embodiment as a schematic of a partial open top chip additionally demonstrating cells in the compartments of the chip (right). Comparative epithelial compartments include intestinal epithelium (enteroid/colonoid derived) from 4 different intestinal segments: duodenum, jejunum, ileum and colon. Stromal compartment includes intestinal fibroblasts immune cells. Vascular compartment includes intestinal microvascular endothelium from small intestine and/or large intestine.
Figure 63C:
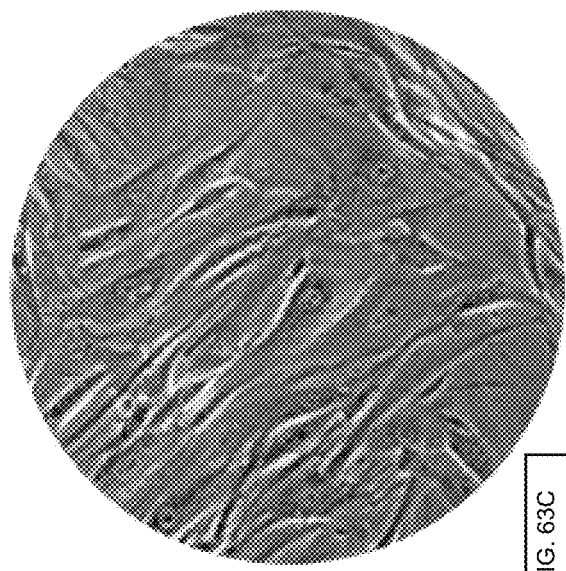
FIGS. 63A-C shows exemplary phase contrast micrographs of Patient-derived Primary Intestinal Cells used Intestinal Mucosa On-Chip.
Figure 63B:
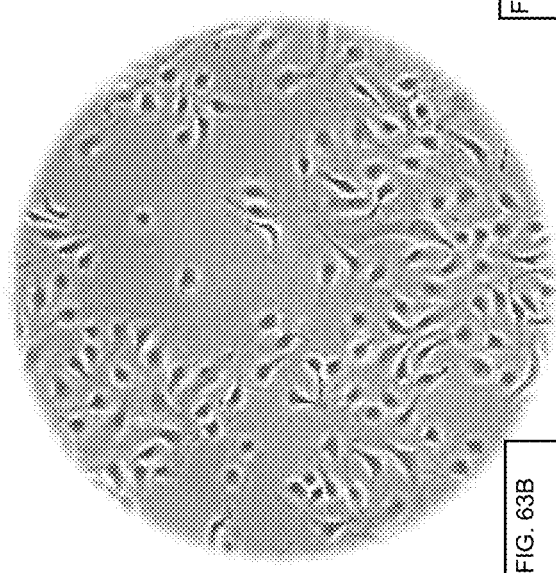
Figure 63A:
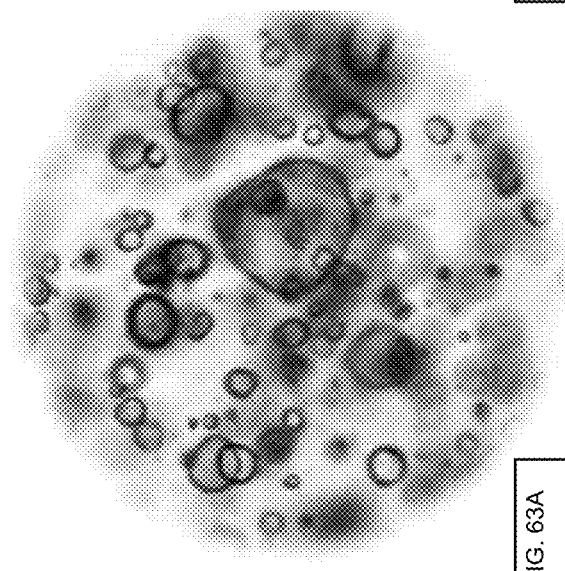
Figure 64:
FIG. 64 shows exemplary results of homogenous 3D villi-like structure formation in phase contrast micrographs (Upper—low magnified image; Lower higher magnified image) of epithelium on-chip in direct contact with fibroblasts in one embodiment of Intestinal Mucosa On-Chip. Direct Contact with Fibroblasts Improves 3D Tissue Architecture.

FIG. 60A-B shows an exemplary comparison of IL-9 production in response to PAM stimulation as an exemplary bacterial agonist, FIG. 60A, and an immunofluorescent micrograph showing IL-9R (receptor) expression in the epithelial layer of one embodiment of an Intestine On-Chip, FIG. 60B. IL-9R is shown in green, tight junctions shown in red and nuclei stained with DAPI are colored blue.

Blocking Inflammatory Cytokines Rescued Barrier Function and Reversed an Exacerbated Diseased State of Intestine On-Chips.

A high level of INF-gamma production and IL-9 production is associated with exacerbated inflammatory responses. Including morphological damage to the intestinal epithelial cell layer barrier, respectively associated with CD4+ $T_H1$ cell populations or CD4+ $T_H9$ cell populations.

Thus, it was contemplated that by blocking the action of either or both INF-gamma and IL-9, the barrier might return to more normal levels of permeability. Further, it is contemplated that blocking antibodies for proinflammatory cytokines, e.g. INF-gamma, IL-9, etc., may reduce exacerbated levels of corresponding cytokine production. Thus, in some embodiments, an exacerbated diseased state of Intestine On-Chips may be reduced. In some preferred embodiments, an exacerbated diseased state of Intestine On-Chips may be reduced to simulating areas of non-inflamed CD and non-inflamed UC, i.e. in part by simulating a return to non-inflamed CD or non-inflamed UC in vivo after effective treatment, e.g. Prednisone.

Thus, in further preferred embodiments, an exacerbated diseased state of Intestine On-Chips may be revered, e.g. in part to resemble non-inflamed areas or to resemble non-inflamed and healthy intestinal tissue.

Figure 49:
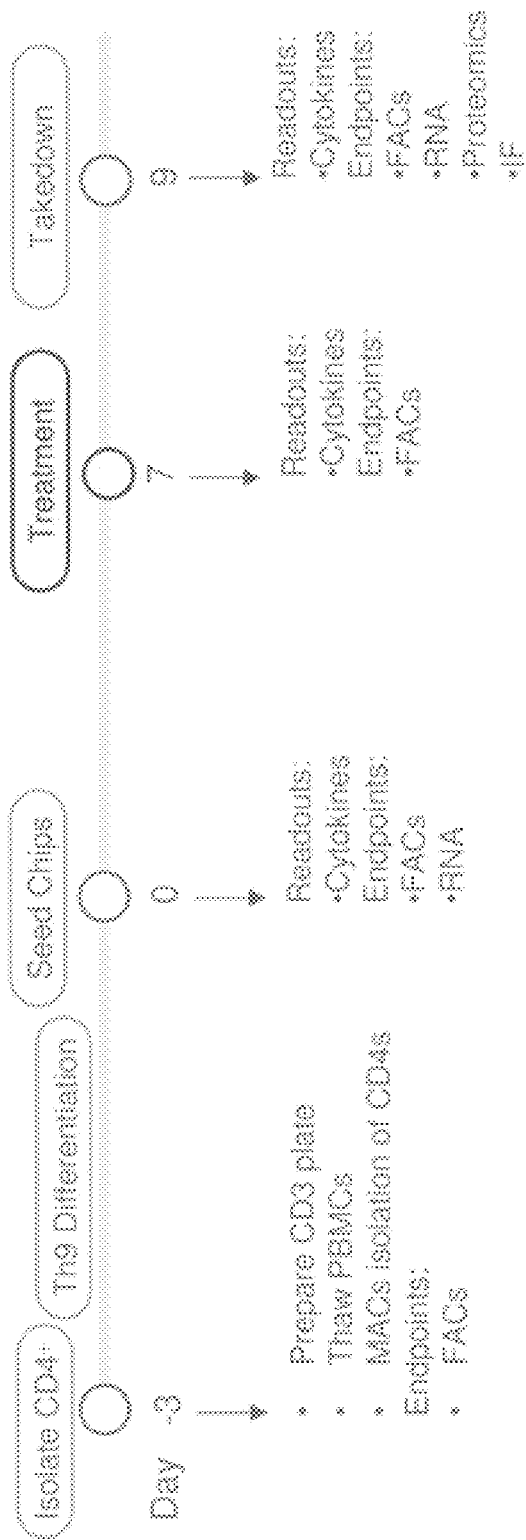
FIG. 49 shows a schematic representation demonstrating an exemplary timeline for immune response blocking experiments.

FIG. 49 shows a schematic representation demonstrating an exemplary timeline for immune response blocking experiments.

Stimulation conditions include but not limited to additional stimulation with PAM2CSK4 (i.e. PAM), with or without additional IL-9 and or IFN-gamma, alternatively with anti-IL-9 and/or blocking anti-IFNgamma. See, Table 13.

TABLE 13

Exemplary experimental conditions for blocking activation of T cells on-chips. Treatments on Day 7 using blocking antibodies, such as anti-IL-9 and/or anti-IFNgamma, in the presence of antigen are shown. Chips were seeded on Day 0 with plate activated and differentiated CD4+ T cell subsets (Day −3 to Day 0). T cells on chips were further stimulated using activated ECM, including activation reagents, e.g. CD3 and CD28 antibodies.

| T-Cells | Factors | Treatment | #Chips |
|---|---|---|---|
| N/A | 1. +CD3/+CD28 | 1. Control | 6 |
|  | 2. +CD3/+CD28 | 2. +PAM (10 ug/mL) | 6 |
|  |  | 3. +PAM, IL-9 | 4 |
|  |  | 4. +IFNg | 4 |
|  |  | 5. +PAM, anti-IFNg/anti-IL9 | 4 |
| Th1 | 1. +CD3/+CD28 | 1. Control | 6 |
|  | 2. +CD3/+CD28 | 2. +anti-IFNg | 6 |
| Th9 | 1. +CD3/+CD28 | 1. +PAM (10 ug/mL) | 6 |
|  | 2. +CD3/+CD28 | 2. +anti-IL-9 + PAM | 6 |

Such exemplary experimental conditions shown in Table 13, e.g. combinations of factors with certain treatments, are contemplated to determine the level of IFN-gamma associated with $T_H1$ intestinal inflammatory responses IL-9 associated with $T_H9$ intestinal inflammatory responses. Blocking of IFNg receptor binding in $T_H1$ and blocking IL-9 receptor binding in $T_H9$ chips is contemplated to, in part, decrease an exacerbated inflammatory response by at least an increase barrier function, in other words, by decreasing apparently permeability.

Example 17

Exemplary Primary Cell Expansion and Differentiation

Primary cells obtained from biopsies were increased in numbers (expanded) after culturing in expansion media, such as shown in Table 14.

In one embodiment, expanded cells were then differentiated into cells reflecting their origin, e.g. intestinal segments: duodenum, jejunum, ileum or colon. In exemplary embodiments for differentiating cells: Cultures were exposed to ALI (Air Liquid Interface); Or the following media components were removed from expansion media for providing a differentiation media, Table 15 for example: Wnt3A, SB2001190 along with reducing the concentration of R-spondin and Noggin CM (obtained from conditioned media) to 10% and 5%, respectively. Additionally, Notch inhibitor (DAPT) is added to further enhance differentiation.

TABLE 14

Exemplary Media Components For Primary Cell Expansion.

| Component | Volume (for 100 ml total) | Dilution factor | Final Concentration |
|---|---|---|---|
| EXPANSION MEDIA (EM) | | | |
| Wnt3A CM | 50 ml | 2x | 50% |
| Noggin CM | 10 ml | 10x | 10% |
| R-spondin CM | 20 ml | 5x | 20% |
| Advanced DMEM/F12 | 14.55 ml | — | — |
| Glutamax | 1 ml | 100x | 1x (2 mM glutamine) |
| HEPES | 1 ml | 100x | 10 mM (stock 1M; 100x) |
| Primocin | 200 ul | 500x | 0.1 mg/ml (stock 50 mg/ml) |
| B27 | 2 ml | 50x | 1x (stock 100x) |
| N2 | 1 ml | 100x | 1x (stock 50x) |
| N-acetyl cysteine | 200 ul | 500x | 1 mM (stock 500 mM) |
| EGF | 10 ul | 10,000x | 50 ng/ml (stock 500 ug/ml) |
| Gastrin | 10 ul | 10,000x | 10 nM (stock 100 uM) |
| A-83-01 | 10 ul | 10,000x | 500 nM (stock 5 mM) |
| SB2001190 | 20 ul | 5,000x | 10 uM (stock 50 mM) |
| Total | 100 ml | — | — |
| ADDITIONAL COMPONENTS (EM+) | | | |
| ROCK inhibitor (Y27632) | 100 ul | 1,000x | 10 uM (stock 10 mM) |
| CHIR 99021 | 50 ul | 2,000x | 5 uM (stock 10 mM) |

TABLE 15

Exemplary Media Components For Primary Cell Differentiation. Differentiation Media (DM)

| Component | Volume (for 100 ml total) | Dilution factor | Final Concentration |
|---|---|---|---|
| Noggin CM | 5 ml | 20 x | 5% |
| R-spondin CM | 10 ml | 10 x | 10% |
| Advanced DMEM/F-12 | 79.57 ml | — | — |
| Glutama X | 1 ml | 100x | 1x (2 mM glutamine) |
| HEPES | 1 ml | 100x | 10 mM (stock 1M; 100x) |
| Primocin | 200 ul | 500x | 0.1 mg/ml (stock 50 mg/ml) |
| B27 | 2 ml | 50x | 1x (stock 100x) |
| N2 | 1 ml | 100x | 1x (stock 50x) |
| N-acetyl cysteine | 200 ul | 500x | 1 mM (stock 500 mM) |
| EGF | 10 ul | 10,000x | 50 ng/ml (stock 500 ug/ml) |
| Gastrin | 10 ul | 10,000x | 10 nM (stock 100 uM) |
| A-83-01 | 10 ul | 1,000x | 500 nM (stock 0.5 mM) |
| Total | 100 ml | — | — |

EXAMPLES

The following examples illustrate some embodiments and Embodiments described herein. It will be apparent to those skilled in the relevant art that various modifications, additions, substitutions, and the like can be performed without altering the spirit or scope of the invention, and such modifications and variations are encompassed within the scope of the invention as defined in the claims which follow. The following examples do not in any way limit the invention.

Example 1

Preparing a Gut-On-Chip

The following exemplary protocol outlines the sterilization/functionalization, coating, media wash, and cell seeding steps for preparing the Intestine-on-Chip with epithelial cells, e.g. Caco-2, human primary epithelial cells, etc., HUVECs, and resident immune cells from lamina propria derived cells.

The following exemplary equipment were used: 3×2.5 inches of tubing (1/32 inch ID Pharmed BPT) per chip; 2×10 mL syringes reservoirs per chip, cut at 4 mL line with plungers removed; 2×1 mL or 3 mL syringes; 2×18G straight connectors per chip; Steriflip filter 0.45 um (Fisher SEIM 003 M00); Tubing clamp, 2 per chip; Razor blade; 70% ethanol; 4×18G" Blunt needles per chip (SM-infusion cat #B19-100); Emulate Chip Paddle; Chemxy Fusion 200 Syringe Pump with multi-channel extender; Hemocytometer; Microscope; Large, round Petri dishes; and Ice.

The following exemplary reagents were used: DMEM Hi Glucose (ThermoFisherSci 11965-118) without FBS (fetal bovine serum); DMEM (Dulbecco's Modified Eagle Medium) Hi Glucose (ThermoFisherSci 11965-118) with 10% FBS; EGM2 Complete with 2% FBS (exclude GA, add Pen Strep); EGM2 Complete with 0.5% FBS (exclude GA, add Pen Strep (Penicillin-Streptomycin antibiotics)); Note: this is used after 3 days of flow; ECM: Collagen 1 (BD Biosciences #A1048301); Matrigel (BD Biosciences #356234)—frozen, 10 mg/mL; Penicillin/Streptomycin (Invitrogen #15140-463); Centrifuge; Trypsin 0.05% EDTA;

PBS; Confluent T75 flask of Caco-2; Confluent T75 flask of HUVECs; aliquot of resident immune cell suspension; and Trypan blue.

The following exemplary procedure was used for incubation of chips and media. For ideal exemplary results, de-gas chips for 10 min followed by incubation in a humidified tissue culture incubator at 37° C., 5% $CO_2$ for 24-48 hours prior to seeding cells; Degas 50 mLs of DMEM/FBS by 0.45 um Steri-Flipping and incubating for 10 mins under vacuum; Once degassed, media should be stored upright in a T75 flask up to 1-week in a cell culture incubator The following exemplary procedure was used for Preparing Chip Connections; Cut 2.5 in of 1/32" ID Pharmed BPT tubing and insert 18 ga straight connectors into one end; Attach tubing clamps; Discard plungers from 10 mL syringes, cut at 4 mL line and retrieve 15 mL conical tube cap; Autoclave tubing, metal connectors on standard dry cycle (10 min; 121 C); and Sterilize cut-reservoirs and 15 mL conical caps with UV exposure.

The following exemplary procedure was used for Preparation of ECM Solution (100 ug/mL Matrigel, 30 ug/mL Rat Tail Collagen I); 10 mL DMEM (no FBS) on ice; (optional) Pre-chill 200 uL tips in −20° C. freezer for 10 min; Add 100 μL Matrigel (thaw on ice or at 4° C.); 30 ug/mL Collagen 1 (stored on ice) note: check collagen concentration, current is 8.3 mg/mL.

The following exemplary procedure was used for Chip Coating: Sterilize chips by plasma treatment (1 min, 100 W plasma; 15 seem) or autoclave on standard dry cycle. Note: remove polycarbonate backing before autoclaving or it will melt.

Optional: Perform Sulfo-SANPAH treatment protocol: Wash both channels of sterilized chips with 200 uL, sterile PBS and remove PBS by aspiration; Place 200 uL pipet tips in outlet ports. With pre-chilled tips, draw 100 μL of coating solution into 200 uL filter pipet tip and load top channel; Repeat above with bottom channel; Examine device by eye to make sure there are no air bubbles anywhere in the chip. Incubate at 37° C. for 1-2 hours. Can store ON at 37 degrees for next step if necessary.

The following exemplary procedure was used for Washing Chips: Remove coated chips from incubator; Remove pipette tips from seeding ports and aspirate off excess coating fluid; Replace 200 ul pipette tips in outlet seeding ports; Wash both channels with DMEM/FBS; Examine the chips and clear out any debris or bubbles; Place chips and media back in incubator until ready to seed cells.

Seeding HUVECs in Bottom Channel.

The following exemplary procedure was used for Seeding HUVECs in Bottom Channel: Prepare approximately 10-20 million/mL cell suspension of HUVECs; Check viability with a hemocytometer; Fill top channel with media and remove media from bottom channel; Place empty 200 uL filter pipette tips in bottom outlet port; Mix cell suspension gently, fill 200 uL pipette with 50-100 uL of cell suspension, load into bottom channel of chip; Gently triturate cells suspension thorough chip a couple times without introducing bubbles; Eject tip into input port; Check to see if channels are seeded with appropriate density of cells (see images below). If not gently mix excess cells in bottom channel pipette tip reservoir thorough channel a few times. If density is still too low, repeat seeding step. Return chips to incubator upside-down or inverted (to allow attachment to porous membrane); incubate cells for 2 hours in 37° C. incubator.

Seeding Resident Immune Cells in Top Channel.

The following exemplary procedure was used for Seeding Resident Immune Cells in Top Channel: Thaw resident immune cell suspension; Dilute to 10 mLs with DMEM/10%FBS; Spin cells 200 g×5 min; Aspirate and discard supernatant; Resuspend cells to between and 1 mil/mL and 5 mil/mL or more; Remove pre-incubated (24-48 hours) media and pre-seeded chips from incubator; Remove media from top channel; Invert cell suspension gently, fill 200 uL pipette with 50 uL of cells, load into apical channel of chip, and return to incubator; Check to see if channels are seeded with appropriate density of cells, if not gently mix excess cells in apical pipette tip through channel a few times. Repeat as necessary; and Incubate cells for 2 hours in incubator.

The following exemplary procedure was used for preparing a Matrigel overlay; Prepare 250 ug/mL Matrigel in DMEM/10%FBS; Gently add 50 uL to top channel and incubate overnight at 37° C. NOTE: seeding HUVECs, resident immune cells, and applying an overlay may be performed in the same day.

Seeding Caco-2 Epithelial Cells in Top Channel.

The following exemplary procedure was used for Seeding Caco-2 Epithelial Cells in Top Channel, however this method may also be used for seeding other types of epithelial cells, such as human primary epithelial cells: Prepare ~3 million/mL cell suspension of Caco-2; Measure viability; Remove pre-incubated (24-48 hours) media and pre-seeded chips from incubator; Remove ECM overlay from top channel; Invert cell suspension gently, fill 200 uL pipette with 50 uL of cells, load into apical channel of chip, and return to incubator; Check to see if channels are seeded with appropriate density of cells, if not gently mix excess cells in apical pipette tip through channel a few times. Repeat as necessary. Incubate cells for 2 hours in incubator.

The following exemplary procedure was used for Connecting to Flow: Assemble syringes on Chemyx pump; Place chips onto Emulate chip paddle; Remove pipette tips from outlet ports; Unclamp 2.5 in tubing segment and insert 18 ga connector into outlet port; Re-clamp tubing; Remove pipette tips from inlet ports; Deposit a large drop of media on outlet ports to allow for drip-2-drip connections; Prime cut-reservoir with pre-incubated media, slowly push media through cut-reservoir to maintain a drip-2-drip connection and attach to chip inlet ports; Triterate the media in the needle base to remove bubbles and inspect that no bubbles are present in reservoir or chip inlet port; Fill media reservoirs with appropriate volume of pre-incubated media; Prime chip by inserting 200 uL pipette tip outlet tubing, unclamping tubing and gently drawing media through to pipette tip. Observe any bubbles in the channels and attempt to clear; Connect outlet tubing to syringes on Chemyx pump; Prime the system by flowing at 300 uL/min for 150 uL; Check to see that media is entering all syringe needles; Set flow rate to 30 uL/hr. Double check flow rates, all tubing clamps are undone, syringes are seated correctly, the pump is set to withdraw, and start flow.

Example 2

One Embodiment of a Chip Culture Timeline and Example of a Gut-On-Chip

An exemplary experimental chip culture schedule is presented as a timeline starting from Day 0 (seeding chips) by adding HUVEC cells and lamina propria-derived cells; Day 1 was seeding a top layer of epithelial cells and connecting to a flow system; by Day 7 treatments, such as adding PAM2CSK4; and starting Day 8 testing layers and/or removing samples for further analysis. A sample such as effluent was tested for cytokine section from cells. Other samples removed were histological samples for fixation and ICC (immunocytochemistry) such as for determining cellular appearance, determination of tight junction integrity, such as by staining for actin, ZO-1, intracellular cytokine co-localization, etc, and physiological testing, such as migration of particles through the extracellular regions of the epidermal layer. Additional tests may include RNA isolation for determining gene expression levels, such as for proteins involved with tight junction formation, cytokine expression, etc. An exemplary timeline is shown in FIG. 6.

An exemplary gut-on-chip was assembled using the protocol described in Example 1 and the chip culture schedule described above. Samples were removed, fixed then immunofluorescently stained as described herein. DAPI was used in solution to identify nuclear DNA. FIG. 5A (left) shows exemplary immunofluorescently stained histological micrographs of three layers in a cross section of FIG. 5B (right) is an epithelial channel of Caco-2 cells which is shown in the top (left) micrograph as cells outlined in red ZO-1 (Zonula occluders-1, also known as Tight junction protein-1) outlining cells with nuclei stained by DAPI (4',6-diamidino-2-phenylindole) fluorescent stain in blue. Note that the apical microvilli are depicted facing away from the other cells in the chip. Underneath the epithelium (right), on the basal side, is the layer of resident immune cells (* lamina propria-derived cells), which in the middle (left) micrograph shows CD45+ (a lymphocyte common antigen expressed on leucocytes) cells in pink, with intracellular green actin fibers and nuclei stained by DAPI in blue. The lower vascular channel (right) shows a channel formed by HUVECs which in the lower (right) micrograph shows red VE-Cadherin (vascular endothelial cadherin) outlining the cells, intracellular green actin fibers, and nuclei stained by DAPI, in blue.

An exemplary morphology timeline was determined based upon appearance of the cells over time in the device and configuration described above. FIG. 8 shows an exemplary morphology of an Intestine-On-Chip (left schematic) along with a morphology timeline based upon appearance of the cells in the device over time: Day 0 (chips seeded) top micrograph of the area identified on the chip channels by a box; Day 1 connecting to flow; Day 2 monolayer developed; Day 7 'Villus' developed (bottom micrograph of the area identified on the chip channels by a box).

Thus, the inventors designed a Quality Control method fir identifying a gut-on-chip that passes minimum requirements for use in embodiments described herein. FIG. 9A-B shows an exemplary embodiment for Intestine-on-Chip: Quality Control. FIG. 9A) permeability ($P_{app}$ (cm/s)) and FIG. 9B) viability (LDH release as a percent of lysis control) of cells over time. This permeability assay method for adsorption across a gut wall, i.e. caco-2 cells in a gut-on-chip, measures the rate of transport of a test compound added to the basal side of the membrane, for example, inulin-FITC, across to the apical side. See an exemplary permeability assay method in Example 4. Conversely, adding a test compound to the apical side may also be used to measure transport to the basal side. The viability assay method used herein is based on the leakage of a cytoplasmic enzyme, i.e. lactate dehydrogenase (LDH), from dying cells.

The use of this inventive gut-on-chip showed that a culture of primary (healthy) leukocytes (LPDCs) was maintained up to 9 days.

Example 3

Use of a Gut-On-Chip for Modeling Ulcerative Colitis (UC)

Resident immune cells (B cells, T cells, dendritic cells, macrophages, and innate lymphoid cells) were isolated from healthy and Ulcerative Colitis (UC) patients including inflamed and non-inflamed regions of patient tissue. These cells were used as lamina propria-derived resident immune cells in a Gut-On-Chip as described above.

A. UC Lamina Propria-Derived Cells Disrupt Epithelial Barrier Function.

Inflamed UC LP resident immune cells increases permeability of epithelial cells when co-cultured in a device of the present inventions.

FIG. 10 shows an exemplary disrupted barrier function of around 0.5×10-7 $P_{app}$ (cm/s) (apparent permeability) by co-culturing caco-2 epithelial cells and HUVECs with leukocytes isolated from inflamed UC tissue. Untreated controls for comparison use healthy LP derived cells and no LP cells in Gut-On-Chips for comparisons. Treated samples used leukocytes isolated from non-inflamed UC LP compared to inflamed UC LP, which induce a weakened barrier function in the co-cultured epithelial cells.

B. Toll-Like Receptor 2 (TLR2) Activation Stimulates an Ulcerative Colitis-Like Response.

The Gut-On-Chip modeling of inflammation was used for testing bacterial antigen effects on barrier function and cytokine production. An exemplary bacteria antigen used was PAM2CSK4. FIG. 7 shows an exemplary Chip Culture Schematic used for testing effects of a representative bacterial antigen as a synthetic TLR2 agonist, PAM2CSK4, on cytokine production and barrier function. PAM2CSK4 refers to a synthetic diacylated lipopeptide.

1. Cytokine Production (IL-6 and IL-9) Induced by a Synthetic TLR2 Agonist, PAM2CSK4.

FIGS. 11A-B shows an exemplary TLR2 activation that stimulates an ulcerative colitis-like response using a co-culture as shown in a schematic in FIG. 7. PAM2CSK4 induce an IL6 response in healthy LP leukocyte co-cultures and in epithelial cells without LP, while PAM2CSK4 induce IL-9 in LP leukocyte co-cultures for each source but not in epithelial cells without LP cells. FIG. 11A) Comparison of IL-6 (pg/ml) production between chips containing healthy LP, UC LP non-inflamed, UC LP inflamed and no LP with plus or minus PAM2CSK4. FIG. 11B) Comparison of IL-9 (pg/ml) production between chips containing healthy LP, UC LP non-inflamed, UC LP inflamed and no LP with plus or minus PAM2CSK4. IL-6 production threshold for chips with UC LP tissue is different (lower) than in control LP and no LP chips; TLR2 activation of IL-9 production is LP dependent; and no priming for IL-9 production is observed for UC LP tissue. Thus, IL-9 production is LP dependent.

2. Loss of Barrier Function is LP Cell Density Dependent in a Bioassay of Immune Activation.

A co-culture configured as described herein was incubated in a device of the present inventions as described in FIG. 7. Effects of resident leukocytes isolated from LP FIG. 13 shows an exemplary lamina propria-derived cell dose dependent bioassay (overnight incubation) of immune activation. Disrupting Barrier Function. Loss of barrier function is shown upon treatment with a PAM2CSK4 at 4 LP mil/ml but not at LP 1 mil/ml or LP 2 mil/ml. There is little loss of barrier function in duplicate samples lacking PAM2CSK4 treatment even at 4 LP mil/ml.

3. Reduced 'Villus' Height in 'Infected' Chips Correlates with a Reduced Barrier Function.

The chips treated with PAM2CSK4 as a model bacterial antigen are considered infected chips. FIG. 14A-B shows an exemplary reduced 'Villus' Height in Infected Chips as representative immunofluorescent micrograph cross-sections of one embodiment of Intestine On-Chip indicating changes in exemplary heights of the Caco-2 epithelial layer as a readout for barrier function. FIG. 14A) Untreated Control Caco-2 epithelial layer (Avg. Z Height (z-arrow) 157+/−1.5 um) and FIG. 14B) Caco-2 epithelial layer+ Bacterial Challenge–PAM2CSK4 Treated (Avg. Z Height (z arrow) 84 um+/−11 um). The epithelial boundary is marked by a think yellow line. Immunohistochemistry shows ZO-1 (red) outlining cells, E-cadherin (green) and nuclei (blue: DAPI stained). A decrease in barrier function in infected chips correlates with reduced 'villus' heights on the chip.

Therefore, inflamed Intestine On-Chip has weakened barrier function and a reduction in epithelial 'villus' heights. Thus, in one embodiment, the height of the intestinal cell layer was contemplated as a faster readout of intestinal permeability. In one embodiment, the height of the intestinal cell layer was contemplated as a location specific readout of intestinal permeability.

4. IL-6 is Induced By Model Bacteria Antigen PAM2CSK4 which Activates TLR2.

Treatment of co-cultures as described in FIG. 7 with PAM2CSK4 at 1, 2 and 4 LP mil/ml showed that PAM2CSK4 induced a higher level of IL-6 production than co-cultures with no PAM2CSK4. This TLR2 activation induced production was observed at 4 LP mil/ml which showed a higher level of IL-6 production over untreated 1 and 2 ml/ml LP densities. This IL-6 (pg/ml) trend of increased production correlates with disrupted barrier function.

FIG. 15 shows an exemplary TLR2 activation stimulates an ulcerative colitis-like response. IL-6 (pg/ml) trend correlates with disrupted barrier function at 1, 2 or 4 LP (ml/ml).

5. IL-9 is Induced by TLR2 Activation and Alters Barrier Function and Stimulates an Ulcerative Calitis-Like IL-9 (pg/ml) Response.

Treatment of co-cultures as described in FIG. 7 with PAM2CSK4 at 1, 2 and 4 LP mil/ml showed that PAM2CSK4 induced a higher level of IL-9 production at 4 LP mil/ml in basal areas (FIG. 16B). However, in apical regions of the epithelial cell layer IL-9 is produced at higher levels without PAM2CSK4 treatment that are increased with PAM2CSK4 treatment at 1 and 2 LP but not at 4 LP mil/ml (FIG. 16A). Loss of barrier function correlates with presence of IL-9 in the basal channel.

FIG. 16A-B shows an exemplary TLR2 Activation Stimulates an Ulcerative Colitis-like IL-9 (pg/ml) response, FIG. 16A) Apical IL-9 (pg/ml) cytokine secretion at 1, 2 or 4 LP (mil/ml). FIG. 16B) Basal IL-9 (pg/ml) cytokine secretion at 1, 2 or 4 LP (mil/ml). Loss of barrier function correlates with presence of IL-9 in the basal channel.

Thus, inflamed UC LP resident immune cells increases permeability of epithelial cells when co-cultured in a device of the present inventions. In one embodiment, a co-culture as described herein is used for testing effects of drug treatments for reducing loss of barrier function, including but not limited to reducing cytokine effects, such as IL-6 and IL-9.

Example 4

Exemplary Caco-2 Permeability Assay

I. Materials: Caco-2 cells, where Caco-2 cells were maintained prior to use at 37° C. in DMEM in a humidified atmosphere of 5% $CO_2$, the medium, was changed every two days; and cells were subcultured at 70-80% confluence by trypsinization to lilt cells for seeding new cultures; a microfluidic device of the present inventions; flow media; Transport buffer: Hank's balanced salt solution (HESS)+10 mM HEPES+0.35 g/ml $NaHCO_3$, pH7.4 (1:100 1 M HEPES in HBSS); DMSO; low permeability control: Inulin-FITC solution (Sigma); high permeability control: atenolol (50%0, propranolol (90%), cimetidine (95%) or terbutaline (73%); test compounds (at 100 µg/ml); and PBS.

II. Cultivation of Caco-2 cells in microfluidic device: Caco-2 cell monolayers were seeded as described herein. Basal regions of cells were exposed to medium under flow.

III. Experimental procedure: Cells were used for this experiment between days 7 and 9 post seeding. Donor solutions (including a 100 µg/ml Inulin-FITC) were prepared, and solutions used in this experiment were prewarmed to 37° C. Inulin-FITC was used as an indicator for the determination of the monolayer integrity.

IV. Inulin-FITC method: 6 mM Inulin-FITC may be added into an apical region of a monolayer; and incubated for 1 hr. A standard curve may be prepared in a separate container, e.g. a 0.5 to 50 µM; HBSS blank containing 1 to 0.5% DMS0 is placed in wells; Aliquots of 200 µl are transferred from the separate container to a solid black plate; Aliquots of 50 µl are transferred from the device to a solid black plate containing 50 µl HBSS with 1-0.5% DMSO; Plates may be read in a fluorescent reader (Excitation/Emission wavelength 480/530 nm); LY rejection ($P_c$) values are calculated.

V. Molecule transport assay: Transport of a molecule across the monolayer may also be determined; a test compound may be added at the apical region of the monolayer then removed from the apical and/or basal media then analyzed using LC-MS method for loss (e.g. apical region) or gain (e.g. basal region).

Example 5

Exemplary Permeability of Epithelial Cells Cultured in Microfluidic Devices with Different Types of Intestinal Tissue LP Derived Cells Microfluidic co-cultures with HUVEC cells in the bottom chamber, LPDCs from human non-inflamed regions of UC tissue biopsies, LPDCs from UC inflamed tissue biopsies, and samples with no LPDCs, were overlaid with Caco-2 epithelial cell layers. Duplicate samples were not treated, treated with prednisone, treated with PAM2CSK4 or treated with both prednisone and PAM2CSK4 added to the microfluidic co-cultures. Prednisone refers to a synthetic corticosteroid compound (a synthetic glucocorticoid derivative of cortisol) used as an immunosuppressant to treat chronic inflammatory disorders, including UC, specifically for reducing systemic inflammation. Because of its relatively short biological half-life, microfluidic co-cultures were treated once for an overnight incubation. After an incubation time, permeability was determined ($P_{app}^{(cm/s)}$) as described in exemplary EXAMPLE 4.

Trends were discovered associated with prednisone treatment, e.g. increased permeability in Caco-2 epithelial cell layers co-cultured with non-inflamed UC LPDC, while inflamed it LPDC showed little difference from the non-inflamed LPDC sample. Yet on the individual sample level there were both increases and decreases in permeability. Treatment with prednisone and bacterial antigen showed a trend for decreasing permeability despite the variability in the results.

However, based upon these responses from individual samples, prednisone is contraindicated as a means of a universal treatment for UC as shown in microfluidic co-cultures of non-inflamed UC LPDCs vs. inflamed UC LPDCs, with or without the presence of bacterial antigens.

However, by extrapolation of the experimental results shown herein, prednisone treatment may show highly beneficial results to inflamed areas while showing undesirable effects in non-inflamed tissue in certain UC patients. Inflamed UC LPDC is on average more inflamed than the corresponding non-inflamed UC LPDC. Prednisone had no significant effect on either the non-inflamed or inflamed UC LPDC.

Therefore, a microfluidic co-culture as described herein, is contemplated for use in predicting whether a specific patient might derive a benefit in both non-infrared and inflamed intestinal tissue, or potentially be harmed in at least one of these areas by treatment with prednisone.

Figure 17A:
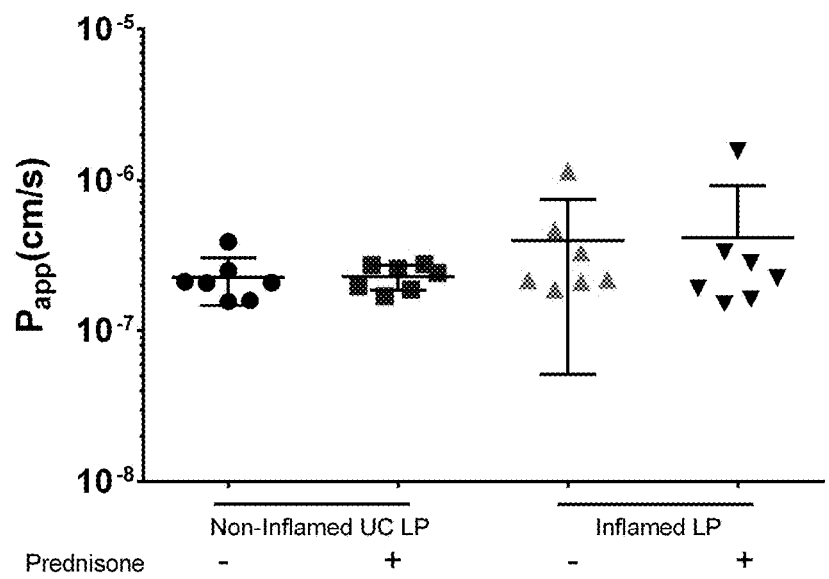
FIGS. 17A-B shows exemplary permeability of FIG. 17A) non-inflamed UC vs. Inflamed LP with and without pretreatment with prednisone, and FIG. 17B) non-inflamed UC vs. Inflamed LP vs. a sample without LP, with and without pretreatment with prednisone with and without treatment with PAM2CSK4 after overnight incubation (treatment).

As shown in FIG. 17A, prednisone treatment of non-inflamed UC LPDC vs. inflamed UC LPDC microfluidic co-cultures shows some benefit in reducing permeability of Caco-2 epithelial cell layer for at least one patients' sample of non-inflamed LPDCs. In contrast, at least one patient sample showed an undesirable increase in Caco-2 epithelial cell layer permeability in a microfluidic co-culture with inflamed UC LPDC treated with prednisone.

Figure 17B:
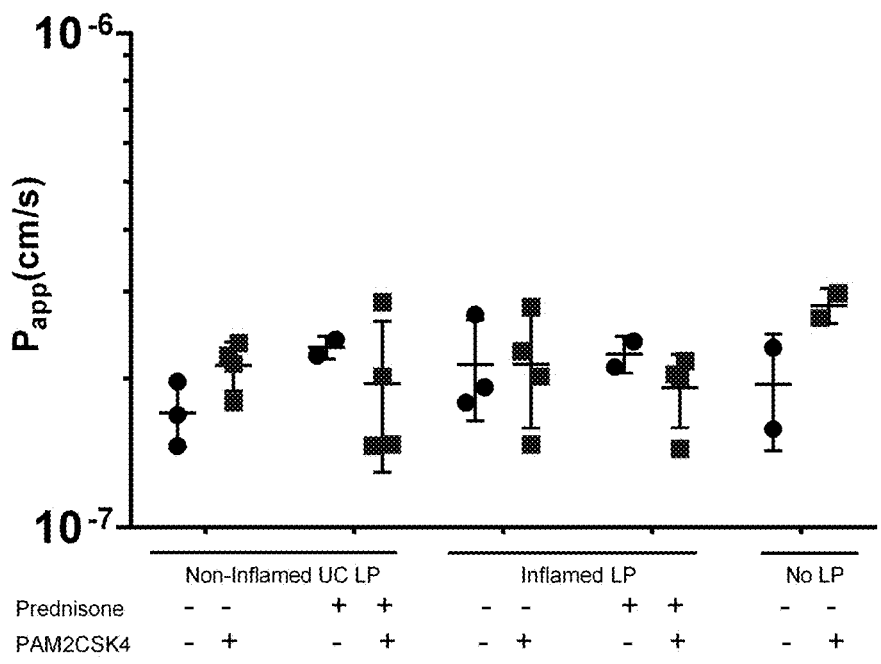

When microfluidic co-cultures are incubated longer term, i.e. overnight, greater differences in responses to prednisone are measured, see, FIG. 17B. For example, the patient samples' non-inflamed UC LPDC co-cultures treated with prednisone showed an undesirable increase in permeability of the associated Caco-2 epithelial cell layer. In contrast, treatment of patients' inflamed UC LPDCs did not induce an increase in permeability when treated with prednisone.

In the presence of an exemplary bacterial antigen, i.e. PAM2CSK4, non-inflamed UC LPDC microfluidic co-cultures show an increase in permeability, as does the microfluidic co-culture containing Caco-2 epithelial cells and endothelial cells without LP derived cells. With prednisone treatment and PAM2CSK4, non-inflamed UC LPDC microfluidic co-cultures show a range of responses, where at least one sample showed an undesirable increase, while other samples showed a desirable decrease in Caco-2 epithelial cell layer permeability.

In contrast, when microfluidic co-cultures are incubated longer term, i.e. overnight, inflamed UC LPDC microfluidic co-culture samples treated with prednisone showed both an increase and a decrease in permeability. However, when inflamed tissue was treated with both prednisone and PAM2CSK4, there appeared to be little benefit in the samples with inflamed UC LPDC.

Example 6

Figure 18A:
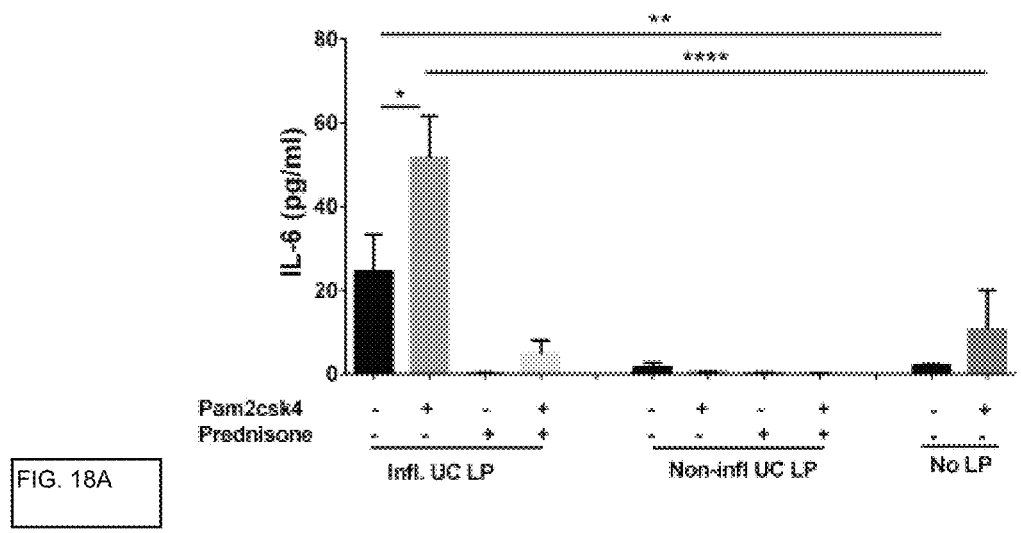
FIGS. 18A-B Shows exemplary cytokine detection of FIG. 18A) IL-6 detected in samples of non-inflamed UC vs. inflamed UC LP vs. a control sample without LP, with and without pretreatment with prednisone; with and without treatment with PAM2CSK4, and FIG. 18B) IL-9 detected in samples of non-inflamed UC vs. inflamed UC LP vs. a control sample without LP, with and without pretreatment with prednisone with and without treatment with PAM2CSK4 after overnight incubation (treatment).
Figure 18B:
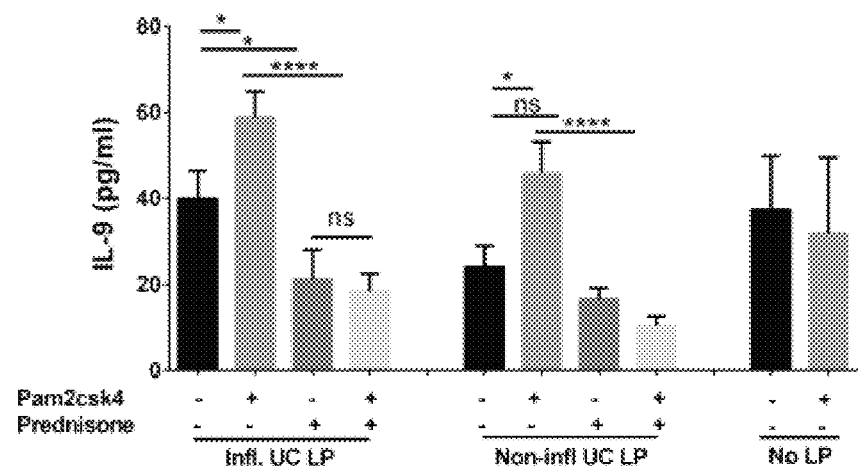
Figure 19A:
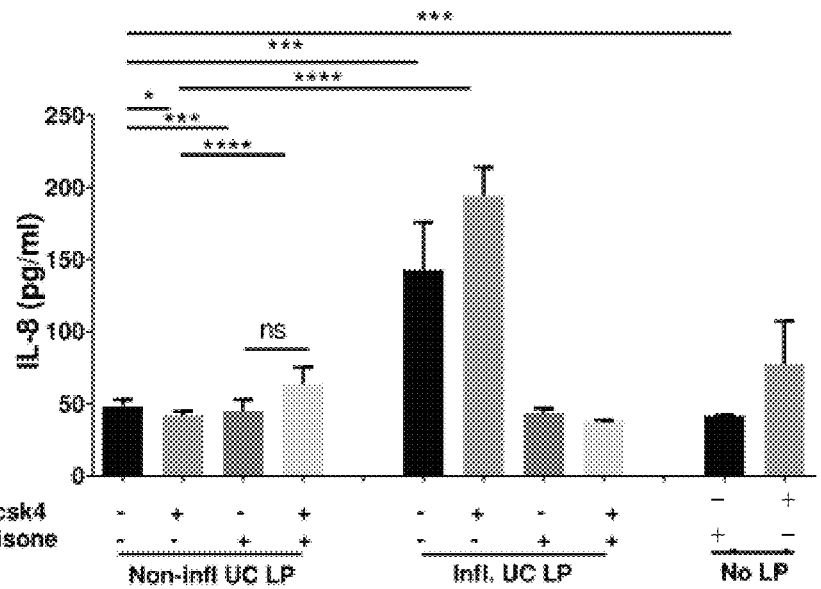
FIGS. 19A-B shows exemplary cytokine detection of FIG. 19A) IL-8 detected in samples of non-inflamed UC vs. Inflamed UC LP vs. a control sample without LP, with and without pretreatment with prednisone; with and without treatment with PAM2CSK4, and FIG. 19B) G-CSF detected in samples of non-inflamed UC vs. inflamed UC LP vs. a control sample without LP, with and without pretreatment with prednisone with and without treatment with PAM2CSK4 after overnight incubation (treatment).
Figure 19B:
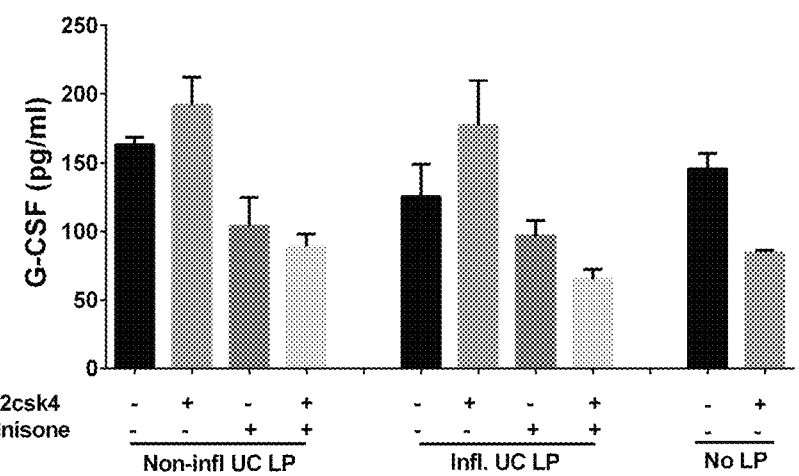
Figure 20A:
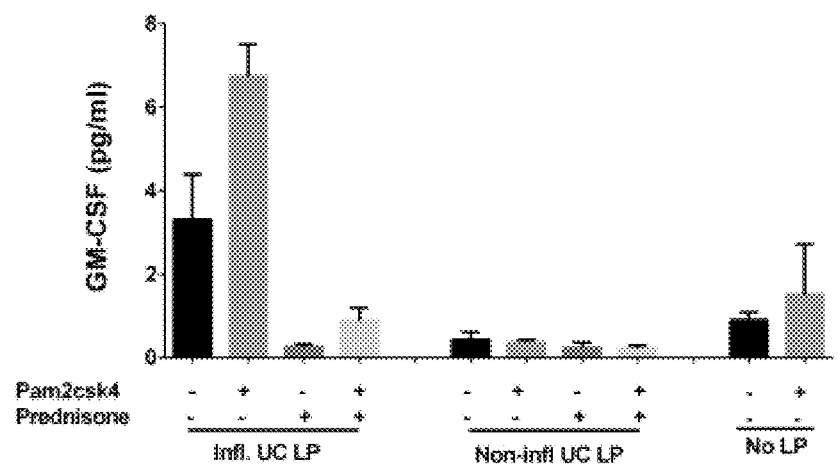
FIGS. 20A-B shows exemplary cytokine detection of FIG. 20A) GM-CSF detected in samples of non-inflamed UC vs. inflamed UC LP vs. a control sample without LP, with and without pretreatment with prednisone; with and without treatment with PAM2CSK4, and FIG. 20B) MCP-1 detected in samples of non-inflamed UC vs. inflamed UC LP vs. a control sample without LP, with and without pretreatment with prednisone with and without treatment with PAM2CSK4 after overnight incubation (treatment).
Figure 20B:
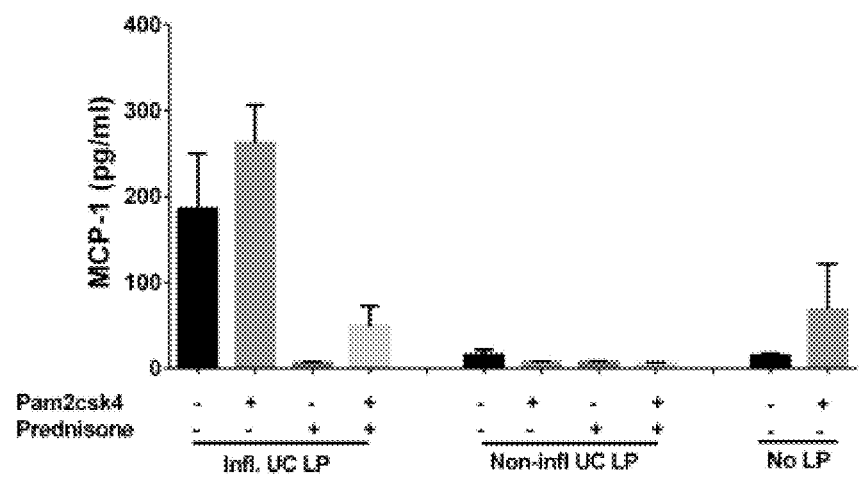
Figure 21A:
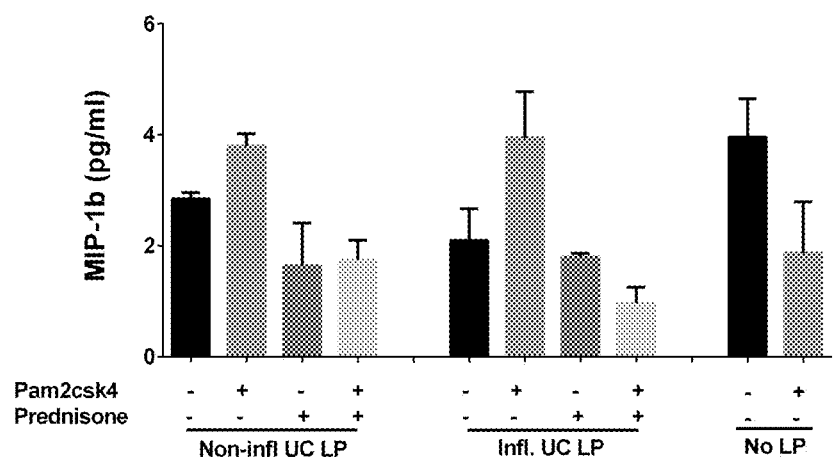
FIGS. 21A-B shows exemplary cytokine detection of FIG. 21A) MIP-1 detected in samples of non-inflamed UC vs. inflamed UC LP vs. a control sample without LP, with and without pretreatment with prednisone; with and without treatment with PAM2CSK4, and FIG. 21B) PDGF-AB/BB detected in samples of non-inflamed UC vs. inflamed UC LP vs. a control sample without LP, with and without pretreatment with prednisone with and without treatment with PAM2CSK4 after overnight incubation (treatment).
Figure 21B:
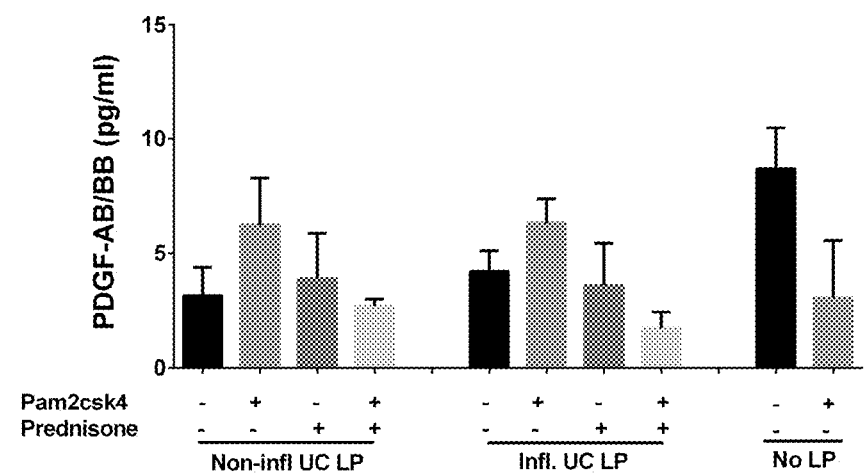
Figure 22:
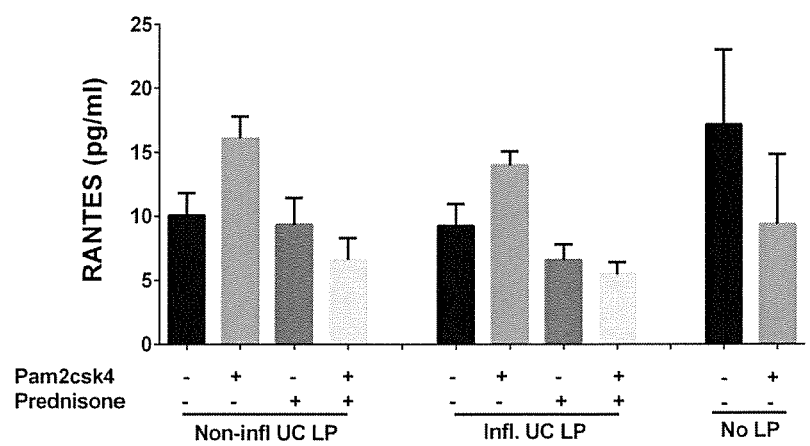
FIG. 22 shows exemplary cytokine detection of RANTES detected in samples of non-inflamed UC vs. inflamed UC LP vs. a control sample without LP, with and without pretreatment with prednisone; with and without treatment with PAM2CSK4

Exemplary Cytokine Production in Co-Cultures of Epithelial Cells Cultured in Microfluidic Devices with Different Types of Intestinal Tissue LP Derived Cells In order to determine contributory factors to the trends in permeability changes observed by combinations of prednisone treatments as in Example 5, cytokine and chemokine production were measured from media samples obtained from the microfluidic cultures as described in EXAMPLE 5. After an incubation time, media samples were extracted from the microfluidic device then used for determining amounts cytokine and chemokine produced, such as IL-6 and IL-9 in FIG. 18A-B; IL-8 and G-CSF in FIG. 19A-B; GM-CSF and MCP-1 in FIG. 20A-B; MIP1b and PDGF-AB/BB in FIG. 21A-B; and RANTES in FIG. 22. Amounts of cytokine and chemokine protein are measure in pg/ml (picogram per milliliter).

Prednisone Reduces IL-6 Production in Microfluidic Co-Cultures with Inflamed LPDCs In general, while PAM2CSK4 induces increases in IL-6 production, prednisone treatment reduces it regardless if it is endogenous to the microfluidic cultures due to the types of co-cultured cells, e.g. larger amounts produced in the inflamed UC LPDC sample compared to a non-inflamed UC LPDC sample, or induced by PAM2CSK4 in the inflamed sample. Significantly, the Caco-2 epithelial cells cultured with inflamed LPDC samples produced greater amounts of IL-6 than did the non-inflamed LPDC co-cultures or cultures without LP cells. PAM2CSK4 treatment in the presence of inflamed LPDC samples also increased IL-6 production but not with the non-inflamed LPDC samples. While IL-6 is known to have both inflammatory and anti-inflammatory effects, depending upon the system, in this microfluidic system for mimicking UC, based upon these results, IL-6 is contemplated as an initiatory factor for inducing inflammation. Further, prednisone is shown to reduce IL-6 production in the inflammatory (potentially pre-inflammatory) microfluidic model. See, FIG. 18A.

In contrast, Prednisone (and/or PAM2CSK4) does not appear to have an effect on IL-6 production in the co-cultures with non-inflamed LPDCs. See, middle section of FIG. 18A.

Prednisone Reduces IL-9 Production in Microfluidic Co-Cultures with Non-Inflamed and Inflamed LPDCs Interleukin 9 (IL-9) production is reduced in the presence of prednisone in the non-inflamed and inflamed UC LPDC microfluidic co-cultured samples, regardless of the presence of PAM2CSK4. See, FIG. 18B.

Further, in both types of co-cultures, PAM2CSK4 significantly induced IL-9 production over endogenous levels in these types of microfluidic co-cultures. This increased IL-9 production was significantly reduced by prednisone treatment, which also tended to reduce IL-9 to levels lower than endogenous levels in these microfluidic co-cultures. Thus, IL-9 is contemplated as a factor for supporting inflammation in this microfluidic UC model co-culture system while prednisone reduces IL-9 production.

Furthermore, because IL-9 is mainly produced by $T_H9$ T cells in other systems, a procedure was used to produce $T_H9$ (Th9) cells for use in these microfluidic co-cultures, see Examples 7 and 8.

Prednisone Reduces IL-8 Production in Microfluidic Co-Cultures with Non-Inflamed LPDCs Microfluidic co-cultures, with treatments as described above, were used to provide media samples for determining production of IL-8.

Prednisone treatment showed a trend for reducing IL-8 production in microfluidic co-cultures with inflamed LPDCs, with and without treatment with PAM2CSK4.

There did not appear to be a reduction in IL-8 for microfluidic non-inflamed LPDC cultures treated with Prednisone alone or PAM2CSK4.

Prednisone Tends to Reduce G-CFS Production in Microfluidic Co-Cultures with Non-Inflamed and Inflamed LPDCs Microfluidic co-cultures, with treatments as described above, were used to provide media samples for determining production of Granulocyte-colony stimulating factor (G-CSF or GCSF), also known as colony-stimulating factor 3 (CSF 3).

Prednisone treatment showed a trend for reducing G-CSF production in microfluidic co-cultures with non-inflamed LPDCs or inflamed LPDCs, with and without treatment with PAM2CSK4.

Prednisone Reduce CM-CFS Production in Microfluidic Co-Cultures with Non-Inflamed LPDCs Microfluidic co-cultures, with treatments as described above, were used to provide media samples for determining production of Granulocyte-macrophage colony-stimulating factor (GM-CSF), also known as colony stimulating factor 2 (CSF2).

Prednisone treatment reduced GM-CSF production in microfluidic co-cultures with inflamed LPDCs with and without treatment with PAM2CSK4. There did not appear to be a reduction in GM-CSF for microfluidic non-inflamed LPDC cultures treated with Prednisone alone, likely because there was such as small amount of GM-CSF produced in these cultures both before and after treatment with PAM2CSK4.

Prednisone Reduce MCP-1 Production in Microfluidic Co-Cultures with Non-Inflamed and Inflamed LPDCs Microfluidic co-cultures, with treatments as described above, were used to provide media samples for determining production of chemokine Monocyte chemoattractant protein-1 (MCP-1 or CCL2).

Prednisone treatment reduced MCP-1 production in microfluidic co-cultures with inflamed LPDCs with and without treatment with PAM2CSK4. There did not appear to be a reduction in MCP-1 for microfluidic non-inflamed LPDC cultures treated with Prednisone alone, likely because there was such as small amount of MCP-1 produced in these cultures both before and after treatment with PAM2CSK4.

Prednisone Tends to Reduce MIP-1b Production in Microfluidic Co-Cultures with Non-Inflamed and Inflamed LPDCs Microfluidic co-cultures, with treatments as described above, were used to provide media samples for determining production of macrophage inflammatory protein 1 beta (MIP-1b).

Prednisone treatment showed a trend for reducing PDGF-AA/BB production in microfluidic co-cultures with non-inflamed LPDCs.

Prednisone treatment showed a trend for reducing PDGF-AA/BB production in microfluidic co-cultures with non-inflamed and inflamed LPDCs treated with PAM2CSK4. There did not appear to be a reduction in PDGF-AA/BB for microfluidic cultures treated with Prednisone alone.

Prednisone Tends to Reduce PDGF-AA/BB Production in Microfluidic Co-Cultures with Non-Inflamed and Inflamed LPDCs Treated with PAM2CSK4

Microfluidic co-cultures, with treatments as described above, were used to provide media samples for determining production of Platelet-derived growth factor (PDGF) including isoforms PDGF-AA, PDGF-BB and PDGF-AB.

Prednisone treatment showed a trend for reducing PDGF-AA/BB production in microfluidic co-cultures with non-inflamed and inflamed LPCs treated with PAM2CSK4. There did not appear to be a reduction in PDGF-AA/BB for microfluidic cultures treated with Prednisone alone.

Prednisone Tends to Reduce RANTES Production in Microfluidic Co-Cultures with Non-Inflamed and Inflamed LPDCs Treated with PAM2CSK4

Microfluidic co-cultures, with treatments as described above, were used to provide media samples for determining production of RANTES chemokine (i.e. "Regulated on Activation, Normal T Expressed and Secreted" or "Chemokine (C-C motif) ligand 5 or "CCL5").

Prednisone treatment showed a trend for reducing RANTES production in microfluidic re-cultures with non-inflamed and inflamed LPDCs treated with PAM2CSK4.

Example 7

Exemplary Isolation of CD4+ Populations of Peripheral White Blood Cells (PBMCs) and Exemplary Plate Activation for Providing a Default $T_H1$ Population (i.e. Subset of T Cells)

A. Isolating Lymphocytes from Peripheral Blood Mononuclear Cells (PBMCs) for Providing Purified CD4+ Lymphocyte Populations.

As indicated by the photographs of whole blood in a centrifuge tube as a solution with a gradient forming reagent, e.g. Ficoll-Hypaque (Pharmacia LKB Biotechnology, Piscataway, N.J.), FIG. 25B left, and after density gradient centrifugation, FIG. 25B right, a lymphocyte population was pippeted out of the buffy coat lymphocyte (T cell) layer. The harvested cells were washed at least 2 times with PBS supplemented with 2% fetal bovine serum and (thylenediaminetetraacetic acid (EDTA), then underwent purification to provide a CD4+ enriched lymphocyte population using positive selection, e.g. MACS® Cell Separation (MACS®) Miltenyi Biotec GmbH), which may include, for e.g., CD4 MicroBeads, one package for each $1 \times 10^9$ total cells. As an exemplary method, MACS MACS® magnetic MicroBeads are added to the washed lymphocytes, cells are separated (e.g. magnetized cells are retained while the remainder are a flow through fraction) in a MACS Column placed in a MACS Separator. The flow-through fraction can be collected as the negative fraction depleted of the labeled cells. Elution of labeled cells is accomplished when the column is removed from the separator. The retained cells are elated as a purified, i.e. enriched, positively selected cell fraction, e.g. CD4+ cells, for use in providing T cell subsets described herein.

In other embodiments, density gradient centrifugation is not used. As another exemplary method, a CD4+ cell population may be obtained by using flow cytometry based cell sorting, either positive or negative selection. As another example, enterocytes in whole blood are lysed, then white blood cells are harvested for use in further CD4+ purification. In yet another embodiment, MACSxpress® Technology may be used to isolate cells directly from whole blood, without density gradient centrifugation and erythrocyte lysis.

In some embodiments, isolated or purified populations of lymphocytes are used directly in activation and differentiation procedures. In some embodiments, isolated or purified populations of lymphocytes are frozen then thawed prior to use with activation procedures. In some embodiments, isolated or purified populations of lymphocytes are used directly in microfluidic chips. In some embodiments, isolated or purified populations of lymphocytes are frozen then thawed prior to use with activation procedures. Freezing methods for human lymphocytes are well known in the art.

B. Plate Activation and Differentiation of a Purified CD4+ Population.

This is an exemplary method for providing an activated and differentiated population of predominantly $T_H1$ cells via a default pathway where no additional cytokines are added to the activation media, over 3 days of incubation. After three days of co-stimulation (activation) and differentiation into a predominant T cell subset, this T cell population was used for seeding microfluidic chips on Day 0 of the chip timeline.

Both CD3 and CD28 antibodies are used in part for providing an on-plate activated population of T cells. In part because absence of co-stimulation during TcR engagement with CD3 activation antibodies is implicated in a state of unresponsiveness (energy) or to pro-grammed cell death (apoptosis) of T cells.

1. A Method for Antibody Immobilization on Tissue Culture Plates

Anti-human CD3 antibodies were used to coat plastic tissue culture plates (or flasks, wells, etc.) prior to adding CD4 purified lymphocyte cell populations. Nonlimiting examples of anti-CD3 antibodies include anti-human CD3 antibody OKT 3, Anti-CD3 (OKT3) MoAb Caitag Corporation (Burlingame, Calif.); BD Bioscience #555336; anti-human CD3 mAb (PharMingen)). Antibodies are immobilized (i.e. attached) to tissue culture plates via CD3 antibody Fc receptors by incubating antibody solutions in tissue culture plates, for one example, at 2 µg/mL in phosphate-buffered saline solution (PBS) for 4 to 18 hours at 37° C. then washing plates with PBS or media to remove unbound antibodies.

2. A Method for Co-Simulation of T cells On-Plates.

Purified human CD4+ cells in tissue culture media, comprising soluble anti-human CD28 mAb (e.g. PharMingen, San Diego, Calif.), were added to CD3 coated plastic tissue culture plates for non-antigen-specific activation. Co-stimulation of the CD3 transmembrane signaling complex and the T cell CD28 molecule results in nonantigen specific stimulation of the TCR (CD3). After three days of incubation, the default T cell population is considered a TH1 population. After three days of co-stimulation, with or without added cytokines, cells are pipetted out of the plates, the plates are washed with media or PBS to remove any remaining cells, then harvested cells are washed at least 3 times to remove cell fragments and culture reagents, prior to use of the activated T cell population for seeding microfluidic chips on Day 0 of the chip timeline.

For production of a nondefault T cell population, cytokines are added to the cell media to inducing differentiation of a nonTH1. Thus, in other examples described herein, cytokines are added in the activation media for producing other types of T cell populations.

FIGS. 25A-C shows an exemplary schematic model for translating in vivo T cell activation and differentiation of T-Cell effector subsets derived from blood to an in vitro method for providing human activated immune cells simulating CD as $T_H1$ subsets and simulating UC gas $T_H9$ subsets. FIG. 25A shows one embodiment as an exemplary schematic of T cell activation in vivo (nature) where antigen presentation in the context of cell bound MHC-antigen complex triggers a CD3 signaling complex on a T cell, while cell bound CD80 and CD86 molecules co-activate CD28 signaling on the same cell, as compared to T cell activation in vivo (laboratory) where activation factors such as anti-CD3 and anti-CD28 antibodies are soluble (in solution) that activate the T cell bound CD3 complex bypassing recognition of TCR (T cell receptor) antigen specific MHC molecules and the CD28 receptor. FIG. 25B shows one embodiment as an exemplary schematic for lymphocyte isolation from peripheral blood (i.e. PBMCs), including T cells, as a buffy coat layer (right) obtained after centrifugation of a mixture of whole blood, i.e. peripheral whole blood mononuclear (PBMCs) cells, in a solution comprising a gradient forming particle (left). FIG. 25C shows one embodiment as an exemplary schematic for post-activation of a population of CD4+ enriched T cells differentiated into T cell subsets depending upon differential levels of cytokine additions for inducing differentiation into the exemplary T cell subsets depicted.

For nonlimiting examples, examples of $T_H1$, $T_H2$ and $T_H9$ differentiated subsets of activated CD4+ T cell populations are shown resulting from either a default subset without exposure to additional cytokines, e.g. a $T_H1$ subset, vs. exposure to IL-2 and IL-4 for producing $T_H2$ CD4+ T cell populations and exposure to IL-4 and TGF-beta for producing $T_H9$ CD4+ T cell populations.

Example 8

Exemplary Differentiation of $T_H9$ Cells from Isolated CD4+ Populations of Peripheral White Blood Cells, i.e. PBMCs T helper 9 ($T_H9$ or Th9) cells refer to CD4+ helper T (CD3+) cells (CD3+CD4+IL-9+) producing IL-9. Because IL-9 was identified as a potential modulatory cytokine in the microfluidic system for UC, and predisone reduced IL-9 production, $T_H9$ cells were produced for identifying additional contributory factors to UC.

A $T_H9$ cell population was produced from a population of T cells isolated from a sample of peripheral blood mononuclear cells (PBMCs), referring to white blood cells isolated from a human. Including but not limited to lymphocytes (T cells, B cells, NK cells), eosinophils, basophils, macrophages, monocytes etc. See, FIG. 25B.

Thus, in one embodiment, the isolated T cells were treated with a combination of TGFB, IL-4, and IFNg for inducing differentiation of $T_H9$ cells. This differentiation procedure produced CD3+/CD28+ T cells (CD3/CD28), where CD28 refers to a receptor for inducing a co-stimulatory pathway. Such co-stimulatory pathways include T cell activation pathways, See, FIG. 25A-C.

Example 9

Cytokine Production from Artificially Produced T$_H$9 Cells

Figure 23A:
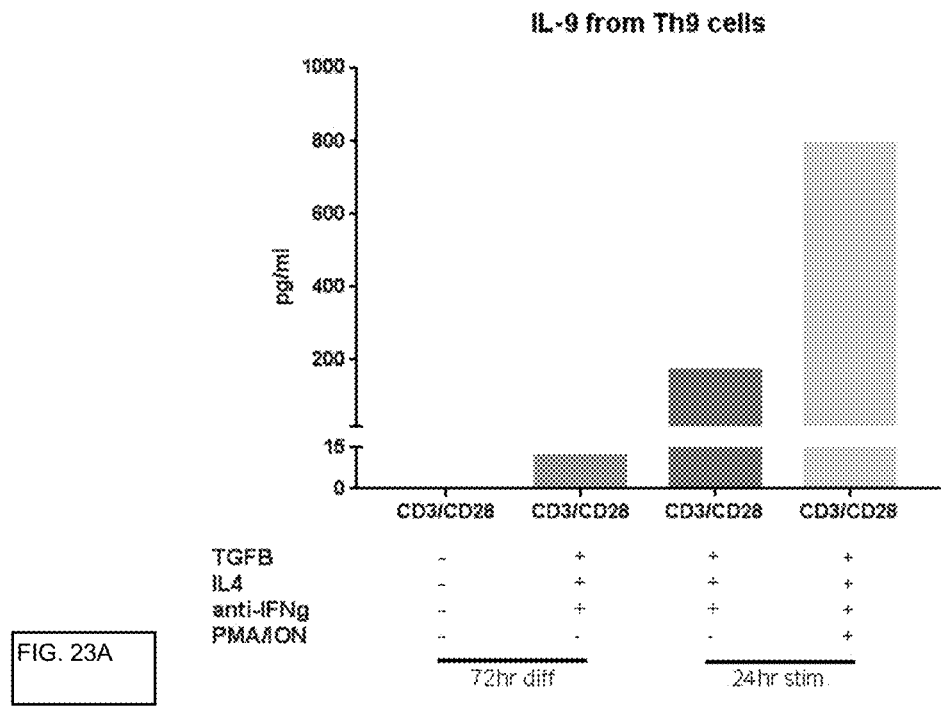
FIGS. 23A-B shows exemplary cytokine detection from populations of Th9 cells, FIG. 23A) IL-9 and FIG. 23B) IL-2 detected in populations of CD3/CD28 T cells isolated from PBMCs, treated with combinations of the agents as shown: TGFB, IL4, anti-IFNgamma (IFNg), and PMA/ION.
Figure 23B:
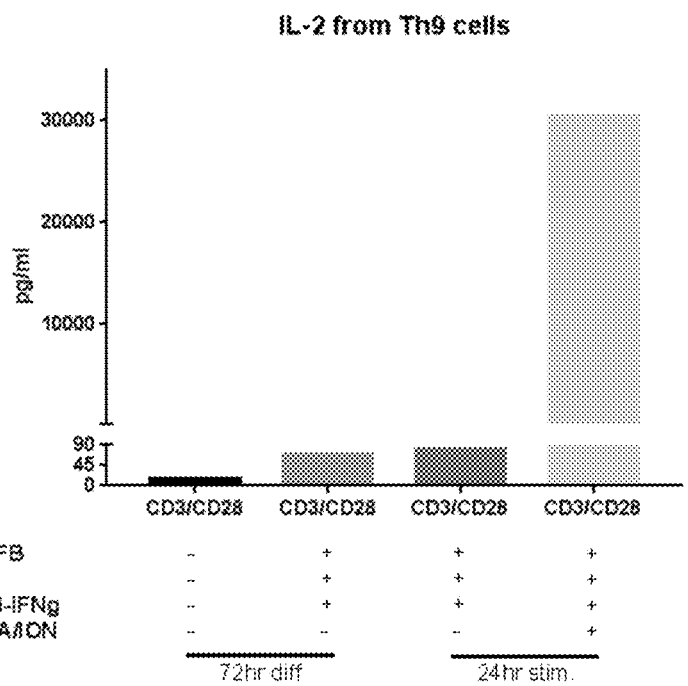

Production of cytokines IL-9 and IL-2 were measured in the CD3+/CD28+ T$_H$9 T cells produced in EXAMPLE 7. After 72 hours of differentiation, as described above, CD3+/CD28+ T cells produced relatively low levels of IL-9 protein. Then subsequetly, these CD3+/CD28+ underwent 24 hours of stimulation with Phorbol 2-myristate 13-acetate/ Ionomycin (PMA/ION). Stimulated CD3/CD28 T cells produced large amounts of IL-9 demonstrating the presence of T$_H$9 cells. See, FIG. 23A. Under the same conditions, these T$_H$9 cells also produced IL-2, See, FIG. 23B. IL-2 refers to a cytokine for supporting T cell survival and activation, typically produced by CD4+ helper T cells. Therefore, this combination of differentiation and stimulation produced an IL-9 and IL-2 producing T$_H$9 population for use in further microfluidic co-culture experiments.

Example 10

T$_H$1 Populations and T$_H$9 Populations for Comparative Bacterial Antigen Stimulation Assays on Cell Culture Plates (On-Plate)

In this example, a T$_H$1 cell population was produced from a population of CD4+ T cells obtained from a sample of PBMCs. This population of CD4+ T cells were co-stimulated with soluble CD3 and CD28 antibodies without added cytokine stimulation for inducing differentiation of T$_H$1 cells. Unlike the co-stimulation with soluble CD3 and CD28 antibodies in the presence of TGFB, IL-4, and IFNg cytokines for inducing differentiation of T$_H$9 cells as described herein.

Thus, in this example, purified CD4+ T cell populations were plated into tissue culture plates for activation and differentiation into one selected T cell subtype, e.g. Th1 in one plate, and Th2 in another plate.

FIGS. 26A-B shows exemplary results comparing post differentiation CD4+ T cell cytokine expression from each of the differentiated CD4+ T cell subsets on-plates. Further cytokine secretion is compared between subtypes after stimulation with an exemplary bacterial agonist, i.e. PAM2CSK4, for mimicking an inflammatory stimulus. FIG. 26A shows exemplary comparative IFNgamma cytokine protein expression. FIG. 26B shows exemplary IL-9 cytokine protein expression. For each CD4+ T cell subset, the left bar represents expression without an additional stimulus whiles the right bar represents expression after exposure to soluble PAM2CSK4. PAM2CSK4 increases in the concentration of protein signaling in both T$_H$1 (CD) and T$_H$9 (UC) cells.

FIG. 27A-B shows exemplary results for additional comparative cytokine production as described in FIGS. 26A-B. FIG. 27A shows exemplary comparative IL-6 cytokine protein. FIG. 27B shows exemplary comparative IL-8 cytokine protein expression. For each CD4+ T cell subset, the left bar represents expression without an additional stimulus while the right bar represents expression after exposure to soluble PAM2CSK4.

FIG. 28A-C shows exemplary results of measuring cytokine expression post differentiation as described in FIGS. 26A-B. FIG. 28A shows exemplary comparative IL-13 cytokine protein expression. FIG. 28B shows exemplary comparative IL-1 beta cytokine protein expression. FIG. 28C shows exemplary comparative TNF-alpha cytokine protein expression.

FIG. 29 shows a schematic representation demonstrating exemplary intracellular signaling pathways in an activated T$_H$9 CD4+ T cell. IL-9 production is triggered by binding of particular cytokines to membrane receptors for TGF-beta, e.g. PU.1 associated signaling pathway(s); IL-4, e.g. parts of the STAT6 associated signaling pathway; and IL-1 and IL-25 e.g. NF-kappaB associated signaling pathway(s), each contributing to the expression of IL-9.

A sample of each T$_H$ cell type was exposed to PAM2CSK4, then log 2 fold changes in protein expression of either pathway molecules or IL-9 were measured and compared to duplicate samples not treated with PAM2CSK4.

FIG. 30A-D shows exemplary results comparing post differentiation CD-4+ T$_H$9 T cell activation factors and IL-9 cytokine secretion from activation of CD4+ T cell subsets using soluble CD3 and CD28 antibodies, with or without stimulation by soluble PAM2CSK4, on-plates, FIG. 30A shows exemplary results for GATA3 mRNA production. FIG. 30B shows exemplary results for SPI1 mRNA production. FIG. 30C shows exemplary results for IRF4 mRNA production. FIG. 30D shows exemplary results for IL-9 protein mRNA.

Upon stimulation with PAM2CSK4, T$_H$1 populations produce measurable IRF4 and IL-9, but not GATA3 car SPI11. Surprisingly, PAM2CSK4 stimulation did not significantly increase IL-9, or IL-9 activation factors associated with inducing IL-9 expression, measured in log 2 fold changes, as demonstrated in populations of T$_H$9 populations in tissue culture plate even though IL-9 mRNA concentrations did significantly increase in T$_H$1 populations, see FIG. 26B.

Example 11

Comparative Co-Stimulation (Using Soluble Reagents) and Exposure to Bacterial Antigen in Intestinal Microfluidic Chips Failed to Provide an Inflammatory Model of IBD In this example, purified CD4+ T cell populations were plated into tissue culture plates for activation and differentiation into one selected T cell subtype, e.g. T$_H$1 in one plate, and T$_H$9 in another plate. A T$_H$1 cell population was produced from a population of CD4+ T cells, as described in Example 7. This population of CD4+ T cells were co-stimulated with soluble CD3 and CD28 antibodies, without added cytokines, for inducing differentiation of T$_H$1 cells. Unlike co-stimulation with soluble CD3 and CD28 antibodies in the presence of TGFB, IL-4, and IFNg cytokines which induced differentiation of T$_H$9 cells, as described herein.

A sample of each T$_H$ cell type was exposed to PAM2CSK4, then log 2 fold changes in protein expression of either pathway molecules or IL-9 were measured and compared to duplicate samples not treated with PAM2CSK4.

In Vitro Activation and Differentiation of T-Cell Effector Subsets Derived from Blood Further Stimulated on-Chip.

FIG. 31 shows a schematic representation demonstrating an exemplary timeline for one embodiment of a microfluidic chip. Chips are seeded at Day 0 in the Endothelial Channel: HUVECs and Epithelial Channel: 1. Immune Cells and 2. Cace-2 epithelial cells then incubated at 37° C. On Day 1 the chips are connected to flow, in some embodiments readouts on Day 1 may include imaging cells attached to the chip surfaces. On Day 3, in some embodiments, a microfluidic chip has an inflammatory challenge (i.e. treatment, including but not limited to a treatment shown in Tables 1, 2, 4, 5, 7, 9, 10, 13, for nonlimiting examples), for one example e.g. adding PAM or IL-9 to media flowing through the chip. In some embodiments, chips are disconnected from flow. In some embodiments, readouts on Day 3 or later, may include imaging cells and permeability assays. In chips disconnected from flow, media may be replenished on Day 6. In chips with closed media flow, media may be replenished on Day 6. Day 6 readouts: may include cell imaging, permeability assays, cytokine analysis, etc. Day 7 or later: collect endpoint samples for readouts: including but not limited to cell imaging, permeability assays, cytokine analysis, etc. Endpoint sample collection (sample collection of cells from chips): including but not limited to FACs, RNA, and immunofluorescence.

Stimulation conditions include but not limited to additional stimulation with PAM2CSK4 (i.e. PAM), with or without additional IL-9. See, Table 1.

FIG. 32A-B shows exemplary results comparing apparent permeability of untreated vs. treated epithelial layers in microfluidic chips over time, after seeding with TH1 or TI-19 T-cells differentiated on plates, shown in FIG. 32A. FIG. 32B shows results from Day 8 microfluidic chips treated with Tofacitinib (citrate) with or without PAM2CSK4 (PAM).

FIGS. 33A-B shows exemplary results comparing pro-inflammatory cytokine production in chips described in FIGS. 32A-B. FIG. 33A shows exemplary IL-6 secretion. FIG. 33B shows exemplary IL-10 secretion.

Thus, methods using soluble CD3, CD28 and PAM2CSK4 provided an activated and differentiated population of $T_H9$ cells but failed to provide a $T_H9$ population capable of further activation when exposed to a soluble bacterial antigen mimic, PAM2CSK4. As this result was puzzling, the following experiment was designed for measuring permeability of the epithelial layer for comparison. Additionally, Tofacitinib (citrate), or Tofa, was tested alongside PAM2CSK4. Tofacitinib (citrate) refers to an inhibitor of the enzymes Janus kinase 1 (JAK1) and Janus kinase 3 (JAK 3), which means that it interferes with the JAK-STAT signaling pathway. A JAK-STAT signaling pathway is involved with transmitting extracellular information into the cell nucleus, influencing DNA transcription related to inflammatory mediators.

Thus, CD4+ T-cells were differentiated on plates and then seeded on chips, that were further stimulated, did not induce a definitive decrease in barrier function unlike intestine on-chips stimulated for inflammation, e.g. PAM2CSK4.

In order to further test whether PBMCs activated and differentiated with soluble factors were capable of inducing inflammation on chips, pro-inflammatory cytokine production was compared between untreated, PAM2CSK4 treated with and without Tofacitinib.

Example 12

Methods of Binding Immune Activating Factors, i.e. Reagents, in the Intestine On-Chip for Providing an Activated ECM FIG. 41C is a schematic representation showing immune activating factors (reagents) covalently attached to the chip membrane, within or on top of the ECM, i.e. activated ECM.

The following examples show the development of providing an activated ECM to immune cell subsets in intestine-on-chips, that provides stimulation for keeping T cells in a responsive state such that in the presence of antigen results in production of significant amounts of prostimulatory cytokines. See, FIG. 35 for a schematic representation demonstrating an exemplary timeline for experiments on chips seeded (Day 0) using $T_H1$ or $T_H9$ populations that were activated and differentiated into subsets using CD3 antibody coated tissue culture plates, co-stimulated with soluble CD28 antibodies.

Stimulation (treatment) conditions on-chips include but are not limited to adding soluble CD3 antibodies, soluble CD28 antibodies, and a combination of soluble CD3 and CD28 antibodies, etc. In some preferred embodiments, soluble activation factors include stimulatory CD28 antibodies. In some embodiments, soluble activation factors include antigen. In some embodiments, soluble activation factors include an antigen for stimulating antigen recognition by T cells that bypasses the MHC-antigen molecule, including but not limited to TLR, Toll-like receptors expressed on T cells. In some embodiments, soluble activation factors include antigen recognition by cells in an epithelial layer expressing TLR receptor molecules. Thus, in some embodiments, soluble antigen, e.g. PAM2CSK4 (i.e. PAM) is added to microfluidic chips, with or without additional IL-9. Wherein, in some embodiments, activated ECM comprises CD3 antibodies capable of binding to and activating human CD3 T cells. In such conditions, CD28 co-stimulatory antibodies are added as a soluble reagent in the upper epithelial channel.

There are several methods for adding stimulatory antibodies to ECM on-chip. In one embodiment, antibodies in solution are added to chips in the epithelial channel prior to coating the chip's plastic membrane with ECM. Thus, after antibodies attach to the chip membrane, see incubation times and solutions for coating plastic tissue culture plates for example, unattached antibodies are washed out, then chip membranes are coated with ECM, as described herein. In some embodiments, antibodies in solution are added to ECM solution prior to coating the chip membrane with the ECM mixture, for creating an activated ECM comprising bound antibodies. In one embodiment, antibodies in solution are added to and incubated on top of ECM coated chip membranes, i.e. preECM coated membranes, after which the unbound antibodies are washed off the ECM prior to adding epithelial cells, for creating an activated ECM comprising bound antibodies. Such activated ECM may be considered "doped", wherein to "dope" the ECM refers to adding a T cell stimulatory reagent to the ECM. In preferred embodiments, CD3 antibodies and CD28 antibodies are capable of binding to and activating human CD3 T cells. Examples of anti-human CD3 antibodies (i.e. CD3 antibodies) include but are not limited to mouse-anti-human OKT3, soluble anti-CD28 Abs. Nonlimiting examples of anti-CD3 antibodies include anti-human CD3 antibody OKT 3, Anti-CD3

(OKT3) MoAb Caltag Corporation (Burlingame, Calif.); BD Bioscience #555336; anti-human CD3 mAb (PharMingen)).

Example 13

Simulating in Vivo Co-Stimulation (Activation) of TH1 Cell Subsets On-Chip in the Presence of Antigen Using Activated ECM Stimulation conditions include but not limited to comparing stimulation effects on barrier function, i.e. apparent permeability, and cytokine expression, as shown in Table 7, with results described below. T cell subsets were purified from PBMCs as described herein, then stimulated in tissue culture plates using plate bound CD3 and soluble CD28 antibodies.

FIG. 42 shows a schematic representation demonstrating an exemplary timeline for activating immune cells on-chip comprising an activated ECM, where chips were seeded using $T_H1$ or $T_H9$ populations activated and differentiated into subsets using CD3 antibody coated tissue culture plates co-stimulated with soluble CD2 antibodies. In this embodiment, the method includes treatment at Day 6 with an endpoint readout at Day 8 (Takedown). See the following Tables for additional embodiments. See, Tables 7-11.

These experiments showed that chips having bound CD3 and bound CD28 (one embodiment of activated ECM) in combination with the presence of a soluble antigen, PAM, causes a significant increase in the apparent permeability of the $T_H1$ Intestine On-Chip epithelial barrier over embodiments of intestine on-chip without an activated ECM embodiment, i.e. no bound CD3 or bound CD28. This embodiment of activated ECM in one embodiment of an intestine on-chip, having ECM bound CD3 and bound CD28, mimics the induction of a weaker barrier function, where a weaker barrier function is one symptom (component) of both IBD subtypes, CD and UC.

FIG. 43 shows exemplary results of measuring barrier function after the addition of bound activation reagents on-chip with exposure to antigen. The graph demonstrates that bound CD3, with soluble or bound CD28, for co-stimulation of $T_H1$ cells in the presence of antigen has a significant impact on decreasing the barrier function of the Intestine On-Chip. The decreasing barrier function is represented as an increase in permeability.

Further, these experiments showed that $T_H1$ Intestine On-Chip having bound CD3 and bound CD28 (one embodiment of activated ECM) in combination with the presence of a soluble antigen, PAM, causes a significant increase (upregulation) of inflammatory cytokine production, e.g. IFN-gamma and IL-10, Intestine On-Chip. This upregulation is in contrast to IL-9, IL-13, IL-6 and IL-8 production from TH1 cells in Intestine On-Chip.

FIGS. 44A-D shows exemplary results of measuring immune cytokine expression alter the addition of bound activation reagents on-chip with exposure to antigen. The graphs demonstrate that bound CD3 with soluble or hound CD28 for co-stimulation of $T_H1$ cells in the presence of antigen. $T_H1$ cells show a significant increased in IFN-gamma but not IL-9 using bound CD3 and CD28 in the presence of soluble antigen. Thus, binding both CD3 and CD28 to the membrane causes a significant upregulation in inflammatory cytokine production on Intestine On-Chip for $T_H1$ cells. FIG. 44A shows IFNgamma production. FIG. 44B shows IL-9 production. FIG. 44C shows IL-10 production. FIG. 44D shows IL-13 production.

FIGS. 45A-B shows exemplary results of measuring epithelial cytokine expression using activated ECM as bound CD3 with soluble or bound CD28 for co-stimulation of TH1 cells in the presence of antigen. FIG. 45A shows IL-6 production. FIG. 45 IL-8 production.

FIGS. 46A-C shows exemplary results of measuring epithelial cytokine expression in the presence of T cells and activated ECM. In this embodiment as intestine on-chips having bound CD3 antibodies. In combination with bound CD28 or soluble CD28 co-stimulation of $T_H1$ cells. FIG. 46A TNF alpha cytokine expression. FIG. 46B IL-1b cytokine expression FIG. 46C shows an exemplary key for experimental conditions: control, antigen stimulation (PAM). In the presence of soluble CD28, bound CD28 and T cells without activated ECM (i.e. inactivated).

Thus, inflammatory cytokine production by immune cell populations differentiated into a $T_H1$ subsets. $T_H1$ subset production of cytokines in intestine on-chips treated with soluble CD28 mimics elevated cytokine levels found in the intestinal mucosa of CD patients'. Addition of bound CD3 and CD28 causes a significant increase in permeability, resulting in a weaker barrier function. A weaker barrier function in the intestine is a major component of both IBD subtypes.

Example 14

Evaluating Effect of Double-Bound (CD3 and CD28) Membrane on Intestine-Chips with $T_H1$ and $T_H9$ Immune Cells This example describes experiments using activated ECM comprising both CD3 and CD28 antibodies in the presence of soluble antigen for $T_H1$ compared to $T_H9$ immune cells. Soluble antigen was added as treatment on Day 7.

FIG. 47 shows a schematic representation demonstrating an exemplary timeline for experiments on chips seeded with $T_H1$ or $T_H9$ populations, activated and differentiated into subsets using CD3 antibody coated tissue culture plates co-stimulated with soluble CD28 antibodies (Day −3 to Day 0). See, FIG. 34 for additional details for the exemplary timeline of providing plate activated and differentiated T cell subsets, i.e. Day −3 to Day 0 of chip seeding. Treatment of immune cells on-chip includes an additional stimulation using bound activation reagents, CD3 antibodies and CD28 antibodies in the presence of antigen.

FIG. 48 shows exemplary results of measuring apparent permeability using a double bound activated ECM, with or without antigen, comparing $T_H1$ and $T_H9$ populations.

The addition of bound CD3 and CD28 has a significant affect on the barrier function of the Intestine-Chip in the presence of $T_H1$ and $T_H9$ cells.

When bound to the Intestine-Chip membrane, CD3 and CD28 are able to activate the $T_H1$ and $T_H9$ immune response, simulating Crohn's and Ulcerative Colitis diseased states, respectively.

Thus, culturing 1 cell subpopulations, e.g. $T_H1$ and $T_H9$, in the presence of ECM bound CD3 and CD28, in an intestine on-chip caused a significant increase in the apparent permeability of the epithelial barriers in both $T_H1$ and $T_H9$ Intestine On-Chips.

Therefore, exacerbation of antigen induced inflammatory reactions in TH populations in an Intestine On-Chip was caused by cell receptor signal activation, i.e. insoluble co-stimulatory molecules. This type of in vitro on-chip exacerbated inflammation response is contemplated to characterize the type of exacerbated inflammation observed in biopsies of inflammatory regions of in vivo IBDs.

Example 15

Blocking Inflammatory Cytokines During an Exacerbated Diseased State of Intestine On-Chips FIG. 49 shows a schematic representation demonstrating an exemplary timeline for immune response blocking experiments.

Stimulation conditions include but not limited to additional stimulation with PAM2CSK4 (i.e. PAM), with or without additional IL-9 and or IFN-gamma, alternatively with anti-IL-9 and/or blocking anti-IFNgamma. See, Table 13.

Such exemplary experimental conditions shown in Table 13. e.g. combinations of factors with certain treatments, are contemplated to determine the level of IFN-gamma associated with TH1 intestinal inflammatory responses IL-9 associated with TH9 intestinal inflammatory responses. Blocking of IFNg receptor binding in $T_H1$ and blocking IL-9 receptor binding in $T_H9$ chips is contemplated to, in part, decrease an exacerbated inflammatory response by at least an increase barrier function, i.e. by decreasing apparently permeability.

Example 16

Immune Cell Inflammatory Profile of CD45+ Resident Immune Cells On-Chip

Lamina propria derived, resident intestinal CD45+ immune cells were labeled with Cell Tracker, seeded onto Chips with HUVEC endothelial cells, and imaged over 8 hours of time-lapse photography. The time-lapse micrographs indicate that the heterogeneous population of CD45+ resident immune cells binds to and stably adhered to the Chip membrane.

FIG. 52A shows an exemplary schematic of one embodiment of an intestine on-chip seeded with CD45+ primary resident immune cells from a patient, FIG. 52B, as one overlapping image. In FIG. 52C, from 8 hours of time-lapse photography of intestinal resident immune cells. Lamina propria derived, resident intestinal immune cells were labeled with Cell Tracker, seeded onto Chips with HUVEC, endothelial cells. CD45+resident immune cells are a heterogeneous population that binds and stably adheres to the Chip membrane. FIG. 52A shows an exemplary schematic of one embodiment of an intestine on-chip with an upper epithelial channel seeded with CD45+ resident immune cells and a lower vascular channel seeded with endothelial cells. FIG. 52B shows an exemplary phase contrast image of the chip where white dots represent immune cells. FIG. 52C shows an exemplary fluorescent micrograph image of the chip where green dots represent immune cells labeled with Cell Tracker.

Secreted cytokine levels are an exemplary readout of inflammation and were measured for primary derived, resident intestinal immune cells (LP) in static culture, see FIG. 12. Therefore, secreted cytokine levels were measured in effluent media after seeding CD45+ resident immune cells on-chip.

FIGS. 53A-C shows exemplary results of measuring an inflammatory response (secreted cytokines) of CD45+ resident immune cells on-chip. FIG. 53A shows exemplary IL-6 protein secretion. FIG. 53B shows exemplary IL-10 protein secretion. FIG. 53C shows exemplary IL-8 protein secretion. FIG. 53D shows a key for experimental conditions. Ctrl LP, Non-Infl LP (Ulcerative Colitis) and Infl LP (Ulcerative Colitis).

Thus, it was summarized that primary resident immune cells remember their in vivo phenotype enabling a model of the mucosal microenvironment in the Intestine On-Chip in a patient-specific fashion. Including for e.g., for use in personalized medicine.

Example 17

LP Derived CD45+ Immune Cells From Additional Donors

Due to the large range in error bars after statistical analysis of some experiments, it was contemplated that more representative statistics having smaller error bars might be obtained using larger numbers of individuals. Thus, effects on in vitro epithelial barrier function, cytokine profile of immune cells, secreted cytokine production, and antigen activation using PAM were done alter adding in vivo activated T cells to an intestine on-chip. These measurements were made across multiple donors of intestinal inflamed UC LP. Thus, it was contemplated to mimic an UC "flare up" inflammatory cell response by adding such in vivo activated T cells from inflamed intestinal regions of UC LP.

Donors included but were not limited to Control (Ctrl LP) and Ulcerative colitis (UC LP). Immune cells were isolated from different regions of Donor 2's LP tissue: Non-Inflamed (Non-infl. UC LP) and Inflamed (Intl. UC LP).

A. Immune Cell Inflammatory Profile.

A cytokine profile of inflamed relative to non-inflamed immune cells was evaluated for on plate expression.

FIG. 54 shows exemplary results of measuring cytokine profile of immune cells isolated from a biopsy of inflamed colon tissues, i.e. inflamed, relative to immune cells isolated from a biopsy of non-inflamed immune cells. These experiments were done with immune cells on-plates.

It was found that Immune cells isolated from inflamed colon tissues have a significantly higher baseline inflammatory state than non-immune cells from non-inflamed colon tissue. Therefore, the inflammatory state of resident intestinal immune cells is highly location dependent.

B. Bacterial Challenge of Resident Immune Cells.

FIGS. 55A-C shows exemplary results of measuring secreted cytokine production from a UC patient's resident immune cells cultured on-plates, in response to 24 hour bacterial challenge as represented by exposure to PAM2CSK4. FIG. 55A shows exemplary TNF alpha protein secretion. FIG. 55B shows exemplary IL-6 protein secretion. FIG. 55C shows exemplary IL-8 protein secretion.

Thus, immune cells from inflamed, UC tissue have a higher baseline inflammatory state and stronger response to PAM2CSK4 activation of TLR2.

C. In Vivo Like Immune Cells Responses to Bacterial Challenge.

FIG. 56 shows exemplary results of measuring secreted cytokine production from a UC patient's isolated resident immune cells, cultured on plates, in response to 24 hour bacterial challenge as represented by exposure to PAM2CSK4. Cytokines expressed by control, healthy patient's resident immune cells are shown in grey dots, while blue dots represent results from UC non-inflamed resident immune cells and red dots represent results from UC inflamed resident immune cells. Significance [−log 10 (p-value)] Increasing Expression Log 2 (Fold-Change).

Thus, immune cells from a healthy patient are not activated by bacterial challenge. Non-inflamed immune cells from the Ulcerative Colitis patient are not significantly activated by bacterial challenge while Inflamed immune cells from the UC patient are significantly activated and primed to respond to bacterial stimuli.

D. Effects of Incorporated Resident Immune Cells in the Intestine-Chip.

FIGS. 57A-C shows exemplary, results of measuring secreted cytokines after incorporation of CD45+ resident immune cells in one embodiment of an intestine on-chip. FIG. 57A shows exemplary IL-6 protein secretion. FIG. 57B shows exemplary IL-8 protein secretion. FIG. 57C shows exemplary apparent permeability increase after CD45+ resident immune cells from an inflammatory region of UC LP.

Thus, Primary immune cells from inflamed tissues incorporated in the Intestine-Chip recapitulate relevant pro-inflammatory characteristics as shown by cytokine secretion and weakened intestinal barrier function.

E. Steroidal Treatment of Intestinal Inflammation.

During the development of the present invention, it was contemplated that immune cells from normal and inflamed regions would respond differently to the same treatment, in part supported by results obtained herein. Prednisone is an exemplary Standard-of-Care treatment for Ulcerative Colitis. However, Prednisone has undesirable Side Effects such as increased Risk of infection, Weight gain, Hyperglycemia, Hypertension, Bone loss. Further, the Efficacy of Prednisone is variable such that around 16% of treated patients are non-responsive, 30% have partial remission and 54% have full remission (Lichtenstein, et al. 2006).

FIGS. 58A-B shows representative schematics as FIG. 58A anti-inflammatory pathways involving glucocorticoid compound (as a red flower) entry through a cell membrane (upper right representation of a lipid bilayer) and FIG. 58B an exemplary Prednisone chemical structure.

When evaluating secreted cytokine production from one embodiment of an Intestine on Chip cultured with a UC patient's resident immune cells in response to bacterial challenge and prophylactic treatment with prednisone, there was no difference in the response of noninflamed vs. inflamed resident immune cells on-chip. In other words, Prednisone treatment on-chip suppresses the inflammatory responses of both noninflamed and inflamed tissues to PAM2CSK4 treatment.

FIGS. 59A-B shows secreted cytokine production from Intestine-Chip cultured with a UC patient's resident immune cells in response to bacterial challenge and prophylactic treatment with prednisone. FIG. 59A shows exemplary IL-8 protein secretion. FIG. 59B shows exemplary IL-9 protein secretion.

F. Interleukin 9 (IL-9) Production in the Pathogenesis of Ulcerative Colitis (UC).

While IL-9 promotes the development of allergic and autoimmune diseases (asthma/UC), IL-9 expression correlates with UC disease severity, but is not correlated with CD severity (Gerlach, et al., 2014). Further, Intestinal epithelial cells of UC patients express more IL-9R than in healthy patients (Nalleweg, et al., 2015) and IL-9 was shown to have a direct effect on the epithelium and promotes pathogenic immune responses in UC (Gerlach, et al. 2015). See, exemplary FIG. 51B showing a schematic representation of immune stimulation in relation to IL-9. In particular, IL-9 and IL-6 are overexpressed in mucosal biopsies from severely inflamed UC patients. See, FIG. 12. Overexpression of IL-9 and IL-6 generally tracks with disease severity.

G. Resident Immunity in the Pathogenesis of Ulcerative Colitis $T_H9$ Mediated Ulcerative Colitis.

As demonstrated herein. Intestine on-chip comprising immune cells isolated from primary LP tissue samples from patients, show that the presence of IL-9 protein and IL-9 receptors in the intestinal epithelial layer is associated with weakening the epithelial barrier and induces inflammatory responses.

FIG. 60A-B shows an exemplary comparison of IL-9 production in response to PAM stimulation as an exemplary bacterial agonist, FIG. 60A, and an immunofluorescent micrograph showing IL-9R (receptor) expression in the epithelial layer of one embodiment of an Intestine On-Chip, FIG. 60B, IL-9R is shown in green, tight junctions shown in red and nuclei stained with DAPI are colored blue.

Example 17

Exemplary Primary Cell Expansion and Differentiation

Primary cells obtained from biopsies were increased in numbers (expanded) after culturing in expansion media, such as shown in Table 14.

In one embodiment, expanded cells were then differentiated into cells reflecting their origin, e.g. intestinal segments: duodenum, jejunum, ileum or colon. In exemplary embodiments for differentiating cells: Cultures were exposed to ALI (Air Liquid Interface); Or the following media components were removed from expansion media for providing a differentiation media, Table 1 for example: Wnt3A, SB2001190 along with reducing the concentration of R-spondin and Noggin CM (obtained from conditioned media) to 10% and 5%, respectively. Additionally, Notch inhibitor (DAPT) is added to further enhance differentiation.

All patents, patent applications, and publications identified are expressly incorporated herein by reference for the purpose of describing and disclosing, for example, the methodologies described in such publications that might be used in connection with the present invention. These publications are provided solely for their disclosure prior to the filing date of the present application. Nothing in this regard should be construed as an admission that the inventors are not entitled to antedate such disclosure by virtue of prior invention or for any other reason. All statements as to the date or representation as to the contents of these documents is based on the information available to the applicants and does not constitute any admission as to the correctness of the dates or contents of these documents.

What is claimed is:

1. A method of stimulating immune cells, comprising:
   a) providing
      i) T helper cells and
      ii) a microfluidic device comprising a microfluidic channel and a membrane in contact with said microfluidic channel, said membrane comprising an extracellular matrix (ECM) comprising one or more extracellular proteins and affinity reagents, said affinity reagents bound to said ECM and configured to stimulate said T helper cells; and
   b) introducing said T helper cells into said microfluidic device under conditions such that said T helper cells become more stimulated in the presence of said affinity reagent bound to said ECM as compared to said affinity reagent that is soluble and not bound to said ECM; and
   c) measuring IL-10 secretion from said stimulated T helper cells.

2. The method of claim 1, wherein said one or more extracellular matrix proteins comprise an overlay, said overlay trapping said affinity reagents.

3. The method of claim 1, wherein said one or more extracellular matrix proteins comprise a gel, said gel trapping said affinity reagents.

4. The method of claim 1, wherein said affinity reagents comprises antibodies or antigen-binding fragments thereof.

5. The method of claim 4, wherein said antibodies are anti-CD3 antibodies.

6. The method of claim 4, wherein said antibodies are anti-CD28 antibodies.

7. The method of claim 4, wherein said antibodies are a combination of anti-CD3 antibodies and anti-CD28 antibodies.

8. The method of claim 1, prior to step b), providing epithelial cells, and adding said epithelial cells to said microfluidic device.

9. The method of claim 1, prior to step b), providing endothelial cells, and adding said endothelial cells to said microfluidic device.

10. The method of claim 1, wherein said T helper cells comprise TH9 cells.

11. The method of claim 1, wherein said device further comprises soluble antigen.

12. The method of claim 1, further comprising step c) introducing a soluble antigen into said microfluidic device.

13. The method of claim 1, further comprising step c) introducing one or more test agents into said microfluidic device.

14. The method of claim 13, wherein said test agent is a drug or candidate drug.

15. The method of claim 14, wherein said drug or candidate drug is tested for inhibiting said T helper cells.

16. A method, comprising:
a) providing:
   i) one or more reagents configured to activate T helper cells,
   ii) T helper cells,
   iii) an extracellular matrix (ECM) solution comprising one or more extracellular matrix proteins, and
   iv) a microfluidic device comprising a membrane;
b) adding said one or more reagents to said ECM solution to create an ECM mixture comprising said affinity reagents bound to said ECM;
c) coating said membrane with the ECM mixture; and
d) adding said T helper cells to said microfluidic device under conditions such that said T helper cells are more activated in the presence of said affinity reagent bound to said ECM as compared to said affinity reagent that is soluble and not bound to said ECM.

17. The method of claim 16, wherein said one or more reagents comprise affinity reagents.

18. The method of claim 17, wherein said one or more affinity reagents comprise antibodies or antigen-binding fragments thereof.

19. The method of claim 16, wherein said microfluidic device further comprises one or more microfluidic channels.

20. The method of claim 16, wherein said T helper cells comprise TH9 cells.

* * * * *